United States Patent
Barnett et al.

(10) Patent No.: US 10,208,123 B2
(45) Date of Patent: Feb. 19, 2019

(54) ANTI-CD70 ANTIBODY DRUG CONJUGATES

(71) Applicant: Ambrx, Inc., La Jolla, CA (US)

(72) Inventors: Richard S. Barnett, San Marcos, CA (US); Nick Knudsen, Escondido, CA (US); Ying Sun, San Diego, CA (US); Sandra Biroc, Alameda, CA (US); Timothy Buss, Carlsbad, CA (US); Tsotne Javahishvili, Del Mar, CA (US); Damien Bresson, San Diego, CA (US); Shailaja Srinagesh, San Mateo, CA (US); Amha Hewet, Chula Vista, CA (US); Jason K. Pinkstaff, San Rafael, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 14/410,021

(22) PCT Filed: Jun. 19, 2013

(86) PCT No.: PCT/US2013/046669
§ 371 (c)(1),
(2) Date: Dec. 19, 2014

(87) PCT Pub. No.: WO2013/192360
PCT Pub. Date: Dec. 27, 2013

(65) Prior Publication Data
US 2015/0141624 A1 May 21, 2015

Related U.S. Application Data

(60) Provisional application No. 61/661,782, filed on Jun. 19, 2012.

(51) Int. Cl.
| | |
|---|---|
| *A61K 38/00* | (2006.01) |
| *A61P 35/00* | (2006.01) |
| *C07K 16/28* | (2006.01) |
| *A61K 47/42* | (2017.01) |
| *C07K 5/062* | (2006.01) |
| *A61K 47/68* | (2017.01) |

(52) U.S. Cl.
CPC .......... *C07K 16/2875* (2013.01); *A61K 47/42* (2013.01); *A61K 47/6817* (2017.08); *A61K 47/6845* (2017.08); *A61K 47/6889* (2017.08); *C07K 5/06052* (2013.01); *C07K 2317/76* (2013.01)

(58) Field of Classification Search
CPC .... A61K 38/07; A61K 38/00; A61K 38/1774; A61P 35/00
See application file for complete search history.

(56) References Cited

FOREIGN PATENT DOCUMENTS

| | | |
|---|---|---|
| WO | WO 2004/073656 A2 | 9/2004 |
| WO | WO 2006/069246 A2 | 6/2006 |
| WO | WO 2008/077079 A1 | 6/2008 |
| WO | WO 2012/166559 A1 | 12/2012 |
| WO | WO 2012/166560 A1 | 12/2012 |
| WO | WO 2013/068874 A1 | 5/2013 |

OTHER PUBLICATIONS

Sapra et al., "Abstract 5691: Novel Site Specific Antibody drug Conjugates Based on Novel Amino Acid Incorporation Technology Have Improved Pharmaceutical Properties Over Conventional Antibody Drug Conjugates" Cancer Research, (2012) 72(8):5691.

*Primary Examiner* — Rachael E Bredefeld
*Assistant Examiner* — Kaipeen E Yang
(74) *Attorney, Agent, or Firm* — Sharon Beresford

(57) ABSTRACT

This invention relates to anti-CD70 antibodies and antibody drug conjugates comprising at least one non-naturally-encoded amino acid. Disclosed herein are αCD70 antibodies with one or more non-naturally encoded amino acids and further disclosed are antibody drug conjugates wherein the αCD70 antibodies of the invention are conjugated to one or more toxins. Further disclosed are methods for using such non-natural amino acid antibody drug conjugates, including therapeutic, diagnostic, and other biotechnology uses.

4 Claims, 8 Drawing Sheets
Specification includes a Sequence Listing.

ANTI-CD70 ANTIBODY DRUG CONJUGATES

CROSS-REFERENCE TO RELATED APPLICATIONS

This application is national phase entry in the United States under 35 U.S.C. § 371 of International Patent Application No. PCT/US13/46669 filed on Jun. 19, 2013, which is incorporated by reference herein in its entirety and claims priority to and the benefit of U.S. Provisional Application Ser. No. 61/661,782 filed on Jun. 19, 2012, the specification and contents of which are incorporated by reference in its entirety for all purposes.

FIELD OF THE INVENTION

This invention relates to anti-CD70 antibodies and antibody drug conjugates comprising at least one non-naturally-encoded amino acid. Disclosed herein are αCD70 antibodies with one or more non-naturally encoded amino acids and further disclosed are antibody drug conjugates wherein the αCD70 antibodies of the invention are conjugated to one or more toxins. Further disclosed are methods for using such non-natural amino acid antibody drug conjugates, including therapeutic, diagnostic, and other biotechnology uses.

BACKGROUND OF THE INVENTION

CD70 is a member of the tumor necrosis factor (TNF) family of cell membrane-bound and secreted molecules that are expressed by a variety of normal and malignant cell types. The primary amino acid (AA) sequence of CD70 predicts a transmembrane type II protein with its carboxyl terminus exposed to the outside of cells and its amino terminus found in the cytosolic side of the plasma membrane (Bowman et al., 1994, J Immunol 152:1756-61; Goodwin et al., 1993, Cell 73:447-56). Human CD70 is composed of a 20 AA cytoplasmic domain, an 18 AA transmembrane domain, and a 155 AA extracytoplasmic domain with two potential N-linked glycosylation sites (Bowman et al., supra; Goodwin et al., supra). Specific immunoprecipitation of radioisotope-labeled CD70-expressing cells by anti-CD70 antibodies yields polypeptides of 29 and 50 kDa (Goodwin et al., supra; Hintzen et al., 1994, J Immunol 152:1762-73). Based on its homology to TNF-alpha and TNF-beta, especially in structural strands C, D, H and I, a trimeric structure is predicted for CD70 (Petsch et al., 1995, Mol Immunol 32:761-72).

Original immunohistological studies revealed that CD70 is expressed on germinal center B cells and rare T cells in tonsils, skin, and gut (Hintzen et al., 1994, Int Immunol 6:477-80). Subsequently, CD70 was reported to be expressed on the cell surface of recently antigen-activated T and B lymphocytes, and its expression wanes after the removal of antigenic stimulation (Lens et al., 1996, Eur J Immunol 26:2964-71; Lens et al., 1997, Immunology 90:38-45). Within the lymphoid system, natural killer cells (Orengo et al., 1997, Clin Exp Immunol 107:608-13) and mouse mature peripheral dendritic cells (Akiba et al., 2000, J Exp Med 191:375-80) also express CD70. In non-lymphoid lineages, CD70 has been detected on thymic medullar epithelial cells (Hintzen et al., 1994, supra; Hishima et al., 2000, Am J Surg Pathol 24:742-46).

In addition to expression on normal cells, CD70 expression has been reported in different types of cancers including lymphomas, carcinomas, and tumors of neural origin. In malignant B cells, 71% of diffuse large B-cell lymphomas, 33% of follicle center lymphomas, 25% of mantle lymphomas, and 50% of B-CLL have been reported to express CD70 (Lens et al., 1999, Br J Haematol 106:491-503). CD70 is frequently expressed together with other lymphoid activation markers on the malignant Hodgkin and Reed-Sternberg cells of Hodgkin's disease (Gruss and Kadin, 1996, Bailieres Clin Haematol 9:417-46). One report demonstrates CD70 expression on 88% (7 of 8 cases) of thymic carcinomas and 20% (1 of 5 cases) of atypical thymomas (Hishima et al., 2000, supra). The second type of carcinoma on to which CD70 has been detected is nasopharyngeal carcinoma. One study reports the presence of CD70 on 80% (16 of 20 cases) of snap-frozen tumor biopsies obtained from undifferentiated nasopharyngeal carcinomas (Agathanggelou et al., 1995, Am J Path 147:1152-60). CD70 has also been detected on brain tumor cells, especially glioma cell lines, solid human gliomas, and meningiomas (Held-Feindt and Mentlein, 2002, Int J Cancer 98:352-56; Wischlusen et al., 2002, Can Res 62:2592-99).

It has been proposed that transforming viruses including the Epstein-Barr virus (EBV) and the human T leukemia virus-1 (HTLV-1) can induce CD70 on cells such as epithelial cells that normally do not express CD70 (Agathanggelou et al., supra; Stein et al., 1989, Oxford University Press, p. 446). Therefore, expression of CD70 on malignant B cells could be a reflection of oncogenic transformation (Lens et al., 1999, supra). Also, since CD70 expression is induced on B cells after antigen encounter (Maurer et al., 1990, Eur J Immunol 20:2679-84; Lens et al., 1996, supra), stable expression of CD70 might reflect prolonged antigenic stimulation. This has been postulated to occur in follicular non-Hodgkin's lymphomas based on ongoing somatic hypermutation (Bahler et al., 1992, Proc Natl Acad Sci USA 89:6770-74; Bahler et al., 1992, Cancer Res 52:suppl. 5547S-51S).

The receptor for CD70 is CD27, a glycosylated type I transmembrane protein of about 55 kDa (Goodwin et al., 1993, Cell 73:447-56; Hintzen et al., 1994, supra). CD70 is sometimes referred to as CD27L. CD27, which exists as a homodimer on the cell surface (Gravestein et al., 1993, Eur J Immunol 23:943-50), is a member of the TNF receptor superfamily as defined by cysteine-rich repeats of about 40 amino acids in the extracellular domain (Smith et al., 1990, Science 248:1019-23; Locksley et al., 2001, Cell 104:487-501). CD27 is typically expressed by thymocytes, NK, T, and B cells (Hintzen et al., 1994, Immunol Today 15:307-11; Lens et al., 1998, Semin Immunol 10:491-99). On resting T cells, CD27 is constitutively expressed, yet antigenic triggering further upregulates CD27 expression (de Jong et al., 1991, J Immunol 146:2488-94; Hintzen et al., 1993, J. Immunol. 151:2426-35). Further, triggering of T cells via their T cell antigen receptor complex alone or in combination with the accessory molecule CD28 releases soluble CD27 from activated T cells (Hintzen et al., 1991, J Immunol 147:29-35). Naive B cells do not express CD27, but its expression is induced and, in contrast to CD70, sustained after antigenic triggering of B cells (Jacquot S et al., 1997 J Immunol 159:2652-57; Kobata T et al., 1995, Proc Natl Acad Sci USA 92:11249-53).

In marked contrast to the restricted expression of CD27 and CD70 in normal B lineage cells, both CD27 and CD70 are frequently co-expressed in many B cell non-Hodgkin's lymphomas and leukemias. This could potentially lead to functional CD27-CD70 interactions on these cells in the form of an autocrine loop, resulting in CD27 signaling and in CD70-induced proliferation, thereby providing a growth advantage to malignant cells (Lens et al., 1999, supra).

The available data supports a model in which ligation of CD27 on activated lymphocytes by CD70 delivers signals to the CD27-expressing cells, including co-stimulatory signals in T, B, and NK cells. (See, e.g., Goodwin et al., supra; Hintzen et al., 1995, J Immunol 154:2612-23; Oshina et al., 1998, Int Immunol 10:517-26; Smith et al., supra; Van Lier et al., 1987, J Immunol 139:1589-96; Gravestein et al., 1995, Int Immunol 7:551-7; Tesselaar et al., 1997, J Immunol 159:4959-65; Jacquot et al., supra; Agematsu et al., 1998, Blood 91:173-80; Kobata et al., supra; Agematsu et al., 1997, Eur J Immunol 27:2073-79; Sugita et al., 1992, J Immunol 149:1199-1203; Orengo et al., 1997, Clin Exp Immunol 107:608-13). Antibodies against both murine and human CD70 have been demonstrated to inhibit such activities, presumably by blocking the CD70/CD27 interaction (Hintzen et al., 1994, supra; Hintzen et al., 1995, supra; Oshima et al., supra).

Limited information is available on the modulation of cellular functions through CD70 signaling upon CD70/CD27 interaction, i.e., 'reverse signaling'. Some CD70 antibodies have the ability to enhance T cell proliferation when they are presented to CD70-expressing T cells either cross-linked with a secondary antibody or immobilized on tissue culture plates (Bowman et al., 1994, J Immunol 152:1756-61; Brugnoni, 1997, Immunol Lett 55:99-104). Such 'reverse signaling' has also been described in a subset of B chronic lymphocytic leukemia (B-CLL) cells, and CD70 can function as a receptor to transduce signals to facilitate proliferation of PMA-stimulated purified B-CLL cells (Lens et al., 1999, supra). These observations suggest situations in which engagement of CD27 and CD70 can result in the delivery of agonistic signals to both the CD27 and CD70 expressing cells.

The role of CD70/CD27 co-stimulation in cell-mediated autoimmune diseases has been investigated in a model of experimental autoimmune encephalomyelitis (EAE) (Nakajima et al., 2000, J Neuroimmunol 109:188-96). In vivo administration of a particular anti-mouse CD70 mAb (clone FR-70) markedly suppressed the onset of EAE by inhibiting antigen-induced TNF-alpha production without affecting T cell priming, Ig production or $T_{H1}/T_{H2}$ cell balance. However, such treatment had little efficacy in established disease. It has been reported that expression of CD70 on T cells was enhanced by TNF-alpha and IL-12 and down regulated by $IL_4$ (Lens et al., 1998, supra). Thus, the CD70/CD27 mediated T cell-T cell interactions may play a role in enhancing $T_{H1}$-mediated immune responses rather than $T_{H2}$-mediated responses. Supporting this hypothesis, the anti-mouse CD70 mAb FR-70 is also effective in inhibiting $T_{H1}$-mediated collagen-induced arthritis (Nakajima et al., 2000, supra). In contrast, the same anti-mouse CD70 mAb did not show any efficacy in modulating lupus in NZB/NZW F1 mice and experimental *Leishmania major* infection in susceptible BALB/c mice, both of which are predominantly $T_{H2}$-mediated autoimmune response (Nakajima et al., 1997, J Immunol 158, 1466-72; Akiba et al., 2000, J Exp Med 191:375-380).

The role of CD70 has not yet been investigated in acute graft versus host disease (aGVHD), another $T_{H1}$-mediated immune response. GVHD is a major and often lethal consequence of allogeneic bone marrow transplantation (BMT) therapy that occurs when histocompatibility antigen differences between the BM donor and the recipient of the transplant are present (den Haan et al., 1995, Science 268:1476). GVHD is caused by mature T cells present in the transplanted marrow, as well as other minor cell populations (Giralt and Champlin, 1994, Blood 84:3603). It is noteworthy that CD70 has been detected in vivo on CD4+ cells in conditions characterized by allogeneic reaction, as in cases of maternal T cell engraftment in severe combined immune deficiency patients (Brugnoni et al., Immunol Lett 55:99-104). Prophylaxis of GVHD is achieved by pan-T cell immunosuppressive agents such as cyclosporine, corticosteroids, or methotrexate. In addition to the lack of specificity, these agents are also associated with significant adverse side effects. To limit these undesirable effects and the disruption of normal T cell functions, other therapeutic interventions based on selective targeting of T cells directly participating in allo-recognition and graft rejection are much needed.

CD70 is a potentially useful target for antibody-directed immunotherapy. As indicated supra, CD70 has a restricted expression pattern in normal cells: CD70 expression is mostly restricted to recently antigen-activated T and B cells under physiological conditions, and its expression is downregulated when antigenic stimulation ceases. The key role of CD70 is believed to be facilitating plasma cell differentiation and contributing to the generation and maintenance of long-term T cell memory. Further, evidence from animal models suggests that unregulated CD70/CD27 interaction may contribute to immunological disorders, and, in humans, experimental data have also pointed towards potential abnormal regulation of the CD70/CD27 pathway in $T_{H1}$-mediated immune disorders such as, e.g., rheumatoid arthritis, psoriasis, and multiple sclerosis. It is of particular interest that CD70 is expressed on a variety of transformed cells including lymphoma B cells, Hodgkin and Reed-Sternberg cells, malignant cells of neural origin, and a number of carcinomas.

Several groups have demonstrated the inhibitory effect of anti-CD70 mAb in both in vitro models of lymphocyte activation and animal models of $T_{H1}$-mediated responses. The focus has been on the use of antibodies to block the CD70/CD27 co-stimulation pathway to achieve therapeutic efficacy. However, one main shortcoming of such an approach is the large number of signaling receptors, e.g., the CD28/CD80/CD86 co-stimulatory pathway, known to participate in immunological diseases. Consequently, blocking one specific signaling pathway may only have minimal impact on disease development. This is supported by the observations that anti-CD70 mAb can only partially inhibit in vitro T cell activation induced by allogeneic stimulator cells (Hintzen et al., 1995, supra) and an anti-CD70 mAb showed no therapeutic efficacy in EAE once the disease is established (Nakajima et al., 2000, supra).

Thus, there is a need in the art for developing an approach for depleting or inhibiting the growth of CD70-expressing cells involved in cancers and/or immunological diseases by means other than or in addition to blocking the CD70/CD27 interaction. As CD70 is expressed on the surface of mature antigen presenting dendritic cells, activated T cells, and activated B cells, agents that can target and inhibit or deplete CD70+ cells may prove to be effective in the removal of antigen presenting cells presenting autoantigens and offending autoreactive activated T or B cells, as wells as CD70-expressing tumor cells.

Approaches that have been used for increasing the therapeutic efficacy of antibodies are radiolabeling and combination with chemotherapy; however, these approaches include associated with undesirable side effects. For example, isotope therapy is associated with myelosuppression (Witzig, 2001, Cancer Chemother Pharmacol 48 (Suppl 1):S91-5), and combining therapy with antibodies and chemotherapeutics is associated with immunosuppression. Further, isotopically labeled substances are difficult to produce, and patients often experience relapse after initial treatment with isotopically labeled substances.

Accordingly, there is a need for anti-CD70 ADCs that are constructed in such a manner so as to be capable exerting a clinically useful cytotoxic, cytostatic, or immunosuppressive effect on CD70-expressing cells, particularly without exerting undesirable effects on non-CD70-expressing cells. Such compounds would be useful therapeutic agents against cancers that express CD70 or immune disorders that are mediated by CD70-expressing cells. More recently, MAbs such as 2H5 have been identified. Anti-CD70 antibody-drug conjugates that can be utilized for imaging, diagnostic and/or therapeutic uses are therefore needed. The present invention provides such antibody-drug conjugates for use in immunology and oncology.

SUMMARY OF THE INVENTION

Disclosed herein are anti-CD70 antibodies linked to toxic moieties through one or more non-natural amino acids with one or more linker(s), and methods for making such non-natural amino acids and polypeptides.

Some embodiments of the present invention provide an anti-CD70 antibody comprising one or more non-naturally encoded amino acids. In some embodiments, the anti-CD70 antibody comprises one non-naturally encoded amion acid. In some embodiments, the anti-CD70 antibody comprises two non-naturally encoded amino acids. In some embodiments, the anti-CD70 antibody comprises two or more non-naturally encoded amino acids. In some embodiments, the anti-CD70 antibody comprises 3, 4, 5, or 6 more non-naturally encoded amino acids. or more post-translational modifications. In some embodiments, the anti-CD70 antibody comprises the heavy chain sequence given in SEQ ID NO. 1. In some embodiments of the present invention, the anti-CD70 antibody comprises SEQ ID NO.1 and 2. In some embodiments, the anti-CD70 antibody is linked to a linker, polymer, or biologically active molecule. In some embodiments, the anti-CD70 antibody is linked to a linker, polymer, or biologically active molecule via a non-naturally encoded amino acid in the anti-CD70 antibody.

Some embodiments of the present invention describe a toxic moiety, or salt thereof, comprising Formula (I):

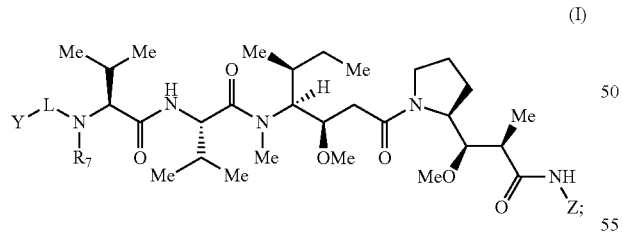

(I)

wherein:

Z has the structure of:

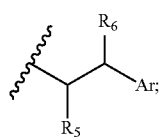

$R_5$ is H, $COR_8$, $C_1$-$C_6$alkyl, or thiazole;

$R^8$ is OH or —NH-(alkylene-O)$_n$—NH$_2$;

$R_6$ is OH or H;

Ar is phenyl or pyridine;

$R_7$ is $C_1$-$C_6$alkyl or hydrogen;

Y is selected from the group consisting of an hydroxylamine, methyl, aldehyde, protected aldehyde, ketone, protected ketone, thioester, ester, dicarbonyl, hydrazine, amidine, imine, diamine, azide, keto-amine, keto-alkyne, alkyne, cycloalkyne, and ene-dione;

L is a linker selected from the group consisting of -alkylene-, -alkylene-C(O)—, -(alkylene-O)$_n$-alkylene-, -(alkylene-O)$_n$-alkylene-C(O)—, -(alkylene-O)$_n$—(CH$_2$)$_{n'}$—NHC(O)CH$_2$)$_{n''}$—C(Me)$_2$—S—S—(CH$_2$)$_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-U-alkylene-C(O)—, and -(alkylene-O)$_n$-alkylene-U-alkylene-;

W has the structure of:

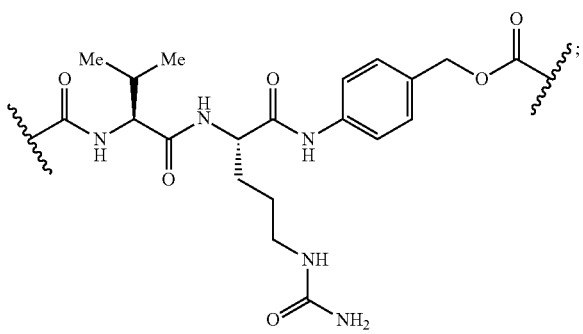 [SMILES: *C(=O)N[C@H](C(=O)N[C@@H](CCCNC(N)=O)C(=O)Nc1ccc(COC(*)=O)cc1)C(C)C]

U has the structure of:

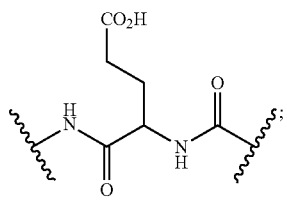 [SMILES: *NC(=O)C(CCC(=O)O)NC(*)=O]

or L is absent, Y is methyl, $R_5$ is $COR_8$, and $R_8$ is —NH-(alkylene-O)$_n$—NH$_2$; and each n, n', n", n'" and n"" are independently integers greater than or equal to one.

In some embodiments, $R_5$ is thiazole. In other embodiments, $R_6$ is H. In certain embodiments, Ar is phenyl. In further or additional embodiments, $R_7$ is methyl. In some embodiments, n is an integer from 0 to 20, 0 to 10 or 0 to 5.

In some embodiments, a compound is described comprising Formula (II):

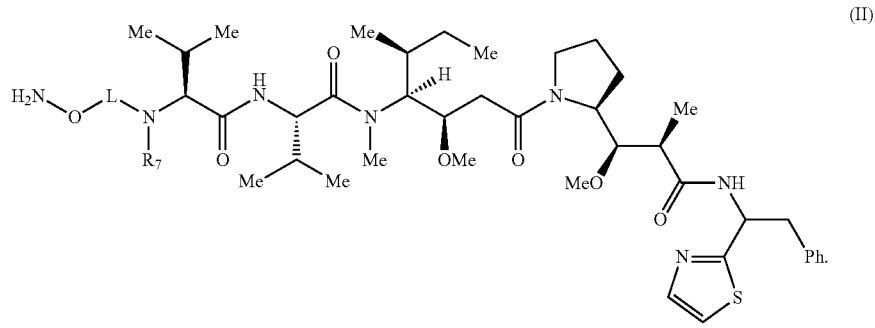

(II)

In certain embodiments, L is -(alkylene-O)$_n$-alkylene-. In specific embodiments, each alkylene is —CH$_2$CH$_2$—, n is equal to 3, and R$_7$ is methyl. In other embodiments, L is -alkylene-. In specific embodiments, each alkylene is —CH$_2$CH$_2$— and R$_7$ is methyl or hydrogen. In certain embodiments, L is -(alkylene-O)$_n$-alkylene-C(O)—. In certain specific embodiments, each alkylene is —CH$_2$CH$_2$—, n is equal to 4, and R$_7$ is methyl. In further or alternative embodiments, L is -(alkylene-O)$_n$—(CH$_2$)$_{n'}$—NHC(O)—(CH$_2$)$_{n''}$—C(Me)$_2$-S—S—(CH$_2$)$_{n'''}$—NHC(O)-(alkylene-O)$_{n''''}$-alkylene-. In specific embodiments, each alkylene is —CH$_2$CH$_2$—, n is equal to 1, n' is equal to 2, n" is equal to 1, n''' is equal to 2, n"" is equal to 4, and R$_7$ is methyl.

In some embodiments, Y is azide. In other embodiments, Y is cyclooctyne. In specific embodiments, the cyclooctyne has a structure of:

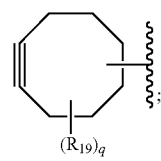

each R$_{19}$ is independently selected from the group consisting of C$_1$-C$_6$ alkyl, C$_1$-C$_6$ alkoxy, ester, ether, thio-ether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro; and q is 0, 1, 2, 3, 4, 5, 6, 7, 8, 9, 10 or 11.

Some embodiments of the present invention describe a compound, or salt thereof, comprising Formula (III), (IV), (V) or (VI):

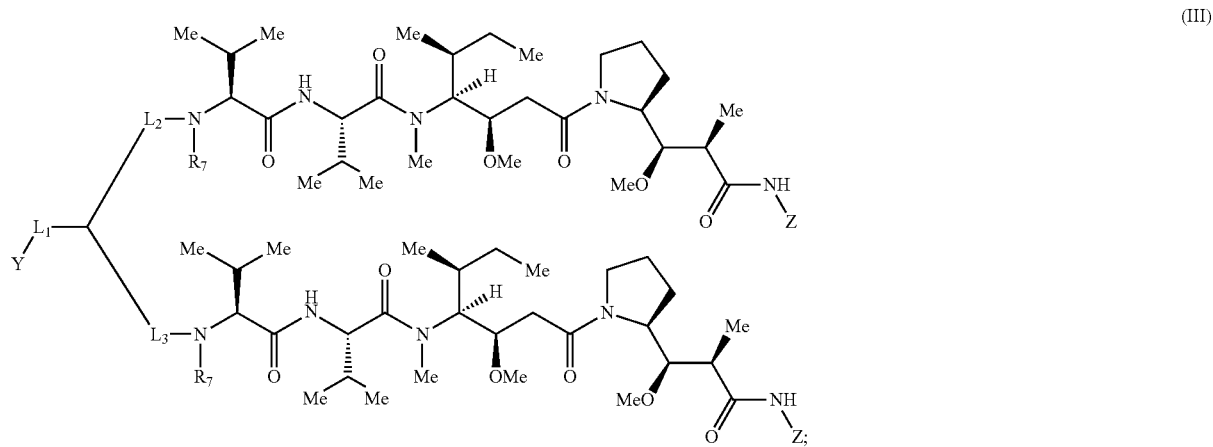

(III)

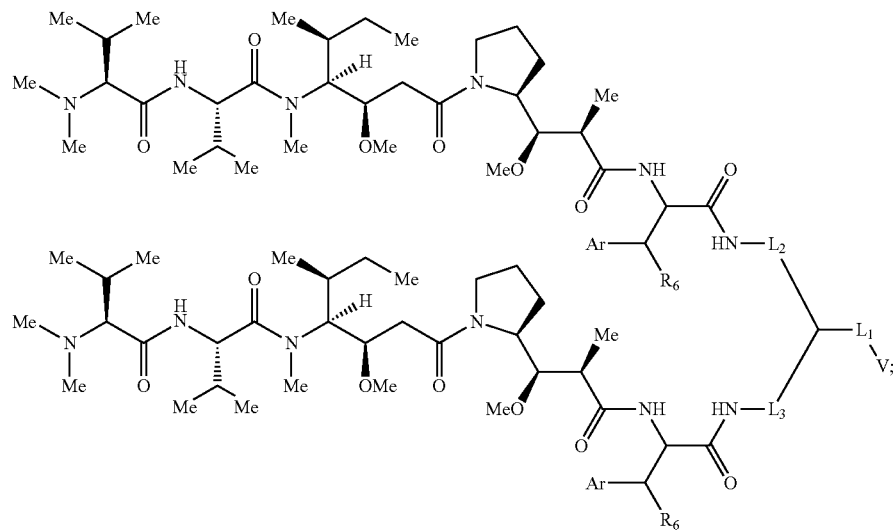
(IV)
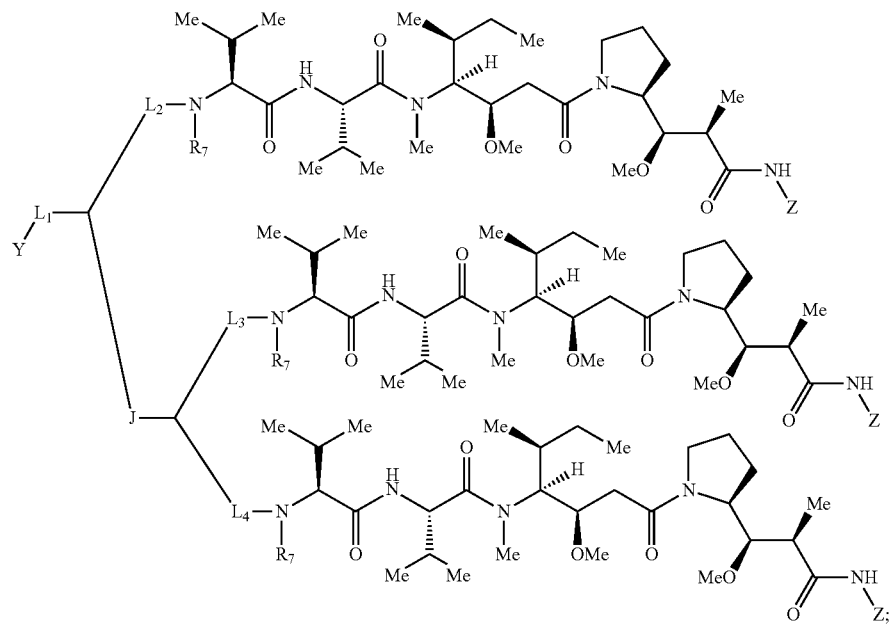
(V)

(VI)

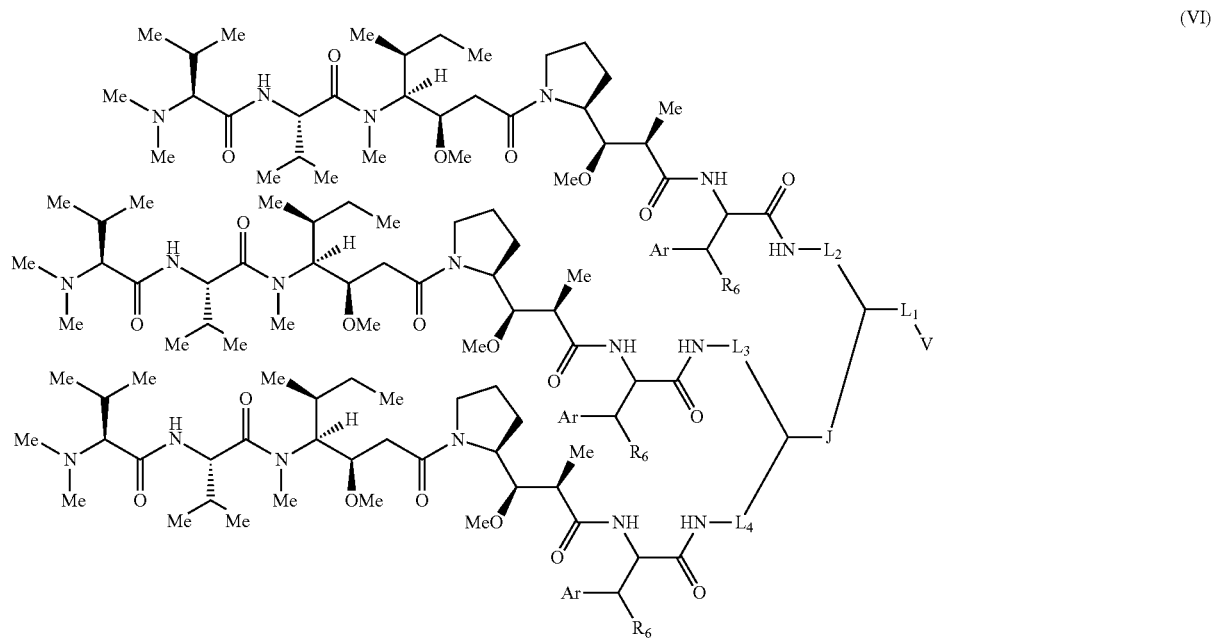

wherein:

Z has the structure of:

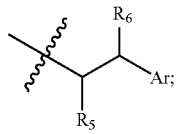

$R_5$ is H, $COR_8$, $C_1$-$C_6$alkyl, or thiazole;

$R_8$ is OH;

$R_6$ is OH or H;

Ar is phenyl or pyridine;

$R_7$ is $C_1$-$C_6$alkyl or hydrogen;

Y and V are each selected from the group consisting of an hydroxylamine, methyl, aldehyde, protected aldehyde, ketone, protected ketone, thioester, ester, dicarbonyl, hydrazine, amidine, imine, diamine, azide, keto-amine, keto-alkyne, alkyne, cycloalkyne, and ene-dione;

$L_1$, $L_2$, $L_3$, and $L_4$ are each linkers independently selected from the group consisting of a bond, -alkylene-, -(alkylene-O)$_n$-alkylene-J-, -alkylene'-J-(alkylene-O)$_n$-alkylene-, -J-(alkylene-O)$_n$-alkylene-, -(alkylene-O)$_n$-alkylene-J-(alkylene-O)$_n$'-alkylene-J'-, -(alkylene-O)$_n$-alkylene-J-alkylene'-, —W—, -alkylene-W—, alkylene'-J-(alkylene-NMe)$_n$-alkylene-W—, -J-(alkylene-NMe)$_n$-alkylene-W—, -J-alkylene-NMe-alkylene'-NMe-alkylene"-W—, and -alkylene-J-alkylene'-NMe-alkylene"-NMe-alkylene'''-W—;

W has the structure of:

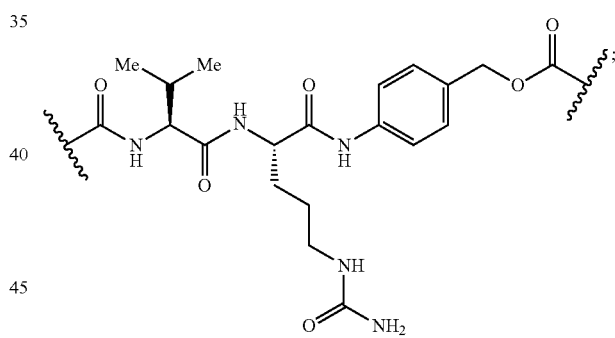

each J and J' independently have the structure of

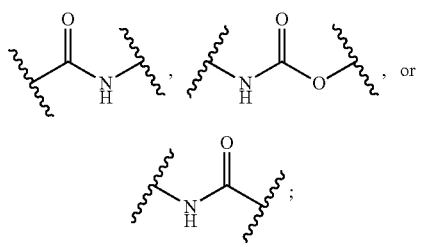

each n and n' are independently integers greater than or equal to one.

In certain embodiments, a compound is described comprising Formula

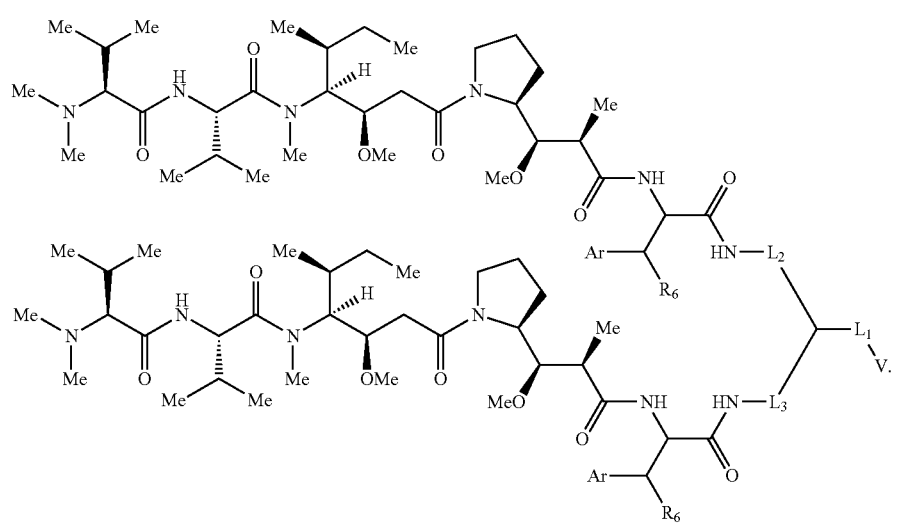

(VII)

In certain embodiments, L$_1$ is -(alkylene-O)$_n$-alkylene-J-, L$_2$ is -alkylene'-J'-(alkylene-O)$_{n'}$-alkylene-, L$_3$ is -J''-(alkylene-O)$_{n''}$-alkylene-, alkylene is —CH$_2$CH$_2$—, alkylene' is —(CH$_2$)$_4$—, n is 1, n' and n'' are 3, J has the structure of

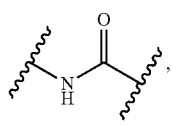,

J' and J'' have the structure of

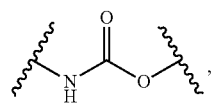, and R$_7$ is methyl. In other embodiments, L$_1$ is -J-(alkylene-O)$_n$-alkylene-, L$_2$ is -(alkylene-O)$_{n'}$-alkylene-J'-alkylene'-, L$_3$ is -(alkylene-O)$_{n''}$-alkylene-J''-, alkylene is —CH$_2$CH$_2$—, alkylene' is —(CH$_2$)$_4$—, n is 1, n' and n'' are 4, and J, J' and J'' have the structure of

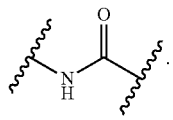 [SMILES: *NC(*)=O].

In some embodiments, Y is azide. In other embodiments, Y is cyclooctyne. In specific embodiments, the cyclooctyne has a structure of:

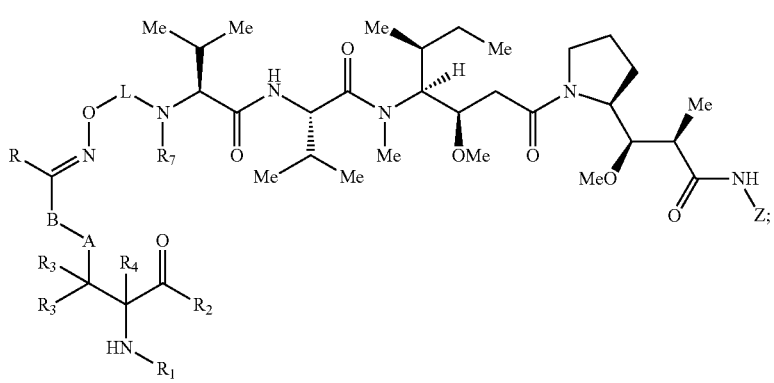

each R$_{19}$ is independently selected from the group consisting of C$_1$-C$_6$ alkyl, C$_1$-C$_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro; and q is 0, 1, 2, 3, 4, 5, 6, 7, 8, 9, 10 or 11.

Certain embodiments of the present invention describe a compound comprising Formula (VIII) or (IX):

(VIII)

-continued

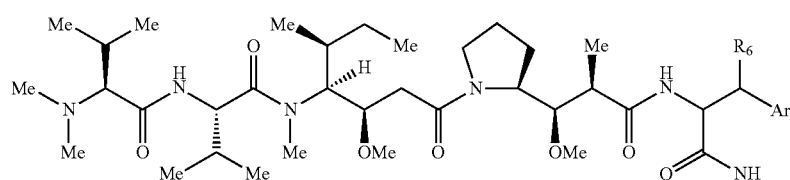

(IX)

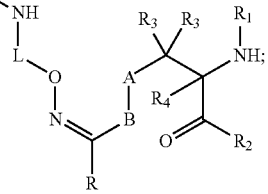

wherein:

- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
- R is H, alkyl, substituted alkyl, cycloalkyl, or substituted cycloalkyl;
- $R_1$ is H, an amino protecting group, resin, at least one amino acid, polypeptide, or polynucleotide;
- $R_2$ is OH, an ester protecting group, resin, at least one amino acid, polypeptide, or polynucleotide;
- $R_3$ and $R_4$ are each independently H, halogen, lower alkyl, or substituted lower alkyl, or $R_3$ and $R_4$ or two $R_3$ groups optionally form a cycloalkyl or a heterocycloalkyl;
- Z has the structure of:

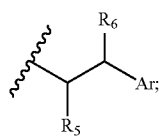

- $R_5$ is H, $CO_2H$, $C_1$-$C_6$alkyl, or thiazole;
- $R_6$ is OH or H;
- Ar is phenyl or pyridine;
- $R_7$ is $C_1$-$C_6$alkyl or hydrogen;
- L is a linker selected from the group consisting of -alkylene-, -alkylene-C(O)—, -(alkylene-O)$_n$-alkylene-, -(alkyleneO)$_n$-alkylene-C(O)—, -(alkylene-O)$_n$—(CH$_2$)$_{n'}$—NHC(O)CH$_2$)$_{n''}$—C(Me)$_2$-S—S—(CH$_2$)$_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-U-alkylene-C(O)—, and -(alkylene-O)$_n$-alkylene-U-alkylene-;
- W has the structure of:

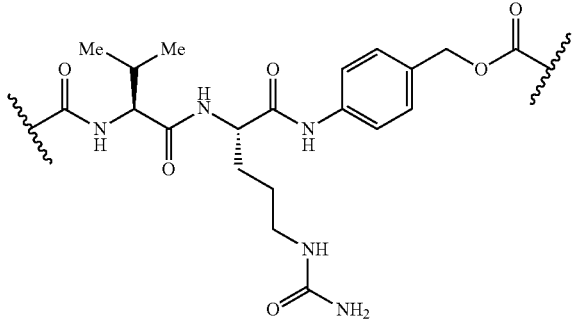

U has the structure of:

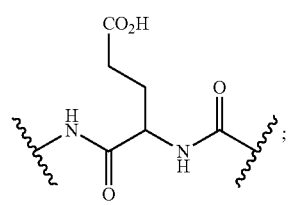 [SMILES: *NC(=O)C(CCC(=O)O)NC(*)=O]

and
each n, n', n", n'" and n"" are independently integers greater than or equal to one;
or an active metabolite, or a pharmaceutically acceptable prodrug or solvate thereof.

In some embodiments, $R_1$ is a polypeptide. In specific embodiments, the polypeptide is an antibody. In some embodiments, the antibody is anti-CD70. In other embodiments, $R_2$ is a polypeptide. In specific embodiments, the polypeptide is an anti-CD70 antibody. In certain specific embodiments, the antibody is CD70-2H5-HA119-NCA1.

Some embodiments of the present invention describe a compound, or salt thereof, comprising Formula (X), (XI), (XII) or (XIII):
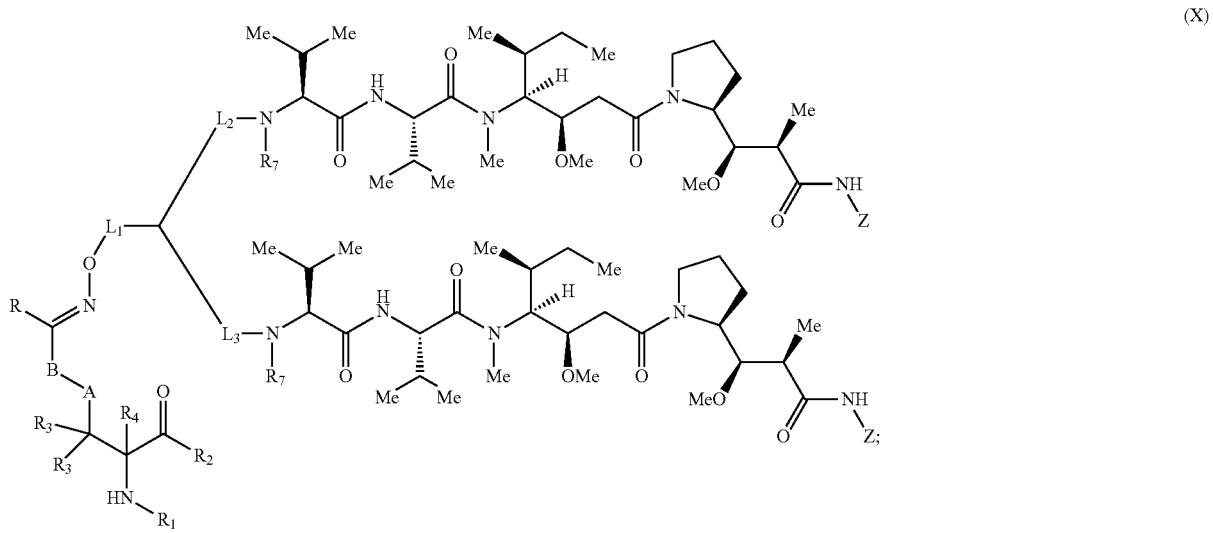
(X)
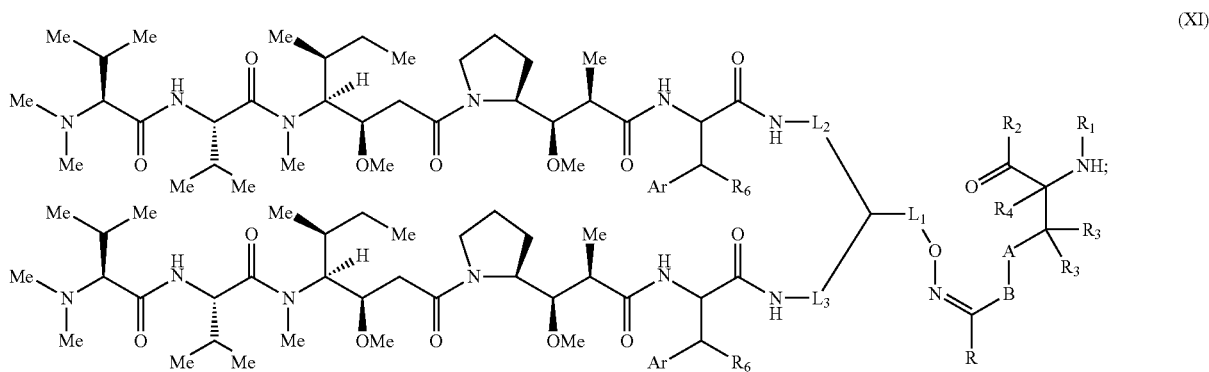
(XI)
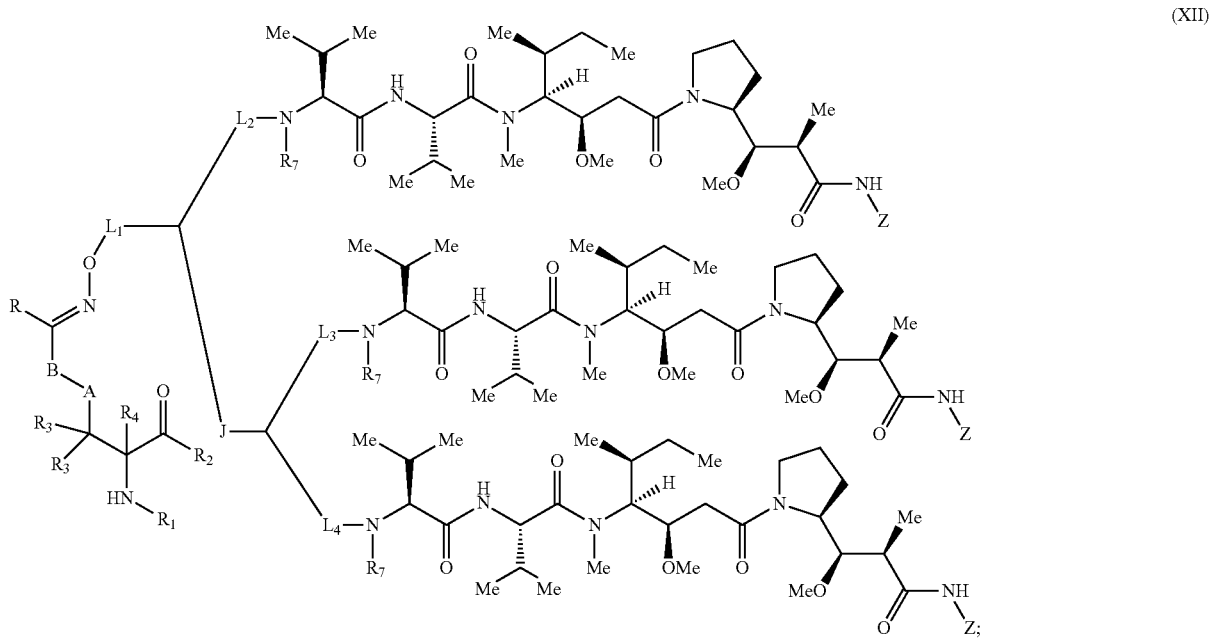
(XII)

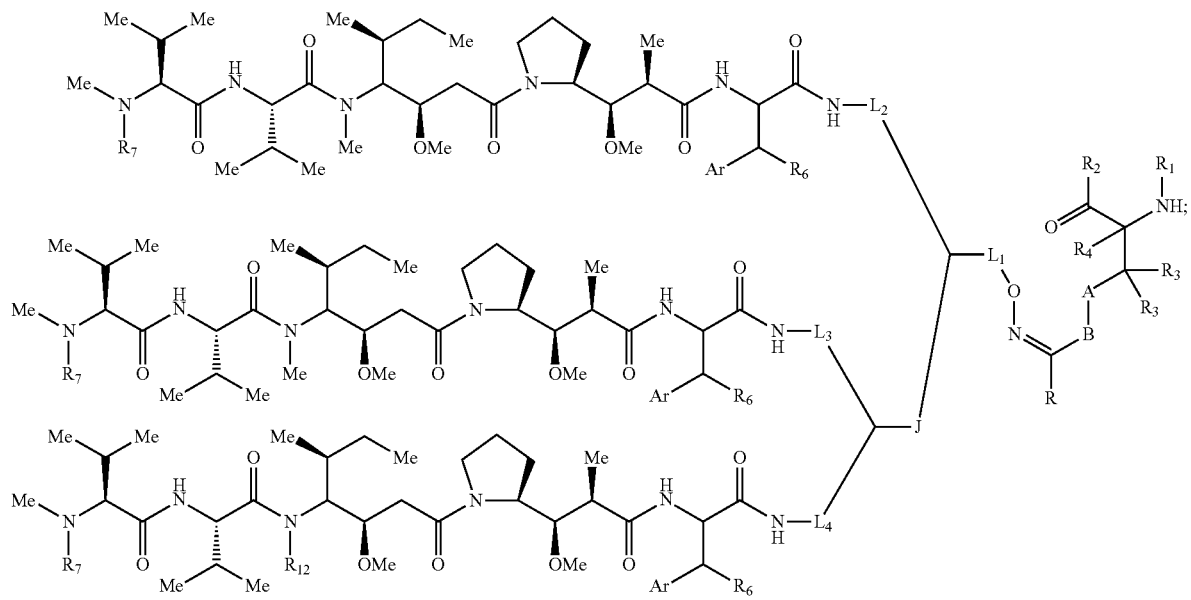

(XIII)

wherein:
A is optional, and when present is lower alkylene, substituted lower alkylene, lower cycloalkylene, substituted lower cycloalkcylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is H, an amino protecting group, resin, at least one amino acid, polypeptide, or polynucleotide;

$R_2$ is OH, an ester protecting group, resin, at least one amino acid, polypeptide, or polynucleotide;

$R_3$ and $R_4$ are each independently H, halogen, lower alkyl, or substituted lower alkyl, or $R_3$ and $R_4$ or two $R_3$ groups optionally form a cycloalkyl or a heterocycloalkyl;

Z has the structure of:

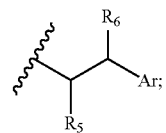

$R_5$ is H, CO$_2$H, C$_1$-C$_6$alkyl, or thiazole;
$R_6$ is OH or H;
Ar is phenyl or pyridine;
$R_7$ is C$_1$-C$_6$alkyl or hydrogen;
$L_1$, $L_2$, $L_3$, and $L_4$ are each linkers independently selected from the group consisting of a bond, -alkylene-, -(alkylene-O)$_n$-alkylene-J-, -alkylene'-J-(alkylene-O)$_n$-alkylene-, -J-(alkylene-O)$_n$-alkylene-, -(alkylene-O)$_n$-alkylene-J-(alkylene-O)$_n$'-alkylene-J'-, -(alkylene-O)$_n$-alkylene-J-alkylene'-, —W—, alkylene-W—, alkylene'-J-(alkylene-NMe)$_n$-alkylene-W—, -J-(alkylene-NMe)$_n$-alkylene-W—, -J-alkylene-NMe-alkylene'-NMe-alkylene''-W—, and -alkylene-J-alkylene'-NMe-alkylene''-NMe-alkylene'''-W—;
W has the structure of:

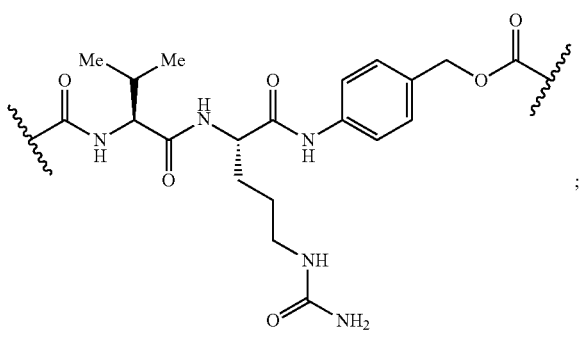 [SMILES: *C(=O)N[C@H](C(=O)N[C@@H](CCCNC(N)=O)C(=O)Nc1ccc(COC(*)=O)cc1)C(C)C]

each J and J' independently have the structure of:

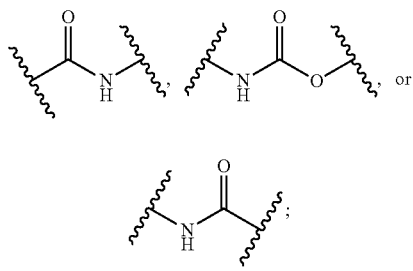

and each n and n' are independently integers greater than or equal to one.

In some embodiments, $R_1$ is a polypeptide. In specific embodiments, the polypeptide is an antibody. In certain specific embodiments, the antibody is herceptin. In other embodiments, $R_2$ is a polypeptide. In specific embodiments, the polypeptide is an antibody. In certain embodiments, the antibody is αCD70. In some embodiments, the antibody is derived from any known αCD70 antibody. In certain specific embodiments, the antibody is ARX-αCD70.

In some embodiments, provided herein is a method for derivatizing a dolastatin analog comprising Formula (I), (III), (IV), (V), or (VI), the method comprising contacting the dolastatin analog with a reagent of Formula (XXXVII), wherein Formula (I), (III), (IV), (V), or (VI) correspond to:

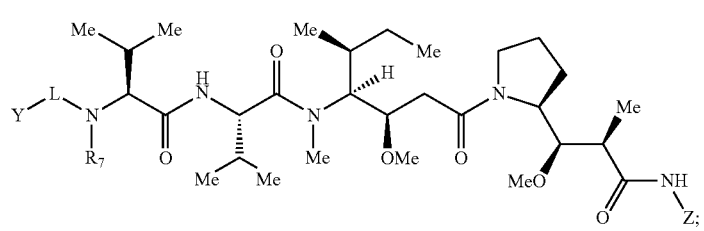

(I)

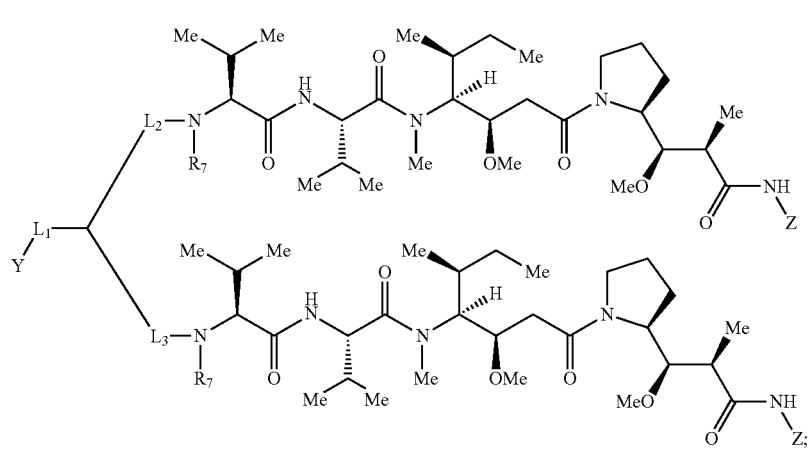

(III)

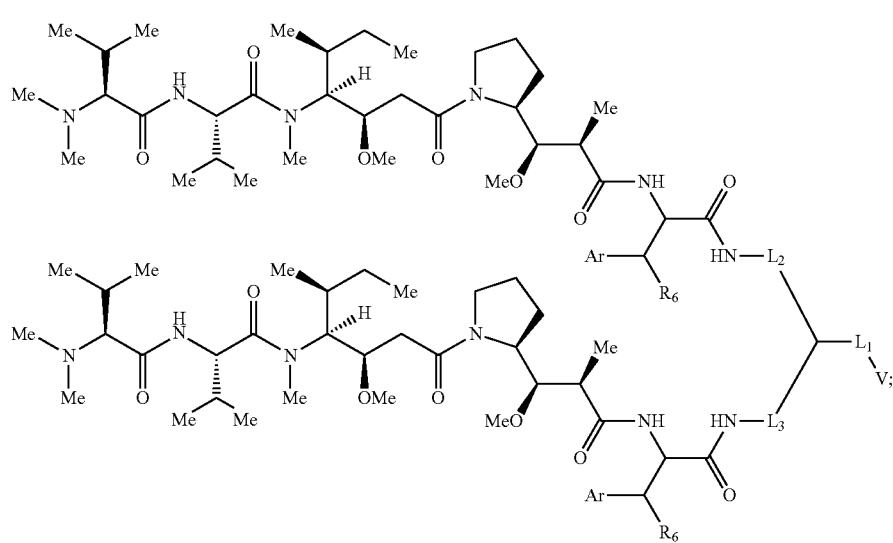

(IV)

-continued

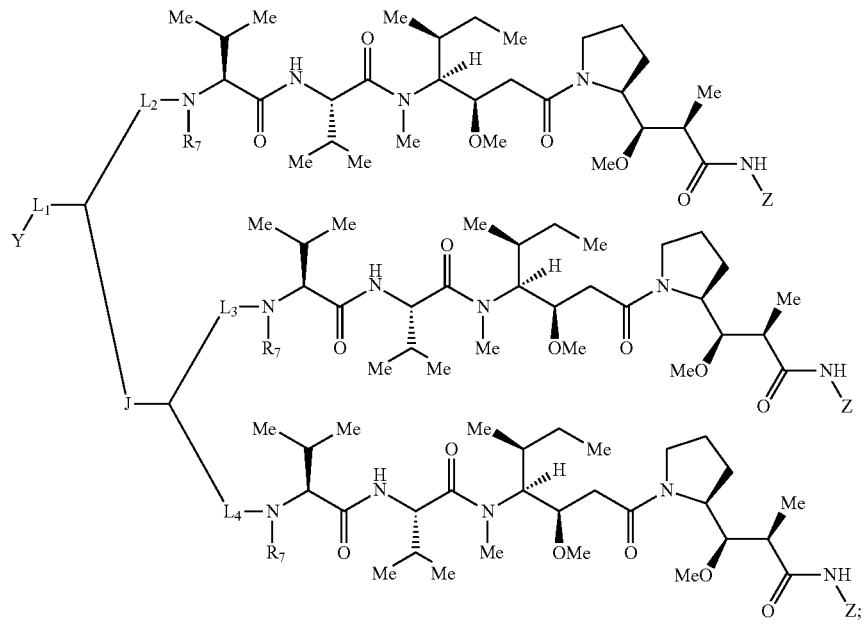

(V)

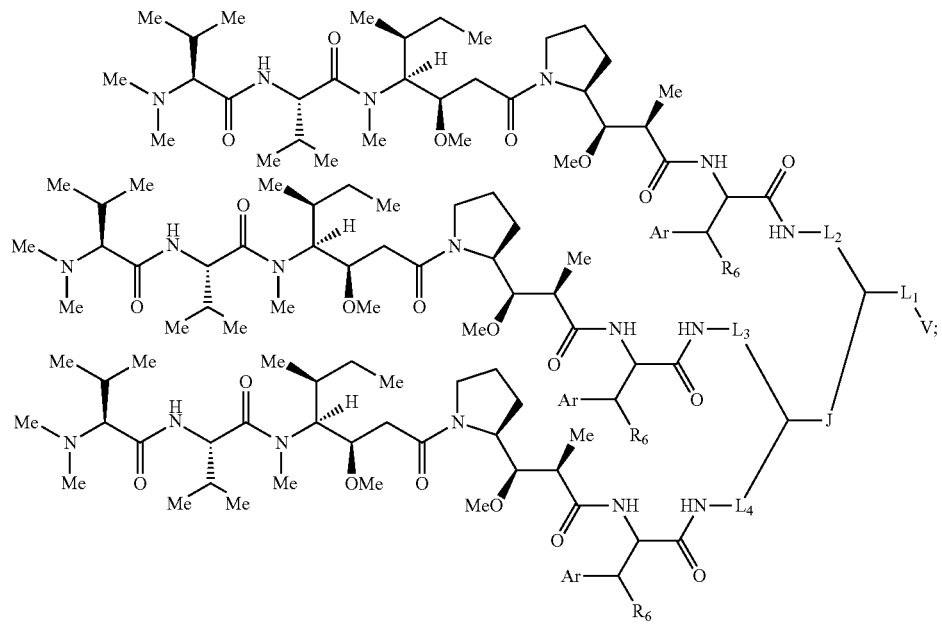

(VI)

wherein:
Z has the structure of:

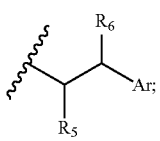

$R_5$ is H, $COR_8$, $C_1$-$C_6$alkyl, or thiazole;
$R_8$ is OH or —NH-(alkylene-O)$_n$—NH$_2$;
$R_6$ is OH or H;
Ar is phenyl or pyridine;

$R_7$ is $C_1$-$C_6$ alkyl or hydrogen;
Y is NH$_2$—O— or methyl;
L, $L_1$, $L_2$, $L_3$, and $L_4$ are each linkers selected from the group consisting of a bond, -alkylene-, -alkylene-C(O)—, -(alkylene-O)$_n$-alkylene-, -(alkylene-O)$_n$-alkylene-C(O)—, -(alkylene-O)$_n$—(CH$_2$)—NHC(OH—CH$_2$)$_{n''}$—C(Me)$_2$-S—S—(CH$_2$)$_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-J-, -alkylene'-J-(alkylene O)$_n$-alkylene-, -(alkylene-O)$_n$-alkylene-J-alkylene', -J-(alkylene-O)$_n$-alkylene-, -(alkylene-O)$_n$-alkylene-J-(alkylene-O)$_n$'-alkylene-J'-, —W—, -alkylene-W—, alkylene'-J-(alkylene-NMe)$_n$-alkylene-W—, and J-(alkylene-NMe)$_n$-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene"-W—, and -alkylene-J-alkylene'-NMe-alkylene"-NMe-alkylene'"W—;

W has the structure of:

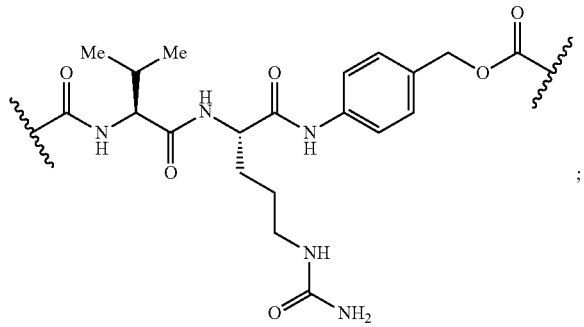 [SMILES: *C(=O)N[C@H](C(=O)N[C@@H](CCCNC(N)=O)C(=O)Nc1ccc(COC(*)=O)cc1)C(C)C]

U has the structure of:

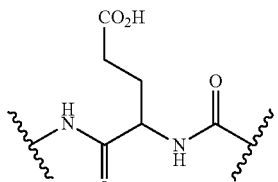

each J and J' independently have the structure of:

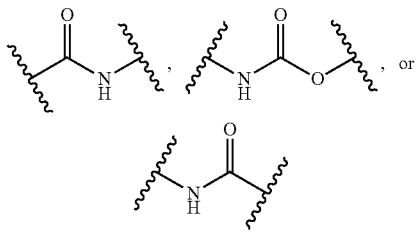

or L is absent, Y is methyl, $R_5$ is $COR_8$, and $R_8$ is —NH-(alkylene-O)$_n$—NH$_2$; and each n, n', n", n'" and n"" are independently integers greater than or equal to one;

wherein Formula (XXXVII) corresponds to:

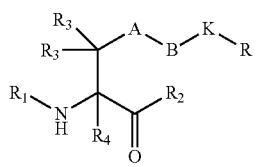

(XXXVII)

wherein:

A is optional, and when present is lower alkylene, substituted lower alkylene, lower alkenylene, substituted lower alkenylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

each R' is independently H, alkyl, or substituted alkyl;

K is

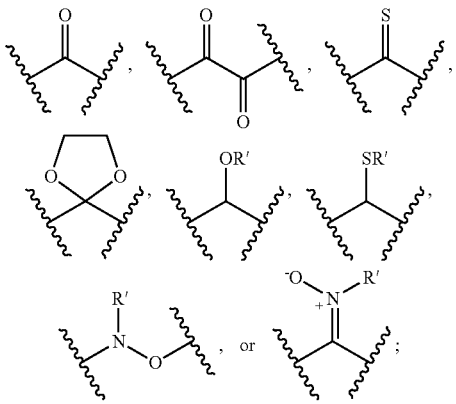

R is H, alkyl, substituted alkyl, cycloalkyl, or substituted cycloalkyl;

$R_1$ is H, an amino protecting group, resin, at least one amino acid, or polynucleotide;

$R_2$ is OH, an ester protecting group, resin, at least one amino acid, or polynucleotide; and $R_3$ and $R_4$ are each independently H, halogen, lower alkyl, or substituted lower alkyl, or $R_3$ and $R_4$ or two $R_3$ groups optionally form a cycloalkyl or a heterocycloalkyl.

In some embodiments, the derivatized dolastatin analog comprises at least one oxime containing amino acid having the structure of Formula (VIII), (IX), (X), (XI), (XII), or (XIII):

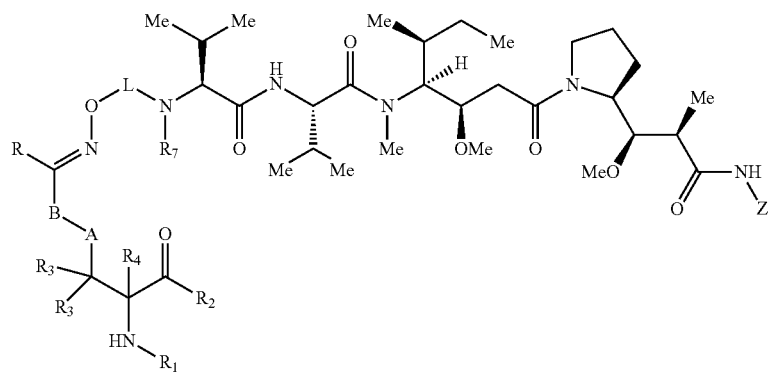
(VIII)
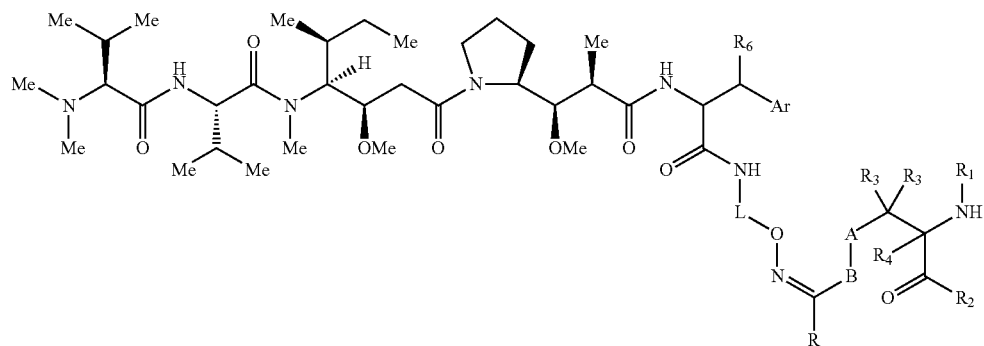
(IX)
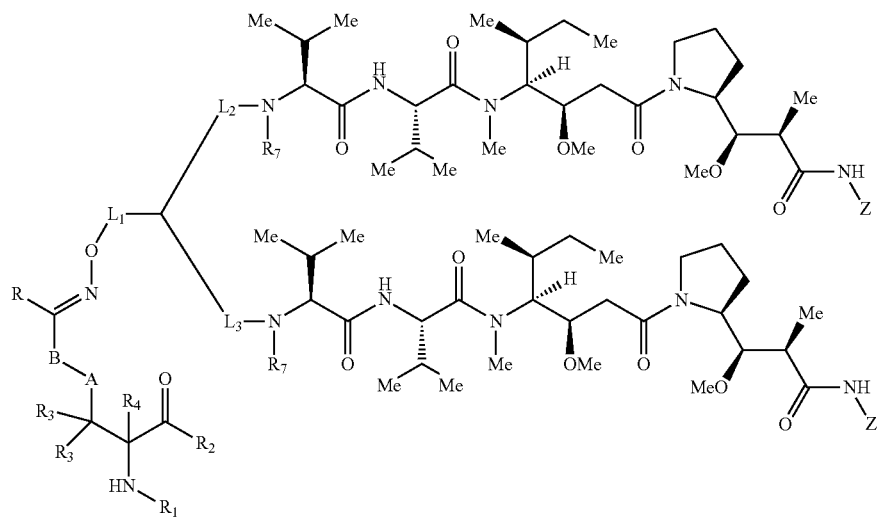
(X)
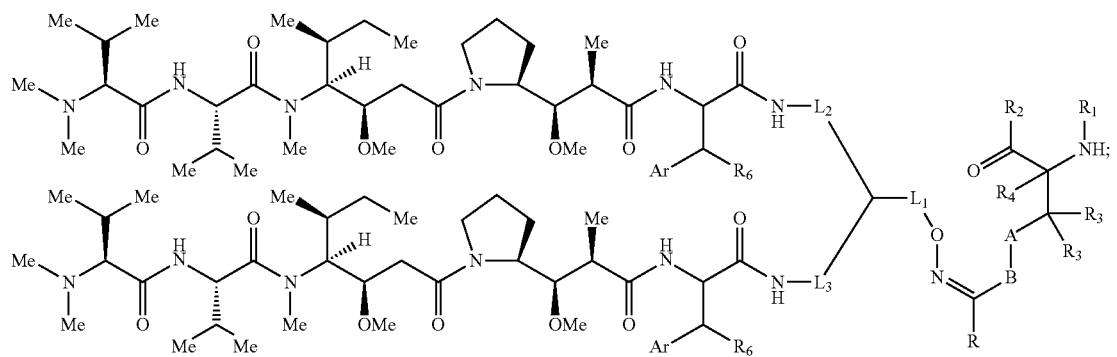
(XI)

(XII)
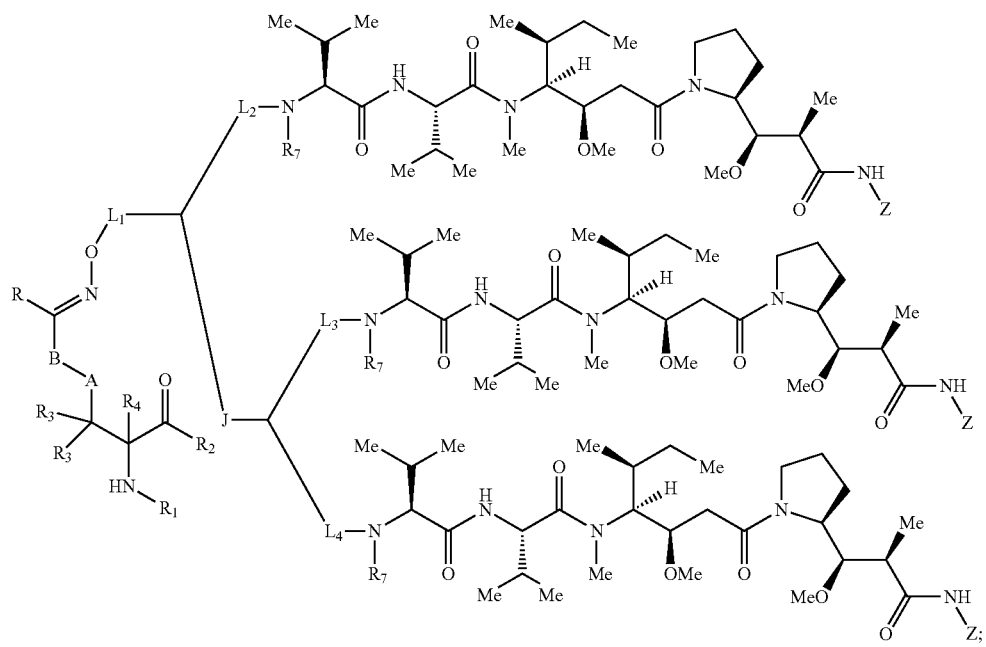
(XIII)
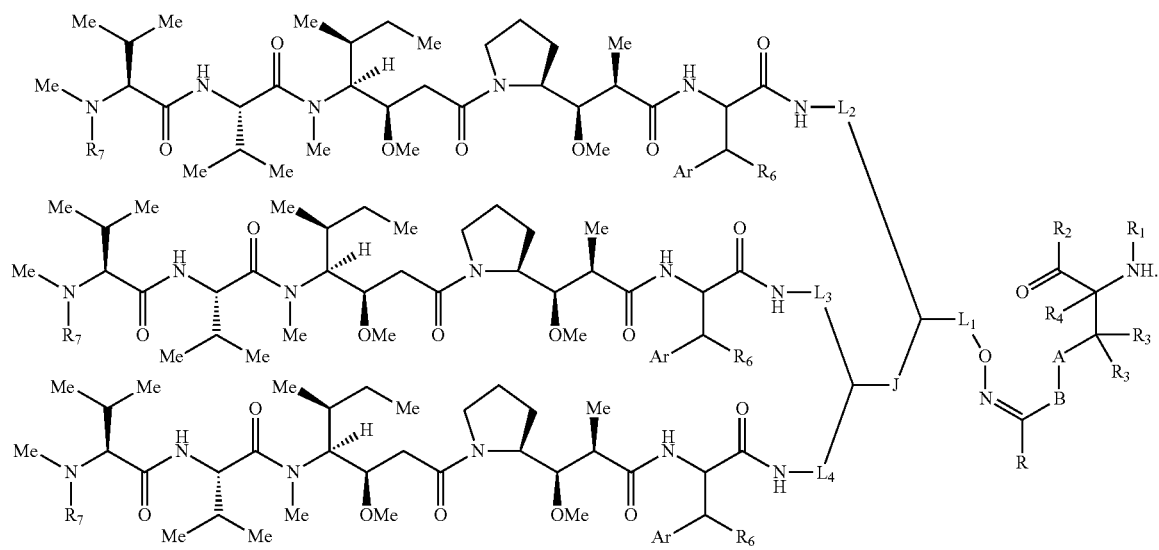
In specific embodiments, the dolastatin analog is contacted with the reagent of Formula (XXXVII) in aqueous solution under mildly acidic conditions.
Certain embodiments of the present invention describe a compound comprising Formula (XXV), (XXVI), (XXVII), (XXVIII), (XXIX), or (XXX):
(XXV)
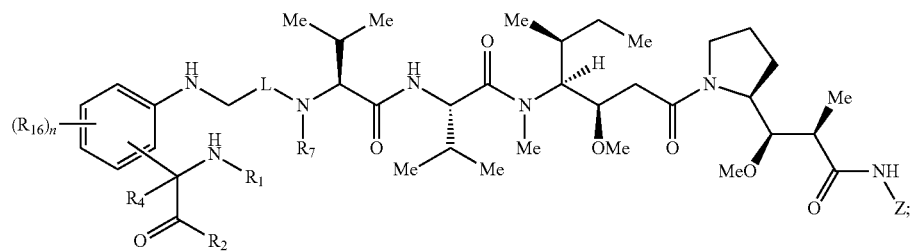

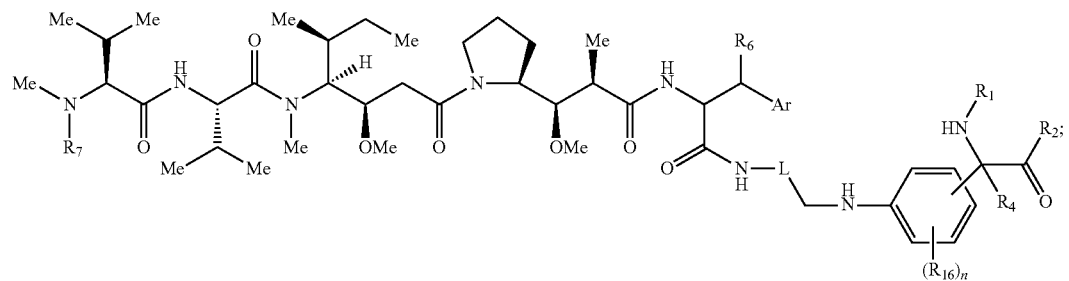
(XXVI)
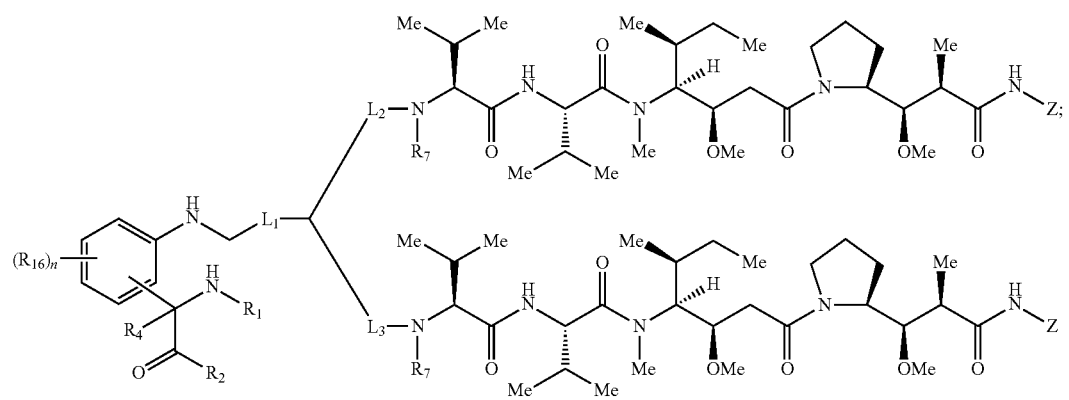
(XXVII)
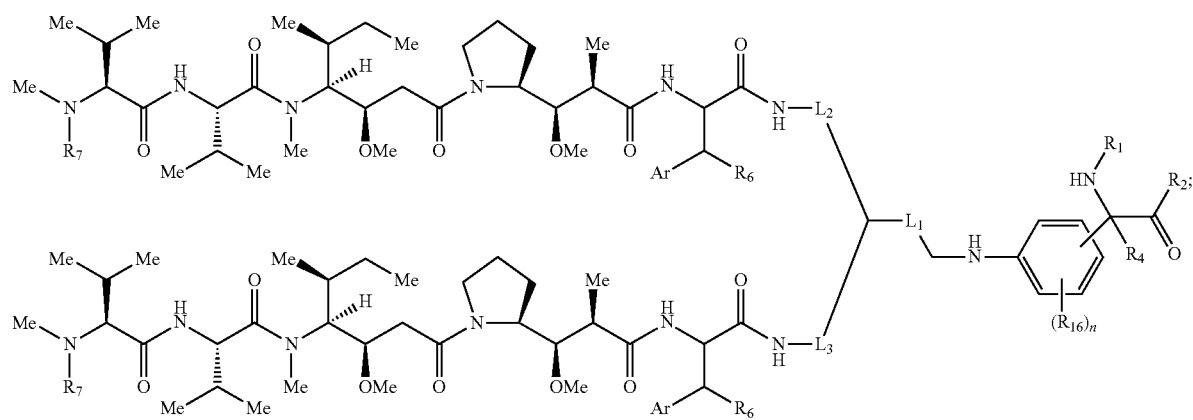
(XXVIII)

-continued

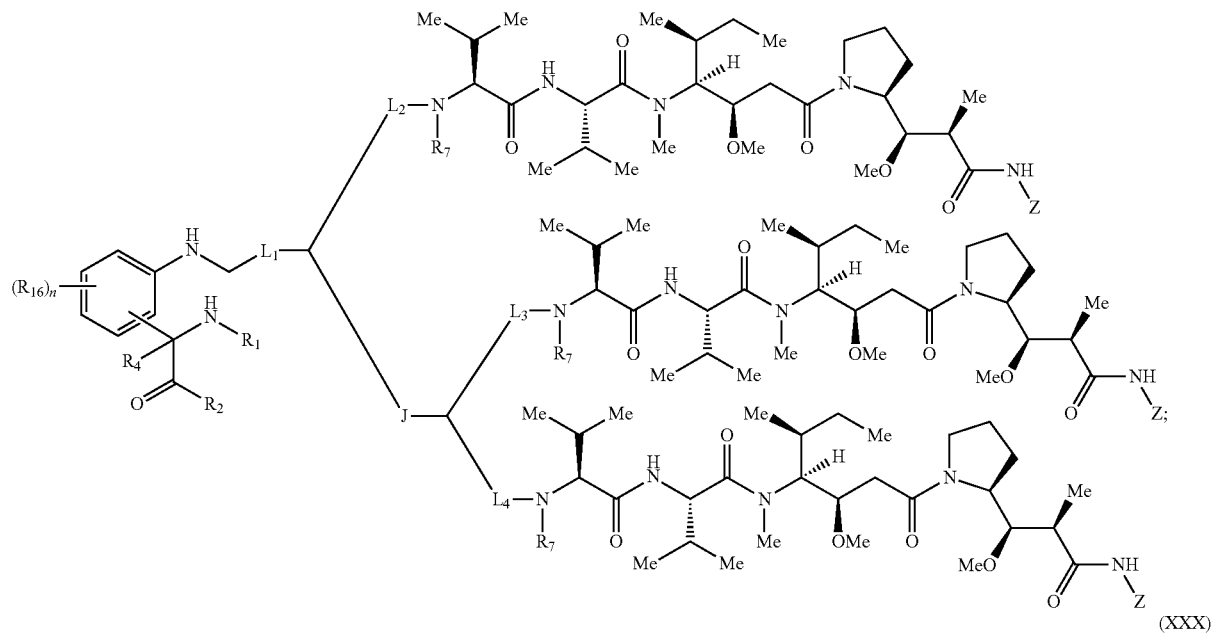

(XXIX)

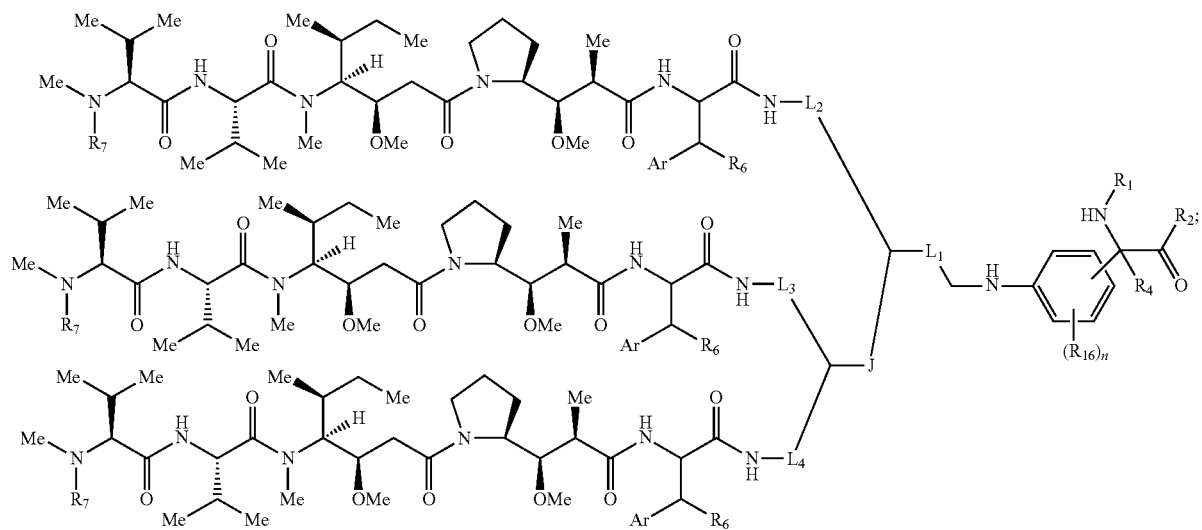

(XXX)

wherein:
Z has the structure of:

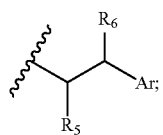

$R_5$ is H, $CO_2H$, $C_1$-$C_6$alkyl, or thiazole;
$R_6$ is OH or H;
Ar is phenyl, or pyridine;
$R_1$ is H, an amino protecting group, resin, at least one amino acid, polypeptide, or polynucleotide;
$R_2$ is OH, an ester protecting group, resin, at least one amino acid, polypeptide, or polynucleotide;
$R_4$ is H, halogen, lower alkyl, or substituted lower alkyl;
$R_7$ is $C_1$-$C_6$alkyl or hydrogen;
L, $L_1$, $L_2$, $L_3$, and $L_4$ are each linkers selected from the group consisting of a bond, -alkylene-, -alkylene-C(O)—, -alkylene-J-, -(alkylene-O)$_n$-alkylene-, -(alkylene-O)$_n$-alkylene-C(O)—, -(alkylene-O)$_n$-J-, -(alkylene-O)$_n$-J-alkylene-, -(alkylene-O)$_n$—(CH$_2$)$_{n'}$—NHC(O)—(CH$_2$)$_{n''}$—C(Me)$_2$-S—S—(CH$_2$)$_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-J-, -alkylene'-J-(alkylene-O)$_n$-alkylene-, -(alkylene-O)$_n$-alkylene-J-alkylene', -J-(alkylene-O)$_n$-alkylene-, -(alkylene-O)$_n$-alkylene-J-(alkylene-O)$_n$'-alkylene-J-, —W—, -alkylene-W—, alkylene'-J-(alkylene-NMe)$_n$-alkylene-W—, -J-(alkylene-NMe)$_n$-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene"-W—, and -alkylene-J-alkylene'-NMe-alkylene"-NMe-alkylene'''-W—;

W has the structure of:

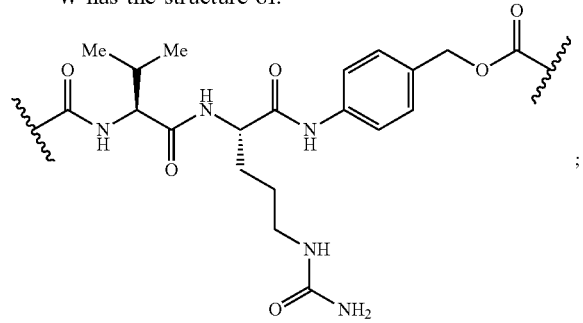

U has the structure of:

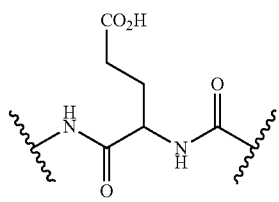 [SMILES: *NC(=O)C(CCC(=O)O)NC(*)=O]

each J and J' independently have the structure of:

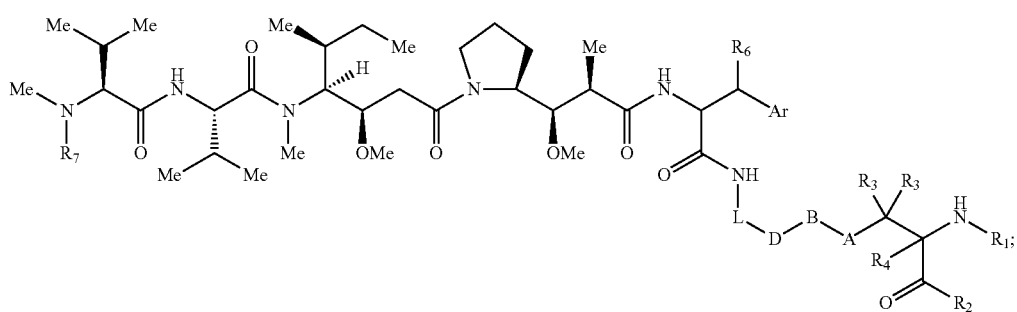

each n and n' are independently integers greater than or equal to one; and each $R_{16}$ is independently selected from the group consisting of hydrogen, halogen, alkyl, $NO_2$, CN, and substituted alkyl.

In some embodiments, $R_1$ is a polypeptide. In specific embodiments, the polypeptide is an antibody. In certain specific embodiments, the antibody is αCD70. In other embodiments, $R_2$ is a polypeptide. In specific embodiments, the polypeptide is an antibody. In certain specific embodiments, the antibody is αCD70.

Some embodiments of the present invention describe a compound comprising Formula (XXXI), (XXXII), (XXXIII), (XXXIV), (XXXV), or (XXXVI):

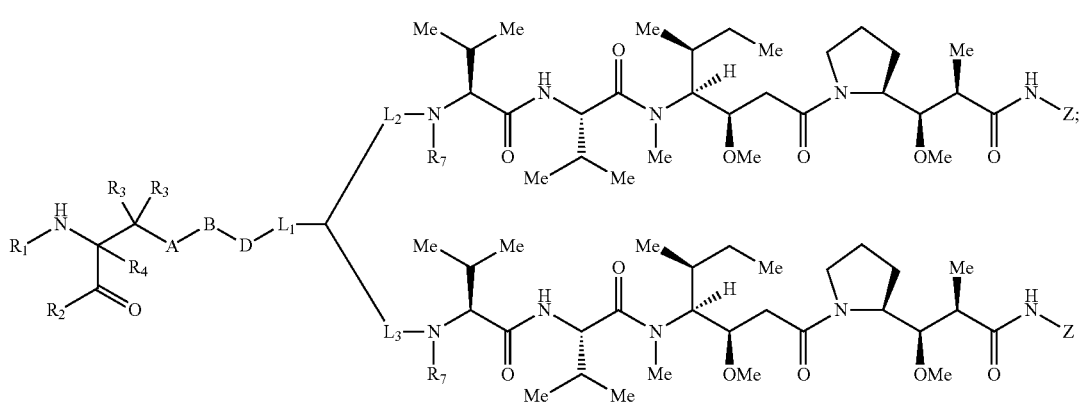

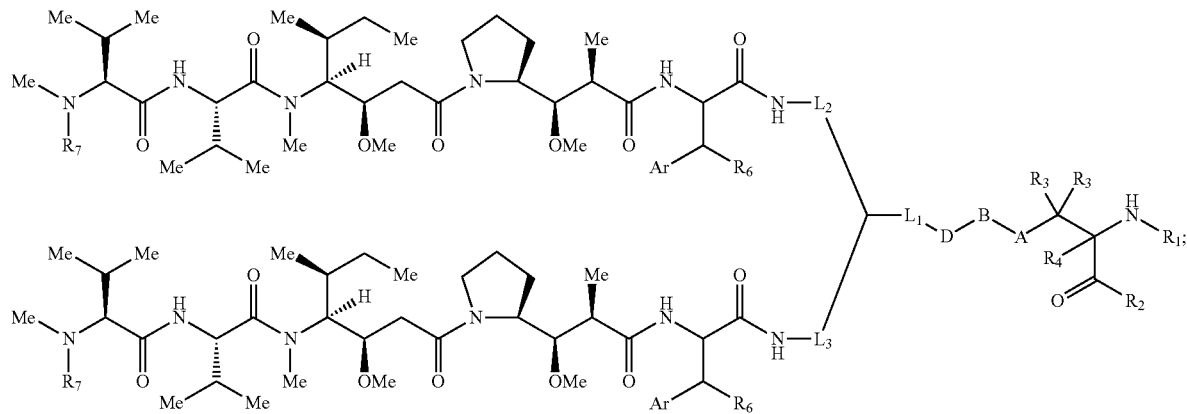
(XXXIII)
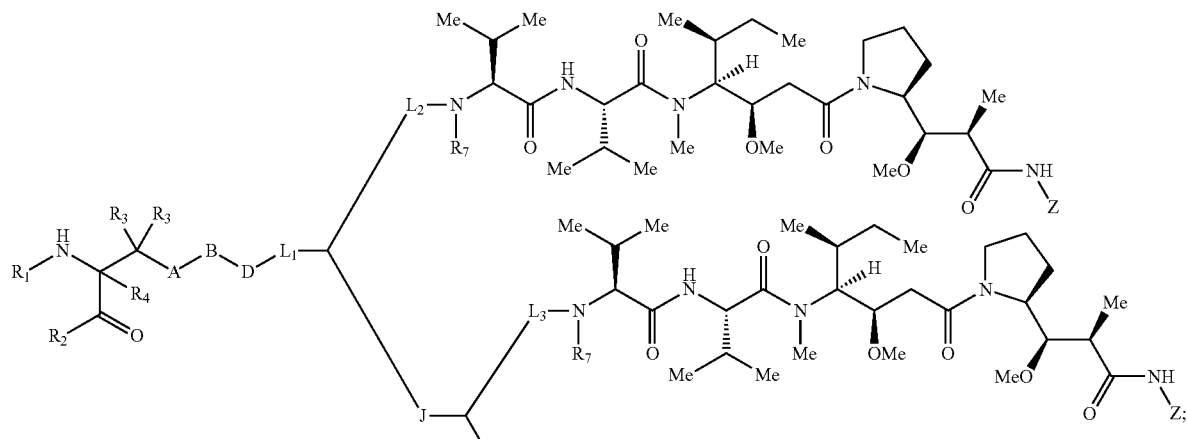
(XXXV)
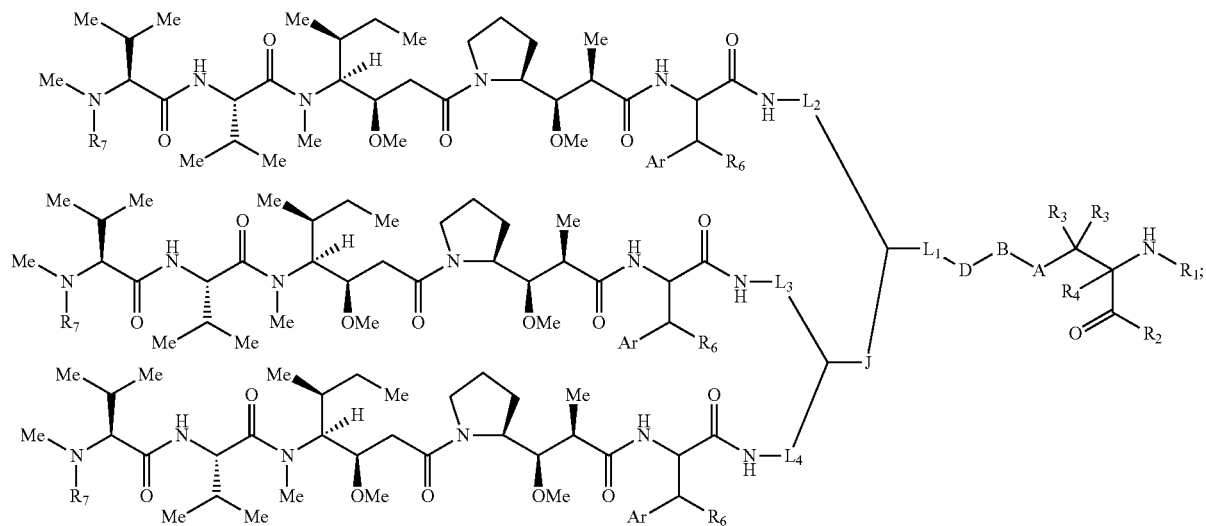
(XXXVI)

wherein:

Z has the structure of:

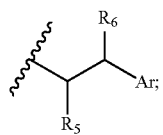

$R_5$ is H, $CO_2H$, $C_1$-$C_6$alkyl, or thiazole;

$R_6$ is OH or H;

Ar is phenyl or pyridine;

$R_1$ is H, an amino protecting group, resin, at least one amino acid, polypeptide, or polynucleotide;

$R_2$ is OH, an ester protecting group, resin, at least one amino acid, polypeptide, or polynucleotide;

$R_4$ is H, halogen, lower alkyl, or substituted lower alkyl;

$R_7$ is $C_1$-$C_6$alkyl or hydrogen;

L, $L_1$, $L_2$, $L_3$, and $L_4$ are each linkers selected from the group consisting of a bond, -alkylene-, -alkylene-C(O)—, -alkylene-J-, -(alkylene-O)$_n$-alkylene-, -(alkylene-O)$_n$-alkylene-C(O)—, -(alkylene-O)$_n$-J-, -(alkylene-O)$_n$-J-alkylene-, -(alkylene-O)$_n$—(CH$_2$)$_{n'}$—NHC(O)—(CH$_2$)$_{n''}$—C(Me)$_2$—S—S—(CH$_2$)$_{n'''}$—NHC(O)-(alkylene-O)$_{n''''}$-alkylene-, -(alkylene-O)-alkylene-W—, -alkylene-C(O)—W—, -(alkylene-O)-alkylene-J-, -alkylene'-J-(alkylene-O)$_n$-alkylene-, -(alkylene-O)$_n$-alkylene-J-alkylene', -J-(alkylene)$_n$-alkylene-, -(alkyleneo-O)$_n$-alkylene-J-(alkylene-O)$_n$'-alkylene-J'-, —W—, -alkylene-W—, alkylene'-J-(alkylene-NMe)$_n$-alkylene-W—, -J-(alkylene-NMe)$_n$-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene"-W—, and -alkylene-J-alkylene'-NMe-alkylene"-NMe-alkylene'"-W—;

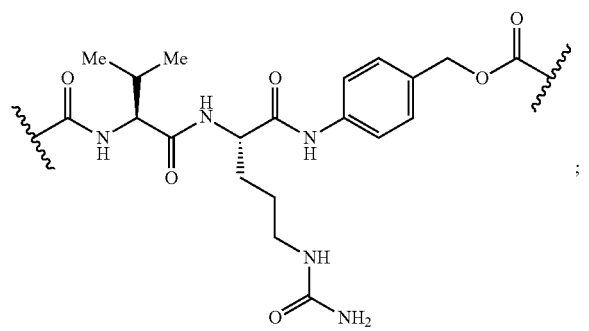 [SMILES: *C(=O)N[C@H](C(=O)N[C@@H](CCCNC(N)=O)C(=O)Nc1ccc(COC(*)=O)cc1)C(C)C]

U has the structure of:

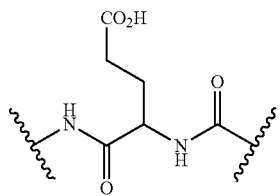 [SMILES: *NC(=O)C(CCC(=O)O)NC(*)=O]

each J and J' independently have the structure of:

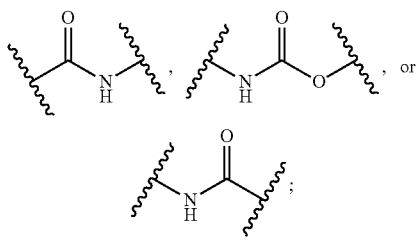

each n and n' are independently integers greater than or equal to one; P D has the structure of:

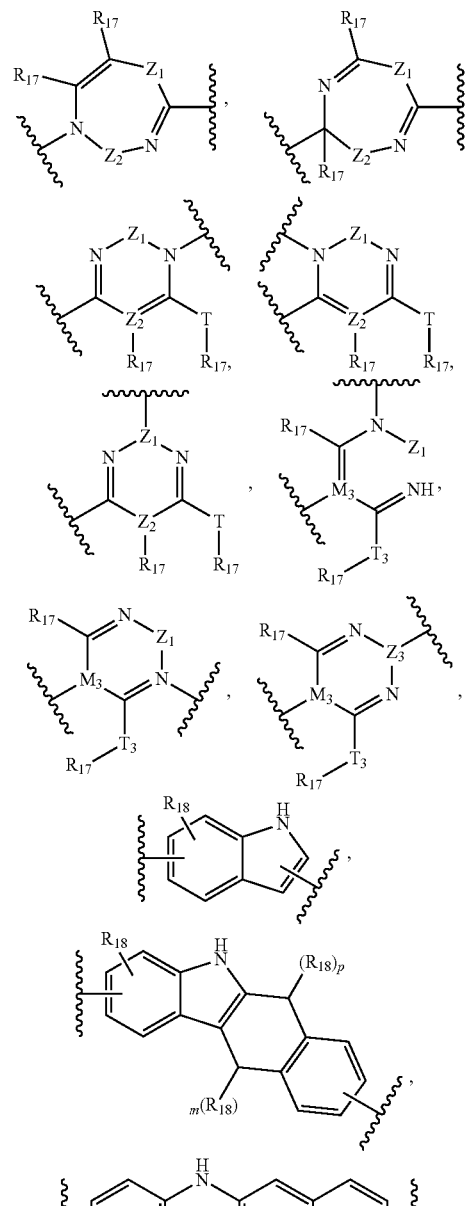

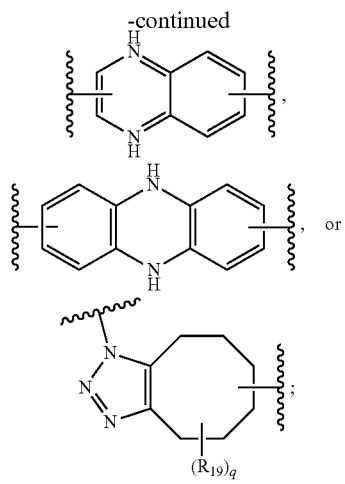

each R$_{17}$ is independently selected from the group consisting of H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$OR", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl;

each Z$_1$ is a bond, CR$_{17}$R$_{17}$, O, S, NR', CR$_{17}$R$_{17}$—CR$_{17}$R$_{17}$, CR$_{17}$R$_{17}$—O, O—CR$_{17}$R$_{17}$, CR$_{17}$R$_{17}$—S, S—CR$_{17}$R$_{17}$, CR$_{17}$R$_{17}$—NR', or NR'—CR$_{17}$R$_{17}$;

each R' is H, alkyl, or substituted alkyl;

each Z$_2$ is selected from the group consisting of a bond, —C(O)—, —C(S)—, optionally substituted C$_1$-C$_3$ alkylene, optionally substituted C$_1$-C$_3$ alkenylene, and optionally substituted heteroalkyl;

each Z$_3$ are independently selected from the group consisting of a bond, optionally substituted C$_1$-C$_4$ alkylene, optionally substituted C$_1$-C$_4$ alkenylene, optionally substituted heteroalkyl, —O—, —S—, —C(O)—, —C(S)—, and —N(R')—;

each T$_3$ is a bond, C(R")(R"), O, or S; with the proviso that when T$_3$ is O or S, R" cannot be halogen;

each R" is H, halogen, alkyl, substituted alkyl, cycloalkyl, or substituted cycloalkyl;

m and p are 0, 1, 2, or 3, provided that at least one of m or p is not 0;

M$_2$ is

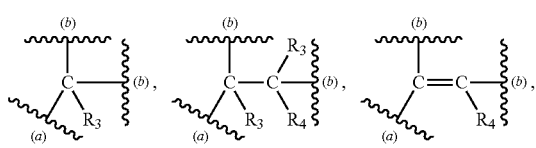

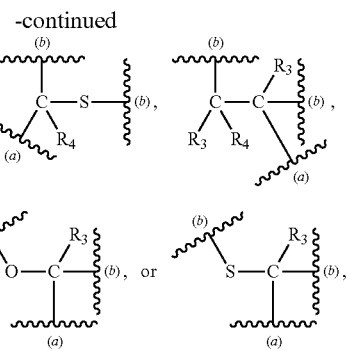

where (a) indicates bonding to the B group and (b) indicates bonding to respective positions within the heterocycle group;

M$_3$ is

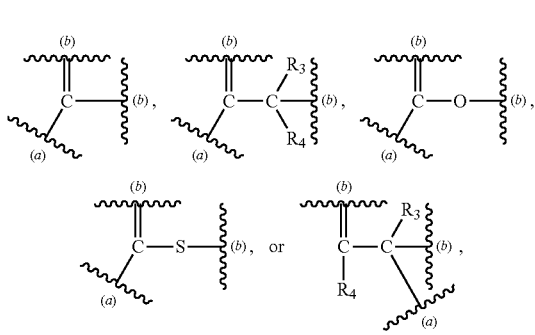

where (a) indicates bonding to the B group and (b) indicates bonding to respective positions within the heterocycle group;

M$_4$ is

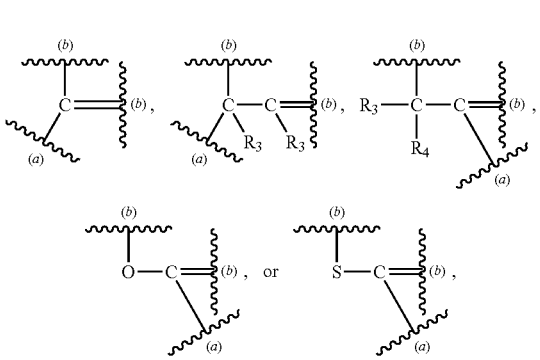

where (a) indicates bonding to the B group and (b) indicates bonding to respective positions within the heterocycle group;

each R$_{19}$ is independently selected from the group consisting of C$_1$-C$_6$ alkyl, C$_1$-C$_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro;

q is 0, 1, 2, 3, 4, 5, 6, 7, 8, 9, 10 or 11; and each R$_{16}$ is independently selected from the group consisting of hydrogen, halogen, alkyl, NO$_2$, CN, and substituted alkyl.

In some embodiments, $R_1$ is a polypeptide. In specific embodiments, the polypeptide is an antibody. In certain specific embodiments, the antibody is αCD70. In other embodiments, $R_2$ is a polypeptide. In specific embodiments, the polypeptide is an antibody. In certain specific embodiments, the antibody is αCD70.

In some embodiments, a compound is described comprising Formula (XXXI-A):

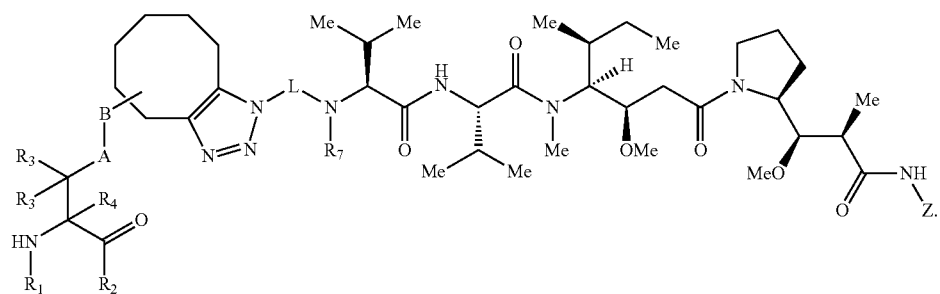

(XXXI-A)

In certain embodiments, a pharmaceutical composition is provided comprising any of the compounds described and a pharmaceutically acceptable carrier, excipient, or binder.

In further or alternative embodiments are methods for detecting the presence of a polypeptide in a patient, the method comprising administering a polypeptide comprising at least one heterocycle-containing non-natural amino acid and the resulting heterocycle-containing non-natural amino acid polypeptide modulates the immunogenicity of the polypeptide relative to the homologous naturally-occurring amino acid polypeptide.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The terms "aldol-based linkage" or "mixed aldol-based linkage" refers to the acid- or base-catalyzed condensation of one carbonyl compound with the enolate/enol of another carbonyl compound, which may or may not be the same, to generate a 3-hydroxy carbonyl compound—an aldol.

The term "affinity label," as used herein, refers to a label which reversibly or irreversibly binds another molecule, either to modify it, destroy it, or form a compound with it. By way of example, affinity labels include enzymes and their substrates, or antibodies and their antigens.

The terms "alkoxy," "alkylamino" and "alkylthio" (or thioalkoxy) are used in their conventional sense, and refer to those alkyl groups linked to molecules via an oxygen atom, an amino group, or a sulfur atom, respectively.

The term "alkyl," by itself or as part of another molecule means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail herein, such as "heteroalkyl", "haloalkyl" and "homoalkyl".

The term "alkylene" by itself or as part of another molecule means a divalent radical derived from an alkane, as exemplified, by ($-CH_2-$)$_n$, wherein n may be 1 to about 24. By way of example only, such groups include, but are not limited to, groups having 10 or fewer carbon atoms such as the structures $-CH_2CH_2-$ and $-CH_2CH_2CH_2CH_2-$. A "lower alkyl" or "lower alkylene" is a shorter chain alkyl or alkylene group, generally having eight or fewer carbon atoms. The term "alkylene," unless otherwise noted, is also meant to include those groups described herein as "heteroalkylene."

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, by way of example only, an α-carbon that is bound to a hydrogen, a carboxyl group, an amino group, and an R group. Such analogs may have modified R groups (by way of example, norleucine) or may have modified peptide backbones while still retaining the same basic chemical structure as a naturally occurring amino acid. Non-limiting examples of amino acid analogs include homoserine, norleucine, methionine sulfoxide, methionine methyl sulfonium.

Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

An "amino terminus modification group" refers to any molecule that can be attached to a terminal amine group. By way of example, such terminal amine groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments, and include antibodies that exist naturally in any organism or are engineered (e.g. are variants).

The term "antibody" refers to intact antibody, monoclonal or polyclonal antibodies. The term "antibody" also encompasses, multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

Anti-CD70 antibodies known in the art are suitable for use with this invention. Non-limiting examples of antibodies include monoclonal antibodies 2H5, 10B4, 8B5, 18E7, 69A7, 69A7Y, and 1F4 and the amino acid sequences are given in U.S. Published Patent Application 20100150950, herein incorporated by reference. The VH amino acid sequences of 2H5, 10B4, 8B5, 18E7, 69A7, 69A7Y and 1F4 are shown in SEQ ID NOs:1, 2, 3, 4, 5, 73, and 6 respectively. The $V_L$ amino acid sequences of 2H5, 10B4, 8B5, 18E7, 69A7, 69A7Y and 1F4 are shown in SEQ ID NOs:7, 8, 9, 10, 11, 11, and 12, respectively of U.S. Published Patent Application 20100150950 (with 69A7 and 69A7Y having the VL amino acid sequence of SEQ ID NO: 11). Any known heavy chain sequence can be combined with light chain sequences and in some embodiments of the present invention there is non-naturally encoded amino acid in the constant region of the antibodies. In some embodiments of the present invention there are two or more non-naturally encoded amino acid in the constant region of the antibodies. Accordingly, in one aspect, this disclosure provides an isolated monoclonal antibody or antigen binding portion thereof comprising:

(a) a heavy chain variable region comprising an amino acid sequence selected from the group consisting of SEQ ID NOs:1, 2, 3, 4, 5, 6, and 73; and (b) a light chain variable region comprising an amino acid sequence selected from the group consisting of SEQ ID NOs: 7, 8, 9, 10, 11, and 12; and (c) a non-naturally encoded amino acid; wherein the antibody specifically binds to CD70.

Anti-CD70 (αCD70) antibodies known in the art are suitable for use in the present invention. For example, sequences for 2H5 antibody are given in U.S. Pat. No. 8,124,738 and is incorporated herein by reference.

The term "antigen-binding fragment", as used herein, refers to one or more fragments of an antibody that retain the ability to bind to an antigen. It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR), e.g., $V_H$ CDRz3 comprising or not additional sequence (linker, framework region(s) etc.) and (v) a combination of two to six isolated CDRs comprising or not additional sequence (linker, framework region(s) etc.). Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

In fact, because CDR sequences are responsible for most antibody-antigen interactions, it is possible to express recombinant antibodies that shows the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized to create an entirely synthetic variable region clone. This process has certain advantages such as elimination or inclusion of particular restriction sites, or optimization of particular codons.

Of course, the totality or portions of the framework region of the antibody described herein may be used in conjunction with the CDRs in order to optimize the affinity, specificity or any other desired properties of the antibody. By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments, and include antibodies that exist naturally in any organism or are engineered (e.g. are variants).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like (Maynard & Georgiou, 2000, Annu. Rev. Biomed. Eng. 2:339-76; Hudson, 1998, Curr. Opin. Biotechnol. 9:395-402). Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments."

By "antibody-drug conjugate, or "ADC", as used herein, refers to an antibody molecule, or fragment thereof, that is covalently bonded to one or more biologically active molecule(s). The biologically active molecule may be conjugated to the antibody through a linker, polymer, or other covalent bond.

The term "aromatic" or "aryl", as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes monocyclic rings linked covalently or fused-ring polycyclic (i.e., rings which share adjacent pairs of carbon atoms) groups. An aromatic group can be unsubstituted or substituted. Non-limiting examples of "aromatic" or "aryl", groups include phenyl, 1-naphthyl, 2-naphthyl, 4-biphenyl, anthracenyl, and phenanthracenyl. Substituents for each of the above noted aryl and heteroaryl ring systems are selected from the group of acceptable substituents described herein.

For brevity, the term "aromatic" or "aryl" when used in combination with other terms (including but not limited to, aryloxy, arylthioxy, aralkyl) includes both aryl and heteroaryl rings as defined above. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by a heteroatom, by way of example only, by an oxygen atom. Examples of such aryl groups include, but are not limited to, phenoxymethyl, 2-pyridyloxymethyl, 3-(1-naphthyloxy) propyl, and the like.

The term "arylene", as used herein, refers to a divalent aryl radical. Non-limiting examples of "arylene" include phenylene, pyridinylene, pyrimidinylene and thiophenylene. Substituents for arylene groups are selected from the group of acceptable substituents described herein.

A "bifunctional polymer", also referred to as a "bifunctional linker", refers to a polymer comprising two functional groups that are capable of reacting specifically with other moieties to form covalent or non-covalent linkages. Such moieties may include, but are not limited to, the side groups on natural or non-natural amino acids or peptides which contain such natural or non-natural amino acids. The other moieties that may be linked to the bifunctional linker or bifunctional polymer may be the same or different moieties. By way of example only, a bifunctional linker may have a functional group reactive with a group on a first peptide, and another functional group which is reactive with a group on a second peptide, whereby forming a conjugate that includes the first peptide, the bifunctional linker and the second peptide. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein in their entirety. A "multi-functional polymer" also referred to as a "multi-functional linker", refers to a polymer comprising two or more functional groups that are capable of reacting with other moieties. Such moieties may include, but are not limited to, the side groups on natural or non-natural amino acids or peptides which contain such natural or non-natural amino acids. (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to a compound and molecules it binds to or the compound.

The term "bioavailability," as used herein, refers to the rate and extent to which a substance or its active moiety is delivered from a pharmaceutical dosage form and becomes available at the site of action or in the general circulation. Increases in bioavailability refers to increasing the rate and extent a substance or its active moiety is delivered from a pharmaceutical dosage form and becomes available at the site of action or in the general circulation. By way of example, an increase in bioavailability may be indicated as an increase in concentration of the substance or its active moiety in the blood when compared to other substances or active moieties. A non-limiting example of a method to evaluate increases in bioavailability is given in examples 21-25. This method may be used for evaluating the bioavailability of any polypeptide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, prodrugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

By "modulating biological activity" is meant increasing or decreasing the reactivity of a polypeptide, altering the selectivity of the polypeptide, enhancing or decreasing the substrate selectivity of the polypeptide. Analysis of modified biological activity can be performed by comparing the biological activity of the non-natural polypeptide to that of the natural polypeptide.

The term "biomaterial," as used herein, refers to a biologically-derived material, including but not limited to material obtained from bioreactors and/or from recombinant methods and techniques.

The term "biophysical probe," as used herein, refers to probes which can detect or monitor structural changes in molecules. Such molecules include, but are not limited to, proteins and the "biophysical probe" may be used to detect or monitor interaction of proteins with other macromolecules. Examples of biophysical probes include, but are not limited to, spin-labels, a fluorophores, and photoactivatible groups.

The term "biosynthetically," as used herein, refers to any method utilizing a translation system (cellular or non-cellular), including use of at least one of the following components: a polynucleotide, a codon, a tRNA, and a ribosome. By way of example, non-natural amino acids may be "biosynthetically incorporated" into non-natural amino acid polypeptides using the methods and techniques described herein, "In vivo generation of polypeptides comprising non-natural amino acids", and in the non-limiting example 20. Additionally, the methods for the selection of useful non-natural amino acids which may be "biosynthetically incorporated" into non-natural amino acid polypeptides are described in the non-limiting examples 20.

The term "biotin analogue," or also referred to as "biotin mimic", as used herein, is any molecule, other than biotin, which bind with high affinity to avidin and/or streptavidin.

The term "carbonyl" as used herein refers to a group containing at a moiety selecting from the group consisting of —C(O)—, —S(O)—, —S(O)2-, and —C(S)—, including, but not limited to, groups containing a least one ketone group, and/or at least one aldehyde groups, and/or at least one ester group, and/or at least one carboxylic acid group, and/or at least one thioester group. Such carbonyl groups include ketones, aldehydes, carboxylic acids, esters, and thioesters. In addition, such groups may be part of linear, branched, or cyclic molecules.

The term "carboxy terminus modification group" refers to any molecule that can be attached to a terminal carboxy group. By way of example, such terminal carboxy groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

The term "chemically cleavable group," also referred to as "chemically labile", as used herein, refers to a group which breaks or cleaves upon exposure to acid, base, oxidizing agents, reducing agents, chemical inititiators, or radical initiators.

The term "chemiluminescent group," as used herein, refers to a group which emits light as a result of a chemical reaction without the addition of heat. By way of example only, luminol (5-amino-2,3-dihydro-1,4-phthalazinedione)

reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "cofactor," as used herein, refers to an atom or molecule essential for the action of a large molecule. Cofactors include, but are not limited to, inorganic ions, coenzymes, proteins, or some other factor necessary for the activity of enzymes. Examples include, heme in hemoglobin, magnesium in chlorophyll, and metal ions for proteins.

"Cofolding," as used herein, refers to refolding processes, reactions, or methods which employ at least two molecules which interact with each other and result in the transformation of unfolded or improperly folded molecules to properly folded molecules. By way of example only, "cofolding," employ at least two polypeptides which interact with each other and result in the transformation of unfolded or improperly folded polypeptides to native, properly folded polypeptides. Such polypeptides may contain natural amino acids and/or at least one non-natural amino acid.

A "comparison window," as used herein, refers a segment of any one of contiguous positions used to compare a sequence to a reference sequence of the same number of contiguous positions after the two sequences are optimally aligned. Such contiguous positions include, but are not limited to a group consisting of from about 20 to about 600 sequential units, including about 50 to about 200 sequential units, and about 100 to about 150 sequential units. By way of example only, such sequences include polypeptides and polypeptides containing non-natural amino acids, with the sequential units include, but are not limited to natural and non-natural amino acids. In addition, by way of example only, such sequences include polynucleotides with nucleotides being the corresponding sequential units. Methods of alignment of sequences for comparison are well-known in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

By way of example, an algorithm which may be used to determine percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, $M=5$, $N=-4$, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus by way of example every natural or non-natural nucleic acid sequence herein which encodes a natural or non-natural polypeptide also describes every possible silent variation of the natural or non-natural nucleic acid. One of ordinary skill in the art will recognize that each codon in a natural or non-natural nucleic acid (except AUG, which is ordinarily the only codon for methionine, and TGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

Conservative substitution tables providing functionally similar amino acids are known to those of ordinary skill in the art. The following eight groups each contain amino acids that are conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, Proteins:Structures and Molecular Properties (W H Freeman & Co.; 2nd edition (December 1993)

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. The heteroatom may include, but is not limited to, oxygen, nitrogen or sulfur. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses multicyclic structures, including but not limited to, bicyclic and tricyclic ring structures. Similarly, the term "heterocycloalkylene" by itself or as part of another molecule means a divalent radical derived from heterocycloalkyl, and the term "cycloalkylene" by itself or as part of another molecule means a divalent radical derived from cycloalkyl.

The term "cyclodextrin," as used herein, refers to cyclic carbohydrates consisting of at least six to eight glucose molecules in a ring formation. The outer part of the ring contains water soluble groups; at the center of the ring is a relatively nonpolar cavity able to accommodate small molecules.

The term "cytotoxic," as used herein, refers to a compound which harms cells.

"Denaturing agent" or "denaturant," as used herein, refers to any compound or material which will cause a reversible unfolding of a polymer. By way of example only, "denaturing agent" or "denaturants," may cause a reversible unfolding of a protein. The strength of a denaturing agent or denaturant will be determined both by the properties and the concentration of the particular denaturing agent or denaturant. By way of example, denaturing agents or denaturants include, but are not limited to, chaotropes, detergents, organic, water miscible solvents, phospholipids, or a combination thereof. Non-limiting examples of chaotropes include, but are not limited to, urea, guanidine, and sodium thiocyanate. Non-limiting examples of detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Non-limiting examples of organic, water miscible solvents include, but are not limited to, acetonitrile, lower alkanols (especially C2-C4 alkanols such as ethanol or isopropanol), or lower alkandiols (C2-C4 alkandiols such as ethylene-glycol) may be used as denaturants. Non-limiting examples of phospholipids include, but are not limited to, naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "desired functionality" as used herein refers to any group selected from a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide, a water-soluble dendrimer, a cyclodextrin, a biomaterial; a nanoparticle; a spin label; a fluorophore; a metal-containing moiety; a radioactive moiety; a novel functional group; a group that covalently or noncovalently interacts with other molecules; a photocaged moiety; an actinic radiation excitable moiety; a ligand; a photoisomerizable moiety; biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent (in which case, the biologically active agent can include an agent with therapeutic activity and the non-natural amino acid polypeptide or modified non-natural amino acid can serve either as a co-therapeutic agent with the attached therapeutic agent or as a means for delivery the therapeutic agent to a desired site within an organism); a detectable label; a small molecule; an inhibitory ribonucleic acid; a radionucleotide; a neutron-capture agent; a derivative of biotin; quantum dot(s); a nanotransmitter; a radiotransmitter; an abzyme, an activated complex activator, a virus, an adjuvant, an aglycan, an allergan, an angiostatin, an antihormone, an antioxidant, an aptamer, a guide RNA, a saponin, a shuttle vector, a macromolecule, a mimotope, a receptor, a reverse micelle, and any combination thereof.

The term "diamine," as used herein, refers to groups/molecules comprising at least two amine functional groups, including, but not limited to, a hydrazine group, an amidine group, an imine group, a 1,1-diamine group, a 1,2-diamine group, a 1,3-diamine group, and a 1,4-diamine group. In addition, such groups may be part of linear, branched, or cyclic molecules.

The term "detectable label," as used herein, refers to a label which may be observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The term "dicarbonyl" as used herein refers to a group containing at least two moieties selected from the group consisting of —C(O)—, —S(O)—, —S(O)$_2$—, and —C(S)—, including, but not limited to, 1,2-dicarbonyl groups, a 1,3-dicarbonyl groups, and 1,4-dicarbonyl groups, and groups containing a least one ketone group, and/or at least one aldehyde groups, and/or at least one ester group, and/or at least one carboxylic acid group, and/or at least one thioester group. Such dicarbonyl groups include diketones, ketoaldehydes, ketoacids, ketoesters, and ketothioesters. In addition, such groups may be part of linear, branched, or cyclic molecules. The two moieties in the dicarbonyl group may be the same or different, and may include substituents that would produce, by way of example only, an ester, a ketone, an aldehyde, a thioester, or an amide, at either of the two moieties.

The term "drug," as used herein, refers to any substance used in the prevention, diagnosis, alleviation, treatment, or cure of a disease or condition.

The term "dye," as used herein, refers to a soluble, coloring substance which contains a chromophore.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The term "electron dense group," as used herein, refers to a group which scatters electrons when irradiated with an electron beam. Such groups include, but are not limited to, ammonium molybdate, bismuth subnitrate cadmium iodide, 99%, carbohydrazide, ferric chloride hexahydrate, hexamethylene tetramine, 98.5%, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which can either donate or accept energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

As used herein, the term "eukaryote" refers to organisms belonging to the phylogenetic domain Eucarya, including but not limited to animals (including but not limited to, mammals, insects, reptiles, birds, etc.), ciliates, plants (including but not limited to, monocots, dicots, and algae), fungi, yeasts, flagellates, microsporidia, and protists.

The term "fatty acid," as used herein, refers to carboxylic acids with about C6 or longer hydrocarbon side chain.

The term "fluorophore," as used herein, refers to a molecule which upon excitation emits photons and is thereby fluorescent.

The terms "functional group", "active moiety", "activating group", "leaving group", "reactive site", "chemically reactive group" and "chemically reactive moiety," as used herein, refer to portions or units of a molecule at which chemical reactions occur. The terms are somewhat synonymous in the chemical arts and are used herein to indicate the portions of molecules that perform some function or activity and are reactive with other molecules.

The term "halogen" includes fluorine, chlorine, iodine, and bromine.

The term "haloacyl," as used herein, refers to acyl groups which contain halogen moieties, including, but not limited to, —C(O)CH$_3$, —C(O)CF$_3$, —C(O)CH$_2$OCH$_3$, and the like.

The term "haloalkyl," as used herein, refers to alkyl groups which contain halogen moieties, including, but not limited to, —CF$_3$ and —CH$_2$CF$_3$ and the like.

The term "heteroalkyl," as used herein, refers to straight or branched chain, or cyclic hydrocarbon radicals, or combinations thereof, consisting of an alkyl group and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$.

The terms "heterocyclic-based linkage" or "heterocycle linkage" refers to a moiety formed from the reaction of a dicarbonyl group with a diamine group. The resulting reaction product is a heterocycle, including a heteroaryl group or a heterocycloalkyl group. The resulting heterocycle group serves as a chemical link between a non-natural amino acid or non-natural amino acid polypeptide and another functional group. In one embodiment, the heterocycle linkage includes a nitrogen-containing heterocycle linkage, including by way of example only a pyrazole linkage, a pyrrole linkage, an indole linkage, a benzodiazepine linkage, and a pyrazalone linkage.

Similarly, the term "heteroalkylene" refers to a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. By way of example, the formula —C(O)₂R'— represents both —C(O)₂R'— and —R'C(O)₂—.

The term "heteroaryl" or "heteroaromatic," as used herein, refers to aryl groups which contain at least one heteroatom selected from N, O, and S; wherein the nitrogen and sulfur atoms may be optionally oxidized, and the nitrogen atom(s) may be optionally quaternized. Heteroaryl groups may be substituted or unsubstituted. A heteroaryl group may be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "homoalkyl," as used herein refers to alkyl groups which are hydrocarbon groups.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75 to about 100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "immunogenicity," as used herein, refers to an antibody response to administration of a therapeutic drug. The immunogenicity toward therapeutic non-natural amino acid polypeptides can be obtained using quantitative and qualitative assays for detection of anti-non-natural amino acid polypeptides antibodies in biological fluids. Such assays include, but are not limited to, Radioimmunoassay (RIA), Enzyme-linked immunosorbent assay (ELISA), luminescent immunoassay (LIA), and fluorescent immunoassay (FIA). Analysis of immunogenicity toward therapeutic non-natural amino acid polypeptides involves comparing the antibody response upon administration of therapeutic non-natural amino acid polypeptides to the antibody response upon administration of therapeutic natural amino acid polypeptides.

The term "intercalating agent," also referred to as "intercalating group," as used herein, refers to a chemical that can insert into the intramolecular space of a molecule or the intermolecular space between molecules. By way of example only an intercalating agent or group may be a molecule which inserts into the stacked bases of the DNA double helix.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high performance liquid chromatography. In addition, when a component of interest is isolated and is the predominant species present in a preparation, the component is described herein as substantially purified. The term "purified," as used herein, may refer to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "label," as used herein, refers to a substance which is incorporated into a compound and is readily detected, whereby its physical distribution may be detected and/or monitored.

The term "linkage," as used herein to refer to bonds or chemical moiety formed from a chemical reaction between the functional group of a linker and another molecule. Such bonds may include, but are not limited to, covalent linkages and non-covalent bonds, while such chemical moieties may include, but are not limited to, esters, carbonates, imines phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. By way of example only, PEG and related polymers may include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The terms "medium" or "media," as used herein, refer to any culture medium used to grow and harvest cells and/or products expressed and/or secreted by such cells. Such "medium" or "media" include, but are not limited to, solution, solid, semi-solid, or rigid supports that may support or contain any host cell, including, by way of example, bacterial host cells, yeast host cells, insect host cells, plant host cells, eukaryotic host cells, mammalian host cells, CHO cells, prokaryotic host cells, E. coli, or Pseudomonas host cells, and cell contents. Such "medium" or "media" includes, but is not limited to, medium or media in which the host cell has been grown into which a polypeptide has been secreted, including medium either before or after a proliferation step. Such "medium" or "media" also includes, but is not limited to, buffers or reagents that contain host cell lysates, by way of example a polypeptide produced intracellularly and the host cells are lysed or disrupted to release the polypeptide.

The term "metabolite," as used herein, refers to a derivative of a compound, by way of example natural amino acid polypeptide, a non-natural amino acid polypeptide, a modified natural amino acid polypeptide, or a modified non-natural amino acid polypeptide, that is formed when the compound, by way of example natural amino acid polypeptide, non-natural amino acid polypeptide, modified natural amino acid polypeptide, or modified non-natural amino acid polypeptide, is metabolized. The term "pharmaceutically active metabolite" or "active metabolite" refers to a biologically active derivative of a compound, by way of example natural amino acid polypeptide, a non-natural amino acid polypeptide, a modified natural amino acid polypeptide, or a modified non-natural amino acid polypeptide, that is formed when such a compound, by way of example a natural amino acid polypeptide, non-natural amino acid polypeptide, modified natural amino acid polypeptide, or modified non-natural amino acid polypeptide, is metabolized.

The term "metabolized," as used herein, refers to the sum of the processes by which a particular substance is changed by an organism. Such processes include, but are not limited to, hydrolysis reactions and reactions catalyzed by enzymes. Further information on metabolism may be obtained from The Pharmacological Basis of Therapeutics, 9th Edition, McGraw-Hill (1996). By way of example only, metabolites of natural amino acid polypeptides, non-natural amino acid polypeptides, modified natural amino acid polypeptides, or modified non-natural amino acid polypeptides may be identified either by administration of the natural amino acid polypeptides, non-natural amino acid polypeptides, modified natural amino acid polypeptides, or modified non-natural amino acid polypeptides to a host and analysis of tissue samples from the host, or by incubation of natural amino acid polypeptides, non-natural amino acid polypeptides, modified natural amino acid polypeptides, or modified non-natural amino acid polypeptides with hepatic cells in vitro and analysis of the resulting compounds.

The term "metal chelator," as used herein, refers to a molecule which forms a metal complex with metal ions. By way of example, such molecules may form two or more coordination bonds with a central metal ion and may form ring structures.

The term "metal-containing moiety," as used herein, refers to a group which contains a metal ion, atom or particle. Such moieties include, but are not limited to, cisplatin, chelated metals ions (such as nickel, iron, and platinum), and metal nanoparticles (such as nickel, iron, and platinum).

The term "moiety incorporating a heavy atom," as used herein, refers to a group which incorporates an ion of atom which is usually heavier than carbon. Such ions or atoms include, but are not limited to, silicon, tungsten, gold, lead, and uranium.

The term "modified," as used herein refers to the presence of a change to a natural amino acid, a non-natural amino acid, a natural amino acid polypeptide or a non-natural amino acid polypeptide. Such changes, or modifications, may be obtained by post synthesis modifications of natural amino acids, non-natural amino acids, natural amino acid polypeptides or non-natural amino acid polypeptides, or by co-translational, or by post-translational modification of natural amino acids, non-natural amino acids, natural amino acid polypeptides or non-natural amino acid polypeptides. The form "modified or unmodified" means that the natural amino acid, non-natural amino acid, natural amino acid polypeptide or non-natural amino acid polypeptide being discussed are optionally modified, that is, the natural amino acid, non-natural amino acid, natural amino acid polypeptide or non-natural amino acid polypeptide under discussion can be modified or unmodified.

As used herein, the term "modulated serum half-life" refers to positive or negative changes in the circulating half-life of a modified biologically active molecule relative to its non-modified form. By way of example, the modified biologically active molecules include, but are not limited to, natural amino acid, non-natural amino acid, natural amino acid polypeptide or non-natural amino acid polypeptide. By way of example, serum half-life is measured by taking blood samples at various time points after administration of the biologically active molecule or modified biologically active molecule, and determining the concentration of that molecule in each sample. Correlation of the serum concentration with time allows calculation of the serum half-life. By way of example, modulated serum half-life may be an increased in serum half-life, which may enable an improved dosing regimens or avoid toxic effects. Such increases in serum may be at least about two fold, at least about three-fold, at least about five-fold, or at least about ten-fold. Methods for evaluating serum half-life are known in the art and may be used for evaluating the serum half-life of antibodies and antibody drug conjugates of the present invention.

The term "modulated therapeutic half-life," as used herein, refers to positive or negative change in the half-life of the therapeutically effective amount of a modified biologically active molecule, relative to its non-modified form. By way of example, the modified biologically active molecules include, but are not limited to, natural amino acid, non-natural amino acid, natural amino acid polypeptide or non-natural amino acid polypeptide. By way of example, therapeutic half-life is measured by measuring pharmacokinetic and/or pharmacodynamic properties of the molecule at various time points after administration. Increased therapeutic half-life may enable a particular beneficial dosing regimen, a particular beneficial total dose, or avoids an undesired effect. By way of example, the increased therapeutic half-life may result from increased potency, increased or decreased binding of the modified molecule to its target, an increase or decrease in another parameter or mechanism of action of the non-modified molecule, or an increased or decreased breakdown of the molecules by enzymes such as, by way of example only, proteases. Methods for evaluating therapeutic half-life are known in the art and may be used for evaluating the therapeutic half-life of antibodies and antibody drug conjugates of the present invention.

The term "nanoparticle," as used herein, refers to a particle which has a particle size between about 500 nm to about 1 nm.

The term "near-stoichiometric," as used herein, refers to the ratio of the moles of compounds participating in a chemical reaction being about 0.75 to about 1.5.

As used herein, the term "non-eukaryote" refers to non-eukaryotic organisms. By way of example, a non-eukaryotic organism may belong to the Eubacteria, (which includes but is not limited to, *Escherichia coli, Thermus thermophilus,* or *Bacillus stearothermophilus, Pseudomonas fluorescens, Pseudomonas aeruginosa, Pseudomonas putida*), phylogenetic domain, or the Archaea, which includes, but is not limited to, *Methanococcus jannaschii, Methanobacterium thermoautotrophicum, Archaeoglobus fulgidus, Pyrococcus furiosus, Pyrococcus horikoshii, Aeuropyrum pernix,* or *Halobacterium* such as *Haloferax volcanii* and *Halobacterium* species NRC-1, or phylogenetic domain.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "oxidizing agent," as used herein, refers to a compound or material which is capable of removing an electron from a compound being oxidized. By way of example oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "photoaffinity label," as used herein, refers to a label with a group, which, upon exposure to light, forms a linkage with a molecule for which the label has an affinity. By way of example only, such a linkage may be covalent or non-covalent.

The term "photocaged moiety," as used herein, refers to a group which, upon illumination at certain wavelengths, covalently or non-covalently binds other ions or molecules.

The term "photocleavable group," as used herein, refers to a group which breaks upon exposure to light.

The term "photocrosslinker," as used herein, refers to a compound comprising two or more functional groups which, upon exposure to light, are reactive and form a covalent or non-covalent linkage with two or more monomeric or polymeric molecules.

The term "photoisomerizable moiety," as used herein, refers to a group wherein upon illumination with light changes from one isomeric form to another.

The term "polyalkylene glycol," as used herein, refers to linear or branched polymeric polyether polyols. Such polyalkylene glycols, including, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 100 Da and about 100,000 Da or more. The molecular weight of the polymer may be between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, 400 Da, about 300 Da, about 200 Da, and about 100 Da. In some embodiments molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 2,000 to about 50,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly (ethylene glycol) molecule is a branched polymer. The molecular weight of the branched chain PEG may be between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. In other embodiments, the molecular weight of the branched chain PEG is between about 2,000 to about 50,000 Da.

The term "polymer," as used herein, refers to a molecule composed of repeated subunits. Such molecules include, but are not limited to, polypeptides, polynucleotides, or polysaccharides or polyalkylene glycols.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds.

The term "post-translationally modified" refers to any modification of a natural or non-natural amino acid which occurs after such an amino acid has been translationally incorporated into a polypeptide chain. Such modifications include, but are not limited to, co-translational in vivo modifications, co-translational in vitro modifications (such as in a cell-free translation system), post-translational in vivo modifications, and post-translational in vitro modifications.

The terms "prodrug" or "pharmaceutically acceptable prodrug," as used herein, refers to an agent that is converted into the parent drug in vivo or in vitro, wherein which does not abrogate the biological activity or properties of the drug, and is relatively nontoxic, i.e., the material may be administered to an individual without causing undesirable biological effects or interacting in a deleterious manner with any of the components of the composition in which it is contained. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug. The benefits of such prodrugs include, but are not limited to, (i) ease of administration compared with the parent drug; (ii) the prodrug may be bioavailable by oral administration whereas the parent is not; and (iii) the prodrug may also have improved solubility in pharmaceutical compositions compared with the parent drug. A pro-drug includes a pharmacologically inactive, or reduced-activity, derivative of an active drug. Prodrugs may be designed to modulate the amount of a drug or biologically active molecule that reaches a desired site of action through the manipulation of the properties of a drug, such as physiochemical, biopharmaceutical, or pharmacokinetic properties. An example, without limitation, of a prodrug would be a non-natural amino acid polypeptide which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial. Prodrugs may be designed as reversible drug derivatives, for use as modifiers to enhance drug transport to site-specific tissues.

The term "prophylactically effective amount," as used herein, refers that amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "protected," as used herein, refers to the presence of a "protecting group" or moiety that prevents reaction of the chemically reactive functional group under certain reaction conditions. The protecting group will vary depending on the type of chemically reactive group being protected. By way of example only, (i) if the chemically reactive group is an amine or a hydrazide, the protecting group may be selected from tert-butyloxycarbonyl (t-Boc) and 9-fluorenylmethoxycarbonyl (Fmoc); (ii) if the chemically reactive group is a thiol, the protecting group may be orthopyridyldisulfide; and (iii) if the chemically reactive group is a carboxylic acid, such as butanoic or propionic acid, or a hydroxyl group, the protecting group may be benzyl or an alkyl group such as methyl, ethyl, or tert-butyl.

By way of example only, blocking/protecting groups may be selected from:

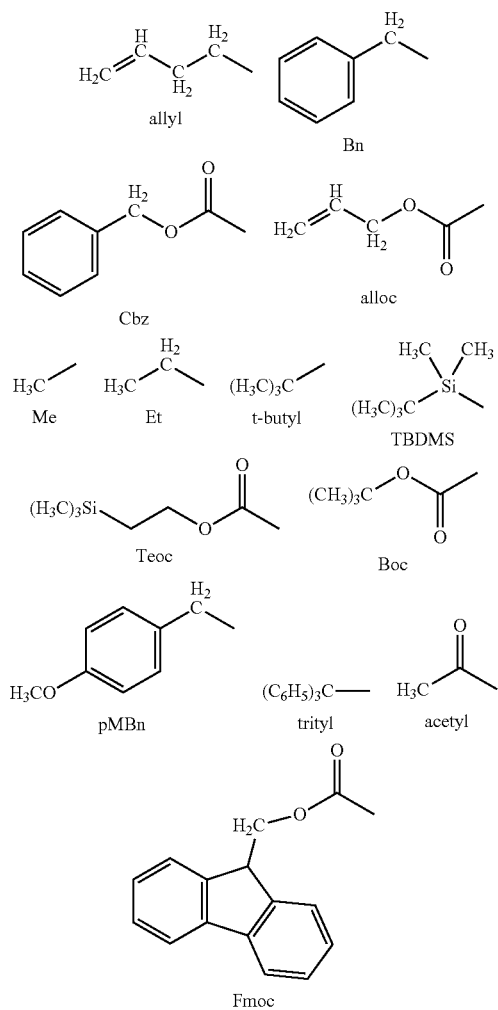

Additionally, protecting groups include, but are not limited to, including photolabile groups such as Nvoc and MeNvoc and other protecting groups known in the art. Other protecting groups are described in Greene and Wuts, Protective Groups in Organic Synthesis, 3rd Ed., John Wiley & Sons, New York, N.Y., 1999, which is incorporated herein by reference in its entirety.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "reactive compound," as used herein, refers to a compound which under appropriate conditions is reactive toward another atom, molecule or compound.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

The term "redox-active agent," as used herein, refers to a molecule which oxidizes or reduces another molecule, whereby the redox active agent becomes reduced or oxidized. Examples of redox active agent include, but are not limited to, ferrocene, quinones, $Ru^{2+/3+}$ complexes, $Co^{2+/+}$ complexes, and $Os^{2+/3+}$ complexes.

The term "reducing agent," as used herein, refers to a compound or material which is capable of adding an electron to a compound being reduced. By way of example reducing agents include, but are not limited to, dithiothreitol (DTT), 2-mercaptoethanol, dithioerythritol, cysteine, cysteoamine (2-aminoethanethiol), and reduced glutathione. Such reducing agents may be used, by way of example only, to maintain sulfhydryl groups in the reduced state and to reduce intra- or intermolecular disulfide bonds.

"Refolding," as used herein describes any process, reaction or method which transforms an improperly folded or unfolded state to a native or properly folded conformation. By way of example only, refolding transforms disulfide bond containing polypeptides from an improperly folded or unfolded state to a native or properly folded conformation with respect to disulfide bonds. Such disulfide bond containing polypeptides to may be natural amino acid polypeptides or non-natural amino acid polypeptides.

The term "resin," as used herein, refers to high molecular weight, insoluble polymer beads. By way of example only, such beads may be used as supports for solid phase peptide synthesis, or sites for attachment of molecules prior to purification.

The term "saccharide," as used herein, refers to a series of carbohydrates including but not limited to sugars, monosaccharides, oligosaccharides, and polysaccharides.

The term "safety" or "safety profile," as used herein, refers to side effects that might be related to administration of a drug relative to the number of times the drug has been administered. By way of example, a drug which has been administered many times and produced only mild or no side effects is said to have an excellent safety profile. A non-limiting example of a method to evaluate the safety profile is given in example 26. This method may be used for evaluating the safety profile of any polypeptide.

The phrase "selectively hybridizes to" or "specifically hybridizes to," as used herein, refers to the binding, duplexing, or hybridizing of a molecule to a particular nucleotide sequence under stringent hybridization conditions when that sequence is present in a complex mixture including but not limited to, total cellular or library DNA or RNA.

The term "spin label," as used herein, refers to molecules which contain an atom or a group of atoms exhibiting an unpaired electron spin (i.e. a stable paramagnetic group) that can be detected by electron spin resonance spectroscopy and can be attached to another molecule. Such spin-label molecules include, but are not limited to, nitryl radicals and nitroxides, and may be single spin-labels or double spin-labels.

The term "stoichiometric," as used herein, refers to the ratio of the moles of compounds participating in a chemical reaction being about 0.9 to about 1.1.

The term "stoichiometric-like," as used herein, refers to a chemical reaction which becomes stoichiometric or near-stoichiometric upon changes in reaction conditions or in the presence of additives. Such changes in reaction conditions include, but are not limited to, an increase in temperature or change in pH. Such additives include, but are not limited to, accelerants.

The phrase "stringent hybridization conditions" refers to hybridization of sequences of DNA, RNA, PNA or other nucleic acid mimics, or combinations thereof, under conditions of low ionic strength and high temperature. By way of example, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. By way of example, longer sequences hybridize specifically at higher temperatures. Stringent hybridization conditions include, but are not limited to, (i) about 5-10° C. lower than the thermal melting point (Tm) for the specific sequence at a defined ionic strength and pH; (ii) the salt concentration is about 0.01 M to about 1.0 M at about pH 7.0 to about pH 8.3 and the temperature is at least about 30° C. for short probes (including but not limited to, about 10 to about 50 nucleotides) and at least about 60° C. for long probes (including but not limited to, greater than 50 nucleotides); (iii) the addition of destabilizing agents including, but not limited to, formamide, (iv) 50% formamide, 5×SSC, and 1% SDS, incubating at 42° C., or 5×SSC, about 1% SDS, incubating at 65° C., with wash in 0.2×SSC, and about 0.1% SDS at 65° C. for between about 5 minutes to about 120 minutes. By way of example only, detection of selective or specific hybridization, includes, but is not limited to, a positive signal at least two times background. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

The term "subject" as used herein, refers to an animal which is the object of treatment, observation or experiment. By way of example only, a subject may be, but is not limited to, a mammal including, but not limited to, a human.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example when a natural amino acid polypeptide or a non-natural amino acid polypeptide is recombinantly produced by host cells, the natural amino acid polypeptide or non-natural amino acid polypeptide may be present at about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85%, about 90%, about 95%, about 99% or greater as determined by appropriate methods, including, but not limited to, SDS/PAGE analysis, RP-HPLC, SEC, and capillary electrophoresis.

The term "substituents" also referred to as "non-interfering substituents" "refers to groups which may be used to replace another group on a molecule. Such groups include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluolyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—$CF_3$, —C(O)$NR_2$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each m is from 1 to 8, —C(O) $NR_2$, —C(S)$NR_2$, —$SO_2NR_2$, —NRC(O)$NR_2$, —NRC(S) $NR_2$, salts thereof, and the like. Each R group in the preceding list includes, but is not limited to, H, alkyl or substituted alkyl, aryl or substituted aryl, or alkaryl. Where substituent groups are specified by their conventional chemical formulas, written from left to right, they equally encompass the chemically identical substituents that would result from writing the structure from right to left; for example, —$CH_2O$— is equivalent to —$OCH_2$—.

By way of example only, substituents for alkyl and heteroalkyl radicals (including those groups referred to as alkylene, alkenyl, heteroalkylene, heteroalkenyl, alkynyl, cycloalkyl, heterocycloalkyl, cycloalkenyl, and heterocycloalkenyl) includes, but is not limited to: —OR, =O, =NR, =N—OR, —$NR_2$, —SR, -halogen, —$SiR_3$, —OC(O)R, —C(O)R, —$CO_2$R, —$CONR_2$, —OC(O)$NR_2$, —NRC(O)R, —NRC(O)$NR_2$, —NR(O)$_2$R, —NR—C($NR_2$)=NR, —S(O)R, —S(O)$_2$R, —S(O)$_2NR_2$, —$NRSO_2$R, —CN and —$NO_2$. Each R group in the preceding list includes, but is not limited to, hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. When two R groups are attached to the same nitrogen atom, they can be combined with the nitrogen atom to form a 5-, 6-, or 7-membered ring. For example, —NR$_2$ is meant to include, but not be limited to, 1-pyrrolidinyl and 4-morpholinyl.

By way of example, substituents for aryl and heteroaryl groups include, but are not limited to, —OR, =O, =NR, =N—OR, —NR$_2$, —SR, -halogen, —SiR$_3$, —OC(O)R, —C(O)R, —CO$_2$R, —CONR$_2$, —OC(O)NR$_2$, —NRC(O)R, —NRC(O)NR$_2$, —NR(O)$_2$R, —NR—C(NR$_2$)=NR, —S(O)R, —S(O)$_2$R, —S(O)$_2$NR$_2$, —NRSO$_2$R, —CN, —NO$_2$, —R, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where each R group in the preceding list includes, but is not limited to, hydrogen, alkyl, heteroalkyl, aryl and heteroaryl.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term "thioalkoxy," as used herein, refers to sulfur containing alkyl groups linked to molecules via an oxygen atom.

The term "thermal melting point" or Tm is the temperature (under defined ionic strength, pH, and nucleic concentration) at which 50% of probes complementary to a target hybridize to the target sequence at equilibrium.

The term "toxic moiety" or "toxic group" as used herein, refers to a compound which can cause harm, disturbances, or death. Toxic moieties include, but are not limited to, NCA1, auristatin, DNA minor groove binding agent, DNA minor groove alkylating agent, enediyne, lexitropsin, duocarmycin, taxane, puromycin, dolastatin, maytansinoid, vinca alkaloid, AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, netropsin, podophyllotoxin (e.g. etoposide, teniposide, etc.), baccatin and its derivatives, anti-tubulin agents, cryptophysin, combretastatin, auristatin E, vincristine, vinblastine, vindesine, vinorelbine, VP-16, camptothecin, epothilone A, epothilone B, nocodazole, colchicines, colcimid, estramustine, cemadotin, discodermolide, maytansine, eleutherobin, mechlorethamine, cyclophosphamide, melphalan, carmustine, lomustine, semustine, streptozocin, chlorozotocin, uracil mustard, chlormethine, ifosfamide, chlorambucil, pipobroman, triethylenemelamine, triethylenethiophosphoramine, busulfan, dacarbazine, and temozolomide, ytarabine, cytosine arabinoside, fluorouracil, floxuridine, 6-thioguanine, 6-mercaptopurine, pentostatin, 5-fluorouracil, methotrexate, 10-propargyl-5,8-dideazafolate, 5,8-dideazatetrahydrofolic acid, leucovorin, fludarabine phosphate, pentostatine, gemcitabine, Ara-C, paclitaxel, docetaxel, deoxycoformycin, mitomycin-C, L-asparaginase, azathioprine, brequinar, antibiotics (e.g., anthracycline, gentamicin, cefalotin, vancomycin, telavancin, daptomycin, azithromycin, erythromycin, rocithromycin, furazolidone, amoxicillin, ampicillin, carbenicillin, flucloxacillin, methicillin, penicillin, ciprofloxacin, moxifloxacin, ofloxacin, doxycycline, minocycline, oxytetracycline, tetracycline, streptomycin, rifabutin, ethambutol, rifaximin, etc.), antiviral drugs (e.g., abacavir, acyclovir, ampligen, cidofovir, delavirdine, didanosine, efavirenz, entecavir, fosfonet, ganciclovir, ibacitabine, immunovir, idoxuridine, inosine, lopinavir, methisazone, nexavir, nevirapine, oseltamivir, penciclovir, stavudine, trifluridine, truvada, valaciclovir, zanamivir, etc.), daunorubicin hydrochloride, daunoriycin, rubidomycin, cerubidine, idarubicin, doxorubicin, epirubicin and morpholino derivatives, phenoxizone biscyclopeptides (e.g., dactinomycin), basic glycopeptides (e.g., bleomycin), anthraquinone glycosides (e.g., plicamycin, mithramycin), anthracenediones (e.g., mitoxantrone), azirinopyrrolo indolediones (e.g., mitomycin), macrocyclic immunosuppressants (e.g., cyclosporine, FK-506, tacrolimus, prograf, rapamycin etc.), navelbene, CPT-11, anastrazole, letrazole, capecitabine, reloxafine, cyclophosphamide, ifosamide, droloxafine, allocolchicine, Halichondrin B, colchicine, colchicine derivatives, maytansine, rhizoxin, paclitaxel, paclitaxel derivatives, docetaxel, thiocolchicine, trityl cysterin, vinblastine sulfate, vincristine sulfate, cisplatin, carboplatin, hydroxyurea, N-methylhydrazine, epidophyllotoxin, procarbazine, mitoxantrone, leucovorin, and tegafur. "Taxanes" include paclitaxel, as well as any active taxane derivative or pro-drug. Chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omega1I; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or to condition. The terms "treat," "treating" or "treatment", include, but are not limited to, prophylactic and/or therapeutic treatments.

As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. By way of example only, coupling of such water soluble polymers to natural amino acid polypeptides or non-natural polypeptides may result in changes including, but not limited to, increased water solubility, increased or modulated serum half-life, increased or modulated therapeutic half-life relative to the unmodified form, increased bioavailability, modulated biological activity, extended circulation time, modulated immunogenicity, modulated physical association characteristics including, but not limited to, aggregation and multimer formation, altered receptor binding, altered binding to one or more binding partners, and altered receptor dimerization or multimerization. In addition, such water soluble polymers may or may not have their own biological activity.

Unless otherwise indicated, conventional methods of mass spectroscopy, NMR, HPLC, protein chemistry, biochemistry, recombinant DNA techniques and pharmacology, within the skill of the art are employed.

Compounds, (including, but not limited to non-natural amino acids, non-natural amino acid polypeptides, modified non-natural amino acid polypeptides, and reagents for producing the aforementioned compounds) presented herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

Some of the compounds herein (including, but not limited to non-natural amino acids, non-natural amino acid polypeptides and modified non-natural amino acid polypeptides, and reagents for producing the aforementioned compounds) have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein (including, but not limited to non-natural amino acids, non-natural amino acid polypeptides and modified non-natural amino acid polypeptides, and reagents for producing the aforementioned compounds) are used in the form of pro-drugs. In additional or further embodiments, the compounds described herein ((including, but not limited to non-natural amino acids, non-natural amino acid polypeptides and modified non-natural amino acid polypeptides, and reagents for producing the aforementioned compounds) are metabolized upon administration to an organism in need to produce a metabolite that is then used to produce a desired effect, including a desired therapeutic effect. In further or additional embodiments are active metabolites of non-natural amino acids and "modified or unmodified" non-natural amino acid polypeptides.

The methods and formulations described herein include the use of N-oxides, crystalline forms (also known as polymorphs), or pharmaceutically acceptable salts of non-natural amino acids, non-natural amino acid polypeptides and modified non-natural amino acid polypeptides. In certain embodiments, non-natural amino acids, non-natural amino acid polypeptides and modified non-natural amino acid polypeptides may exist as tautomers. All tautomers are included within the scope of the non-natural amino acids, non-natural amino acid polypeptides and modified non-natural amino acid polypeptides presented herein. In addition, the non-natural amino acids, non-natural amino acid polypeptides and modified non-natural amino acid polypeptides described herein can exist in unsolvated as well as solvated forms with pharmaceutically acceptable solvents such as water, ethanol, and the like. The solvated forms of the non-natural amino acids, non-natural amino acid polypeptides and modified non-natural amino acid polypeptides presented herein are also considered to be disclosed herein.

Some of the compounds herein (including, but not limited to non-natural amino acids, non-natural amino acid polypeptides and modified non-natural amino acid polypeptides and reagents for producing the aforementioned compounds) may exist in several tautomeric forms. All such tautomeric forms are considered as part of the compositions described herein. Also, for example all enol-keto forms of any compounds (including, but not limited to non-natural amino acids, non-natural amino acid polypeptides and modified non-natural amino acid polypeptides and reagents for producing the aforementioned compounds) herein are considered as part of the compositions described herein.

Some of the compounds herein (including, but not limited to non-natural amino acids, non-natural amino acid polypeptides and modified non-natural amino acid polypeptides and reagents for producing either of the aforementioned compounds) are acidic and may form a salt with a pharmaceutically acceptable cation. Some of the compounds herein (including, but not limited to non-natural amino acids, non-natural amino acid polypeptides and modified non-natural amino acid polypeptides and reagents for producing the aforementioned compounds) can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Pharmaceutically acceptable salts of the non-natural amino acid polypeptides disclosed herein may be formed when an acidic proton present in the parent non-natural amino acid polypeptides either is replaced by a metal ion, by way of example an alkali metal ion, an alkaline earth ion, or an aluminum ion; or coordinates with an organic base. In addition, the salt forms of the disclosed non-natural amino acid polypeptides can be prepared using salts of the starting materials or intermediates. The non-natural amino acid polypeptides described herein may be prepared as a pharmaceutically acceptable acid addition salt (which is a type of a pharmaceutically acceptable salt) by reacting the free base form of non-natural amino acid polypeptides described herein with a pharmaceutically acceptable inorganic or organic acid. Alternatively, the non-natural amino acid polypeptides described herein may be prepared as pharmaceutically acceptable base addition salts (which are a type of a pharmaceutically acceptable salt) by reacting the free acid form of non-natural amino acid polypeptides described herein with a pharmaceutically acceptable inorganic or organic base.

The type of pharmaceutical acceptable salts, include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the non-natural amino acid polypeptide pharmaceutical acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof. In addition, the therapeutic activity of such non-natural amino acid polypeptide pharmaceutical acceptable salts may be tested using the techniques and methods described in examples 87-91.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of non-natural amino acid polypeptide pharmaceutical acceptable salts polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
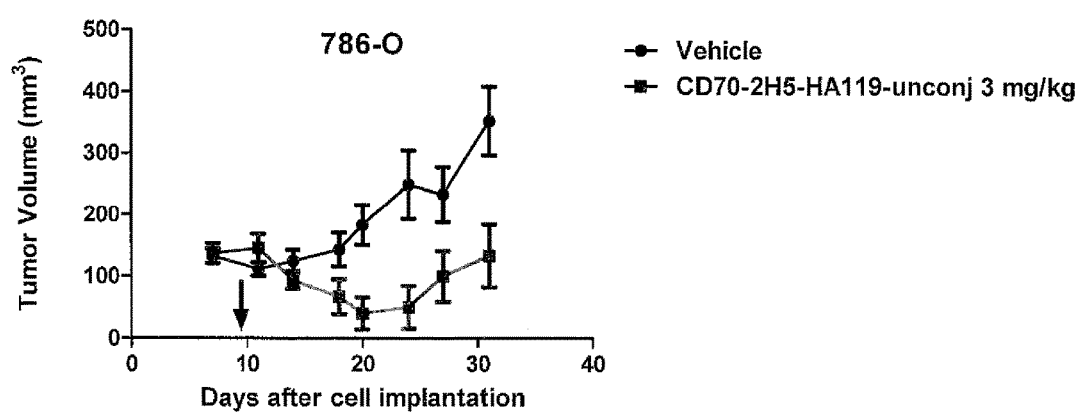
FIG. 1 presents a graphical illustration of anti-tumor efficacy of unconjugated ARX-αCD70 antibody CD70-2H5-HA119 administered in a single dose to female nude mice 7 days following implantation of a 786-O tumor fragment in a dose of 3 mg/kg) against control vehicle.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I. Introduction

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-natural amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society*

124:9026-9027 (incorporated by reference in its entirety); J. W. Chin, & P. G. Schultz, (2002), *ChemBioChem* 3(11): 1135-1137 (incorporated by reference in its entirety); J. W. Chin, et al., (2002), *PNAS United States of America* 99(17): 11020-11024 (incorporated by reference in its entirety); and, L. Wang, & P. G. Schultz, (2002), *Chem. Comm.*, 1-11 (incorporated by reference in its entirety). These studies have demonstrated that it is possible to selectively and routinely introduce chemical functional groups that are not found in proteins, that are chemically inert to all of the functional groups found in the 20 common, genetically-encoded amino acids and that may be used to react efficiently and selectively to form stable covalent linkages.

II. Overview

The present invention provides αCD70 antibodies having a non-naturally encoded amino acid that facilitate antibody conjugation to a drug (e.g. a drug, toxin, marker molecule). In one embodiment, the ADC comprise an αCD70 antibody conjugated to a drug wherein the conjugation occurs via a non-naturally encoded amino acid in the antibody. In one embodiment, the ADC comprise an αCD70 antibody conjugated to a drug wherein the conjugation occurs via a non-naturally encoded amino acid in the heavy chain of the antibody. In one embodiment, the ADC comprise an αCD70 antibody conjugated to a drug wherein the conjugation occurs via a non-naturally encoded amino acid in the light chain of the antibody. In one embodiment, the ADC comprise a full-length antibody conjugated to a drug wherein the conjugation occurs via a non-naturally encoded amino acid in the antibody.

In one embodiment, the ADC comprise a full-length antibody conjugated to a drug wherein the conjugation occurs via a non-naturally encoded amino acid in the heavy chain of the antibody. In one embodiment, the ADC comprise a full-length antibody conjugated to a drug wherein the conjugation occurs via a non-naturally encoded amino acid in the light chain of the antibody.

In some embodiments, the drug of the ADC is a cytotoxic drug. In some aspects of the invention, the cytotoxic drug is selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In some aspects of the invention, the cytotoxic drug is

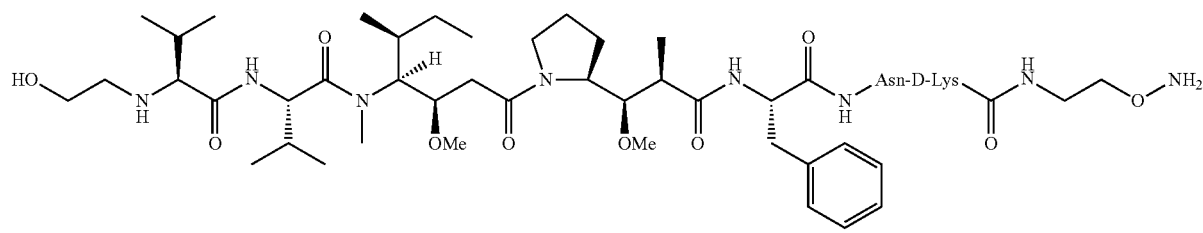

In other embodiments of the present invention, the cytotoxic drug is chosen from the group comprising:

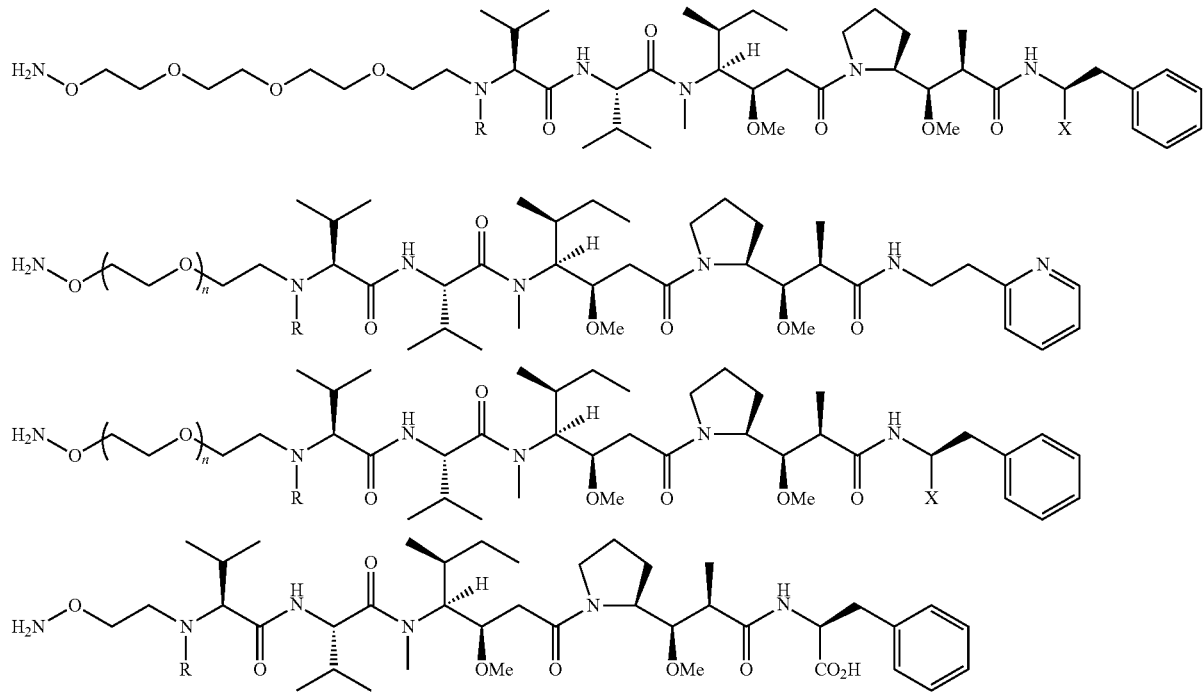

-continued
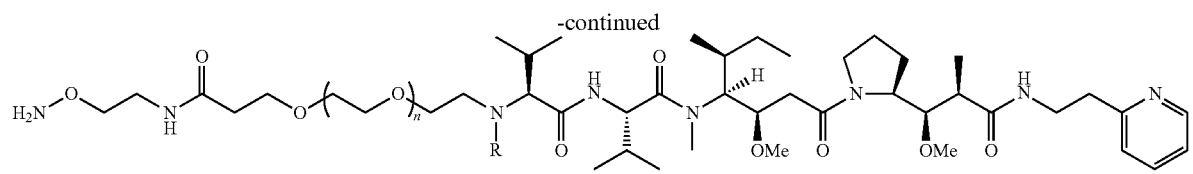
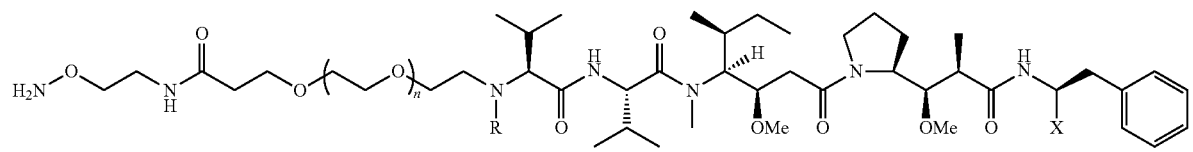
In some embodiments of the present invention, the cytotoxic drug is chosen from the group consisting of
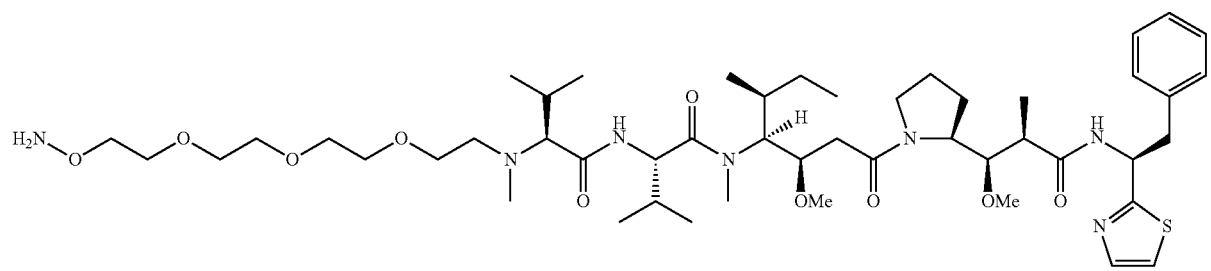
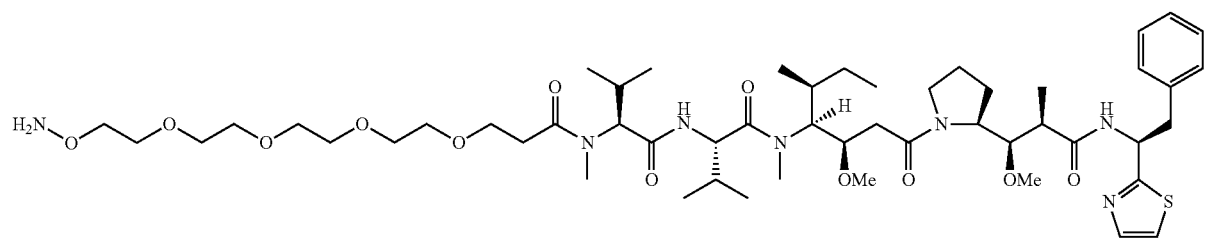
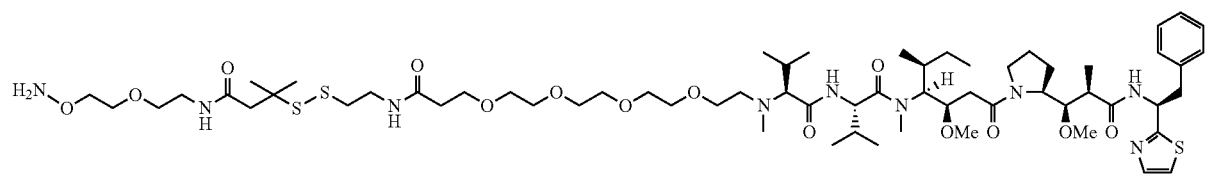
In other aspects of the present invention, the cytotoxic drug is chosen from the group consisting of:
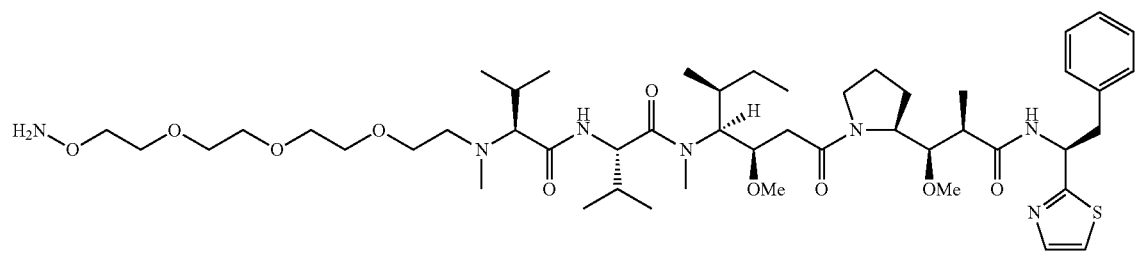

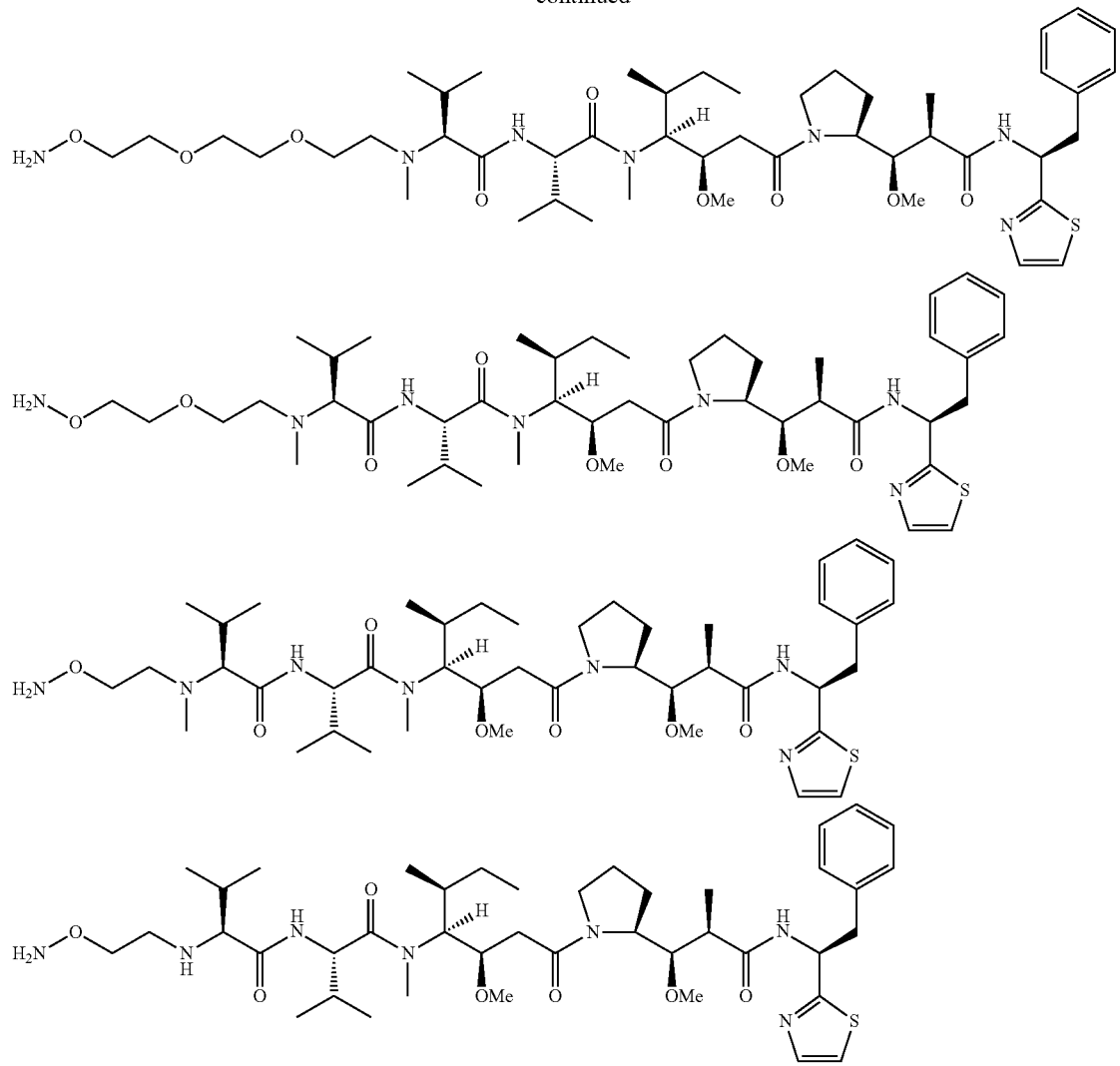
In other aspects of the present invention, the cytotoxic drug is chosen from the group consisting of
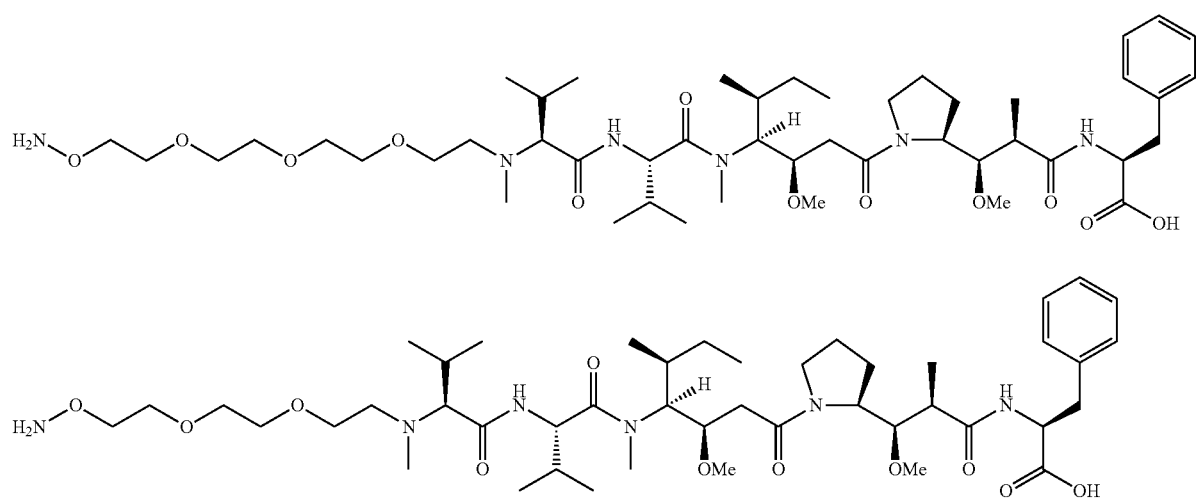

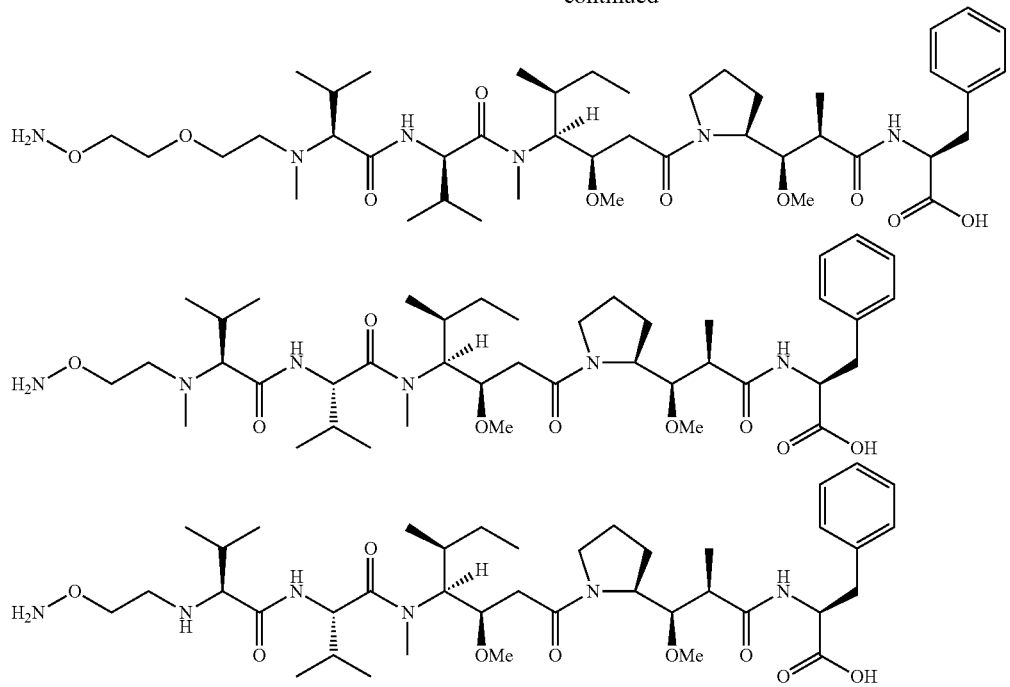

In other aspects of the present invention, the cytotoxic drug is chosen from the group consisting of AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin.

In some aspects of the invention, the cytotoxic drug is an anti-tubulin agent. In some embodiments, the anti-tubulin agent is an auristatin, a vinca alkaloid, a podophyllotoxin, a taxane, a baccatin derivative, a cryptophysin, a maytansinoid, a combretastatin, or a dolastatin. In other aspects of the invention, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodennolide, maytansine, DM-1, or eleutherobin.

In other aspects of the invention, the cytotoxic drug of the ADC is gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-ipoxygenase inhibitor, or a leukotriene receptor antagonist.

In some embodiments of the invention, the antibody of the ADC comprises a full length antibody that: (a) binds to CD70, and (b) is conjugated to a cytotoxic agent or an immunosuppressive agent, wherein the antibody-drug conjugate exerts: (a) a cytotoxic or cytostatic effect on a CD70-expressing cancer cell line, or (b) a cytotoxic, cytostatic, or immunosuppressive effect on a CD70-expressing immune cell, wherein the conjugation occurs at a non-naturally encoded amino acid in the antibody.

At one level, described herein are the tools (methods, compositions, techniques) for creating and using dolastatin linker derivatives or analogs comprising at least one carbonyl, dicarbonyl, oxime, hydroxylamine, aldehyde, protected aldehyde, ketone, protected ketone, thioester, ester, dicarbonyl, hydrazine, azide, amidine, imine, diamine, keto-amine, keto-alkyne, alkyne, cycloalkyne, or ene-dione. At another level, described herein are the tools (methods, compositions, techniques) for creating and using dolastatin linker derivatives or analogs comprising at least one non-natural amino acid or modified non-natural amino acid with an oxime, aromatic amine, heterocycle (e.g., indole, quinoxaline, phenazine, pyrazole, triazole, etc.).

Such dolastatin linker derivatives comprising non-natural amino acids may contain further functionality, including but not limited to, a polymer; a water-soluble polymer; a derivative of polyethylene glycol; a second protein or polypeptide or polypeptide analog; an antibody or antibody fragment; and any combination thereof. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

Provided herein in some embodiments, is a toxic group linker derivative comprising a carbonyl, dicarbonyl, oxime, hydroxylamine, aldehyde, protected aldehyde, ketone, protected ketone, thioester, ester, dicarbonyl, hydrazine, azide, amidine, imine, diamine, keto-amine, keto-alkyne, alkyne, cycloalkyne, or ene-dione. In some embodiments, the toxic group derivative comprises any of the linkers disclosed herein. In other embodiments, described herein are the tools (methods, compositions, techniques) for creating and using toxic group derivatives or analogs comprising at least one non-natural amino acid or modified non-natural amino acid with an oxime, aromatic amine, heterocycle (e.g., indole, quinoxaline, phenazine, pyrazole, triazole, etc.).

In some embodiments, such toxic derivatives comprising non-natural amino acids may contain further functionality, including but not limited to, a polymer; a water-soluble polymer; a derivative of polyethylene glycol; a second protein or polypeptide or polypeptide analog; an antibody or antibody fragment; and any combination thereof. In specific embodiments, the toxic group is a tubulin inhibitor. In certain specific embodiments, the toxic group is dolastatin or auristatin. In other specific embodiments, the toxic group is dolastatin or auristatin derivative. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

Certain embodiments of the present invention describe preparations of certain toxic moieties with linkers that reduce the toxicity of the moiety in vivo while the toxic moiety retains pharmacological activity. In some embodiments, the toxicity of the linked toxic group, when administered to an animal or human, is reduced or eliminated compared to the free toxic group or toxic group derivatives comprising labile linkages, while retaining pharmacological activity. In some embodiments, increased doses of the linked toxic group (e.g., dolastatin linker derivatives, non-natural amino acid linked dolastatin derivatives) may be administered to animals or humans with greater safety. In certain embodiments, the non-natural amino acid polypeptides linked to a toxic moiety (e.g., dolastatin derivative) provides in vitro and in vivo stability. In some embodiments, the non-natural amino acid polypeptides linked to a toxic moiety (e.g., tubulin inhibitor, dolastatin-10 derivative) are efficacious and less toxic compared to the free toxic moiety (e.g., tubulin inhibitor, dolastatin-10).

III. Dolastatin Linker Derivatives

At one level, described herein are the tools (methods, compositions, techniques) for creating and using a dolastatin linker derivatives or analogs comprising at least one non-natural amino acid or modified non-natural amino acid with a carbonyl, dicarbonyl, oxime or hydroxylamine group. Such dolastatin linker derivatives comprising non-natural amino acids may contain further functionality, including but not limited to, a polymer; a water-soluble polymer; a derivative of polyethylene glycol; a second protein or polypeptide or polypeptide analog; an antibody or antibody fragment; and any combination thereof. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

In one aspect are methods for selecting and designing a dolastatin linker derivative to be modified using the methods, compositions and techniques described herein. The new dolastatin linker derivative may be designed de novo, including by way of example only, as part of high-throughput screening process (in which case numerous polypeptides may be designed, synthesized, characterized and/or tested) or based on the interests of the researcher. The new dolastatin linker derivative may also be designed based on the structure of a known or partially characterized polypeptide. By way of example only, dolastatin has been the subject of intense study by the scientific community; a new compound may be designed based on the structure of dolastatin. The principles for selecting which amino acid(s) to substitute and/or modify are described separately herein. The choice of which modification to employ is also described herein, and can be used to meet the need of the experimenter or end user. Such needs may include, but are not limited to, manipulating the therapeutic effectiveness of the polypeptide, improving the safety profile of the polypeptide, adjusting the pharmacokinetics, pharmacologics and/or pharmacodynamics of the polypeptide, such as, by way of example only, increasing water solubility, bioavailability, increasing serum half-life, increasing therapeutic half-life, modulating immunogenicity, modulating biological activity, or extending the circulation time. In addition, such modifications include, by way of example only, providing additional functionality to the polypeptide, incorporating an antibody, and any combination of the aforementioned modifications.

Also described herein are dolastatin linker derivatives that have or can be modified to contain an oxime, carbonyl, dicarbonyl, or hydroxylamine group. Included with this aspect are methods for producing, purifying, characterizing and using such dolastatin linker derivatives The dolastatin linker derivative may contain at least one, at least two, at least three, at least four, at least five, at least six, at least seven, at least eight, at least nine, or ten or more of a carbonyl or dicarbonyl group, oxime group, hydroxylamine group, or protected forms thereof. The dolastatin linker derivative can be the same or different, for example, there can be 1, 2, 3, 4, 5, 6, 7, 8, 9, 10, 11, 12, 13, 14, 15, 16, 17, 18, 19, 20, or more different sites in the derivative that comprise 1, 2, 3, 4, 5, 6, 7, 8, 9, 10, 11, 12, 13, 14, 15, 16, 17, 18, 19, 20, or more different reactive groups.

A. Structure and Synthesis of Dolastatin Linker Derivatives: Electrophilc and Nucleophilic Groups Dolastatin derivatives with linkers containing a hydroxylamine (also called an aminooxy) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain carbonyl- or dicarbonyl-groups, including but not limited to, ketones, aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34(9): 727-736 (2001). Whereas the result of reaction with a hydrazine group is the corresponding hydrazone, however, an oxime results generally from the reaction of an aminooxy group with a carbonyl- or dicarbonyl-containing group such as, by way of example, a ketones, aldehydes or other functional groups with similar chemical reactivity. In some embodiments, dolastatin derivatives with linkers comprising an azide, alkyne or cycloalkyne allow for linking of molecules via cycloaddition reactions (e.g., 1,3-dipolar cycloadditions, azide-alkyne Huisgen cycloaddition, etc.). (Described in U.S. Pat. No. 7,807,619 which is incorporated by reference herein to the extent relative to the reaction).

Thus, in certain embodiments described herein are dolastatin derivatives with linkers comprising a hydroxylamine, aldehyde, protected aldehyde, ketone, protected ketone, thioester, ester, dicarbonyl, hydrazine, amidine, imine, diamine, keto-amine, keto-alkyne, and ene-dione hydroxylamine group, a hydroxylamine-like group (which has reactivity similar to a hydroxylamine group and is structurally similar to a hydroxylamine group), a masked hydroxylamine group (which can be readily converted into a hydroxylamine group), or a protected hydroxylamine group (which has reactivity similar to a hydroxylamine group upon deprotection). In some embodiments, the dolastatin derivatives with linkers comprise azides, alkynes or cycloalkynes. Such dolastatin linker derivatives include compounds having the structure of Formula (I), (III), (IV), (V), and (VI):
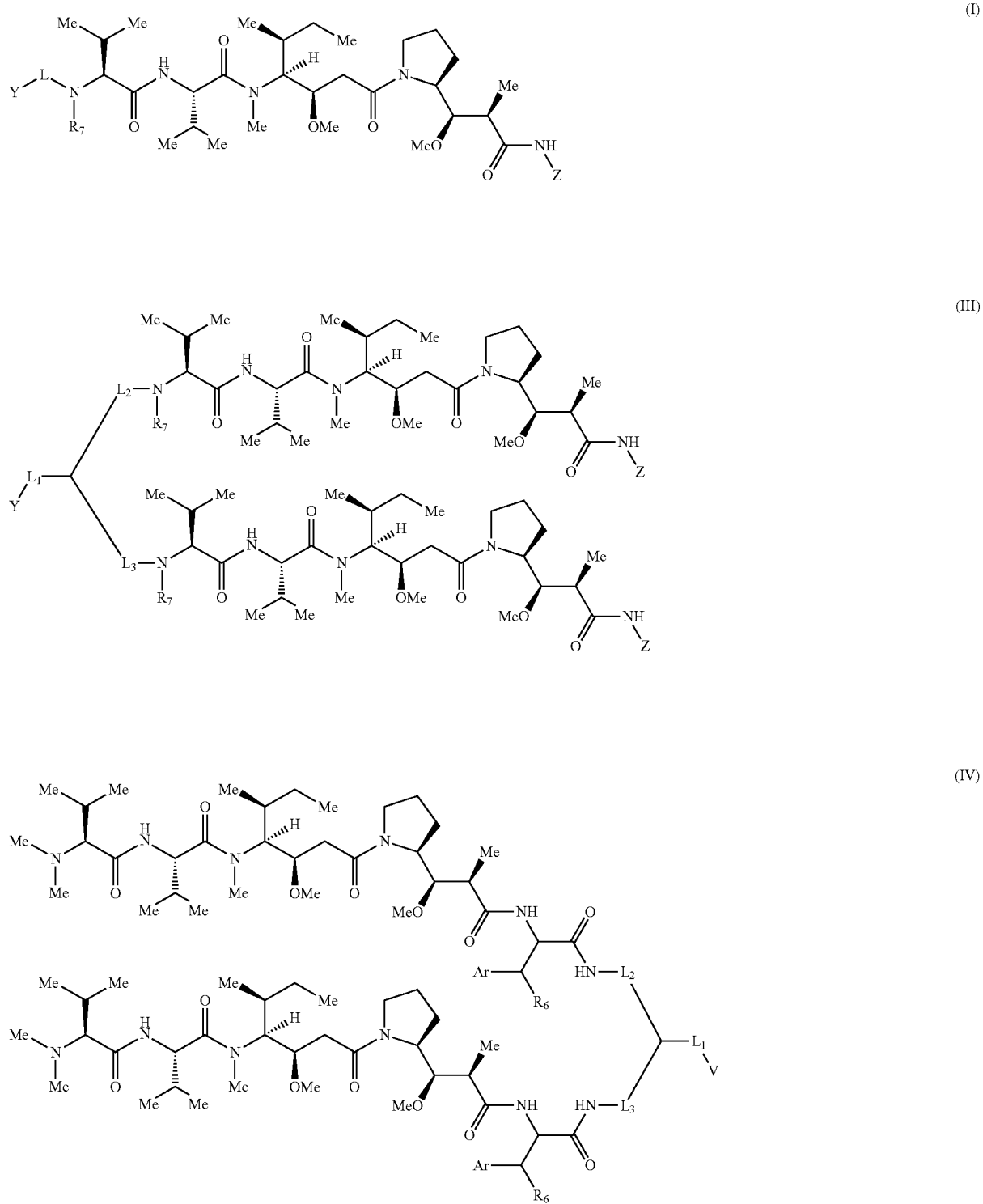

-continued (V)

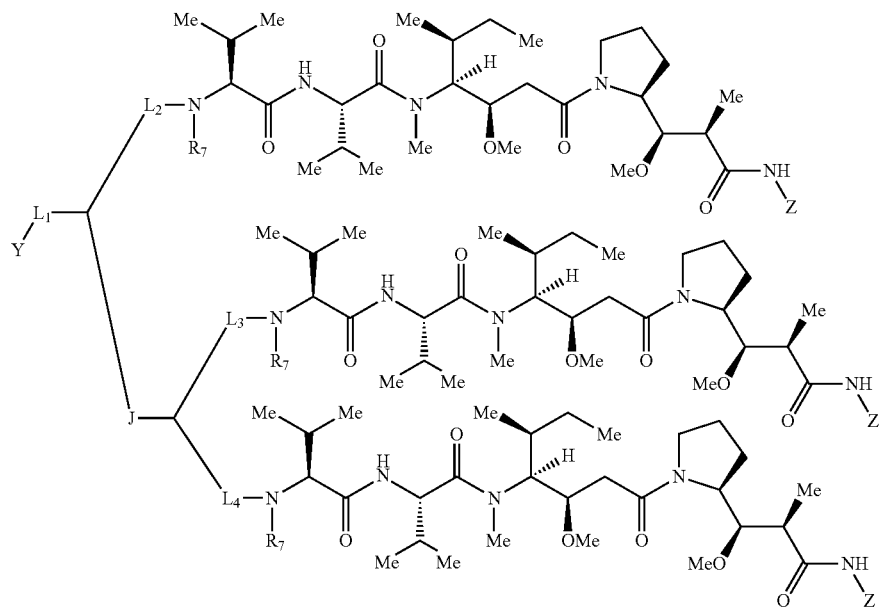

(VI)

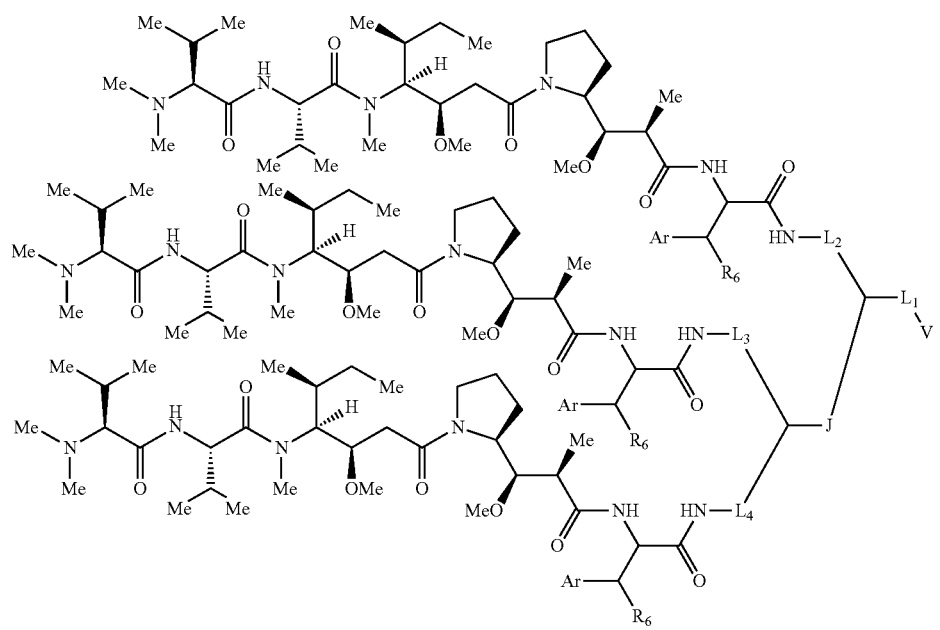

wherein:

Z has the structure of:

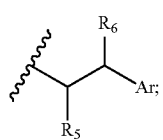

R₅ is H, COR₈, C₁-C₆alkyl, or thiazole;

R₈ is OH or —NH-(alkylene-O)ₙ—NH₂;

R₆ is OH or H;

Ar is phenyl or pyridine;

R₇ is C₁-C₆alkyl or hydrogen;

Y and V are each selected from the group consisting of an hydroxylamine, methyl, aldehyde, protected aldehyde, ketone, protected ketone, thioester, ester, dicarbonyl, hydrazine, azide, amidine, imine, diamine, keto-amine, keto-alkyne, alkyne, cycloalkyne, and ene-dione;

L, L₁, L₂, L₃, and L₄ are each linkers selected from the group consisting of a bond, -alkylene-, -alkylene-C(O)—, -alkylene-J-, -(alkylene-O)ₙ-alkylene-, -(alkylene-O)ₙ-alkylene-C(O)—, -(alkylene-O)ₙ-J-, -(alkylene-O)ₙ-J-alkylene-, -(alkylene-O)ₙ—(CH₂)ₙ′—NHC(O)—(CH₂)ₙ″—C(Me)₂-S—S—(CH₂)ₙ‴—NHC(O)-(alkylene-O)ₙ‴′-alkylene-, -(alkylene-O)ₙ-alkylene-W—, -alkylene-C(O)—W—, -(alkylene-O)ₙ-alkylene-J-, -alkylene'-J-(alkylene-O)ₙ-alkylene-, -(alkylene-O)ₙ-alkylene-J-alkylene', -J-(alkylene-O)ₙ-alkylene-, -(alkylene-O)ₙ-alkylene-J-(alkylene-O)ₙ'-alkylene-J'-, —W—, -alkylene-W—, alkylene'-J-(alkylene-NMe)$_n$-alkylene-W—, -J-(alkylene-NMe)$_n$-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene"-W—, and -alkylene-J-alylene'-NMe-alkylene"-NMe-alkylene'"-W—;

W has the structure of:

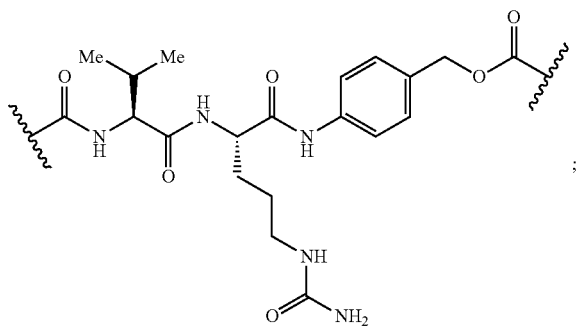 [SMILES: *C(=O)N[C@H](C(=O)N[C@@H](CCCNC(N)=O)C(=O)Nc1ccc(COC(*)=O)cc1)C(C)C]

U has the structure of:

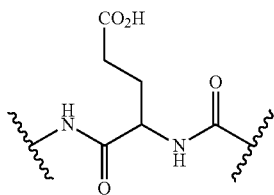 [SMILES: *NC(=O)C(CCC(=O)O)NC(*)=O]

each J and J' independently have the structure of:

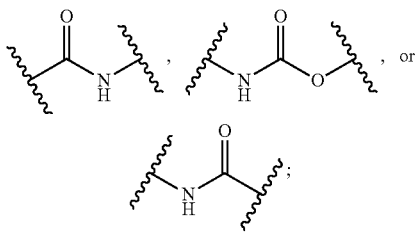

each n, n'n", n'" and n"" are independently integers greater than or equal to one; and or L is absent, Y is methyl, $R_5$ is $COR_8$, and $R_8$ is —NH-(alkylene-O)$_n$—NH$_2$.

Such dolastatin linker derivatives may be in the form of a salt, or may be incorporated into a non-natural amino acid polypeptide, polymer, polysaccharide, or a polynucleotide and optionally post translationally modified.

In certain embodiments of compounds of Formula (I), (III), and (V), $R_5$ is thiazole or carboxylic acid. In certain embodiments of compounds of Formula (I), (III), and (V), $R_5$ is hydrogen. In certain embodiments of compounds of Formula (I), (III), and (V), $R_5$ is methyl, ethyl, propyl, iso-propyl, butyl, iso-butyl, sec-butyl, tert-butyl, pentyl, or hexyl. In certain embodiments of compounds of Formula (I), (III), and (V), $R_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, CH$_2$CH$_2$CH$_2$CHzCH$_2$CH$_2$CH$_2$CH$_2$CH$_2$CH$_2$CH—, or —CH$_2$CH$_2$CH$_2$CH$_2$CH$_2$CH$_2$CH$_2$CH$_2$CH$_2$CH$_2$CH$_2$CH—.

In certain embodiments of compounds of Formula (IV) and (VI), $R_5$ is —NH-(alkylene-O)$_n$—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In some embodiments, Y is azide. In other embodiments, Y is cycloalkyne. In specific embodiments, the cyclooctyne has a structure of:

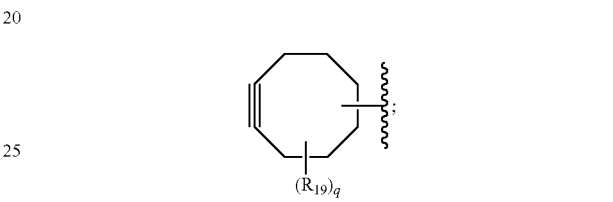

each $R_{19}$ is independently selected from the group consisting of $C_1$-$C_6$ alkyl, $C_1$-$C_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro; and q is 0, 1, 2, 3, 4, 5, 6, 7, 8, 9, 10 or 11.

In certain embodiments of compounds of Formula (I), (III), and (V), $R_6$ is H. In some embodiments of compounds of Formula (I), (III), and (V), $R_6$ is hydroxy.

In certain embodiments of compounds of Formula (I), (III), and (V), Ar is phenyl.

In certain embodiments of compounds of Formula (I), (III), (IV), (V), and (VI), $R_7$ is methyl, ethyl, propyl, iso-propyl, butyl, sec-butyl iso-butyl, tert-butyl, pentyl, or hexyl. In certain embodiments of compounds of Formula (I), (III), (IV), (V), and (VI), $R_7$ is hydrogen.

In certain embodiments of compounds of Formula (I), (III), and (V), Y is hydroxylamine, aldehyde, protected aldehyde, ketone, protected ketone, thioester, ester, dicarbonyl, hydrazine, amidine, imine, diamine, keto-amine, keto-alkyne, or ene-dione.

In certain embodiments of compounds of Formula (IV) and (VI), V is a hydroxylamine, methyl, aldehyde, protected aldehyde, ketone, protected ketone, thioester, ester, dicarbonyl, hydrazine, amidine, imine, diamine, keto-amine, keto-alkyne, and ene-dione.

In certain embodiments of compounds of Formula (I), (III), (IV), (V), and (VI), each L, $L_1$, $L_2$, $L_3$, and $L_4$ is independently a cleavable linker or non-cleavable linker. In certain embodiments of compounds of Formula (I), (III), (IV), (V), and (VI), each L, $L_1$, $L_2$, $L_3$, and $L_4$ is independently a oligo(ethylene glycol) derivatized linker.

In certain embodiments of compounds of Formula (I), (III), (IV), (V), and (VI), each alkylene, alkylene', alkylene", and alkylene'" independently is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$—,
—CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$CH$_2$—, or
—CH$_2$CH$_2$CH$_2$CH$_2$CH$_2$CH$_2$CH$_2$CH$_2$CH$_2$CH$_2$CH$_2$CH$_2$—.

In certain embodiments of compounds of Formula (XIV), (XV), (XVI), (XVII), and (XVIII), each n, n', n", n'", and n"" is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

B. Structure and Synthesis of Dolastatin Linker Derivatives: Hydroxylamine Groups Thus, in certain embodiments described herein are dolastatin derivatives with linkers comprising a hydroxylamine group, a hydroxylamine-like group (which has reactivity similar to a hydroxylamine group and is structurally similar to a hydroxylamine group), a masked hydroxylamine group (which can be readily converted into a hydroxylamine group), or a protected hydroxylamine group (which has reactivity similar to a hydroxylamine group upon deprotection). Such dolastatin linker derivatives include compounds having the structure of Formula (I):

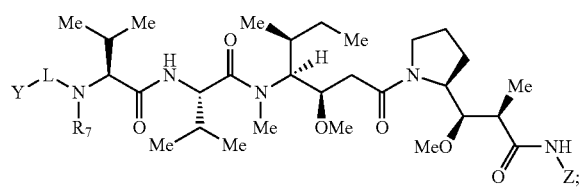

(I)

wherein:

Z has the structure of:

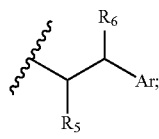

R$_5$ is H, COR$_8$, C$_1$-C$_6$alkyl, or thiazole;
  R$_8$ is OH or —NH-(alkylene-O)$_n$—NH$_2$;
R$_6$ is OH or H;
Ar is phenyl or pyridine;
R$_7$ is C$_1$-C$_6$alkyl or hydrogen;
Y is NH$_2$—O— or methyl;
L is a linker selected from the group consisting of alkylene-, -alkylene-C(O)—, -(alkylene-O)$_n$-alkylene-, -(alkylene-O)$_n$-alkylene-C(O)—, -(alkylene-O)$_n$—(CH$_2$)$_n$'—NHC(O)—(CH$_2$)$_n$"—CMe)$_2$-S—S—(CH$_2$)$_n$'"—NHC(O)-(alkylene-O)$_n$""-alkylene-, -(alkylene-O)$_n$-alkylene-W—, -alkylene-C(O)—W—, -(alkylene-O)$_n$-alkylene-U-alkylene-C(O)—, and -(alkylene-O)$_n$-alkylene-U-alkylene-;

W has the structure of:

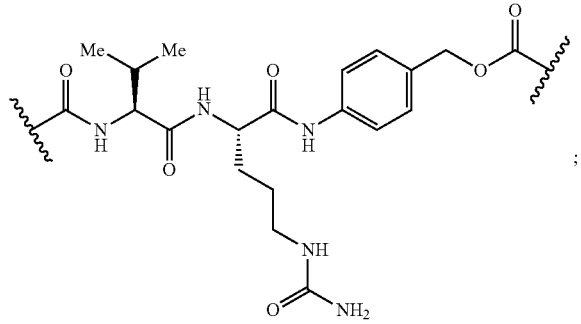 [SMILES: *C(=O)N[C@H](C(=O)N[C@@H](CCCNC(N)=O)C(=O)Nc1ccc(COC(*)=O)cc1)C(C)C]

U has the structure of:

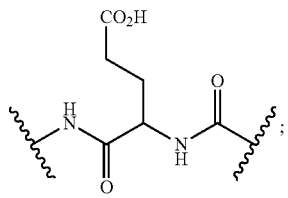 [SMILES: *NC(=O)C(CCC(=O)O)NC(*)=O]

or L is absent, Y is methyl, R$_5$ is COR$_8$, and R$_8$ is —NH-(alkylene-O)$_n$—NH$_2$; and each n, n', n", n'" and n"" are independently integers greater than or equal to one. Such dolastatin linker derivatives may be in the form of a salt, or may be incorporated into a non-natural amino acid polypeptide, polymer, polysaccharide, or a polynucleotide and optionally post translationally modified.

In certain embodiments of compounds of Formula (I), R$_5$ is thiazole. In certain embodiments of compounds of Formula (I), R$_5$ is hydrogen. In certain embodiments of compounds of Formula (I), R$_5$ is methyl, ethyl, propyl, iso-propyl, butyl, iso-butyl, sec-butyl, tert-butyl, pentyl, or hexyl. In certain embodiments of compounds of Formula (I), R$_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—.

In certain embodiments of compounds of Formula (I), R$_5$ is —NH-(alkylene-O)$_n$—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (I), R$_6$ is H. In some embodiments of compounds of Formula (I), R$_6$ is hydroxy.

In certain embodiments of compounds of Formula (I), Ar is phenyl.

In certain embodiments of compounds of Formula (I), R$_7$ is methyl, ethyl, propyl, iso-propyl, butyl, sec-butyl isobutyl, tert-butyl, pentyl, or hexyl. In certain embodiments of compounds of Formula (I), $R_7$ is hydrogen.

In certain embodiments of compounds of Formula (I), Y is hydroxylamine, aldehyde, protected aldehyde, ketone, protected ketone, thioester, ester, dicarbonyl, hydrazine, amidine, imine, diamine, keto-amine, keto-alkyne, or ene-dione. In certain embodiments of compounds of Formula (I), V is a hydroxylamine, methyl, aldehyde, protected aldehyde, ketone, protected ketone, thioester, ester, dicarbonyl, hydrazine, amidine, imine, diamine, keto-amine, keto-alkyne, and ene-dione.

In certain embodiments of compounds of Formula (I), each L is independently a cleavable linker or non-cleavable linker. In certain embodiments of compounds of Formula (I), each L is independently a oligo(ethylene glycol) derivatized linker.

In certain embodiments of compounds of Formula (I), alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH—, —CH$_2$CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—. In certain embodiments of compounds of Formula (I), each n, n', n", n'", and n"" is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments, dolastatin linker derivatives include compounds having the structure of Formula (II):

O)$_n$-alkylene-C(O)—. In some embodiments of compounds of Formula (II), each alkylene is —CH$_2$CH$_2$—, n is equal to 4, and $R_7$ is methyl. In some embodiments of compounds of Formula (II), L is -(alkylene-O)$_n$—(CH$_2$)$_{n'}$—NHC(O)—(CH$_2$)$_{n''}$—C(Me)$_2$-S—S—(CH$_2$)$_{n'''}$—NHC(O)-(alkylene-O)$_{n''''}$-alkylene-. In some embodiments of compounds of Formula (II), each alkylene is —CH$_2$CH$_2$—, n is equal to 1, n' is equal to 2, n" is equal to 1, n'" is equal to 2, n"" is equal to 4, and $R_7$ is methyl. Such dolastatin linker derivatives may be in the form of a salt, or may be incorporated into a non-natural amino acid polypeptide, polymer, polysaccharide, or a polynucleotide and optionally post translationally modified.

In certain embodiments of compounds of Formula (II), each L is independently a cleavable linker or non-cleavable linker. In certain embodiments of compounds of Formula (II), each L is independently a oligo(ethylene glycol) derivatized linker.

In certain embodiments of compounds of Formula (II), $R_7$ is methyl, ethyl, propyl, iso-propyl, butyl, sec-butyl iso-butyl, tert-butyl, pentyl, or hexyl. In certain embodiments of compounds of Formula (II), $R_7$ is hydrogen.

In certain embodiments of compounds of Formula (II), alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, CH$_2$CH$_2$CH$_2$CH$_2$CH$_2$CH$_2$CH$_2$CH$_2$CH$_2$CH$_2$CH$_2$—, or CH$_2$CH$_2$CH$_2$CH$_2$CH$_2$CH$_2$CH$_2$CH$_2$CH$_2$CH$_2$CH$_2$CH$_2$—. In certain embodiments of compounds of Formula (II), each n, n', n", n'", and n"" is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29,

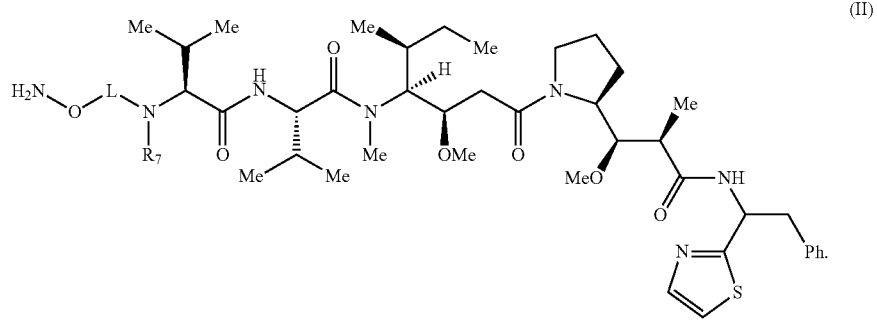

(II)

In some embodiments of compounds of Formula (II), L is -(alkylene-O)$_n$-alkylene-. In some embodiments, each alkylene is —CH$_2$CH$_2$—, n is equal to 3, and $R_7$ is methyl. In some embodiments, L is -alkylene-. In some embodiments of compounds of Formula (II), each alkylene is —CH$_2$CH$_2$— and $R_7$ is methyl or hydrogen. In some embodiments of compounds of Formula (II), L is -(alkylene- 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

Such dolastatin linker derivatives include compounds having the structure of Formula (III), (IV), (V) or (VI):

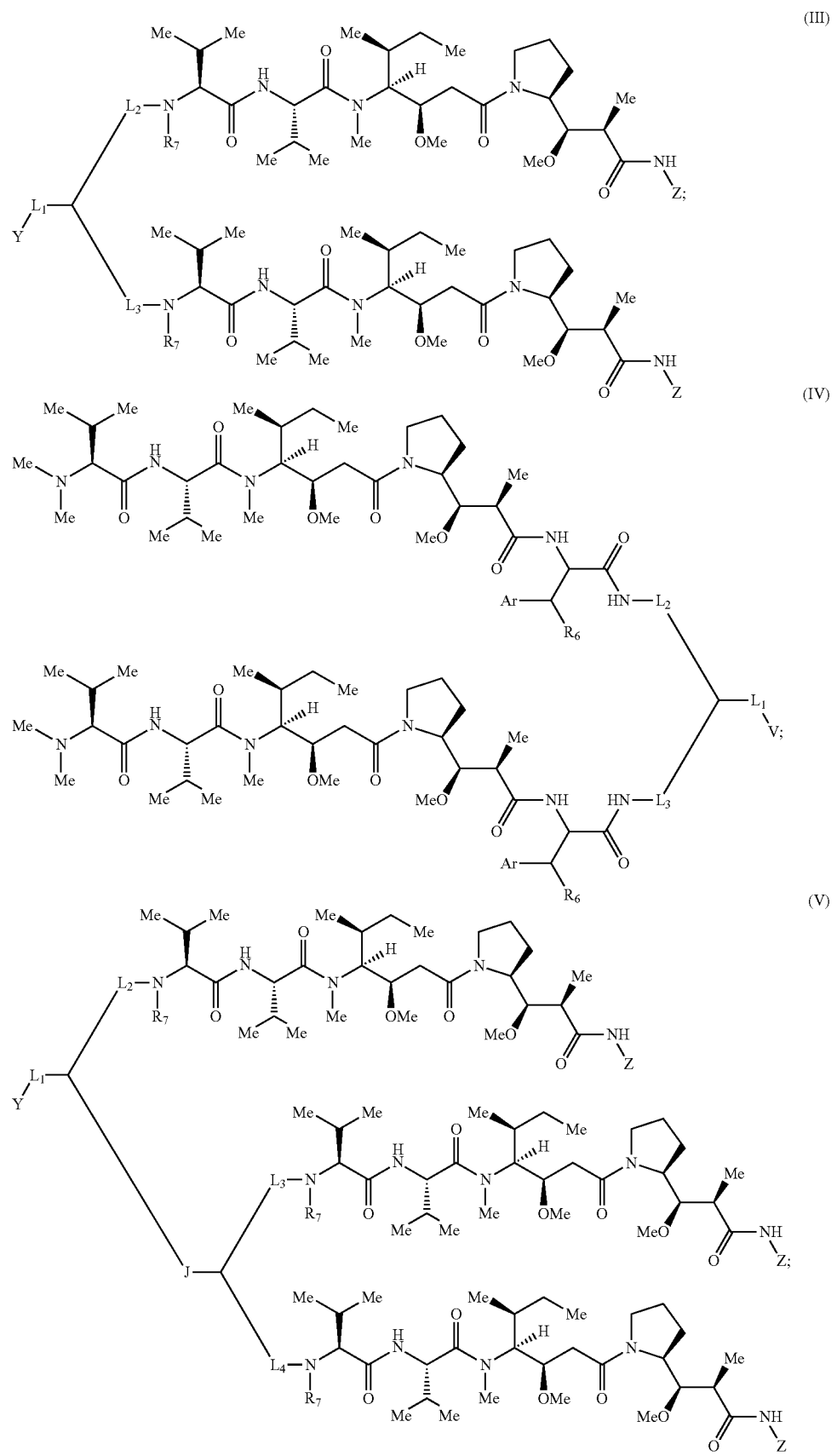

-continued

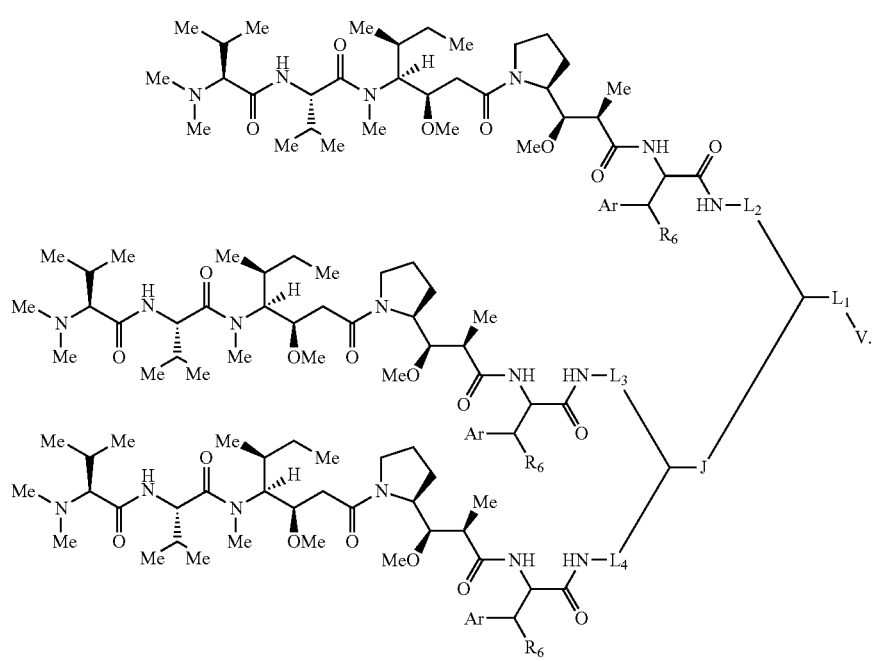

(VI)

wherein:

Z has the structure of:

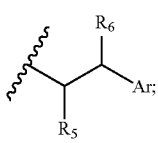

$R_5$ is H, $COR_8$, $C_1$-$C_6$alkyl, or thiazole;

$R_8$ is OH;

$R_6$ is OH or H;

Ar is phenyl or pyridine;

$R_7$ is $C_1$-$C_6$alkyl or hydrogen;

Y is $NH_2$—O—;

V is —O—$NH_2$ $L_1$, $L_2$, $L_3$, and $L_4$ are each linkers independently selected from the group consisting of a bond, -alkylene-, -(alkylene-O)$_n$-alkylene-J-, -alkylene'-J-(alkylene-O)$_n$-alkylene-, -J-(alkylene-O)$_n$-alkylene-, -(alkylene-O)$_n$-alkylene-J-(alkylene-O)$_n$'-alkylene-J'-, -(alkylene-O)$_n$-alkylene-J-alkylene'-, —W—, -alkylene-W—, alkylene'-J-(alkylene-NMe)$_n$-alkylene-W—, -J-(alkylene-NMe)$_n$-alkylene-W—, -J-alkylene-NMe-alkylene'-NMe-alkylene''-W—, and -alkylene-J-alkylene'-NMe-alkylene''-NMe-alkylene'''-W—;

W has the structure of:

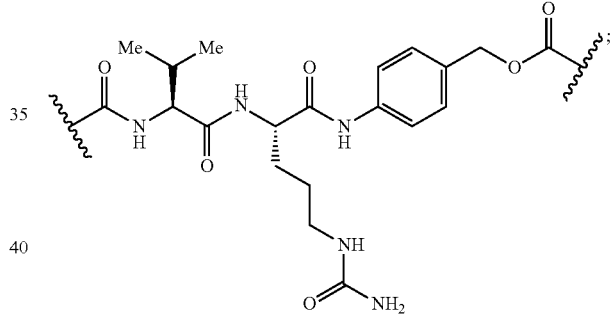

each J and J' independently have the structure of:

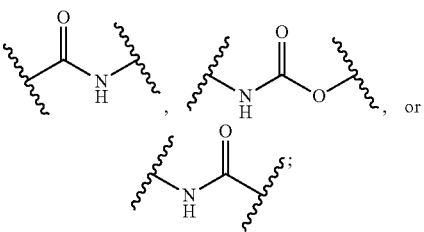

each n and n' are independently integers greater than or equal to one.

Such dolastatin linker derivatives may be in the form of a salt, or may be incorporated into a non-natural amino acid polypeptide, polymer, polysaccharide, or a polynucleotide and optionally post translationally modified.

In certain embodiments of compounds of Formula (III), (IV), (V) or (VI), $R_5$ is thiazole. In certain embodiments of compounds of Formula (III), (IV), (V) or (VI), $R_6$ is H. In certain embodiments of compounds of Formula (III), (IV), (V) or (VI), Ar is phenyl. In certain embodiments of compounds of Formula (III), (IV), (V) or (VI), $R_7$ is methyl. In certain embodiments of compounds of Formula (III), (IV), (V) or (VI), n and n' are integers from 0 to 20. In certain embodiments of compounds of Formula (III), (IV), (V) or (VI), n and n' are integers from 0 to 10. In certain embodiments of compounds of Formula (III), (IV), (V) or (VI), n and n' are integers from 0 to 5.

In certain embodiments of compounds of Formula (III) and (V), $R_5$ is thiazole or carboxylic acid. In certain embodiments of compounds of Formula (III) and (V), $R_5$ is hydrogen. In certain embodiments of compounds of Formula (III) and (V), $R_5$ is methyl, ethyl, propyl, iso-propyl, butyl, iso-butyl, sec-butyl, tert-butyl, pentyl, or hexyl. In certain embodiments of compounds of Formula (III) and (V), $R_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—. In certain embodiments of compounds to of Formula (III) and (V), $R_5$ is —NH-(alkylene-O)$_n$—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (III), (IV), (V) and (VI), $R_6$ is H. In some embodiments of compounds of Formula (III), (IV), (V) and (VI), $R_6$ is hydroxy.

In certain embodiments of compounds of Formula (III), (IV), (V) and (VI), Ar is phenyl.

In certain embodiments of compounds of Formula (III), (IV), (V) and (VI), $R_7$ is methyl, ethyl, propyl, iso-propyl, butyl, sec-butyl iso-butyl, tert-butyl, pentyl, or hexyl. In certain embodiments of compounds of Formula (III), (IV), (V) and (VI), $R_7$ is hydrogen.

In certain embodiments of compounds of Formula (III) and (V), Y is hydroxylamine, aldehyde, protected aldehyde, ketone, protected ketone, thioester, ester, dicarbonyl, hydrazine, amidine, imine, diamine, keto-amine, keto-alkyne, or ene-dione. In certain embodiments of compounds of Formula (IV) and (VI), V is a hydroxylamine, methyl, aldehyde, protected aldehyde, ketone, protected ketone, thioester, ester, dicarbonyl, hydrazine, amidine, imine, diamine, keto-amine, keto-alkyne, and ene-dione.

In certain embodiments of compounds of Formula (XIV), (XV), (XVI), (XVII), and (XVIII), each L, $L_1$, $L_2$, $L_3$, and $L_4$ is independently a cleavable linker or non-cleavable linker. In certain embodiments of compounds of Formula (XIV), (XV), (XVI), (XVII), and (XVIII), each L, $L_1$, $L_2$, $L_3$, and $L_4$ is independently a oligo(ethylene glycol) derivatized linker.

In certain embodiments of compounds of Formula (III), (IV), (V) and (VI), each alkylene, alkylene', alkylene", and alkylene'" independently is —CH—, —CH$_2$CH$_2$—, —CH$_2$CH$_2$CH—, —CH$_2$CH$_2$CH$_2$CH$_2$, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—. In certain embodiments of compounds of Formula (III), (IV), (V) and (VI), alkylene is methylene, ethylene, propylene, butylenes, pentylene, hexylene, or heptylene.

In certain embodiments of compounds of Formula (III), (IV), (V) and (VI), each n and n' independently is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments, dolastatin linker derivatives include compounds having the structure of Formula (VII):

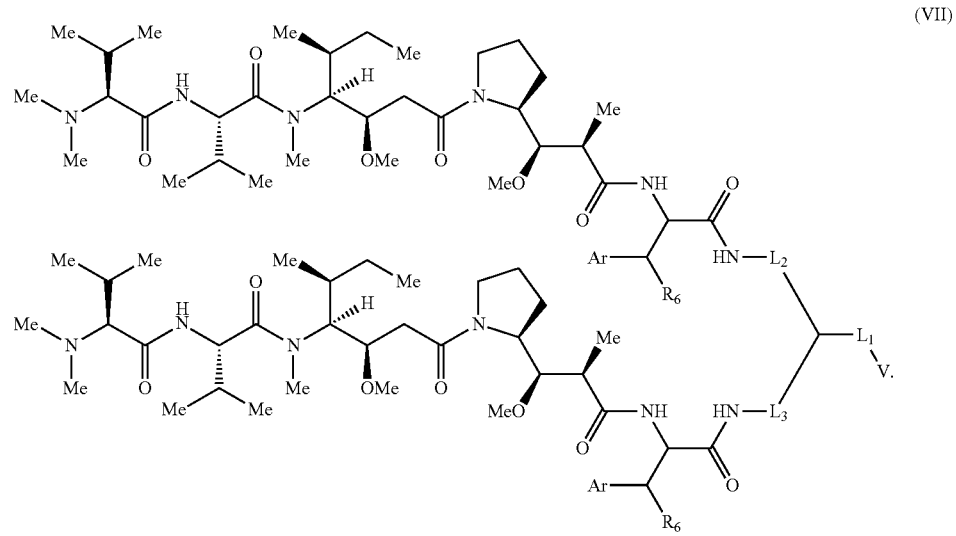

(VII)

In certain embodiments of compounds of Formula (VII), L₁ is -(alkylene-O)$_n$-alkylene-J-, L₂ is -alkylene'-J'-(alkylene-O)$_{n'}$-alkylene-, L₃ is -J"-(alkylene-O)$_{n''}$-alkylene-, alkylene is —CH₂CH₂—, alkylene' is —(CH₂)₄—, n is 1, n' and n" are 3, J has the structure of

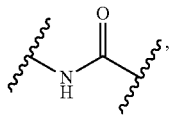

J' and J" have the structure of

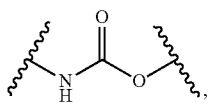 [SMILES: *NC(=O)O*]

and R₇ is methyl. In certain embodiments of compounds of Formula (VII), L₁ is -J-(alkylene-O)$_n$-alkylene-, L₂ is -(alkylene-O)$_{n'}$-alkylene-J'-alkylene'-, L₃ is -(alkylene-O)$_{n''}$-alkylene-J"-, alkylene is —CH₂CH₂—, alkylene' is —(CH₂)₄—, n is 1, n' and n" are 4, and J, J' and J" have the structure of

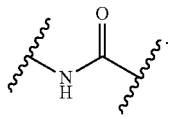

Such dolastatin linker derivatives may be in the form of a salt, or may be incorporated into a non-natural amino acid polypeptide, polymer, polysaccharide, or a polynucleotide and optionally post translationally modified.

In certain embodiments, compounds of Formula (I)-(VII) are stable in aqueous solution for at least 1 month under mildly acidic conditions. In certain embodiments, compounds of Formula (I)-(VII) are stable for at least 2 weeks under mildly acidic conditions. In certain embodiments, compound of Formula (I)-(VII) are stable for at least 5 days under mildly acidic conditions. In certain embodiments, such acidic conditions are pH 2 to 8.

The methods and compositions provided and described herein include polypeptides comprising dolastatin linker derivative containing at least one carbonyl or dicarbonyl group, oxime group, hydroxylamine group, or protected or masked forms thereof. Introduction of at least one reactive group into a dolastatin linker derivative can allow for the application of conjugation chemistries that involve specific chemical reactions, including, but not limited to, with one or more dolastatin linker derivative(s) while not reacting with the commonly occurring amino acids. Once incorporated, the dolastatin linker derivative side chains can also be modified by utilizing chemistry methodologies described herein or suitable for the particular functional groups or substituents present in the dolastatin linker derivative.

The dolastatin linker derivative methods and compositions described herein provide conjugates of substances having a wide variety of functional groups, substituents or moieties, with other substances including but not limited to a polymer; a water-soluble polymer; a derivative of polyethylene glycol; a second protein or polypeptide or polypeptide analog; an antibody or antibody fragment; and any combination thereof.

In certain embodiments, the dolastatin linker derivatives, linkers and reagents described herein, including compounds of Formulas (I)-(VII) are stable in aqueous solution under mildly acidic conditions (including but not limited to pH 2 to 8). In other embodiments, such compounds are stable for at least one month under mildly acidic conditions. In other embodiments, such compounds are stable for at least 2 weeks under mildly acidic conditions. In other embodiments, such compounds are stable for at least 5 days under mildly acidic conditions.

In another aspect of the compositions, methods, techniques and strategies described herein are methods for studying or using any of the aforementioned "modified or unmodified" non-natural amino acid dolastatin linker derivatives. Included within this aspect, by way of example only, are therapeutic, diagnostic, assay-based, industrial, cosmetic, plant biology, environmental, energy-production, consumer-products, and/or military uses which would benefit from a dolastatin linker derivative comprising a "modified or unmodified" non-natural amino acid polypeptide or protein.

Non-limiting examples of dolastatin linker derivatives include:

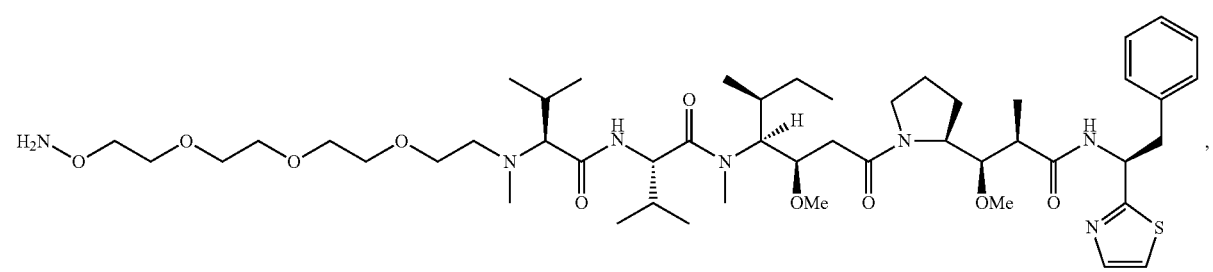

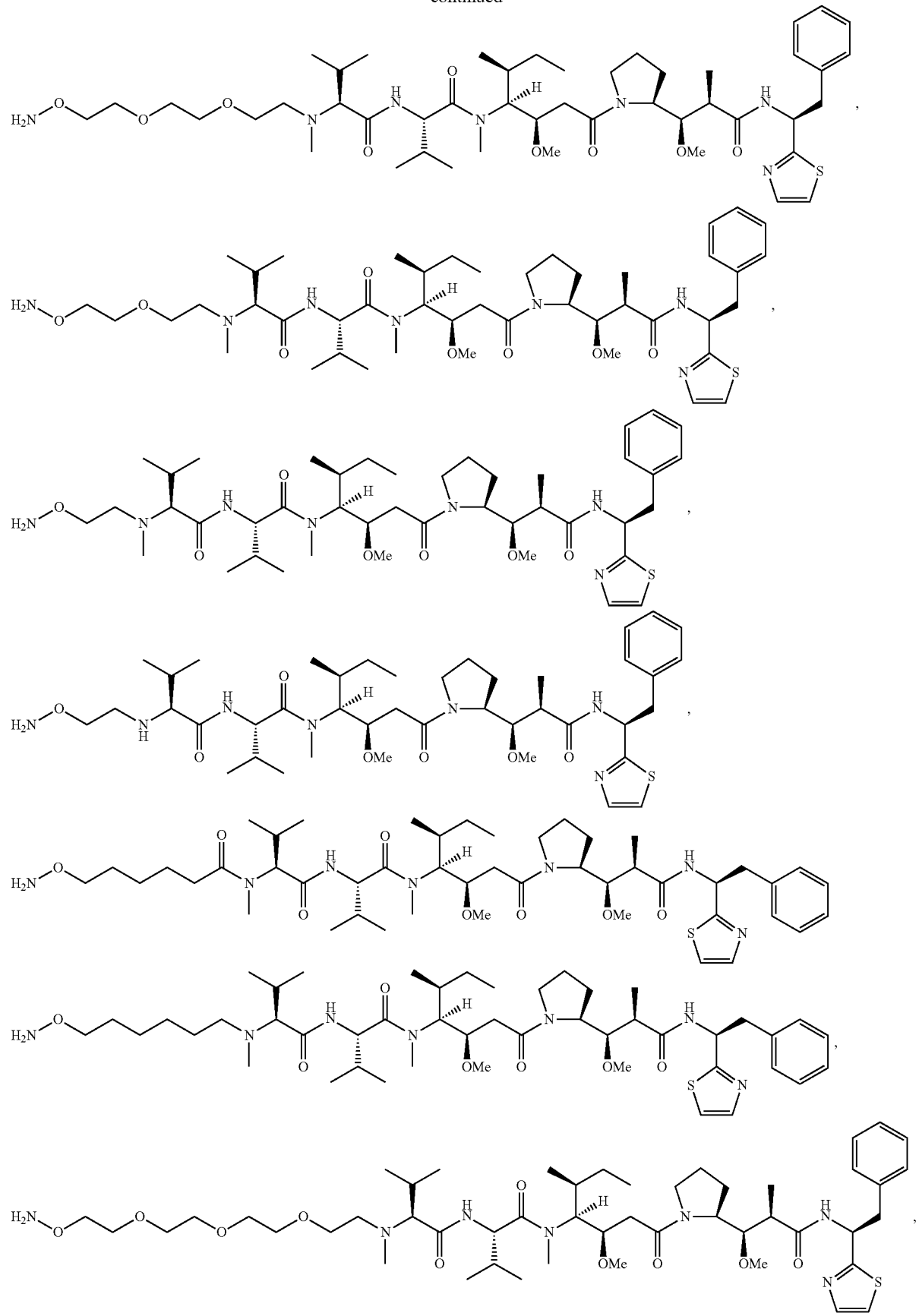

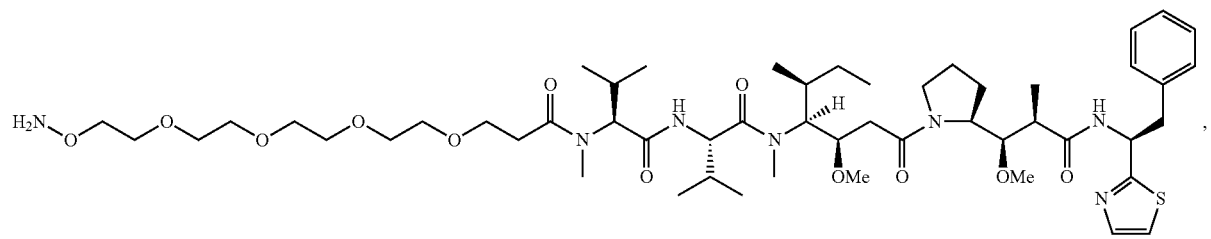,
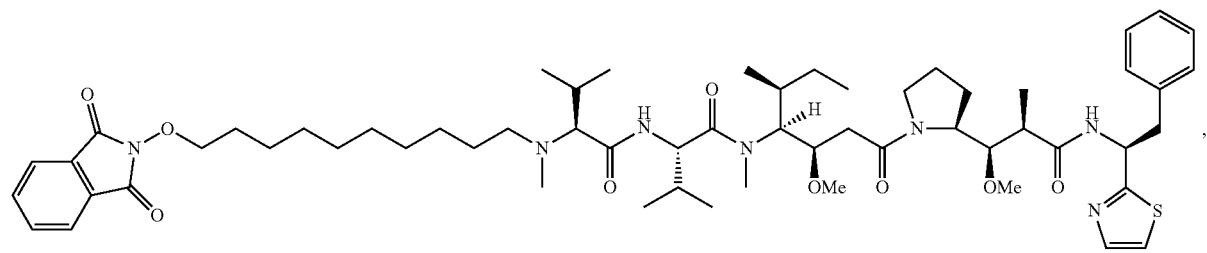,
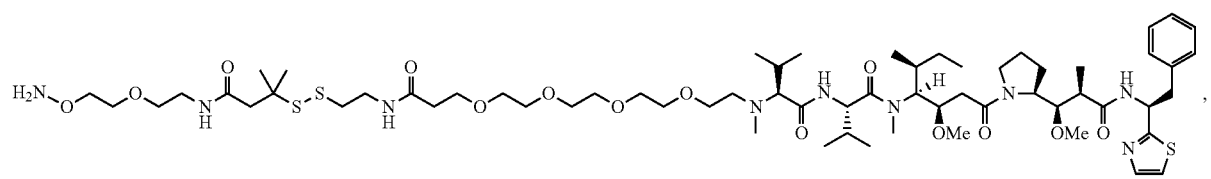,
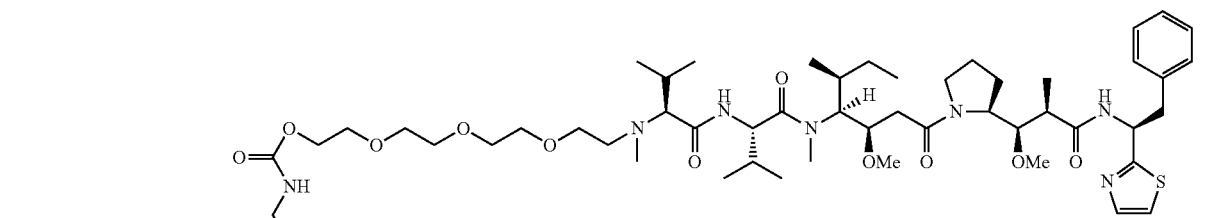,
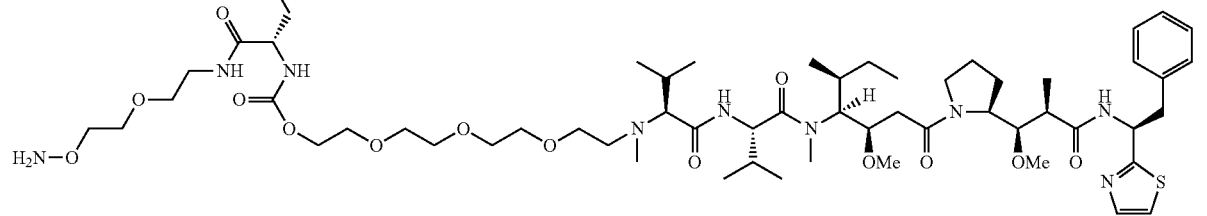,

-continued
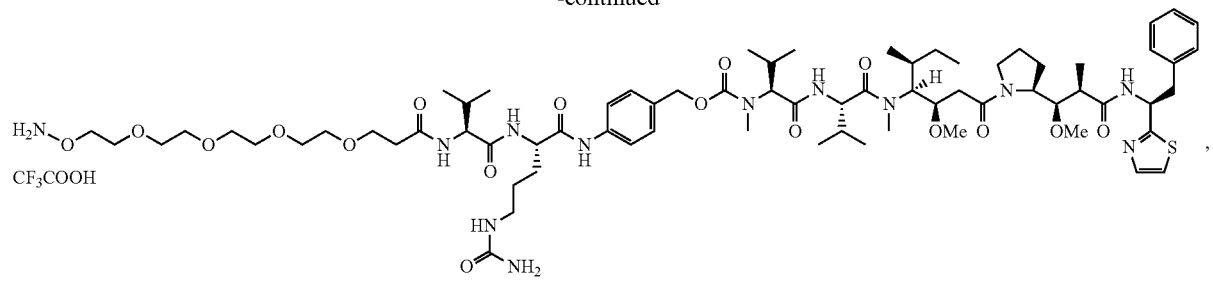
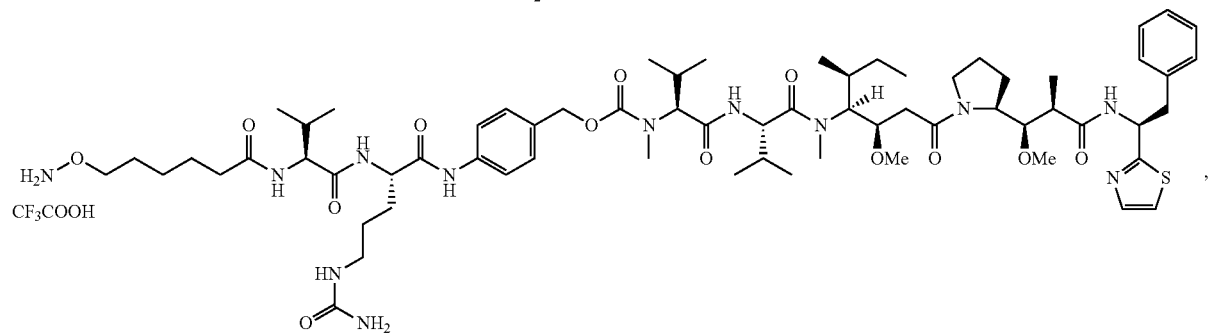
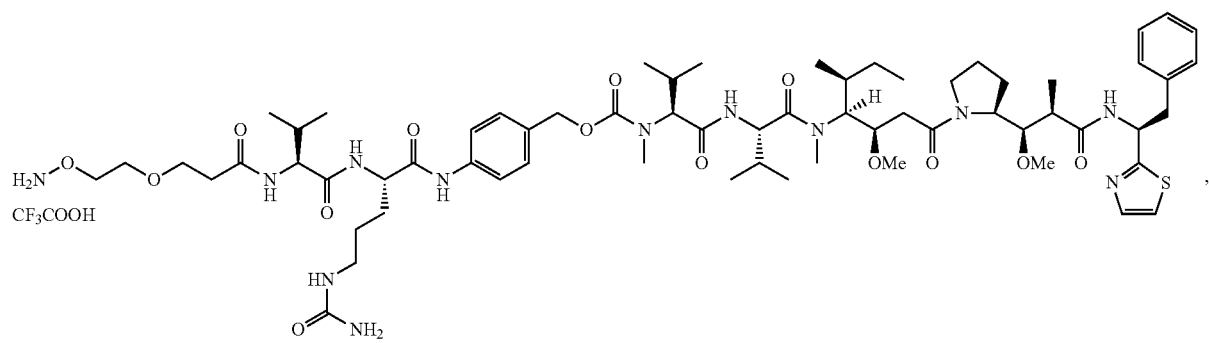
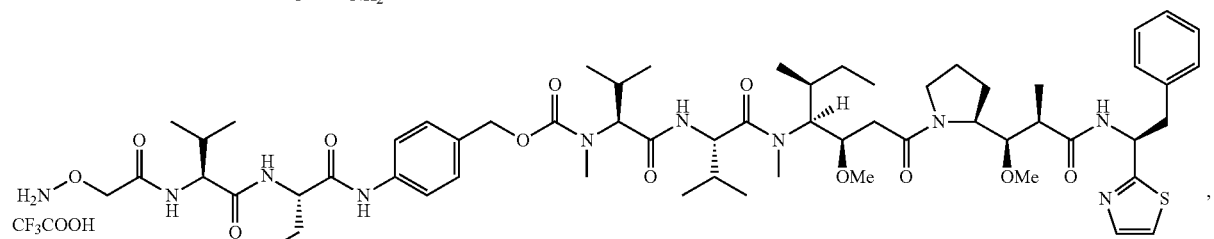
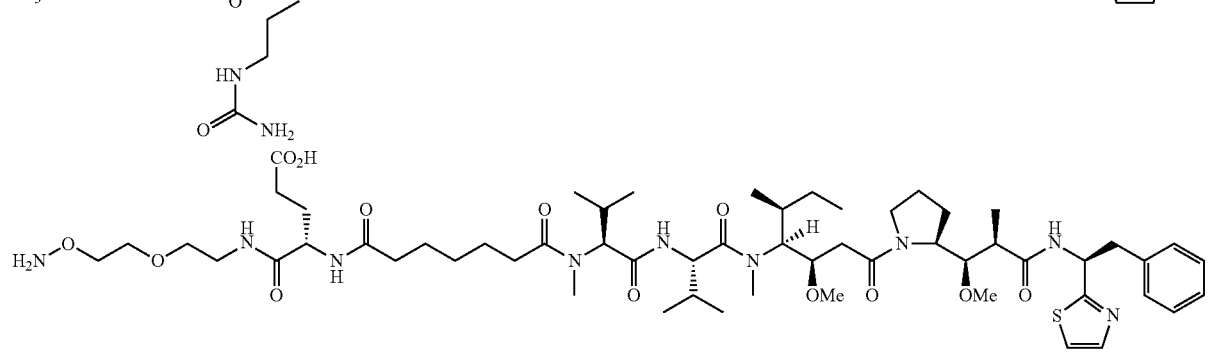
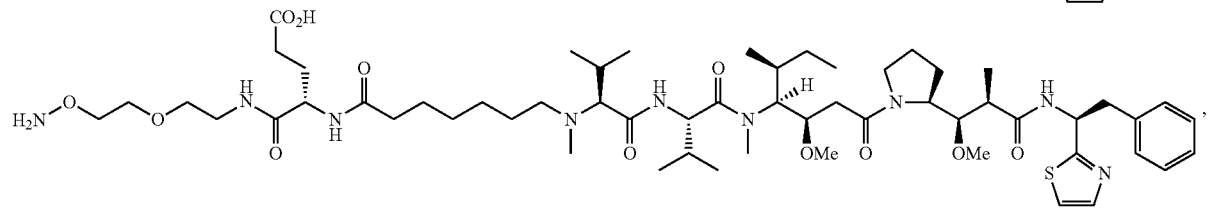

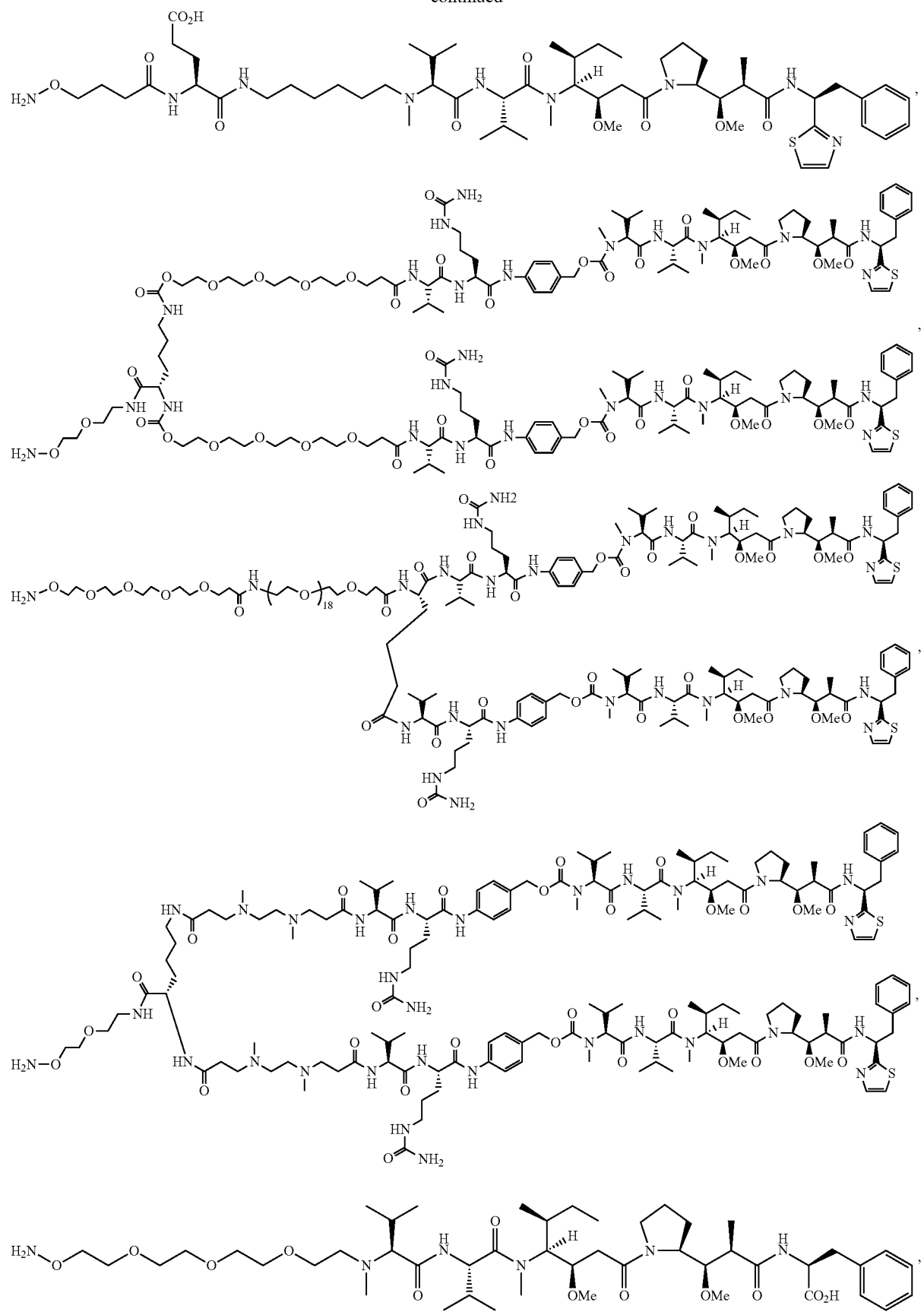

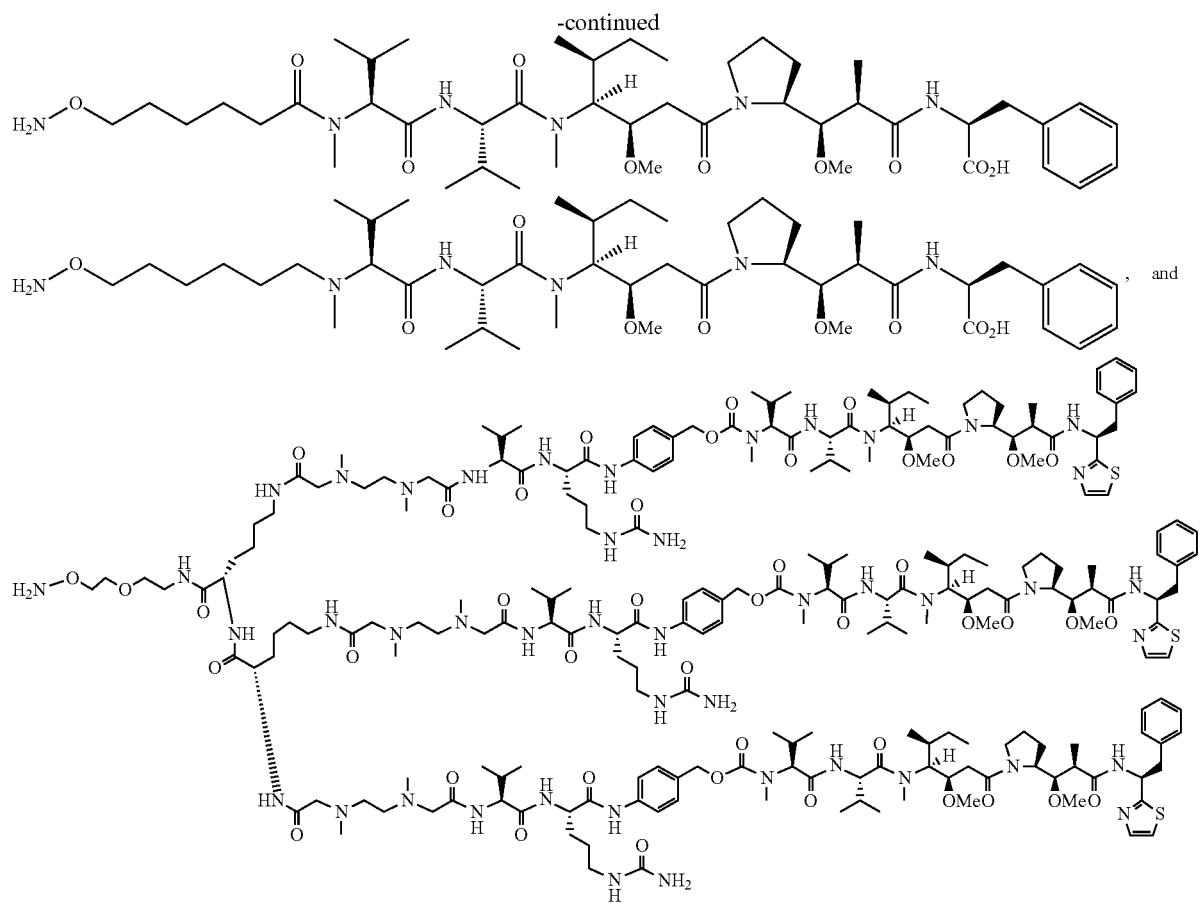

In another aspect of the present invention, the drug conjugated to the anti-CD70 antibody is dexamethasone. In another aspect of the present invention, the drug conjugated to the anti-CD70 antibody is dasantinib. In another aspect of the present invention, the drug conjugated to the anti-CD70 antibody is FK506. In another aspect of the present invention, the drug conjugated to the anti-CD70 antibody is a derivative of dexamethasone. In another aspect of the present invention, the drug conjugated to the anti-CD70 antibody is a derivative of dasantinib. In another aspect of the present invention, the drug conjugated to the anti-CD70 antibody is a derivative of FK506.

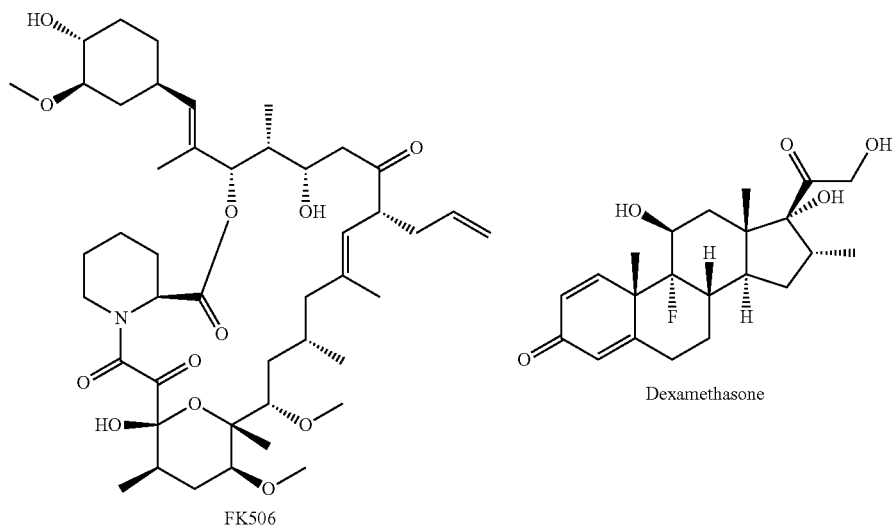

-continued
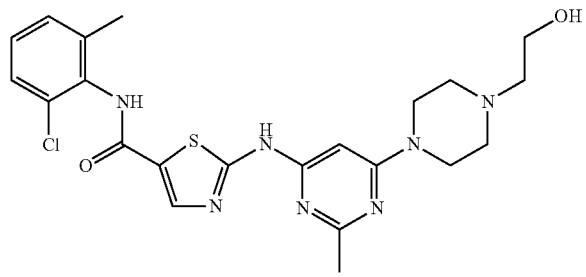
Dasatinib
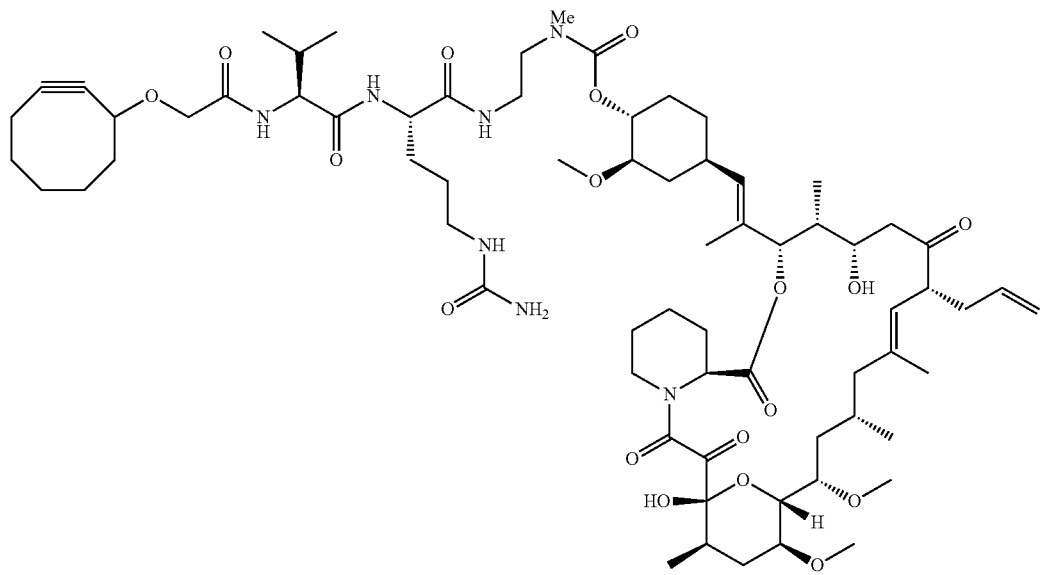
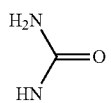
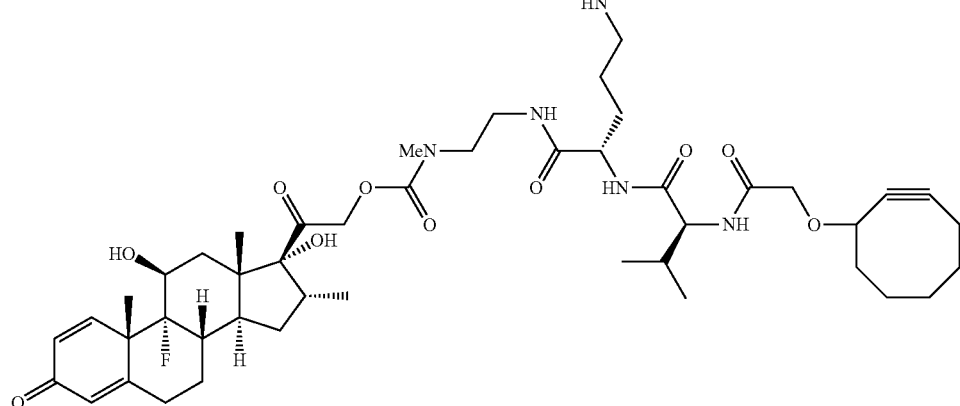
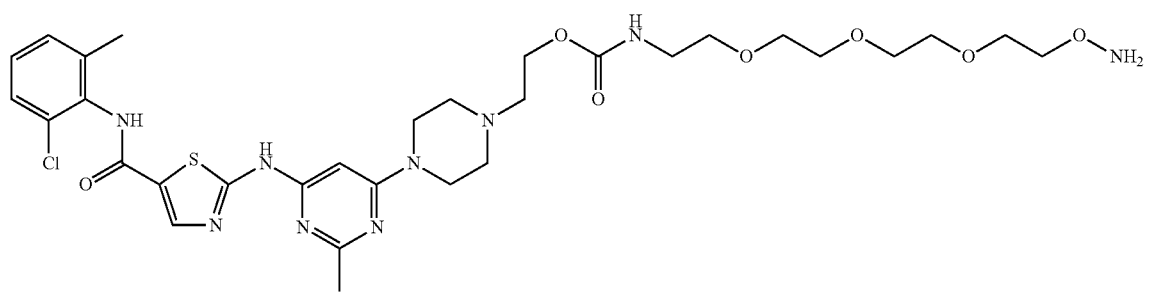

In other aspects of the present invention, the linker-drug portion of the anti-CD70 antibody drug conjugate is chosen from one of the following non-limiting examples:

aspartic acid, cysteine, glutamine, glutamic acid, glycine, histidine, isoleucine, leucine, lysine, methionine, phenylalanine, proline, serine, threonine, tryptophan, tyrosine, and

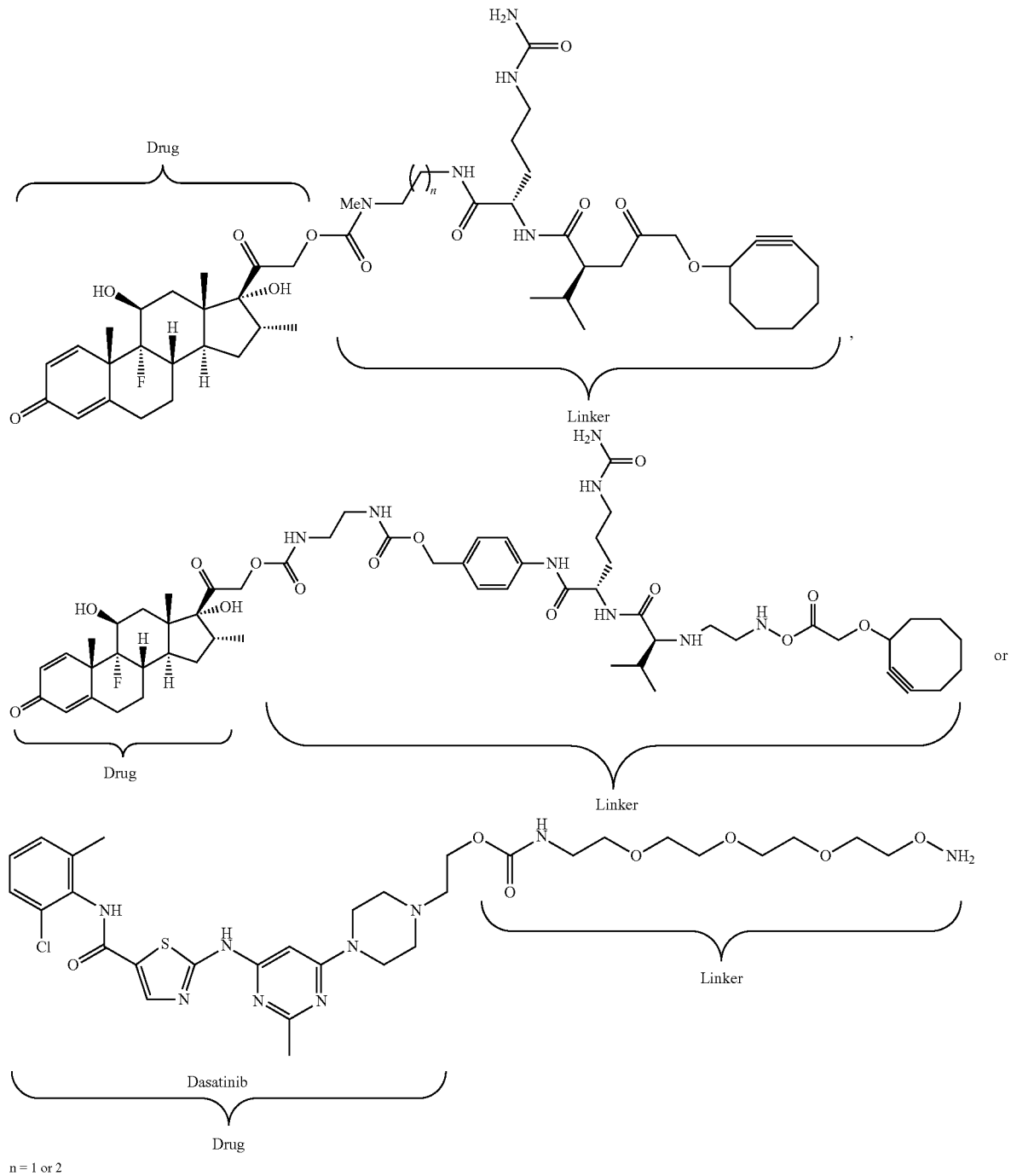

n = 1 or 2

IV. Non-Natural Amino Acid Derivatives

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

Non-natural amino acids that may be used in the methods and compositions described herein include, but are not limited to, amino acids comprising a amino acids with novel functional groups, amino acids that covalently or noncovalently interact with other molecules, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into polypeptides via incorporation of non-natural amino acids into such polypeptides offer a variety of advantages and manipulations of polypeptides. For example, the unique reactivity of a carbonyl or dicarbonyl functional group (including a keto- or aldehyde-functional group) allows selective modification of proteins with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photo-crosslinking of polypeptides. Examples of photoreactive non-natural amino acids include, but are not limited to, p-azido-phenylalanine and p-benzoyl-phenylalanine. The polypeptide with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

A. Structure and Synthesis of Non-Natural Amino Acid Derivatives: Carbonyl, Carbonyl like, Masked Carbonyl, and Protected Carbonyl Groups Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids having the structure of Formula (XXXVII):

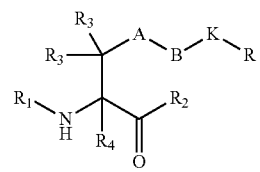

(XXXVII)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N (R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

K is

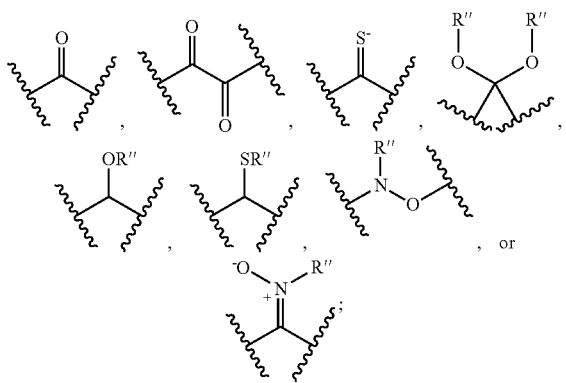

R is H, alkyl, substituted alkyl, cycloalkyl, or substituted cycloalkyl;

each R" is independently H, alkyl, substituted alkyl, or a protecting group, or when more than one R" group is present, two R" optionally form a heterocycloalkyl;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B—K—R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the —K—R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —(CH$_2$)$_4$— and each $R_3$ is H, B is not —NHC(O)(CH$_2$CH$_2$)—; and that when A and B are absent and each $R_3$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (XXXVII) are stable in aqueous solution for at least 1 month under mildly acidic conditions. In certain embodiments, compounds of Formula (XXXVII) are stable for at least 2 weeks under mildly acidic conditions. In certain embodiments, compound of Formula (XXXVII) are stable for at least 5 days under mildly acidic conditions. In certain embodiments, such acidic conditions are pH 2 to 8.

In certain embodiments of compounds of Formula (XXXVII), B is lower alkylene, substituted lower alkylene, —O-(alkylene or substituted alkylene)-, —C(R')=N—N (R')—, —N(R')CO—, —C(O)—, —C(R')=N—, —C(O)-(alkylene or substituted alkylene)-, —CON(R')-(alkylene or substituted alkylene)-, —S(alkylene or substituted alkylene)-, —S(O)(alkylene or substituted alkylene)-, or —S(O)$_2$(alkylene or substituted alkylene)-. In certain embodiments of compounds of Formula (XXXVII), B is —O(CH$_2$)—, —CH=N—, —CH=N—NH—, —NHCH$_2$—, —NHCO—, —C(O)—, —C(O)—(CH$_2$)—, —CONH—(CH$_2$)—, —SCH$_2$—, —S(=O)CH$_2$—, or —S(O)$_2$CH$_2$—. In certain embodiments of compounds of Formula (XXXVII), R is C$_{1-6}$ alkyl or cycloalkyl. In certain embodiments of compounds of Formula (XXXVII) R is —CH$_3$, —CH(CH$_3$)$_2$, or cyclopropyl. In certain embodiments of compounds of Formula (XXXVII), $R_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (XXXVII), $R_1$ is a resin, amino acid, polypeptide, antibody, or polynucleotide. In certain embodiments of compounds of Formula (XXXVII), $R_2$ is OH, O-methyl, O-ethyl, or O-t-butyl. In certain embodiments of compounds of Formula (XXXVII), $R_2$ is a resin, amino acid, polypeptide, antibody, or polynucleotide. In certain embodiments of compounds of Formula (XXXVII), $R_2$ is a polynucleotide. In certain embodiments of compounds of Formula (XXXVII), $R_2$ is ribonucleic acid (RNA).

In certain embodiments of compounds of Formula (XXXVII),

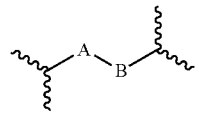

is selected from the group consisting of:
(i) A is substituted lower alkylene, C$_4$-arylene, substituted arylene, heteroarylene, substituted heteroarylene, alkarylene, substituted alkarylene, aralkylene, or substituted aralkylene;

B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N (R')—, —N(R')S(O)N(R')—, —N(R')S(O)$_2$N(R')—, —N(R')—N=, —C(R')=N—N(R')—, —C(R') =N—N=, —C(R')$_2$—N=N—, and —C(R')$_2$—N (R')—N(R')—;

(ii) A is optional, and when present is substituted lower alkylene, C$_4$-arylene, substituted arylene, heteroarylene, substituted heteroarylene, alkarylene, substituted alkarylene, aralkylene, or substituted aralkylene;

B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N=, —C(R')=N—N(R')—, —C(R')=N—N=, —C(R')$_2$—N=N—, and —C(R')$_2$—N(R')—N(R')—;

(iii) A is lower alkylene;
B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CSN(R')—, —CON(R')-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N=, —C(R')=N—N(R')—, —C(R')=N—N=, —C(R')$_2$—N=N—, and —C(R')$_2$—N(R')—N(R')—; and (iv) A is phenylene;
B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)$_2$—, —NS(O)$_2$—, —OS(O)$_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)$_2$N(R'), —N(R')C(O)N(R')—, —N(R')C(S)N(R')—, —N(R')S(O)N(R')—, —N(R')S(O)$_2$N(R')—, —N(R')—N=, —C(R')=N—N(R')—, —C(R')=N—N=, —C(R')$_2$—N=N—, and —C(R')$_2$—N(R')—N(R')—;

K is

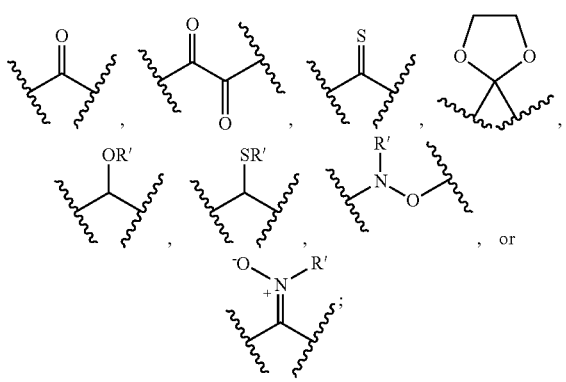

each R' is independently H, alkyl, or substituted alkyl;
R$_1$ is optional, and when present, is H, an amino protecting group, resin, amino acid, polypeptide, or polynucleotide; and
R$_2$ is optional, and when present, is OH, an ester protecting group, resin, amino acid, polypeptide, or polynucleotide; and each R$_3$ and R$_4$ is independently H, halogen, lower alkyl, or substituted lower alkyl;
R is H, alkyl, substituted alkyl, cycloalkyl, or substituted cycloalkyl;

In addition, amino acids having the structure of Formula (XXXVIII) are included:

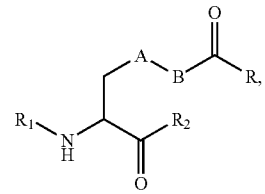

(XXXVIII)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;
R$_1$ is H, an amino protecting group, resin, at least one amino acid, polypeptide, or polynucleotide; and
R$_2$ is OH, an ester protecting group, resin, at least one amino acid, polypeptide, or polynucleotide;

with a proviso that when A is phenylene, B is present; and that when A is —(CH$_2$)$_4$—, B is not —NHC(O)(CH$_2$CH$_2$)—; and that when A and B are absent, R is not methyl. Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXIX) are included:

(XXXIX)

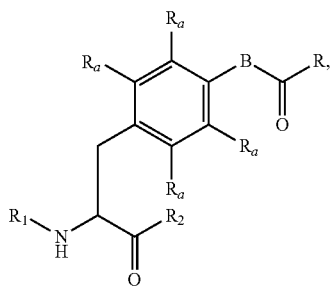

wherein:
B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;
R is H, alkyl, substituted alkyl, cycloalkyl, or substituted cycloalkyl;
R$_1$ is H, an amino protecting group, resin, amino acid, polypeptide, or polynucleotide; and
R$_2$ is OH, an ester protecting group, resin, amino acid, polypeptide, or polynucleotide;
each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl. Such non-natural amino acids may be in the form of a salt, or may be incorporated into a non-natural amino acid polypeptide, polymer, polysaccharide, or a polynucleotide and optionally post translationally modified.
In addition, the following amino acids are included:

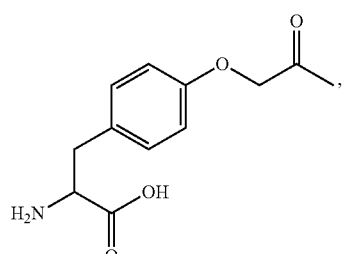

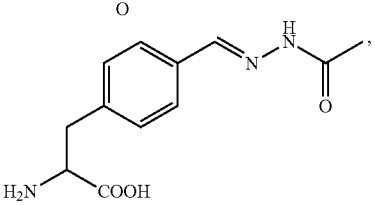

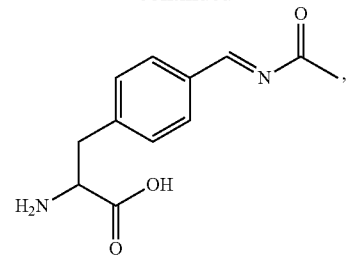

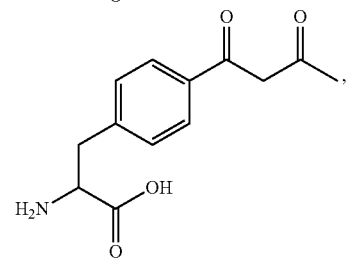

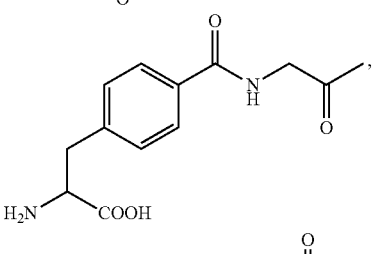

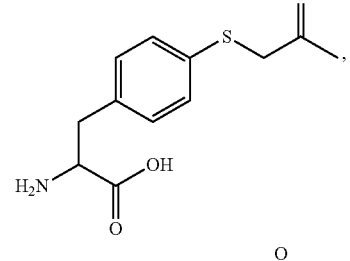

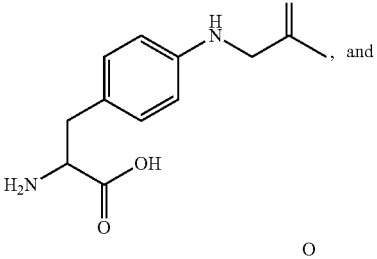

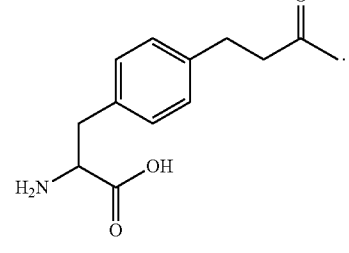

Such non-natural amino acids may be are optionally amino protected group, carboxyl protected and/or in the form of a salt, or may be incorporated into a non-natural amino acid polypeptide, polymer, polysaccharide, or a polynucleotide and optionally post translationally modified.
In addition, the following amino acids having the structure of Formula (XXXX) are included:

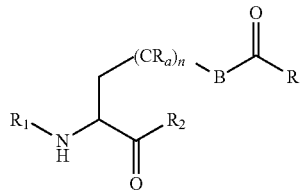

(XXXX)

wherein

—NS(O)$_2$—, —OS(O)$_2$—, optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, an amino protecting group, resin, amino acid, polypeptide, or polynucleotide; and R$_2$ is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8;

with a proviso that when A is —(CH$_2$)$_4$—, B is not —NHC(O)(CH$_2$CH$_2$)—. Such non-natural amino acids may be in the form of a salt, or may be incorporated into a non-natural amino acid polypeptide, polymer, polysaccharide, or a polynucleotide and optionally post translationally modified.

In addition, the following amino acids are included:

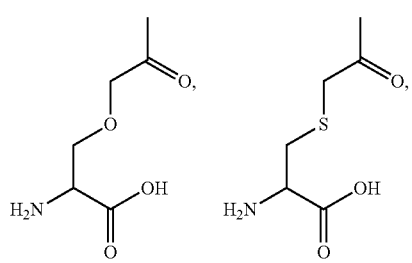

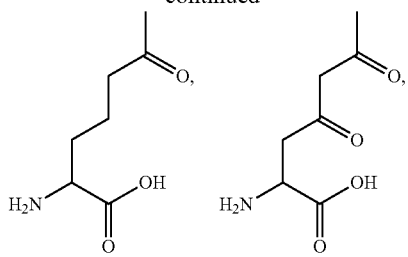

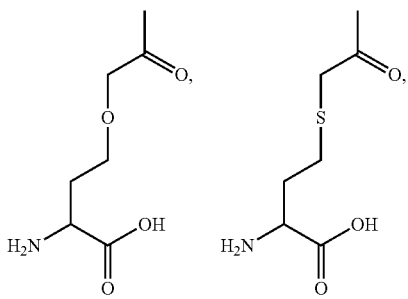

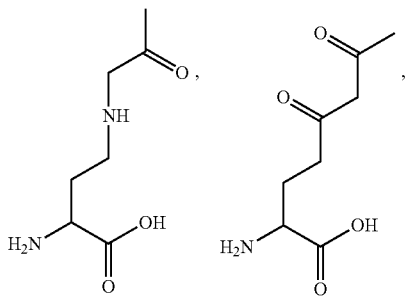

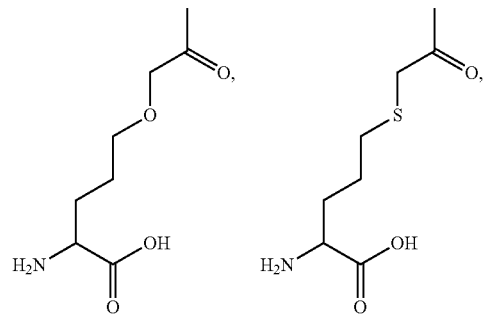

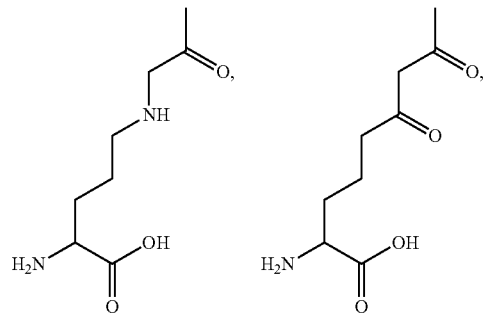

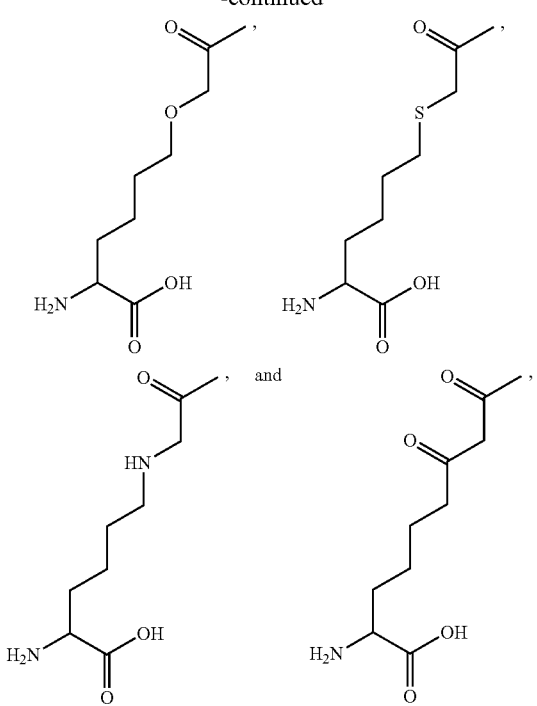

wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (XXXXI) are included:

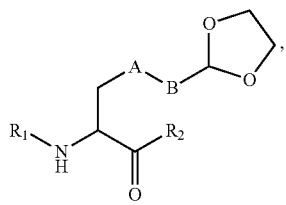

(XXXXI)

wherein,
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
R$_1$ is H, an amino protecting group, resin, amino acid, polypeptide, or polynucleotide; and
R$_2$ is OH, an ester protecting group, resin, amino acid, polypeptide, or polynucleotide.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXII) are included:

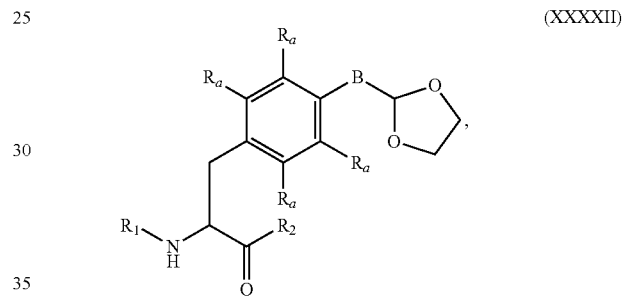

(XXXXII)

wherein,
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
R is H, alkyl, substituted alkyl, cycloalkyl, or substituted cycloalkyl;
R$_1$ is H, an amino protecting group, resin, amino acid, polypeptide, or polynucleotide; and
R$_2$ is OH, an ester protecting group, resin, amino acid, polypeptide, or polynucleotide; wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

Such non-natural amino acids may be in the form of a salt, or may be incorporated into a non-natural amino acid polypeptide, polymer, polysaccharide, or a polynucleotide and optionally post translationally modified.

In addition, the following amino acids are included:

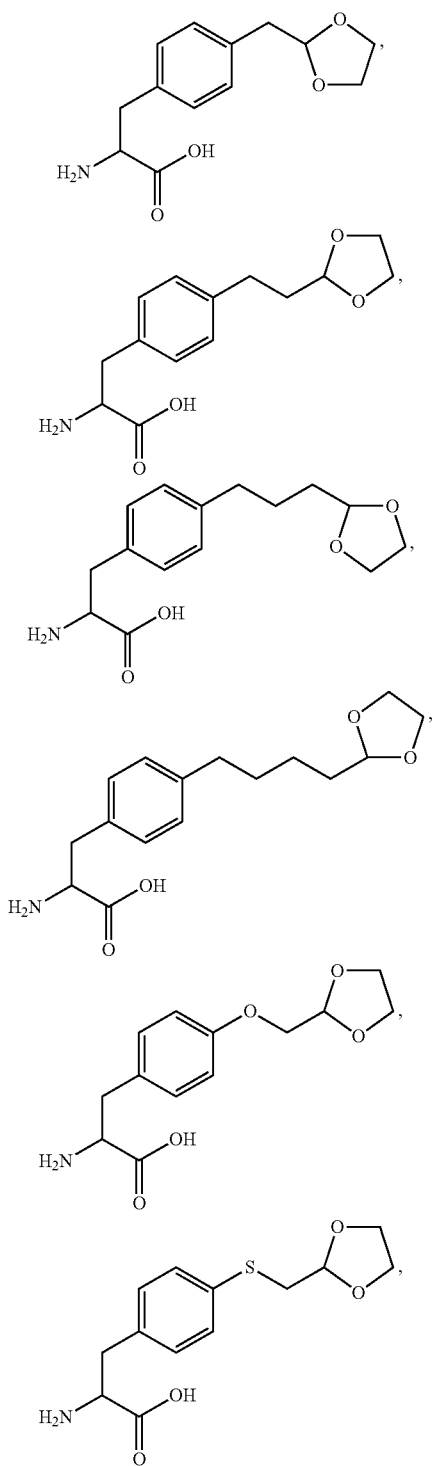

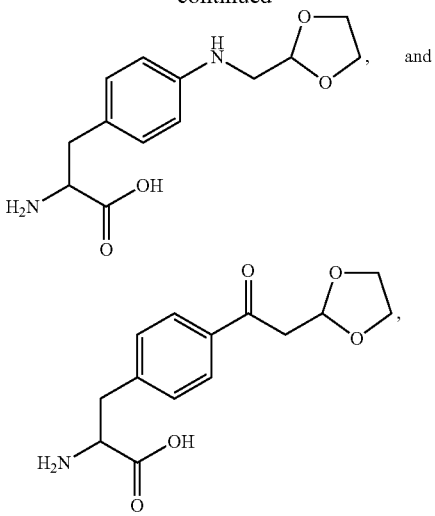

wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (XXXXIV) are included:

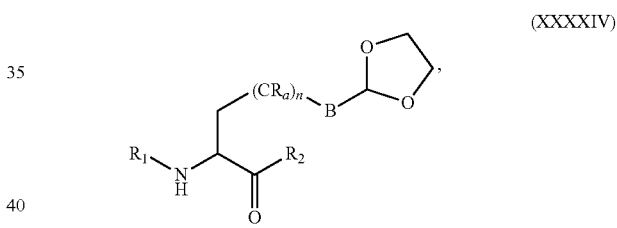

(XXXXIV)

wherein,

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, an amino protecting group, resin, amino acid, polypeptide, or polynucleotide; and R$_2$ is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

Such non-natural amino acids may be in the form of a salt, or may be incorporated into a non-natural amino acid polypeptide, polymer, polysaccharide, or a polynucleotide and optionally post translationally modified.

In addition, the following amino acids are included:

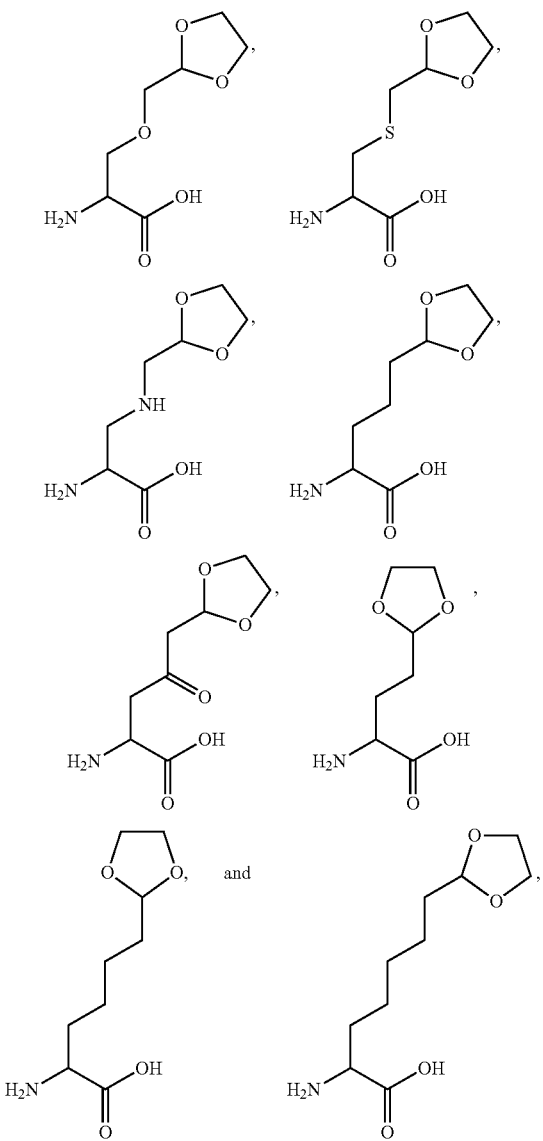

wherein such compounds are optionally amino protected, optionally carboxyl protected, optionally amino protected and carboxyl protected, or a salt thereof, or may be incorporated into a non-natural amino acid polypeptide, polymer, polysaccharide, or a polynucleotide and optionally post translationally modified.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XXXXV) are included:

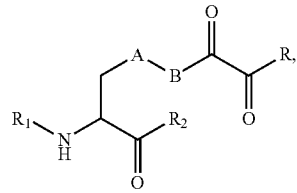

(XXXXV)

wherein,

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, an amino protecting group, resin, amino acid, polypeptide, or polynucleotide; and R$_2$ is OH, an ester protecting group, resin, amino acid, polypeptide, or polynucleotide.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXVI) are included:

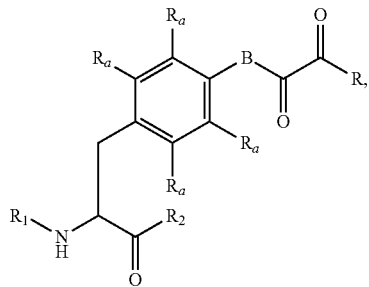

(XXXXVI)

wherein,

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, an amino protecting group, resin, amino acid, polypeptide, or polynucleotide; and R$_2$ is OH, an ester protecting group, resin, amino acid, polypeptide, or polynucleotide; wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

Such non-natural amino acids may be in the form of a salt, or may be incorporated into a non-natural amino acid polypeptide, polymer, polysaccharide, or a polynucleotide and optionally post translationally modified.

In addition, the following amino acids are included:

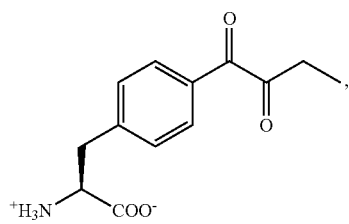

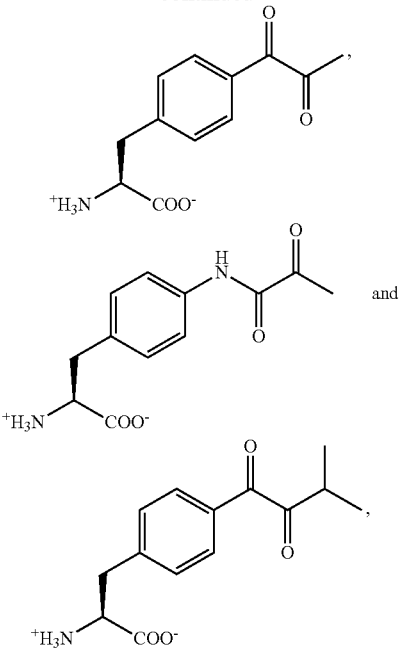

wherein such compounds are optionally amino protected and carboxyl protected, or a salt thereof. Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXVII) are included:

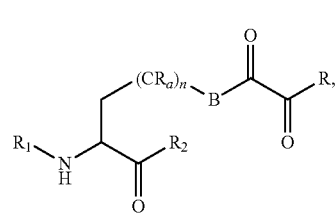

(XXXXVII)

wherein,

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is H, an amino protecting group, resin, amino acid, polypeptide, or polynucleotide; and $R_2$ is OH, an ester protecting group, resin, amino acid, polypeptide, or polynucleotide; each $R^a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

Such non-natural amino acids may be in the form of a salt, or may be incorporated into a non-natural amino acid polypeptide, polymer, polysaccharide, or a polynucleotide and optionally post translationally modified.

In addition, the following amino acids are included:

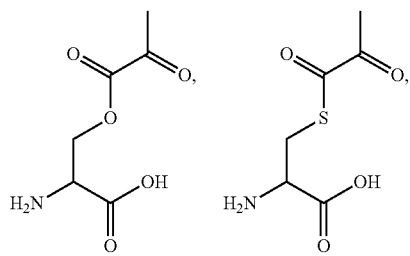

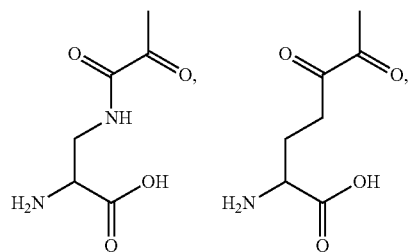

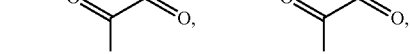

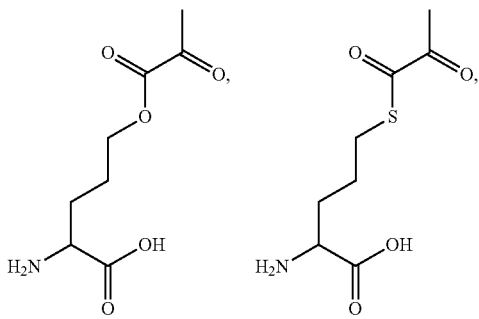

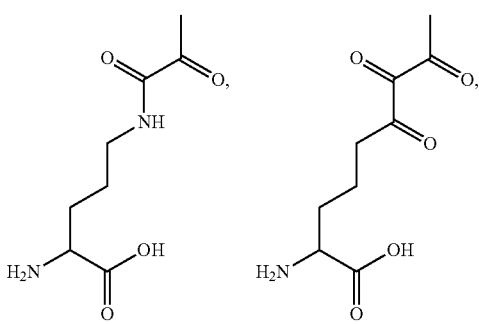

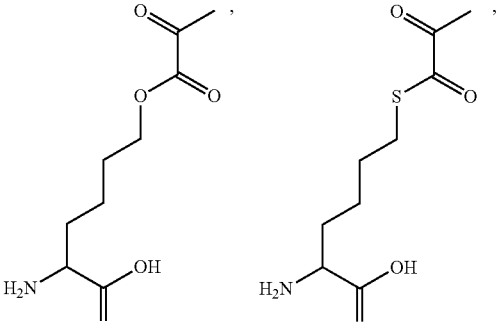

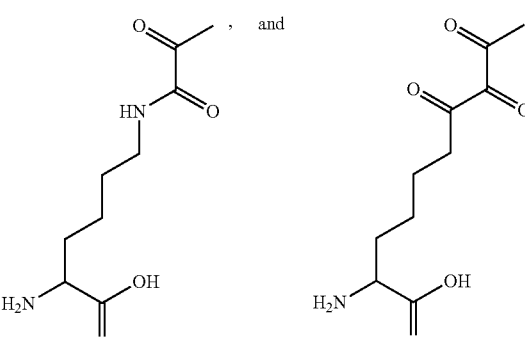

wherein such compounds are optionally amino protected and carboxyl protected, or a salt thereof, or may be incorporated into a non-natural amino acid polypeptide, polymer, polysaccharide, or a polynucleotide and optionally post translationally modified.

In addition, the following amino acids having the structure of Formula (XXXXVIII) are included:

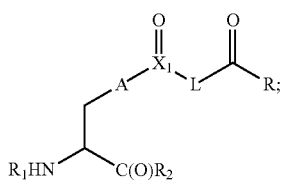

(XXXXVIII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXIX) are included:

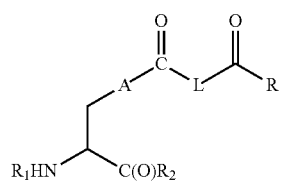

(XXXXIX)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
L is alkylene, substituted alkylene, N(R')alkylene) or N(R') (substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXX) are included:

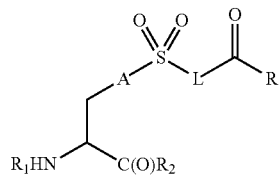

(XXXXX)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
L is alkylene, substituted alkylene, N(R')(alkylene) or N(R') (substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXI) are included:

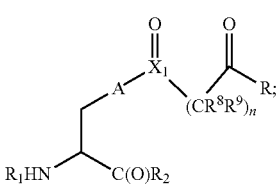

(XXXXXI)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is H, an amino protecting group, resin, amino acid, polypeptide, or polynucleotide; and
$R_2$ is OH, an ester protecting group, resin, amino acid, polypeptide, or polynucleotide;
$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any R⁸ and R⁹ can together form =O or a cycloalkyl, or any to adjacent R⁸ groups can together form a cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXII) are included:

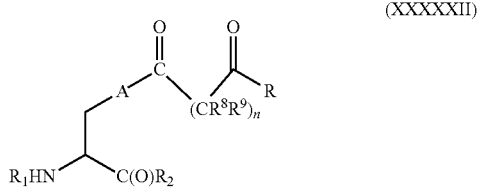

(XXXXXII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
R₁ is H, an amino protecting group, resin, amino acid, polypeptide, or polynucleotide; and
R₂ is OH, an ester protecting group, resin, amino acid, polypeptide, or polynucleotide; n is 0, 1, 2, 3, 4, or 5; and each R⁸ and R⁹ on each CR⁸R⁹ group is independently selected from the group consisting of H, alkoxy, alkylamine, halogen, alkyl, aryl, or any R⁸ and R⁹ can together form =O or a cycloalkyl, or any to adjacent R⁸ groups can together form a cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXIII) are included:

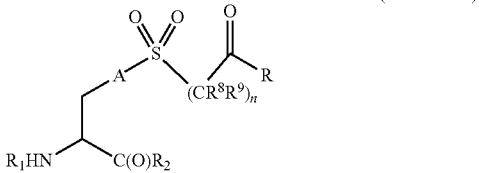

(XXXXXIII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;
R₁ is H, an amino protecting group, resin, amino acid, polypeptide, or polynucleotide; and
R₂ is OH, an ester protecting group, resin, amino acid, polypeptide, or polynucleotide; n is 0, 1, 2, 3, 4, or 5; and each R⁸ and R⁹ on each CR⁸R⁹ group is independently selected from the group consisting of H, alkoxy, alkylamine, halogen, alkyl, aryl, or any R⁸ and R⁹ can together form =O or a cycloalkyl, or any to adjacent R⁸ groups can together form a cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXIV) are included:

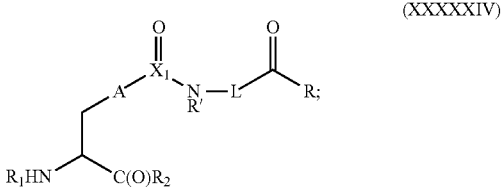

(XXXXXIV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
R₁ is H, an amino protecting group, resin, amino acid, polypeptide, or polynucleotide; and
R₂ is OH, an ester protecting group, resin, amino acid, polypeptide, or polynucleotide;
X₁ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXV) are included:

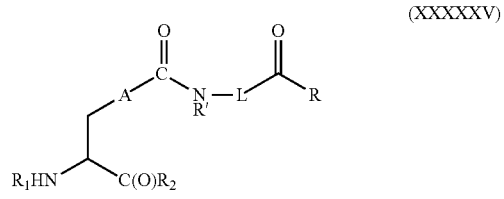

(XXXXXV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

R₁ is H, an amino protecting group, resin, amino acid, polypeptide, or polynucleotide; and R₂ is OH, an ester protecting group, resin, amino acid, polypeptide, or polynucleotide;

L is alkylene, substituted alkylene, N(R')(alkylene) or N(R') (substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, the following amino acids having the structure of Formula (XXXXXVI) are included:

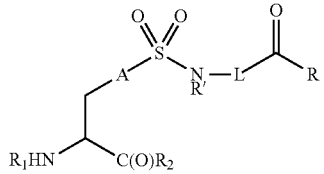

(XXXXXVI)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

R₁ is H, an amino protecting group, resin, amino acid, polypeptide, or polynucleotide; and R₂ is OH, an ester protecting group, resin, amino acid, polypeptide, or polynucleotide;

L is alkylene, substituted alkylene, N(R')(alkylene) or N(R') (substituted alkylene), where R' is H, alkyl, substituted alkyl, cycloalkyl, or substituted cycloalkyl.

Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXXVII) are included:

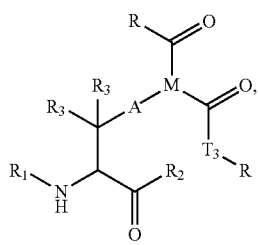

(XXXXXVII)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is —C(R₃)—,

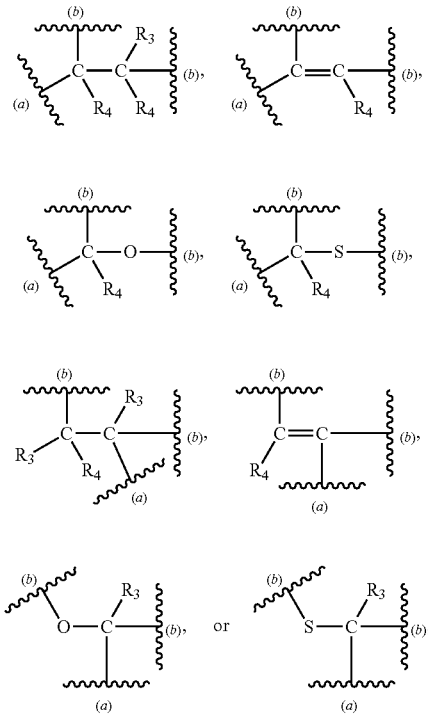

where (a) indicates bonding to the A group and (b) indicates bonding to respective carbonyl groups, R₃ and R₄ are independently chosen from H, halogen, alkyl, substituted alkyl, cycloalkyl, or substituted cycloalkyl, or R₃ and R₄ or two R₃ groups or two R₄ groups optionally form a cycloalkyl or a heterocycloalkyl;

R is H, halogen, alkyl, substituted alkyl, cycloalkyl, or substituted cycloalkyl;

T₃ is a bond, C(R)(R), O, or S, and R is H, halogen, alkyl, substituted alkyl, cycloalkyl, or substituted cycloalkyl;

R₁ is H, an amino protecting group, resin, amino acid, polypeptide, or polynucleotide; and R₂ is OH, an ester protecting group, resin, amino acid, polypeptide, or polynucleotide.

Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXXVIII) are included:

(XXXXXVIII)

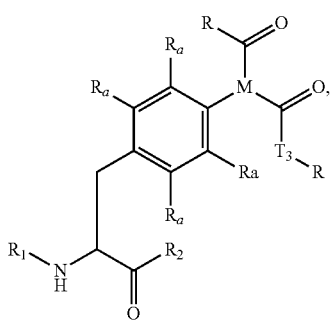

wherein:

M is —C(R$_3$)—,

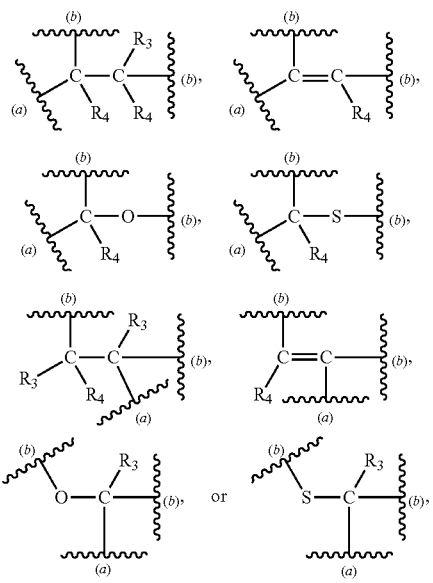

where (a) indicates bonding to the A group and (b) indicates bonding to respective carbonyl groups, R$_3$ and R$_4$ are independently chosen from H, halogen, alkyl, substituted alkyl, cycloalkyl, or substituted cycloalkyl, or R$_3$ and R$_4$ or two R$_3$ groups or two R$_4$ groups optionally form a cycloalkyl or a heterocycloalkyl;

R is H, halogen, alkyl, substituted alkyl, cycloalkyl, or substituted cycloalkyl;

T$_3$ is a bond, C(R)(R), O, or S, and R is H, halogen, alkyl, substituted alkyl, cycloalkyl, or substituted cycloalkyl;

R$_1$ is H, an amino protecting group, resin, amino acid, polypeptide, or polynucleotide; and R$_2$ is OH, an ester protecting group, resin, amino acid, polypeptide, or polynucleotide; each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXXIX) are included:

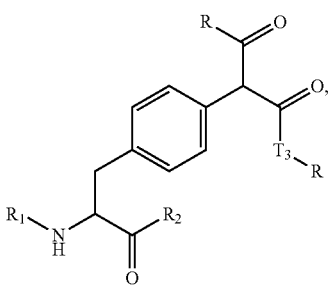

wherein:

R is H, halogen, alkyl, substituted alkyl, cycloalkyl, or substituted cycloalkyl; and T$_3$ is O, or S.

Such non-natural amino acids may be in the form of a salt, or may be incorporated into a non-natural amino acid polypeptide, polymer, polysaccharide, or a polynucleotide and optionally post translationally modified.

In addition, amino acids having the structure of Formula (XXXXXX) are included:

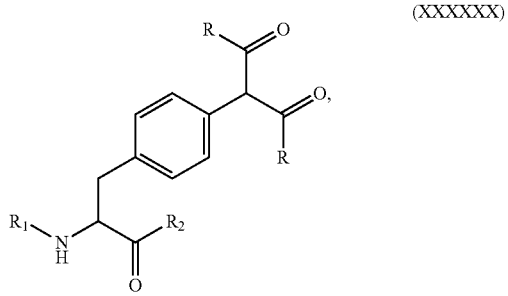

wherein:

R is H, halogen, alkyl, substituted alkyl, cycloalkyl, or substituted cycloalkyl.

In addition, the following amino acids having structures of Formula (XXXXXX) are included:

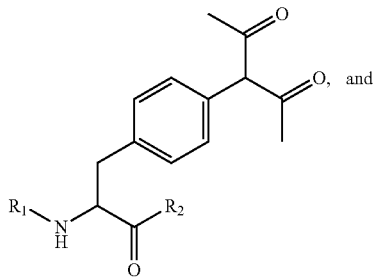

147

-continued

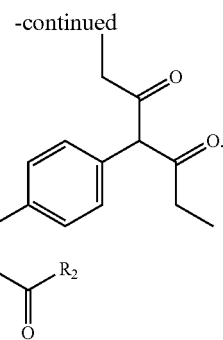

Such non-natural amino acids may be in the form of a salt, or may be incorporated into a non-natural amino acid polypeptide, polymer, polysaccharide, or a polynucleotide and optionally post translationally modified.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117(14):3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

The synthesis of p-acetyl-(+/−)-phenylalanine and m-acetyl-(+/−)-phenylalanine is described in Zhang, Z., et al., Biochemistry 42: 6735-6746 (2003), incorporated by reference. Other carbonyl- or dicarbonyl-containing amino acids can be similarly prepared.

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

Additionally, by way of example a non-natural amino acid bearing adjacent hydroxyl and amino groups can be incorporated into a polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

148

B. Structure and Synthesis of Non-Natural Amino Acids: Dicarbonyl, Dicarbonyl-Like, Masked Dicarbonyl, and Protected Dicarbonyl Groups Amino acids with an electrophilic reactive group allow for a variety of reactions to link molecules via nucleophilic addition reactions among others. Such electrophilic reactive groups include a dicarbonyl group (including a diketone group, a ketoaldehyde group, a ketoacid group, a ketoester group, and a ketothioester group), a dicarbonyl-like group (which has reactivity similar to a dicarbonyl group and is structurally similar to a dicarbonyl group), a masked dicarbonyl group (which can be readily converted into a dicarbonyl group), or a protected dicarbonyl group (which has reactivity similar to a dicarbonyl group upon deprotection). Such amino acids include amino acids having the structure of Formula (XXXVII):

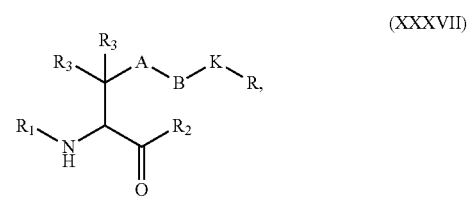

(XXXVII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
B is optional, and when present is a linker linked at one end to a diamine containing moiety, the linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, —C(O)R"—, —S(O)$_k$(alkylene or substituted alkylene)-, where k is 1, 2, or 3, —C(O)-(alkylene or substituted alkylene)-, —C(S)-(alkylene or substituted alkylene)-, —NR"-(alkylene or substituted alkylene)-, —CON(R")-(alkylene or substituted alkylene)-, —CSN(R")-(alkylene or substituted alkylene)-, and —N(R")CO-(alkylene or substituted alkylene)-, where each R" is independently H, alkyl, or substituted alkyl;
K is

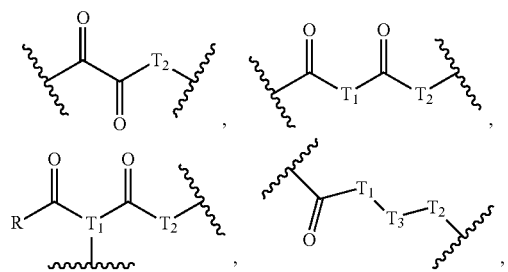

-continued

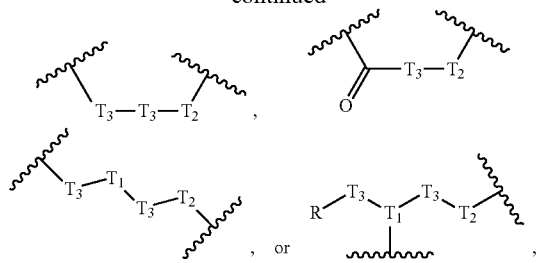

where,

T₁ is a bond, optionally substituted $C_1$-$C_4$ alkylene, optionally substituted $C_1$-$C_4$ alkenylene, or optionally substituted heteroalkyl;

wherein each optional substituents is independently selected from lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

T₂, is selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

T₃ is

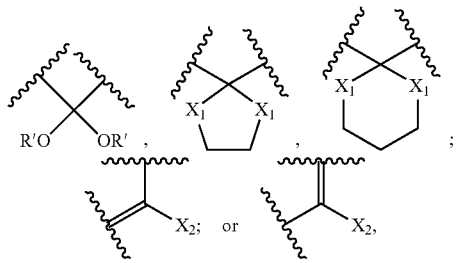

where each X₁ is independently selected from the group consisting of —O—, —S—, —N(H)—, —N(R)—, —N(Ac)—, and —N(OMe)-; X₂ is —OR, —OAc, —SR, —N(R)$_2$, —N(R)(Ac), —N(R)(OMe), or N₃, and where each R' is independently H, alkyl, or substituted alkyl;

R is H, halogen, alkyl, substituted alkyl, cycloalkyl, or substituted cycloalkyl;

R₁ is H, an amino protecting group, resin, amino acid, polypeptide, or polynucleotide; and R₂ is OH, an ester protecting group, resin, amino acid, polypeptide, or polynucleotide;

or the -A-B—K—R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the —K—R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group.

Non-limiting example of dicarbonyl amino acids having the structure of Formula (XXXVII) include:

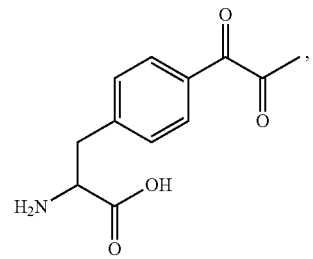

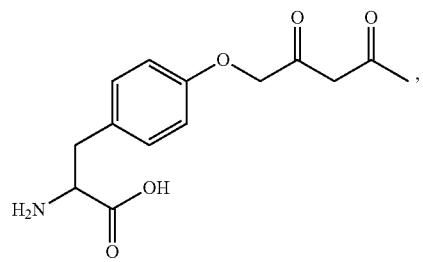

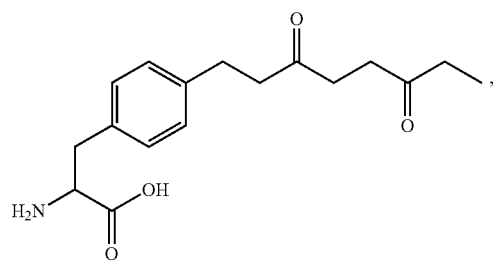

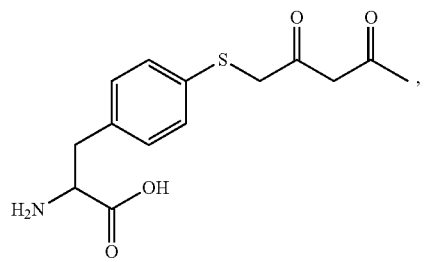

151
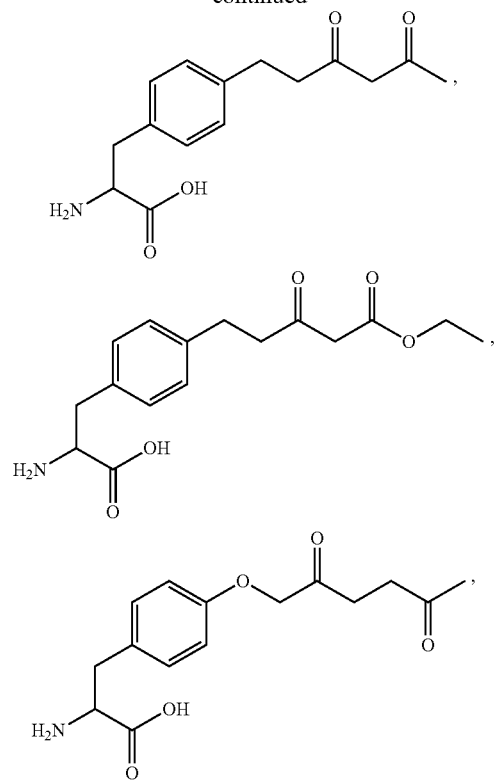
152
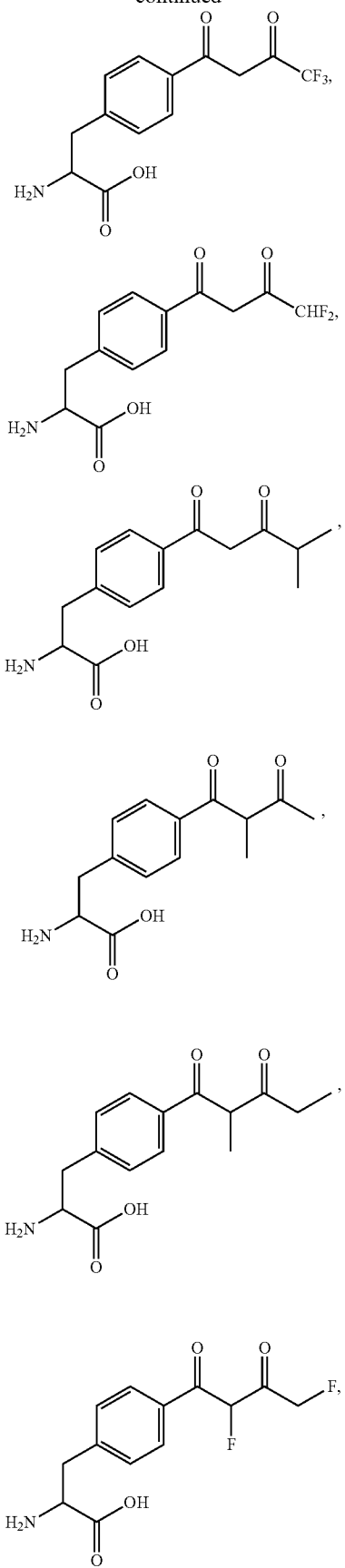

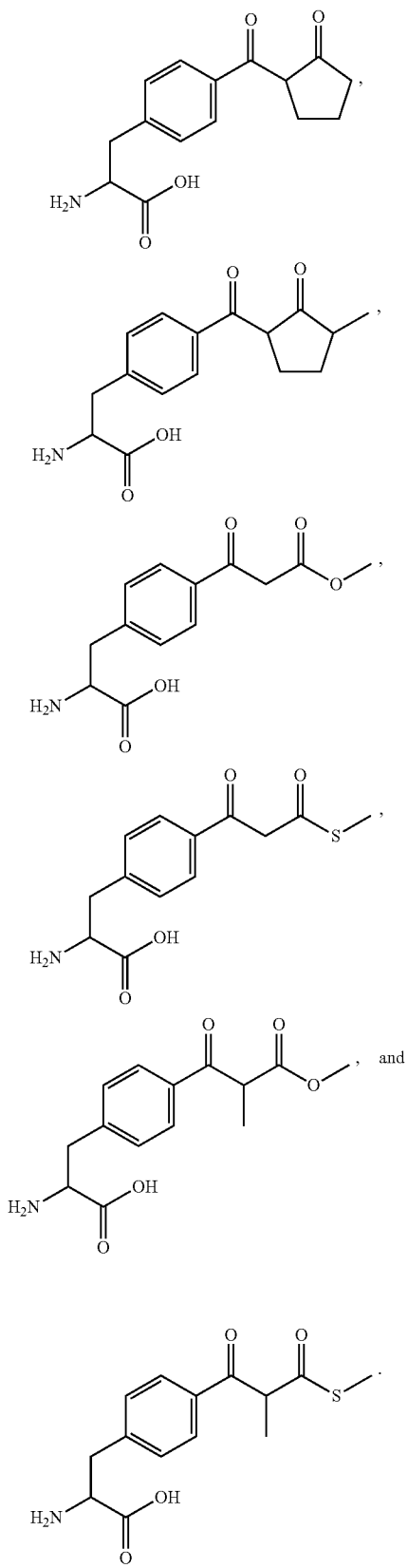
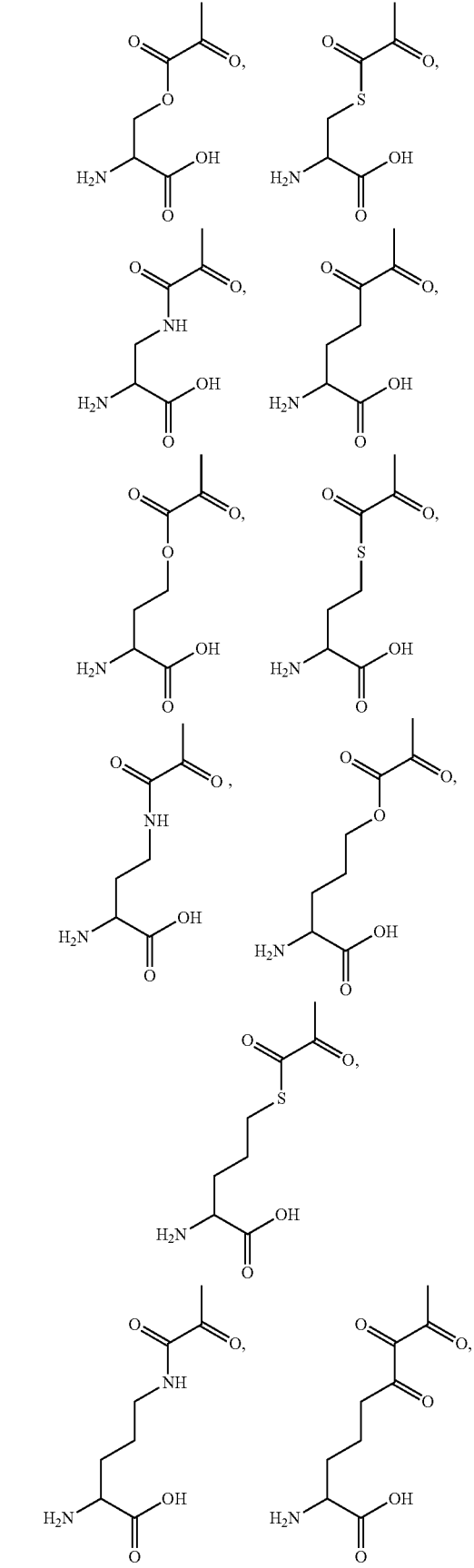
The following amino acids having structures of Formula (XXXVII) are also included:

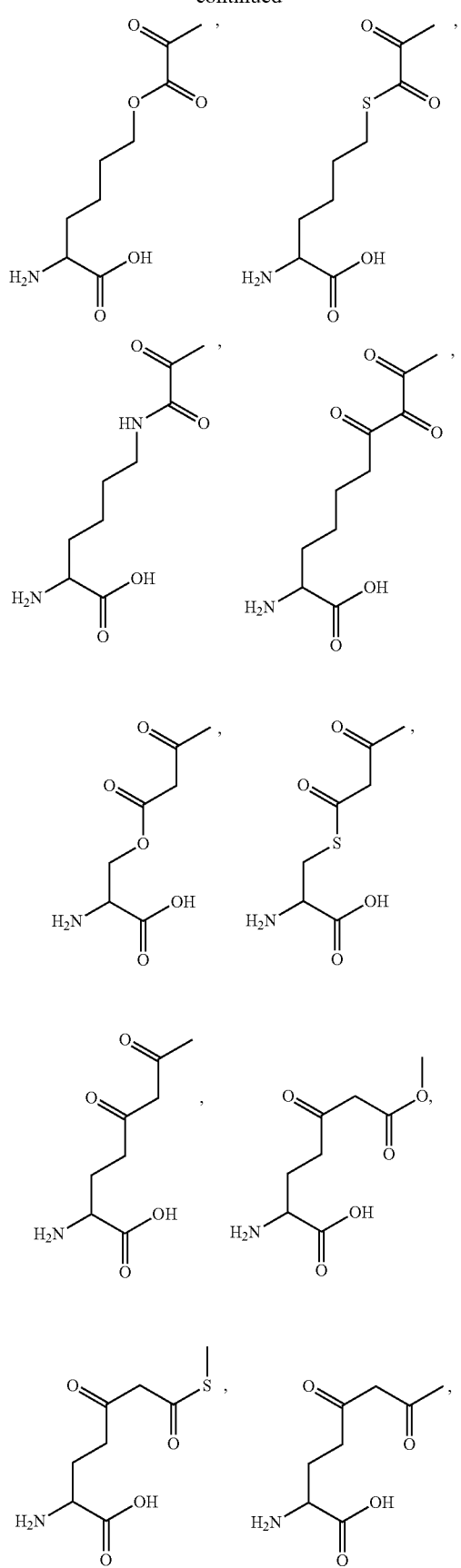
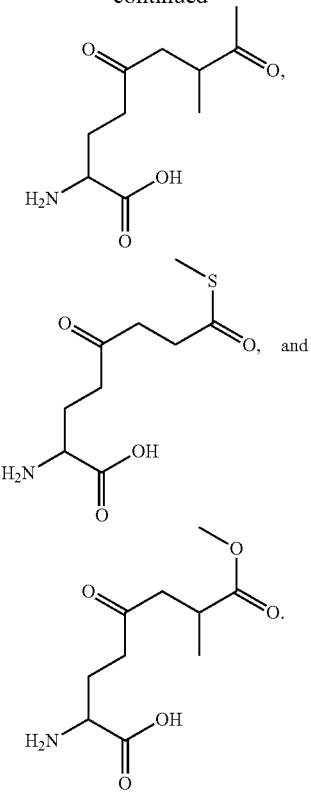

Such non-natural amino acids may be in the form of a salt, or may be incorporated into a non-natural amino acid polypeptide, polymer, polysaccharide, or a polynucleotide and optionally post translationally modified.

C. Structure and Synthesis of Non-Natural Amino Acids: Ketoalkyne, Ketoalkyne-Like, Masked Ketoalkyne, Protected Ketoalkyne Group, Alkyne, and Cycloalkyne Groups Amino acids containing reactive groups with dicarbonyl-like reactivity allow for the linking of molecules via nucleophilic addition reactions. Such electrophilic reactive reactiveonally groups include a ketoalkyne group, a ketoalkyne-like group (which has reactivity similar to a ketoalkyne group and is structurally similar to a ketoalkyne group), a masked ketoalkyne group (which can be readily converted into a ketoalkyne group), or a protected ketoalkyne group (which has reactivity similar to a ketoalkyne group upon deprotection). In some embodiments, amino acids containing reactive groups with a terminal alkyne, internal alkyne or cycloalkyne allow for linking of molecules via cycloaddition reactions (e.g., 1,3-dipolar cycloadditions, azide-alkyne Huisgen cycloaddition, etc.) Such amino acids include amino acids having the structure of Formula (XXXXXXI-A) or (XXXXXXI-B):

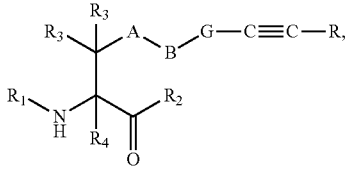

(XXXXXXI-A)

157
-continued

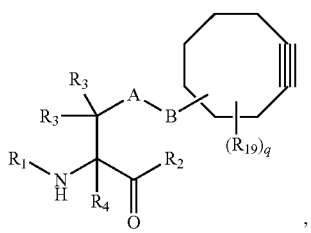
(XXXXXXI-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker linked at one end to a diamine containing moiety, the linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, —C(O)R"—, —S(O)$_k$(alkylene or substituted alkylene)-, where k is 1, 2, or 3, —C(O)-(alkylene or substituted alkylene)-, —C(S)-(alkylene or substituted alkylene)-, —NR"-(alkylene or substituted alkylene)-, —CON(R")-(alkylene or substituted alkylene)-, —CSN(R")-(alkylene or substituted alkylene)-, and —N(R")CO-(alkylene or substituted alkylene)-, where each R" is independently H, alkyl, or substituted alkyl;

G is optional, and when present is

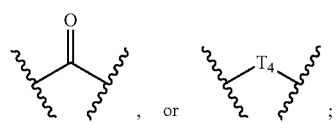
, or ;

$T_4$ is a carbonyl protecting group including, but not limited to

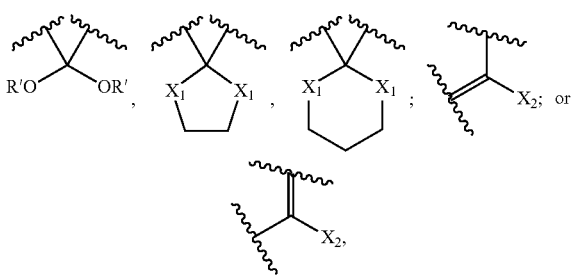

where each $X_1$ is independently selected from the group consisting of —O—, —S—, —N(H)—, —N(R)—, —N(Ac)—, and —N(OMe)-; $X_2$ is —OR, —OAc, —SR, —N(R)$_2$, —N(R)(Ac), —N(R)(OMe), or $N_3$, and where each R' is independently H, alkyl, or substituted alkyl;

158

R is H, halogen, alkyl, substituted alkyl, cycloalkyl, or substituted cycloalkyl;

$R_1$ is H, an amino protecting group, resin, amino acid, polypeptide, or polynucleotide;

$R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

each $R_{19}$ is independently selected from the group consisting of $C_1$-$C_6$ alkyl, $C_1$-$C_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro; and q is 0, 1, 2, 3, 4, 5, 6, 7, 8, 9, 10 or 11.

D. Structure and Synthesis of Non-Natural Amino Acids: Ketoamine, Ketoamine-like, Masked Ketoamine, and Protected Ketoamine Groups Amino acids containing reactive groups with dicarbonyl-like reactivity allow for the linking of molecules via nucleophilic addition reactions. Such reactive groups include a ketoamine group, a ketoamine-like group (which has reactivity similar to a ketoamine group and is structurally similar to a ketoamine group), a masked ketoamine group (which can be readily converted into a ketoamine group), or a protected ketoamine group (which has reactivity similar to a ketoamine group upon deprotection). Such amino acids include amino acids having the structure of Formula (XXXXXXII):

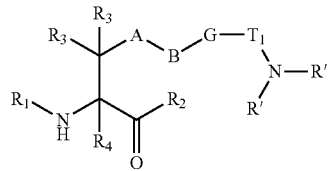
(XXXXXXII)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker linked at one end to a diamine containing moiety, the linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, —C(O)R"—, —S(O)$_k$(alkylene or substituted alkylene)-, where k is 1, 2, or 3, —C(O)-(alkylene or substituted alkylene)-, —C(S)-(alkylene or substituted alkylene)-, —NR"-(alkylene or substituted alkylene)-, —CON(R")-(alkylene or substituted alkylene)-, —CSN(R")-(alkylene or substituted alkylene)-, and —N(R")CO-(alkylene or substituted alkylene)-, where each R" is independently H, alkyl, or substituted alkyl;

G is

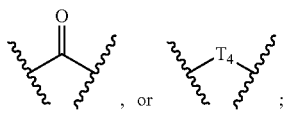

T₁ is an optionally substituted $C_1$-$C_4$ alkylene, an optionally substituted $C_1$-$C_4$ alkenylene, or an optionally substituted heteroalkyl;

T₄ is a carbonyl protecting group including, but not limited to,

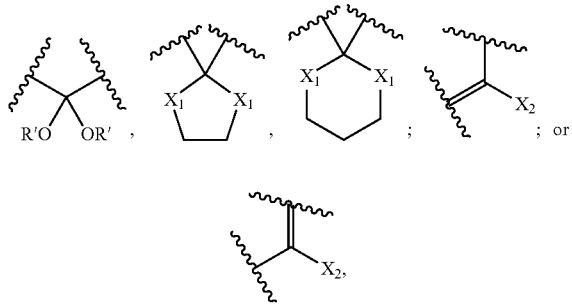

where each $X_1$ is independently selected from the group consisting of —O—, —S—, —N(H)—, —N(R')—, —N(Ac)—, and —N(OMe)-; $X_2$ is —OR, —OAc, —SR, —N(R')₂, —N(R')(Ac), —N(R')(OMe), or $N_3$, and where each R' is independently H, alkyl, or substituted alkyl;

R is H, halogen, alkyl, substituted alkyl, cycloalkyl, or substituted cycloalkyl;

$R_1$ is H, an amino protecting group, resin, amino acid, polypeptide, or polynucleotide; and $R_2$ is OH, an ester projecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl.

Amino acids having the structure of Formula (XXXXXXII) include amino acids having the structure of Formula (XXXXXXII) and Formula (XXXXXXIV):

(XXXXXXIII)

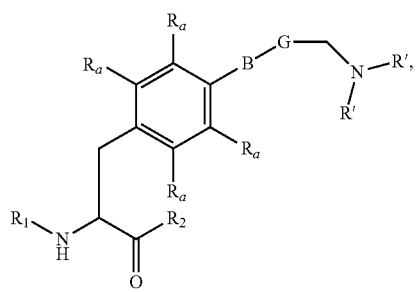

(XXXXXXIV)

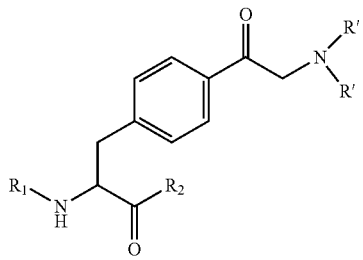

wherein each $R_a$ is independently selected from the group consisting of H, halogen, alkyl, substituted alkyl, —N(R')₂, —C(O)$_k$R' where k is 1, 2, or 3, —C(O)N(R')₂, —OR', and —S(O)$_k$R', where each R' is independently H, alkyl, or substituted alkyl.

E. Structure and Synthesis of Non-Natural Amino Acids: Diamine, Diamine-like, Masked Diamine, Protected Amines and Azides Amino acids with a nucleophilic reactive group allow for a variety of reactions to link molecules via electrophilic addition reactions among others. Such nucleophilic reactive groups include a diamine group (including a hydrazine group, an amidine group, an imine group, a 1,1-diamine group, a 1,2-diamine group, a 1,3-diamine group, and a 1,4-diamine group), a diamine-like group (which has reactivity similar to a diamine group and is structurally similar to a diamine group), a masked diamine group (which can be readily converted into a diamine group), or a protected diamine group (which has reactivity similar to a diamine group upon deprotection). In some embodiments, amino acids containing reactive groups with azides allow for linking of molecules via cycloaddition reactions (e.g., 1,3-dipolar cycloadditions, azide-alkyne Huisgen cycloaddition, etc.).

In another aspect are methods for the chemical synthesis of hydrazine-substituted molecules for the derivatization of carbonyl-substituted dolastatin derivatives. In one embodiment, the hydrazine-substituted molecule can dolastatin linked derivatives. In one embodiment are methods for the preparation of hydrazine-substituted molecules suitable for the derivatization of carbonyl-containing non-natural amino acid polypeptides, including by way of example only, ketone-, or aldehyde-containing non-natural amino acid polypeptides. In a further or additional embodiment, the non-natural amino acids are incorporated site-specifically during the in vivo translation of proteins. In a further or additional embodiment, the hydrazine-substituted dolastatin derivatives allow for the site-specific derivatization of carbonyl-containing non-natural amino acids via nucleophilic attack of each carbonyl group to form a heterocycle-derivatized polypeptide, including a nitrogen-containing heterocycle-derivatized polypeptide in a site-specific fashion. In a further or additional embodiment, the method for the preparation of hydrazine-substituted dolastatin derivatives provides access to a wide variety of site-specifically derivatized polypeptides. In a further or additional embodiment are methods for synthesizing hydrazine-functionalized polyethyleneglycol (PEG) linked dolastatin derivatives.

Such amino acids include amino acids having the structure of Formula (XXXVII-A) or (XXXVII-B):

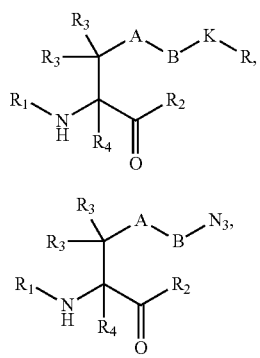

(XXXVII)

(XXXVII-B)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- B is optional, and when present is a linker linked at one end to a diamine containing moiety, the linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, —C(O)R"—, —C(O)R"—, —S(O)$_k$(alkylene or substituted alkylene)-, where k is 1, 2, or 3, —C(O)-(alkylene or substituted alkylene)-, —C(S)-(alkylene or substituted alkylene)-, —NR"-(alkylene or substituted alkylene)-, —CON(R")-(alkylene or substituted alkylene)-, —CSN(R")-(alkylene or substituted alkylene)-, and —N(R")CO-(alkylene or substituted alkylene)-, where each R" is independently H, alkyl, or substituted alkyl;
- K is

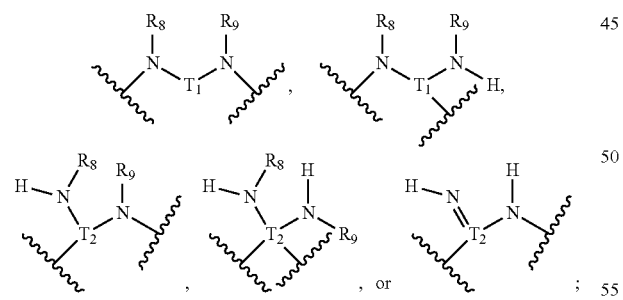

where:
- $R_8$ and $R_9$ are independently selected from H, alkyl, substituted alkyl, cycloalkyl, substituted cycloalkyl, or amine protecting group;
- $T_1$ is a bond, optionally substituted $C_1$-$C_4$ alkylene, optionally substituted $C_1$-$C_4$ alkenylene, or optionally substituted heteroalkyl;
- $T_2$ is optionally substituted $C_1$-$C_4$ alkylene, optionally substituted $C_1$-$C_4$ alkenylene, optionally substituted heteroalkyl, optionally substituted aryl, or optionally substituted heteroaryl;

wherein each optional substituents is independently selected from lower alkyl, substituted lower alkyl, lower cycloalkyl, substituted lower cycloalkyl, lower alkenyl, substituted lower alkenyl, alkynyl, lower heteroalkyl, substituted heteroalkyl, lower heterocycloalkyl, substituted lower heterocycloallyl, aryl, substituted aryl, heteroaryl, substituted heteroaryl, alkaryl, substituted alkaryl, aralkyl, or substituted aralkyl;

R is H, alkyl, substituted alkyl, cycloalkyl, or substituted cycloalkyl;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B—K—R groups together form a bicyclic or tricyclic cycloalkyl or heterocycloalkyl comprising at least one diamine group, protected diamine group or masked diamine group;

or the —B—K—R groups together form a bicyclic or tricyclic cycloalkyl or cycloaryl or heterocycloalkyl comprising at least one diamine group, protected diamine group or masked diamine group;

or the —K—R group together forms a monocyclic or bicyclic cycloalkyl or heterocycloalkyl comprising at least one diamine group, protected diamine group or masked diamine group;

wherein at least one amine group on -A-B—K—R is optionally a protected amine.

In one aspect are compounds comprising the structures 1 or 2:

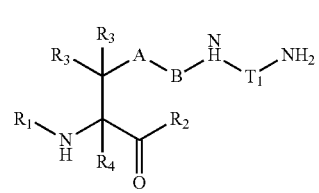

1

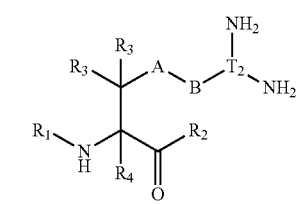

2 wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- B is optional, and when present is a linker linked at one end to a diamine containing moiety, the linker selected from the group consisting of lower alkylene, substituted lower alkylene, lower alkenylene, substituted lower alkenylene, lower heteroalkylene, substituted lower heteroalkylene, —O-(alkylene or substituted alkylene)-, —S-(alkylene or substituted alkylene)-, —C(O)R''—, —S(O)$_k$(alkylene or substituted alkylene)-, where k is 1, 2, or 3, —C(O)-(alkylene or substituted alkylene)-, —C(S)-(alkylene or substituted alkylene)-, —NR''-(alkylene or substituted alkylene)-, —CON(R'')-(alkylene or substituted alkylene)-, —CSN(R'')-(alkylene or substituted alkylene)-, and —N(R'')CO-(alkylene or substituted alkylene)-, where each R'' is independently H, alkyl, or substituted alkyl;

$T_1$ is a bond or $CH_2$; and $T_2$ is CH;

wherein each optional substituents is independently selected from lower alkyl, substituted lower alkyl, lower cycloalkyl, substituted lower cycloalkyl, lower alkenyl, substituted lower alkenyl, alkynyl, lower heteroalkyl, substituted heteroalkyl, lower heterocycloalkyl, substituted lower heterocycloalkyl, aryl, substituted aryl, heteroaryl, substituted heteroaryl, alkaryl, substituted alkaryl, aralkyl, or substituted aralkyl;

$R_1$ is H, an amino protecting group, resin, amino acid, polypeptide, or polynucleotide; and $R_2$ is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B-diamine containing moiety together form a bicyclic cycloalkyl or heterocycloalkyl comprising at least one diamine group, protected diamine group or masked diamine group;

or the —B-diamine containing moiety groups together form a bicyclic or tricyclic cycloalkyl or cycloaryl or heterocycloalkyl comprising at least one diamine group, protected diamine group or masked diamine group;

wherein at least one amine group on -A-B-diamine containing moiety is optionally a protected amine;

or an active metabolite, salt, or a pharmaceutically acceptable prodrug or solvate thereof.

The following non-limiting examples of amino acids having the structure of Formula (XXXVII) are included:

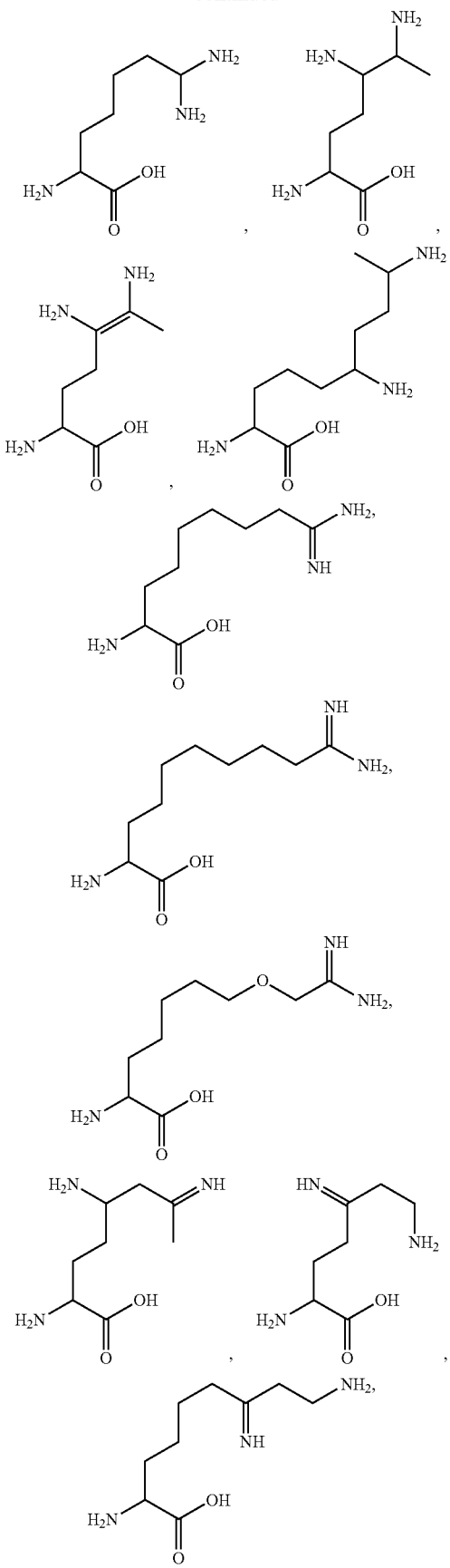

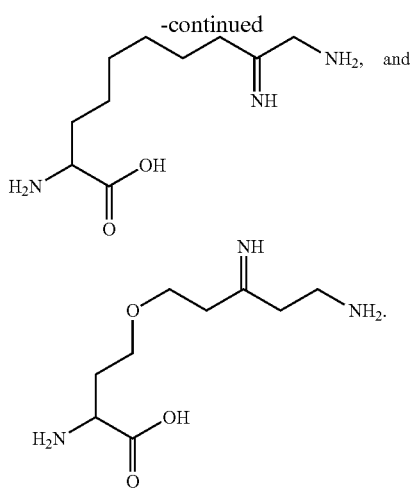

Such non-natural amino acids may also be in the form of a salt or may be incorporated into a non-natural amino acid polypeptide, polymer, polysaccharide, or a polynucleotide and/or optionally post translationally modified.

In certain embodiments, compounds of Formula (XXXVII) are stable in aqueous solution for at least 1 month under mildly acidic conditions. In certain embodiments, compounds of Formula (XXXVII) are stable for at least 2 weeks under mildly acidic conditions. In certain embodiments, compound of Formula (XXXVII) are stable for at least 5 days under mildly acidic conditions. In certain embodiments, such acidic conditions are pH about 2 to about 8.

In certain embodiments of compounds of Formula (XXXVII), B is lower alkylene, substituted lower alkylene, O-(alkylene or substituted alkylene)-, C(R')=NN(R')—, —N(R')CO—, C(O)—, —C(R')=N—, C(O)-(alkylene or substituted alkylene)-, CON(R')alkylene or substituted alkylene)-, —S(alkylene or substituted alkylene)-, —S(O)(alkylene or substituted alkylene)-, or —S(O)$_2$(alkylene or substituted alkylene)-. In certain embodiments of compounds of Formula (XXXVII), B is —O(CH$_2$)—, —CH=N—, CH=NNH—, —NHCH$_2$—, —NHCO—, C(O)—, C(O)(CH$_2$)—, CONH(CH$_2$)—, —SCH$_2$—, —S(—O)CH$_2$—, or —S(O)$_2$CH$_2$—. In certain embodiments of compounds of Formula (XXXVII), R is C$_{1-6}$alkyl or cycloalkyl. In certain embodiments of compounds of Formula (XXXVII) R is —CH$_3$, —CH(CH3)$_2$, or cyclopropyl. In certain embodiments of compounds of Formula (XXXVII), R$_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (XXXVII), R$_1$ is a resin, amino acid, polypeptide, or polynucleotide. In certain embodiments of compounds of Formula (XXXVII), R$_1$ is an antibody, antibody fragment or monoclonal antibody. In certain embodiments of compounds of Formula (XXXVII), R$_2$ is OH, O-methyl, O-ethyl, or O-t-butyl. In certain embodiments of compounds of Formula (XXXVII), R$_2$ is a resin, at least one amino acid, polypeptide, or polynucleotide. In certain embodiments of compounds of Formula (XXXVII), R$_2$ is an antibody, antibody fragment or monoclonal antibody.

The following non-limiting examples of amino acids having the structure of Formula (XXXVII) are also included:

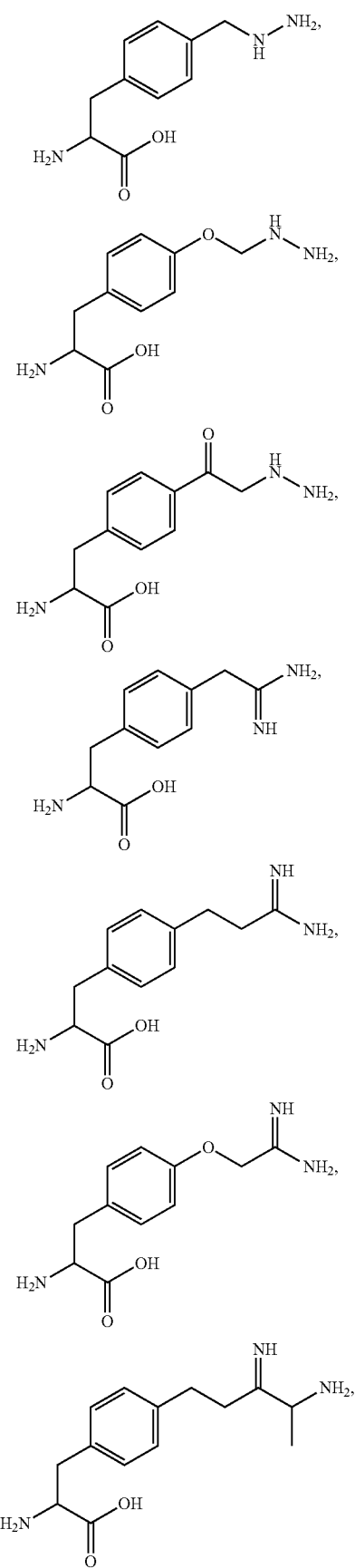

-continued

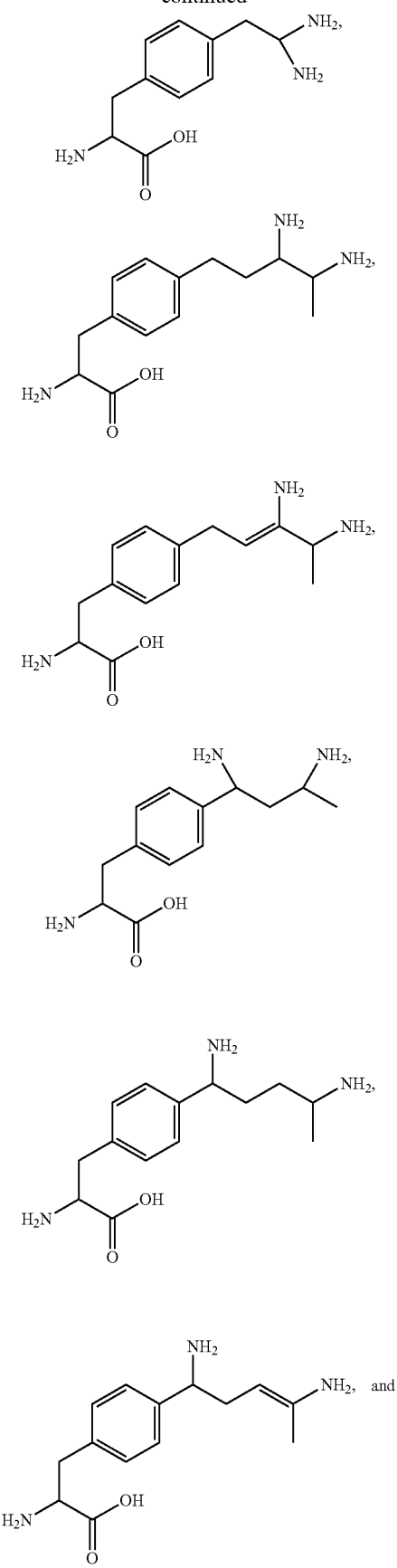

-continued

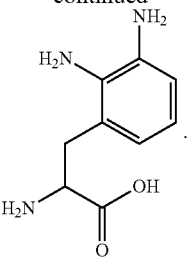

Non-limiting examples of protected amino acids having the structure of Formula (XXXVII) include:

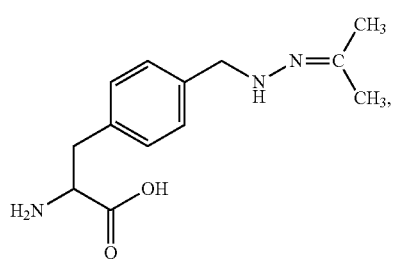

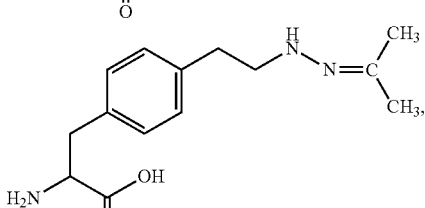

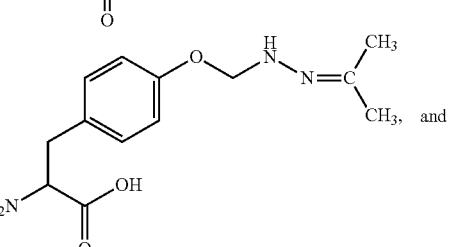

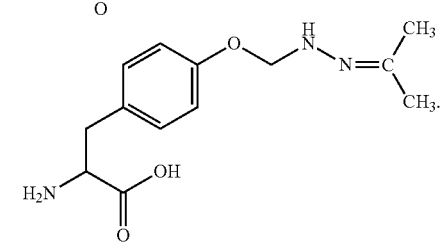

F. Structure and Synthesis of Non-Natural Amino Acids: Aromatic Amines

Non-natural amino acids with nucleophilic reactive groups, such as, by way of example only, an aromatic amine group (including secondary and tertiary amine groups), a masked aromatic amine group (which can be readily converted into a aromatic amine group), or a protected aromatic amine group (which has reactivity similar to an aromatic amine group upon deprotection) allow for a variety of reactions to link molecules via various reactions, including but not limited to, reductive alkylation reactions with aldehyde containing dolastatin linker derivatives. Such aromatic amine containing non-natural amino acids include amino acids having the structure of Formula (XXXXXXV):

(XXXXXXV)

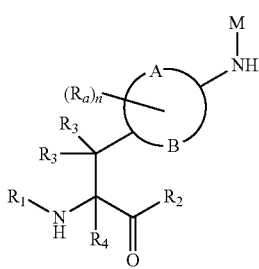

wherein:

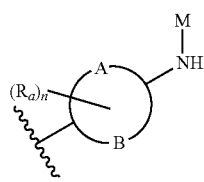

is selected from the group consisting of a monocyclic aryl ring, a bicyclic aryl ring, a multicyclic aryl ring, a monocyclic heteroaryl ring, a bicyclic heteroaryl ring, and a multicyclic heteroaryl ring;

A is independently $CR_a$, or N;

B is independently $CR_a$, N, O, or S;

each $R_a$ is independently selected from the group consisting of H, halogen, alkyl, —$NO_2$, —CN, substituted alkyl, —$N(R')_2$, —$C(O)_kR'$, —$C(O)N(R')_2$, —OR', and —$S(O)_kR'$, where k is 1, 2, or 3; and n is 0, 1, 2, 3, 4, 5, or 6;

$R_1$ is H, an amino protecting group, resin, at least one amino acid, polypeptide, or polynucleotide; and $R_2$ is OH, an ester protecting group, resin, at least one amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

M is H or —$CH_2R_5$; or the M-N—$C(R_5)$ moiety may form a 4 to 7 membered ring structure;

$R_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —$C(O)N(R")_2$, —$C(O)NHCH(R")_2$, -(alkylene or substituted alkylene)-$N(R")_2$, -(alkenylene or substituted alkenylene)-$N(R")_2$, -(alkylene or substituted alkylene)-(aryl or substituted aryl), -(alkenylene or substituted alkenylene)-(aryl or substituted aryl), -(alkylene or substituted alkylene)-$ON(R")_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or two $R_5$ groups optionally form a cycloalkyl or a heterocycloalkyl;

or $R_5$ and any $R_a$ optionally form a cycloalkyl or a heterocycloalkyl; and each R' is independently H, alkyl, or substituted alkyl.

Such non-natural amino acids may also be in the form of a salt, or may be incorporated into a non-natural amino acid polypeptide, polymer, polysaccharide, or a polynucleotide and optionally reductively alkylated.

The structure

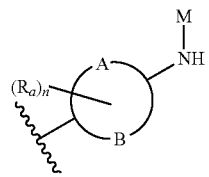

(as presented in all examples herein) does not present the relative orientations of "A," "B," "NH-M" and "$R_a$"; rather these four features of this structure may be oriented in any chemically-sound manner (along with other features of this structure), as illustrated by example herein.

Non-natural amino acids containing an aromatic amine moiety having the structure of Formula (A) include non-natural amino acids having the structures:

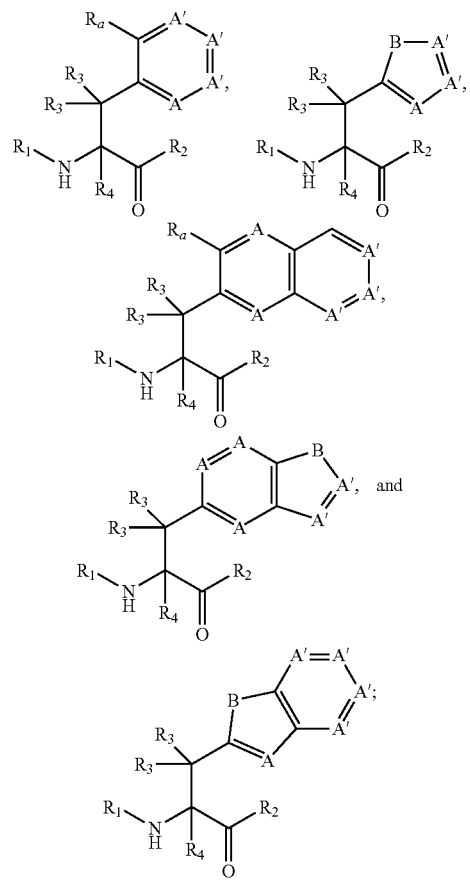

wherein, each A' is independently selected from $CR_a$, N, or

and up to two A' may be

with the remaining A' selected from $CR_a$, or

Such non-natural amino acids may also be in the form of a salt, or may be incorporated into a non-natural amino acid polypeptide, polymer, polysaccharide, or a polynucleotide and optionally reductively alkylated.

Non-limiting examples of non-natural amino acids containing an aromatic amine moiety having the structure of Formula (XXXXXXV) include non-natural amino acids having the structure of Formula (XXXXXXVI), and Formula (XXXXXXVII),

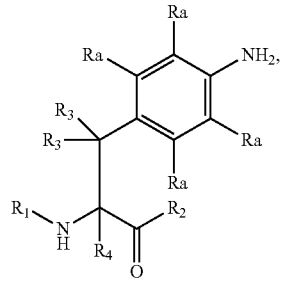
(XXXXXXVI)

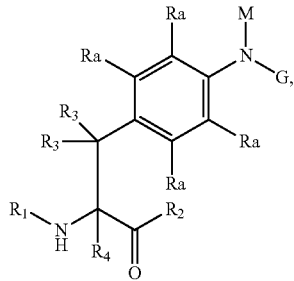
(XXXXXXVII)

wherein; G is an amine protecting group, including, but not limited to,

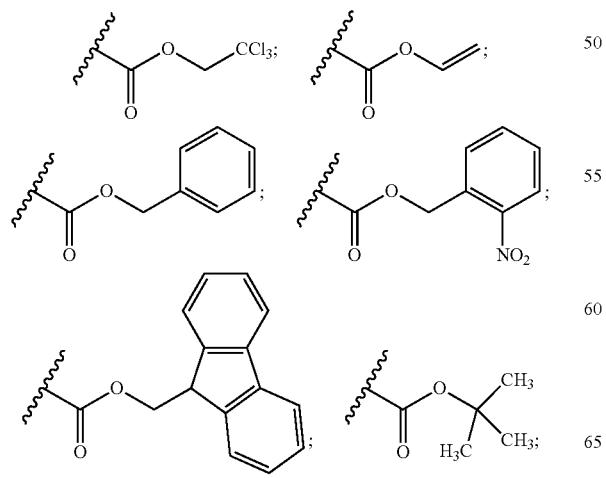

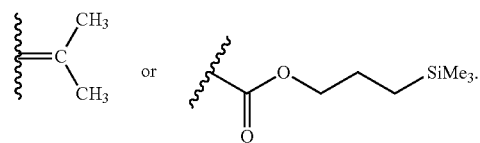

Such non-natural amino acids may be in the form of a salt, or may be incorporated into a non-natural amino acid polypeptide, polymer, polysaccharide, or a polynucleotide and optionally reductively alkylated.

Non-natural amino acids containing an aromatic amine moiety have the following structures:

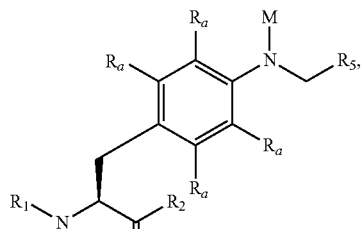

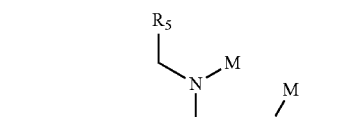

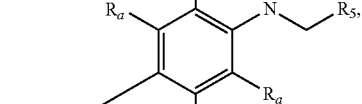

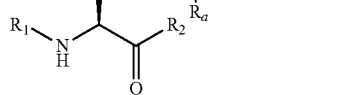

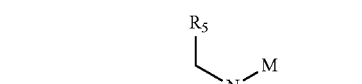

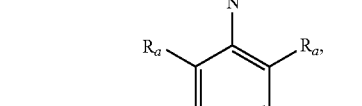

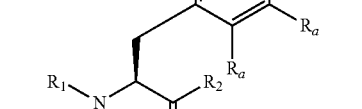

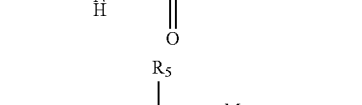

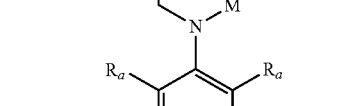

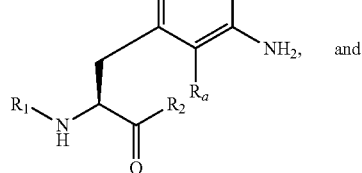

-continued

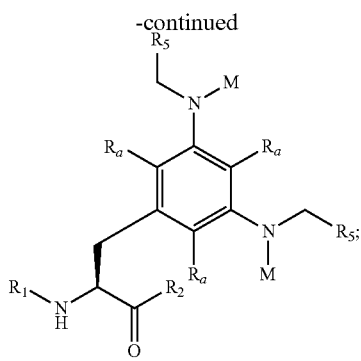

wherein each $R_a$ is independently selected from the group consisting of H, halogen, alkyl, —NO$_2$, —CN, substituted alkyl, —N(R')$_2$, —C(O)$_k$R', —C(O)N(R')$_2$, —OR', and —S(O)$_k$R', where k is 1, 2, or 3;

M is H or —CH$_2$R$_5$; or the M-N—C(R$_5$) moiety may form a 4 to 7 membered ring structure;

R$_1$ is H, an amino protecting group, resin, amino acid, polypeptide, or polynucleotide;

R$_2$ is OH, an ester protecting group, resin, amino acid, polypeptide, or polynucleotide;

R$_5$ is alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, cycloalkyl, substituted cycloalkyl, aryl, substituted aryl, heteroaryl, substituted heteroaryl, heterocycle, substituted heterocycle, alkaryl, substituted alkaryl, aralkyl, substituted aralkyl, —C(O)R", —C(O)OR", —C(O)N(R")$_2$, —C(O)NHCH(R")$_2$, -(alkylene or substituted alkylene)-N(R")$_2$, -(alkenylene or substituted alkenylene)-N(R")$_2$, -(alkylene or substituted alkylene)-(aryl or substituted aryl), -(alkenylene or substituted alkenylene)-(aryl or substituted aryl), -(alkylene or substituted alkylene)-ON(R")$_2$, -(alkylene or substituted alkylene)-C(O)SR", -(alkylene or substituted alkylene)-S—S-(aryl or substituted aryl), wherein each R" is independently hydrogen, alkyl, substituted alkyl, alkenyl, substituted alkenyl, alkoxy, substituted alkoxy, aryl, substituted aryl, heteroaryl, substituted heteroaryl, heterocycle, substituted heterocycle, alkaryl, substituted alkaryl, aralkyl, substituted aralkyl, or —C(O)OR';

or R$_5$ and any R$_a$ optionally form a cycloalkyl or a heterocycloalkyl; and each R' is independently H, alkyl, or substituted alkyl. Such non-natural amino acids may also be in the form of a salt, or may be incorporated into a non-natural amino acid polypeptide, polymer, polysaccharide, or a polynucleotide.

Such non-natural amino acids of Formula (XXXXXXV) may be formed by reduction of protected or masked amine moieties on the aromatic moiety of a non-natural amino acid. Such protected or masked amine moieties include, but are not limited to, imines, hydrazines, nitro, or azide substituents. The reducing agents used to reduce such protected or masked amine moieties include, but are not limited to, TCEP, Na$_2$S, Na$_2$S$_2$O$_4$, LiAH$_4$, NaBH$_4$ or NaBCNH$_3$.

V. Non-Natural Amino Acid Linked Dolastatin Derivatives

In another aspect described herein are methods, strategies and techniques for incorporating at least one such dolastatin linker derivatives into a non-natural amino acid. Also included with this aspect are methods for producing, purifying, characterizing and using such dolastatin linker derivatives containing at least one such non-natural amino acid.

Also included with this aspect are compositions of and methods for producing, purifying, characterizing and using oligonucleotides (including DNA and RNA) that can be used to produce, at least in part, a dolastatin linker derivative containing at least one non-natural amino acid. Also included with this aspect are compositions of and methods for producing, purifying, characterizing and using cells that can express such oligonucleotides that can be used to produce, at least in part, a dolastatin linker derivative containing at least one non-natural amino acid.

Thus, dolastatin linker derivatives comprising at least one non-natural amino acid or modified non-natural amino acid with a carbonyl, dicarbonyl, alkyne, cycloalkyne, azide, oxime or hydroxylamine group are provided and described herein. In certain embodiments, dolastatin linker derivatives with at least one non-natural amino acid or modified non-natural amino acid with a carbonyl, dicarbonyl, alkyne, cycloalkyne, azide, oxime or hydroxylamine group include at least one post-translational modification at some position on the polypeptide. In some embodiments the co-translational or post-translational modification occurs via the cellular machinery (e.g., glycosylation, acetylation, acylation, lipid-modification, palmitoylation, palmitate addition, phosphorylation, glycolipid-linkage modification, and the like), in many instances, such cellular-machinery-based co-translational or post-translational modifications occur at the naturally occurring amino acid sites on the polypeptide, however, in certain embodiments, the cellular-machinery-based co-translational or post-translational modifications occur on the non-natural amino acid site(s) on the polypeptide.

In other embodiments, the post-translational modification does not utilize the cellular machinery, but the functionality is instead provided by attachment of a molecule (a polymer; a water-soluble polymer; a derivative of polyethylene glycol; a second protein or polypeptide or polypeptide analog; an antibody or antibody fragment; and any combination thereof) comprising a second reactive group to the at least one non-natural amino acid comprising a first reactive group (including but not limited to, non-natural amino acid containing a ketone, aldehyde, acetal, hemiacetal, alkyne, cycloalkyne, azide, oxime, or hydroxylamine functional group) utilizing chemistry methodology described herein, or others suitable for the particular reactive groups. In certain embodiments, the co-translational or post-translational modification is made in vivo in a eukaryotic cell or in a non-eukaryotic cell. In certain embodiments, the post-translational modification is made in vitro not utilizing the cellular machinery. Also included with this aspect are methods for producing, purifying, characterizing and using such dolastatin linker derivatives containing at least one such co-translationally or post-translationally modified non-natural amino acids.

Also included within the scope of the methods, compositions, strategies and techniques described herein are reagents capable of reacting with a dolastatin linker derivative (containing a carbonyl or dicarbonyl group, oxime group, alkyne, cycloalkyne, azide, hydroxylamine group, or masked or protected forms thereof) that is part of a polypeptide so as to produce any of the aforementioned post-translational modifications. In certain embodiments, the resulting post-translationally modified dolastatin linker derivative will contain at least one oxime group; the resulting modified oxime-containing dolastatin linker derivative may undergo subsequent modification reactions. Also included with this aspect are methods for producing, purifying, characterizing and using such reagents that are capable of any such post-translational modifications of such dolastatin linker derivative(s).

In certain embodiments, the polypeptide or non-natural amino acid linked dolastatin derivative includes at least one co-translational or post-translational modification that is made in vivo by one host cell, where the post-translational modification is not normally made by another host cell type. In certain embodiments, the polypeptide includes at least one co-translational or post-translational modification that is made in vivo by a eukaryotic cell, where the co-translational or post-translational modification is not normally made by a non-eukaryotic cell. Examples of such co-translational or post-translational modifications include, but are not limited to, glycosylation, acetylation, acylation, lipid-modification, palmitoylation, palmitate addition, phosphorylation, glyco-lipid-linkage modification, and the like. In one embodiment, the co-translational or post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the co-translational or post-translational modification comprises attachment of an oligosaccharide (including but not limited to, Gal-GalNAc, Gal-GlcNAc, etc.) to a serine or threonine by a GalNAc-serine, a to GalNAc-threonine, a GlcNAc-serine, or a GlcNAc-threonine linkage. In certain embodiments, a protein or polypeptide can comprise a secretion or localization sequence, an epitope tag, a FLAG tag, a poly-histidine tag, a GST fusion, and/or the like. Also included with this aspect are methods for producing, purifying, characterizing and using such polypeptides containing at least one such co-translational or post-translational modification. In other embodiments, the glycosylated non-natural amino acid polypeptide is produced in a non-glycosylated form. Such a non-glycosylated form of a glycosylated non-natural amino acid may be produced by methods that include chemical or enzymatic removal of oligosaccharide groups from an isolated or substantially purified or unpurified glycosylated non-natural amino acid polypeptide; production of the non-natural amino acid in a host that does not glycosylate such a non-natural amino acid polypeptide (such a host including, prokaryotes or eukaryotes engineered or mutated to not glycosylate such a polypeptide), the introduction of a glycosylation inhibitor into the cell culture medium in which such a non-natural amino acid polypeptide is being produced by a eukaryote that normally would glycosylate such a polypeptide, or a combination of any such methods. Also described herein are such non-glycosylated forms of normally-glycosylated non-natural amino acid polypeptides (by normally-glycosylated is meant a polypeptide that would be glycosylated when produced under conditions in which naturally-occurring polypeptides are glycosylated). Of course, such non-glycosylated forms of normally-glycosylated non-natural amino acid polypeptides (or indeed any polypeptide described herein) may be in an unpurified form, a substantially purified form, or in an isolated form.

In certain embodiments, the non-natural amino acid polypeptide includes at least one post-translational modification that is made in the presence of an accelerant, wherein the post-translational modification is stoichiometric, stoichiometric-like, or near-stoichiometric. In other embodiments the polypeptide is contacted with a reagent of Formula (XIX) in the presence of an accelerant. In other embodiments the accelerant is selected from the group consisting of:

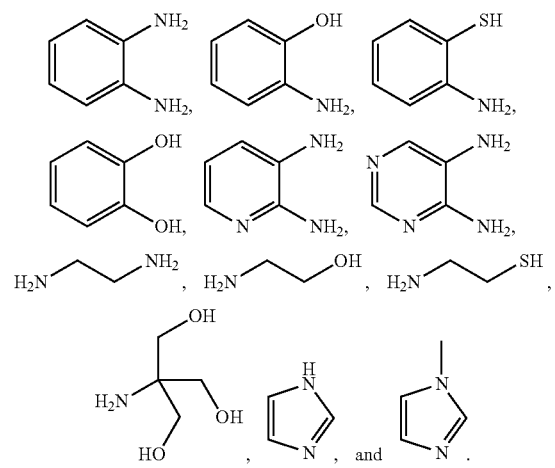

A. Chemical Synthesis of Non-Natural Amino Acid Linked Dolastatin Derivatives: Oxime-Containing Linked Dolastatin Derivatives Non-natural amino acid dolastatin linked derivatives containing an oxime group allow for reaction with a variety of reagents that contain certain reactive carbonyl- or dicarbonyl-groups (including but not limited to, ketones, aldehydes, or other groups with similar reactivity) to form new non-natural amino acids comprising a new oxime group. Such an oxime exchange reaction allows for the further functionalization of dolastatin linked derivatives. Further, the original dolastatin linked derivative containing an oxime group may be useful in their own right as long as the oxime linkage is stable under conditions necessary to incorporate the amino acid into a polypeptide (e.g., the in vivo, in vitro and chemical synthetic methods described herein).

Thus, in certain embodiments described herein are non-natural amino acid dolastatin linked derivatives with sidechains comprising an oxime group, an oxime-like group (which has reactivity similar to an oxime group and is structurally similar to an oxime group), a masked oxime group (which can be readily converted into an oxime group), or a protected oxime group (which has reactivity similar to an oxime group upon deprotection).

Such non-natural amino acid dolastatin linked derivatives include dolastatin linked derivatives having the structure of Formula (VIII) or (IX):

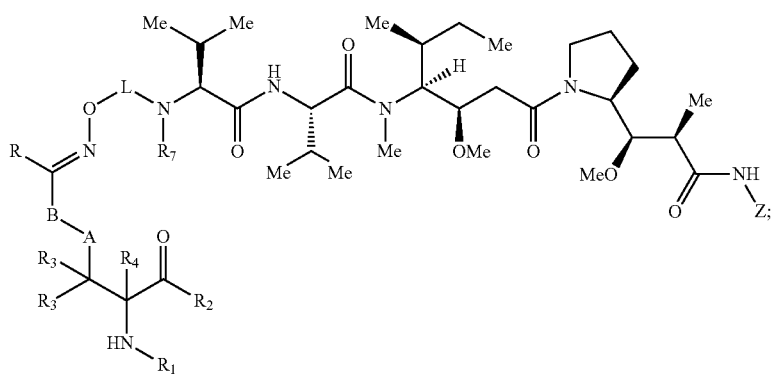

(VIII)

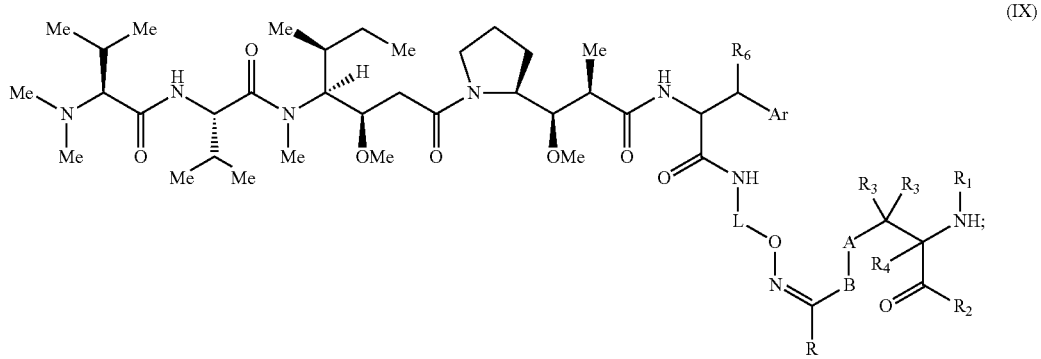

(IX)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$-(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is H, an amino protecting group, resin, at least one amino acid, polypeptide, or polynucleotide;

$R_2$ is OH, an ester protecting group, resin, at least one amino acid, polypeptide, or polynucleotide;

$R_3$ and $R_4$ are each independently H, halogen, lower alkyl, or substituted lower alkyl, or $R_3$ and $R_4$ or two $R_3$ groups optionally form a cycloalkyl or a heterocycloalkyl;

Z has the structure of:

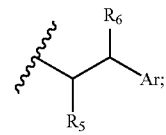

$R_5$ is H, COR$_8$, $C_1$-$C_6$alkyl, or thiazole;

$R_8$ is OH $R_6$ is OH or H;

Ar is phenyl or pyridine;

$R_7$ is $C_1$-$C_6$alkyl or hydrogen;

L is a linker selected from the group consisting of -alkylene-, -alkylene-C(O)—, -(alkylene-O)$_n$-alkylene-, -(alkylene-O)$_n$-alkylene-C(O)—, -(alkylene-O)$_n$—(CH$_2$)$_{n'}$—NHC(O)(CH$_2$)$_{n''}$—C(Me)$_2$-S—S—CH$_2$)$_{n'''}$—NHC(O)-(alkylene-O)$_{n''''}$-alkylene-, -(alkylene-O)$_n$-alkylene-W—, -alkylene-C(O)—W—, -alkylene-O)$_n$-alkylene-U-alkylene-C(O)—, and -(alkylene-O)$_n$-alkylene-U-alkylene-;

W has the structure of:

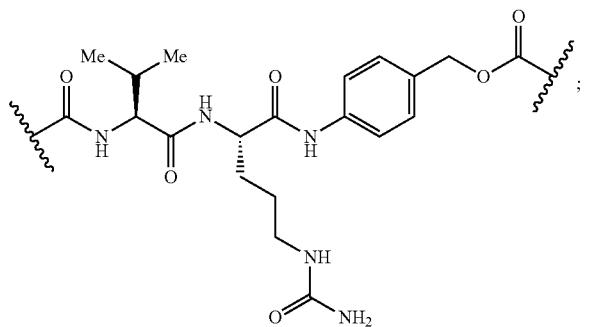 [SMILES: *C(=O)N[C@H](C(=O)N[C@@H](CCCNC(N)=O)C(=O)Nc1ccc(COC(*)=O)cc1)C(C)C]

U has the structure of:

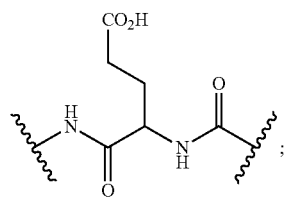 [SMILES: *NC(=O)C(CCC(=O)O)NC(*)=O]

and
each n, n', n', n''' and n'''' are independently integers greater than or equal to one; or an active metabolite, or a pharmaceutically acceptable prodrug or solvate thereof.

In certain embodiments of compounds of Formula (VIII) and (IX), $R_5$ is thiazole. In certain embodiments of compounds of Formula (VIII) and (IX), $R_6$ is H. In certain embodiments of compounds of Formula (VIII) and (IX), Ar is phenyl. In certain embodiments of compounds of Formula (VIII) and (IX), $R_7$ is methyl. In certain embodiments of compounds of Formula (VIII) and (IX), n is an integer from 0 to 20. In certain embodiments of compounds of Formula (VIII) and (IX), n is an integer from 0 to 10. In certain embodiments of compounds of Formula (VIII) and (IX), n is an integer from 0 to 5.

In certain embodiments of compounds of Formula (VIII) and (IX), $R_5$ is thiazole. In certain embodiments of compounds of Formula (VIII) and (IX), $R_5$ is hydrogen. In certain embodiments of compounds of Formula (VIII) and (IX), $R_5$ is methyl, ethyl, propyl, iso-propyl, butyl, iso-butyl, sec-butyl, tert-butyl, pentyl, or hexyl. In certain embodiments of compounds of Formula (VIII) and (IX), $R_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—.
In certain embodiments of Formula (VIII) and (IX), alkylene is methylene, ethylene, propylene, butylenes, pentylene, hexylene, or heptylene.

In certain embodiments of compounds of Formula (VIII) and (IX), $R_5$ is —NH-(alkylene-O)$_n$—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (VIII) and (IX), $R_6$ is H.

In certain embodiments of compounds of Formula (VIII) and (IX), Ar is phenyl.

In certain embodiments of compounds of Formula (VIII) and (IX), $R_7$ is methyl, ethyl, propyl, iso-propyl, butyl, sec-butyl iso-butyl, tert-butyl, pentyl, or hexyl. In certain embodiments of compounds of Formula (VIII) and (IX), $R_7$ is hydrogen.

In certain embodiments of compounds of Formula (VIII) and (IX), each L is independently a cleavable linker or non-cleavable linker. In certain embodiments of compounds of Formula (VIII) and (IX), each L is independently a oligo(ethylene glycol) derivatized linker.

In certain embodiments of compounds of Formula (VIII) and (IX), each alkylene, alkylene', alkylene'', and alkylene''' independently is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$Cl$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—.
In certain embodiments of compounds of Formula (VIII) and (IX), alkylene is methylene, ethylene, propylene, butylenes, pentylene, hexylene, or heptylene.

In certain embodiments of compounds of Formula (VIII) and (IX), each n, n', n'', n''', and n'''' independently is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (VIII) or (IX), $R_1$ is a polypeptide. In certain embodiments of compounds of Formula (VIII) or (IX), $R_2$ is a polypeptide. In certain embodiments of compounds of Formula (VIII) or (IX), the polypeptide is an antibody. In certain embodiments of compounds of Formula (VIII) or (IX), the antibody is herceptin.

Such non-natural amino acid dolastatin linked derivatives include dolastatin linked derivatives having the structure of Formula (X), (XI), (XII) or (XIII):

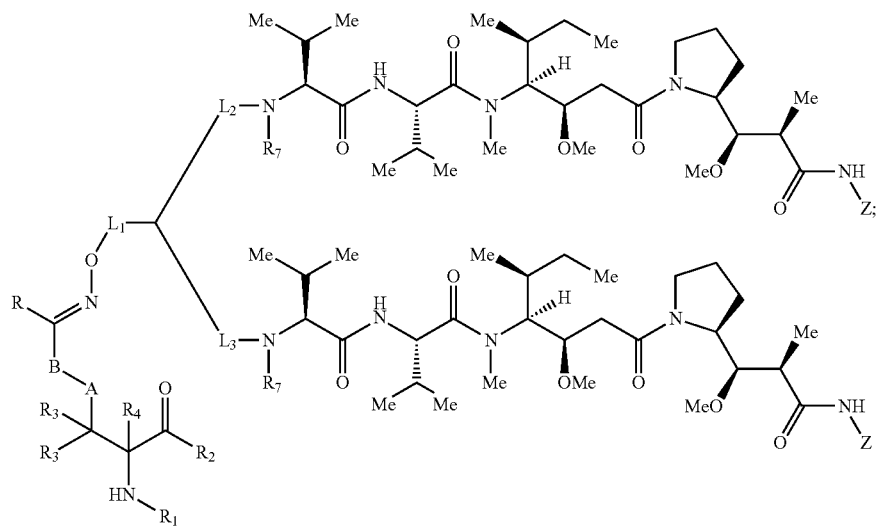
(X)
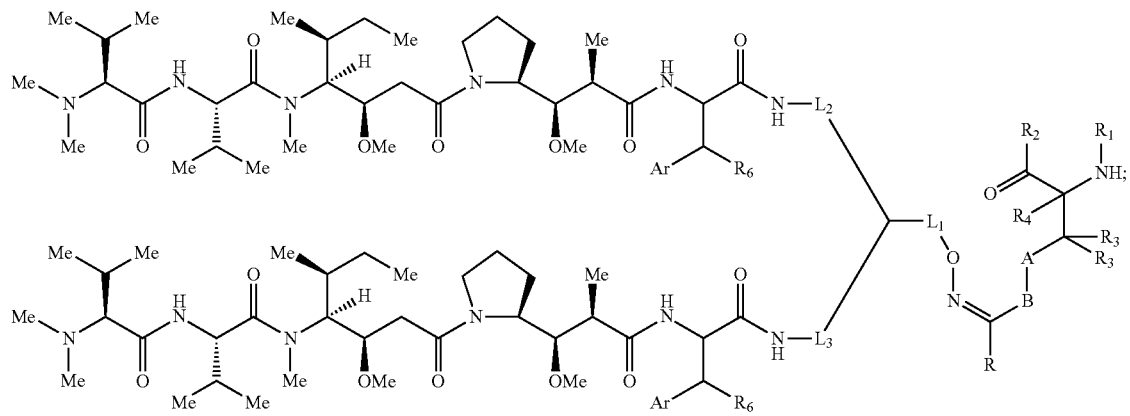
(XI)
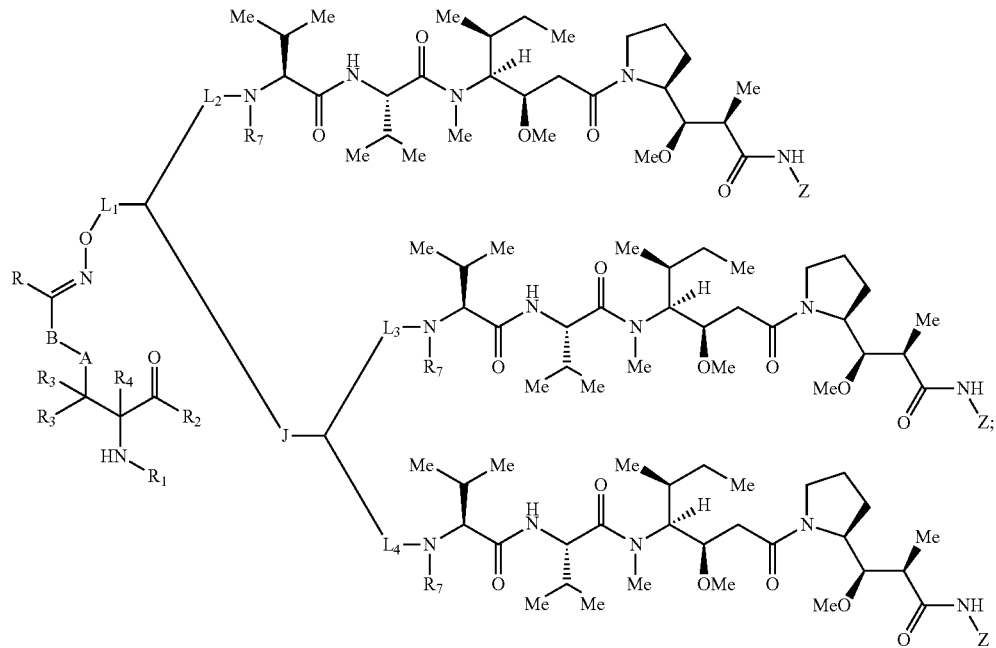
(XII)

-continued (XIII)

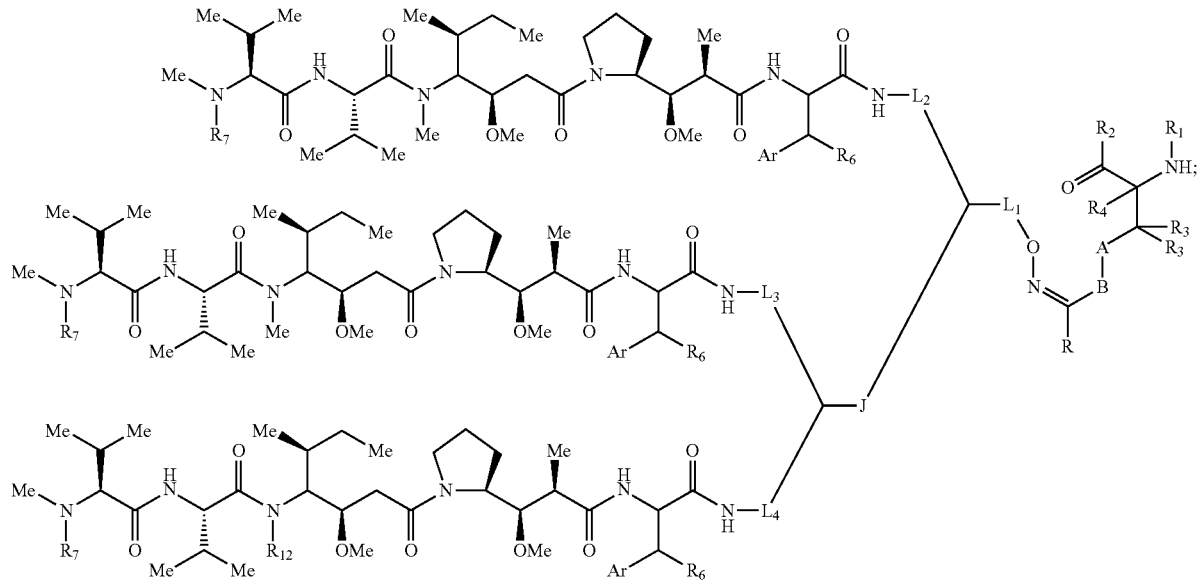

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is H, an amino protecting group, resin, at least one amino acid, polypeptide, or polynucleotide;

$R_2$ is OH, an ester protecting group, resin, at least one amino acid, polypeptide, or polynucleotide;

$R_3$ and $R_4$ are each independently H, halogen, lower alkyl, or substituted lower alkyl, or $R_3$ and $R_4$ or two $R_3$ groups optionally form a cycloalkyl or a heterocycloalkyl;

Z has the structure of:

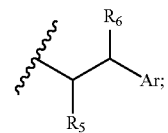

$R_5$ is H, CO$_2$H, C$_1$-C$_6$alkyl, or thiazole;
$R_6$ is OH or H;
Ar is phenyl or pyridine;
$R_7$ is C$_1$-C$_6$alkyl or hydrogen;
$L_1$, $L_2$, $L_3$, and $L_4$ are each linkers independently selected from the group consisting of a bond, -alkylene-, -(alkylene-O)$_n$-alkylene-J-, -alkylene'-J-(alkylene-O)$_n$-alkylene-, -J-(alkylene-O)$_n$-alkylene-, -(alkylene-O)$_n$-alkylene-J-(alkylene-O)$_n$'-alkylene-J'-, -(alkylene-O)$_n$-alkylene-J-alkylene'-, —W—, -alkylene-W—, alkylene'-J-(alkylene-NMe)$_n$-alkylene-W—, -J-(alkylene-NMe)$_n$-alkylene-W—, -J-alkylene-NMe-alkylene'-NMe-alkylene''-W—, and -alkylene-J-alkylene'-NMe-alkylene''-NMe-alkylene'''-W—;

W has the structure of:

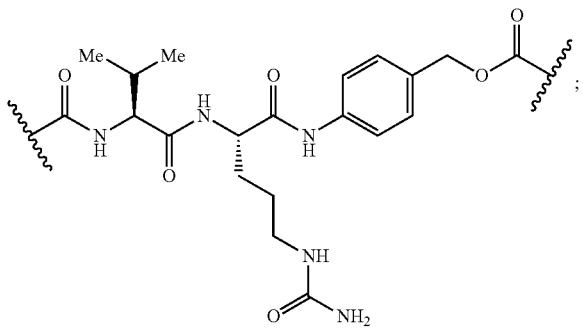 [SMILES: *C(=O)N[C@H](C(=O)N[C@@H](CCCNC(N)=O)C(=O)Nc1ccc(COC(*)=O)cc1)C(C)C]

each J and J' independently have the structure of:

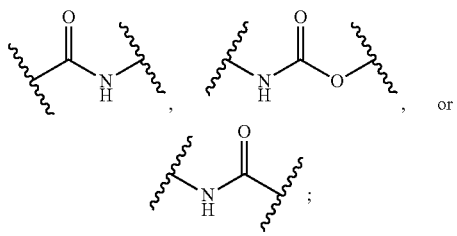

and
each n and n' are independently integers greater than or equal to one.

In certain embodiments of compounds of Formula (X), (XI), (XII) or (XIII), $R_5$ is thiazole or carboxylic acid. In certain embodiments of compounds of Formula (X), (XI), (XII) or (XIII), $R_6$ is H. In certain embodiments of compounds of Formula (X), (XI), (XII) or (XIII), Ar is phenyl. In certain embodiments of compounds of Formula (X), (XI), (XII) or (XIII), $R_7$ is methyl. In certain embodiments of compounds of Formula (X), (XI), (XII) or (XIII), n and n' are integers from 0 to 20. In certain embodiments of compounds of Formula (X), (XI), (XII) or (XIII), n and n' are integers from 0 to 10. In certain embodiments of compounds of Formula (X), (XI), (XII) or (XIII), n and n' are integers from 0 to 5.

In certain embodiments of compounds of Formula (X), (XI), (XII) or (XIII), $R_5$ is thiazole. In certain embodiments of compounds of Formula (X), (XI), (XII) or (XIII), $R_5$ is hydrogen. In certain embodiments of compounds of Formula (X), (XI), (XII) or (XIII), $R_5$ is methyl, ethyl, propyl, iso-propyl, butyl, iso-butyl, sec-butyl, tert-butyl, pentyl, or hexyl. In certain embodiments of compounds of Formula (X), (XI), (XII) or (XIII), $R_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$—CH—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$—. In certain embodiments of Formula (X), (XI), (XII) or (XIII), alkylene is methylene, ethylene, propylene, butylenes, pentylene, hexylene, or heptylene.

In certain embodiments of compounds of Formula (X), (XI), (XII) or (XIII), $R_5$ is —NH-(alkylene-O)$_n$—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (X), (XI), (XII) or (XIII), $R_6$ is H. In some embodiments of compounds of Formula (X), (XI), (XII) or (XIII), $R_6$ is hydroxy.

In certain embodiments of compounds of Formula (X), (XI), (XII) or (XIII), Ar is phenyl.

In certain embodiments of compounds of Formula (X), (XI), (XII) or (XIII), $R_7$ is methyl, ethyl, propyl, iso-propyl, butyl, sec-butyl iso-butyl, tert-butyl, pentyl, or hexyl. In certain embodiments of compounds of Formula (X), (XI), (XII) or (XIII), $R_7$ is hydrogen.

In certain embodiments of compounds of Formula (X), (XI), (XII) or (XIII), each $L_1$, $L_2$, $L_3$, and $L_4$ is independently a cleavable linker or non-cleavable linker. In certain embodiments of compounds of Formula (X), (XI), (XII) or (XIII), each $L_1$, $L_2$, $L_3$, and $L_4$ is independently a oligo(ethylene glycol) derivatized linker.

In certain embodiments of compounds of Formula (X), (XI), (XII) or (XIII), each alkylene, alkylene', alkylene'', and alkylene''' independently is —CH$_2$—, —CH$_2$CH$_2$—, —CH$_2$CH$_2$CH$_2$—, —CH$_2$CH$_2$CH$_2$, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, or —CH$_2$CH$_2$CH$_2$CH$_2$CH$_2$CH$_2$CH$_2$CH$_2$CH$_2$CH$_2$CH$_2$CH$_2$—. In certain embodiments of compounds of Formula (X), (XI), (XII) or (XIII), alkylene is methylene, ethylene, propylene, butylenes, pentylene, hexylene, or heptylene.

In certain embodiments of compounds of Formula (X), (XI), (XII) or (XIII), each n and n' independently is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (X), (XI), (XII) or (XIII), $R_1$ is a polypeptide. In certain embodiments of compounds of Formula (X), (XI), (XII) or (XIII), $R_2$ is a polypeptide. In certain embodiments of compounds of Formula (X), (XI), (XII) or (XIII), the polypeptide is an antibody. In certain embodiments of compounds of Formula (X), (XI), (XII) or (XIII), the antibody is herceptin.

In certain embodiments, compounds of Formula (X), (XI), (XII) or (XIII) are stable in aqueous solution for at least 1 month under mildly acidic conditions. In certain embodiments, compounds of Formula (X), (XI), (XII) or (XIII) are stable for at least 2 weeks under mildly acidic conditions. In certain embodiments, compound of Formula (X), (XI), (XII) or (XIII) are stable for at least 5 days under mildly acidic conditions. In certain embodiments, such acidic conditions are pH 2 to 8. Such non-natural amino acids may be in the form of a salt, or may be incorporated into a non-natural amino acid polypeptide, polymer, polysaccharide, or a polynucleotide and optionally post translationally modified.

Oxime-based non-natural amino acids may be synthesized by methods already described in the art, or by methods described herein, including: (a) reaction of a hydroxylamine-containing non-natural amino acid with a carbonyl- or dicarbonyl-containing reagent; (b) reaction of a carbonyl- or dicarbonyl-containing non-natural amino acid with a hydroxylamine-containing reagent; or (c) reaction of an oxime-containing non-natural amino acid with certain carbonyl- or dicarbonyl-containing reagents.

B. Chemical Structure and Synthesis of Non-Natural Amino Acid Linked Dolastatin Derivatives: Alkylated Aromatic Amine Linked Dolastatin Derivatives In one aspect are dolastatin linker derivatives for the chemical derivatization of non-natural amino acids based upon the reactivity of an aromatic amine group. In further or additional embodiments, at least one of the aforementioned non-natural amino acids is incorporated into a dolastatin linker derivative, that is, such embodiments are non-natural amino acid linked dolastatin derivatives. In further or additional embodiments, the dolastatin linker derivatives are functionalized on their sidechains such that their reaction with a derivatizing non-natural amino acid generates an amine linkage. In further or additional embodiments, the dolastatin linker derivatives are selected from dolastatin linker derivatives having aromatic amine sidechains. In further or additional embodiments, the dolastatin linker derivatives comprise a masked sidechain, including a masked aromatic amine group. In further or additional embodiments, the non-natural amino acids are selected from amino acids having aromatic amine sidechains. In further or additional embodiments, the non-natural amino acids comprise a masked sidechain, including a masked aromatic amine group.

In another aspect are carbonyl-substituted dolastatin linker derivatives such as, by way of example, aldehydes, and ketones, for the production of derivatized non-natural amino acid polypeptides based upon an amine linkage. In a further embodiment are aldehyde-substituted dolastatin linker derivatives used to derivatize aromatic amine-containing non-natural amino acid polypeptides via the formation of an amine linkage between the derivatizing dolastatin linker and the aromatic amine-containing non-natural amino acid polypeptide.

In further or additional embodiments, the non-natural amino acids comprise aromatic amine sidechains where the aromatic amine is selected from an aryl amine or a heteroaryl amine. In a further or additional embodiment, the non-natural amino acids resemble a natural amino acid in structure but contain aromatic amine groups. In another or further embodiment the non-natural amino acids resemble phenylalanine or tyrosine (aromatic amino acids). In one embodiment, the non-natural amino acids have properties that are distinct from those of the natural amino acids. In one embodiment, such distinct properties are the chemical reactivity of the sidechain; in a further embodiment this distinct chemical reactivity permits the sidechain of the non-natural amino acid to undergo a reaction while being a unit of a polypeptide even though the sidechains of the naturally-occurring amino acid units in the same polypeptide do not undergo the aforementioned reaction. In a further embodiment, the sidechain of the non-natural amino acid has a chemistry orthogonal to those of the naturally-occurring amino acids. In a further embodiment, the sidechain of the non-natural amino acid comprises a nucleophile-containing moiety; in a further embodiment, the nucleophile-containing moiety on the sidechain of the non-natural amino acid can undergo a reaction to generate an amine-linked derivatized dolastatin. In a further embodiment, the sidechain of the non-natural amino acid comprises an electrophile-containing moiety; in a further embodiment, the electrophile-containing moiety on the sidechain of the non-natural amino acid can undergo nucleophilic attack to generate an amine-linked derivatized dolastatin. In any of the aforementioned embodiments in this paragraph, the non-natural amino acid may exist as a separate molecule or may be incorporated into a polypeptide of any length; if the latter, then the polypeptide may further incorporate naturally-occurring or non-natural amino acids.

Modification of non-natural amino acids described herein using reductive alkylation or reductive amination reactions have any or all of the following advantages. First, aromatic amines can be reductively alkylated with carbonyl-containing compounds, including aldehydes, and ketones, in a pH range of about 4 to about 10 (and in certain embodiments in a pH range of about 4 to about 7) to generate substituted amine, including secondary and tertiary amine, linkages. Second, under these reaction conditions the chemistry is selective for non-natural amino acids as the sidechains of naturally occurring amino acids are unreactive. This allows for site-specific derivatization of polypeptides which have incorporated non-natural amino acids containing aromatic amine moieties or protected aldehyde moieties, including, by way of example, recombinant proteins. Such derivatized polypeptides and proteins can thereby be prepared as defined homogeneous products. Third, the mild conditions needed to effect the reaction of an aromatic amine moiety on an amino acid, which has been incorporated into a polypeptide, with an aldehyde-containing reagent generally do not irreversibly destroy the tertiary structure of the polypeptide (excepting, of course, where the purpose of the reaction is to destroy such tertiary structure). Similarly, the mild conditions needed to effect the reaction of an aldehyde moiety on an amino acid, which has been to incorporated into a polypeptide and deprotected, with an aromatic amine-containing reagent generally do not irreversibly destroy the tertiary structure of the polypeptide (excepting, of course, where the purpose of the reaction is to destroy such tertiary structure). Fourth, the reaction occurs rapidly at room temperature, which allows the use of many types of polypeptides or reagents that would otherwise be unstable at higher temperatures. Fifth, the reaction occurs readily is aqueous conditions, again allowing use of polypeptides and reagents incompatible (to any extent) with non-aqueous solutions. Six, the reaction occurs readily even when the ratio of polypeptide or amino acid to reagent is stoichiometric, stoichiometric-like, or near-stoichiometric, so that it is unnecessary to add excess reagent or polypeptide to obtain a useful amount of reaction product. Seventh, the resulting amine can be produced regioselectively and/or regiospecifically, depending upon the design of the amine and carbonyl portions of the reactants. Finally, the reductive alkylation of aromatic amines with aldehyde-containing reagents, and the reductive amination of aldehydes with aromatic amine containing reagents, generates amine, including secondary and tertiary amine, linkages which are stable under biological conditions.

Non-natural amino acids with nucleophilic reactive groups, such as, by way of example only, an aromatic amine group (including secondary and tertiary amine groups), a masked aromatic amine group (which can be readily converted into a aromatic amine group), or a protected aromatic amine group (which has reactivity similar to a aromatic amine group upon deprotection) allow for a variety of reactions to link molecules via various reactions, including but not limited to, reductive alkylation reactions with aldehyde containing dolastatin linked derivatives. Such alkylated non-natural amino acid linked dolastatin derivatives include amino acids having the structure of Formula (XXV), (XXVI), (XXVII), (XXVIII), (XXIX), or (XXX):

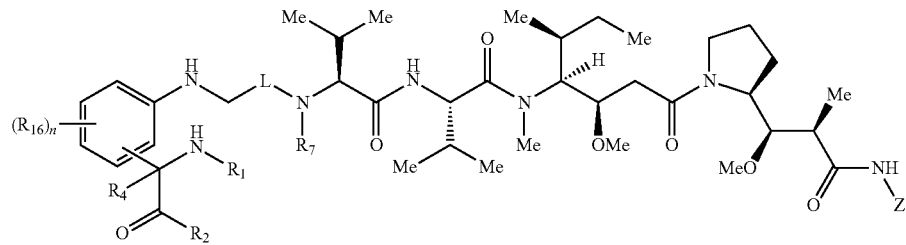
(XXV)
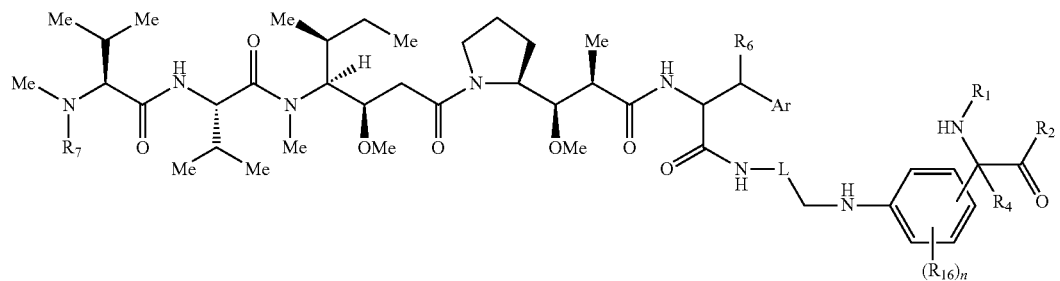
(XXVI)
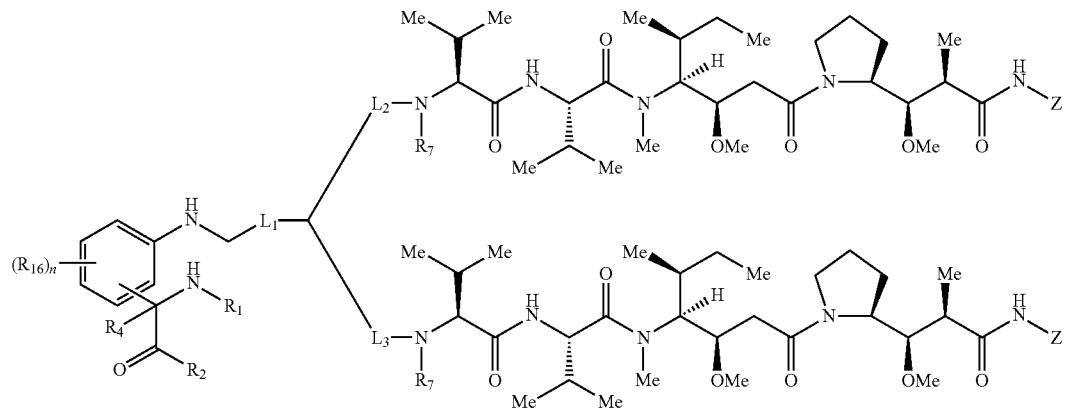
(XXVII)
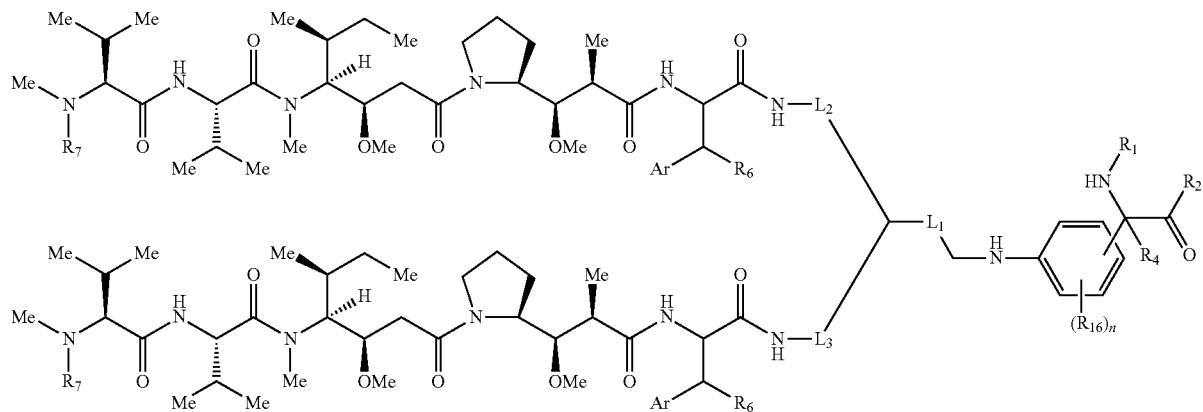
(XXVIII)

-continued (XXIX)

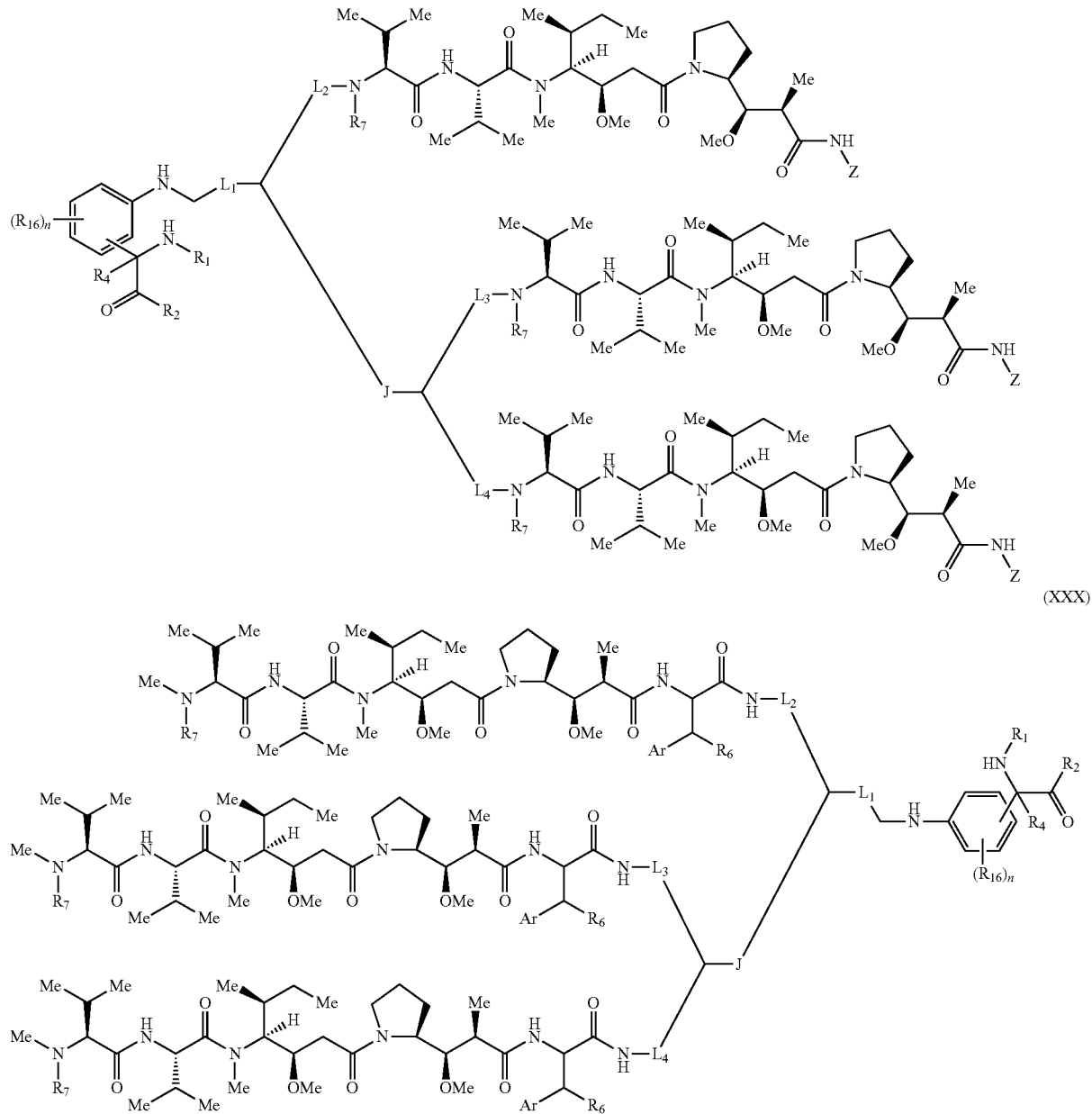

(XXX)

wherein:
Z has the structure of:

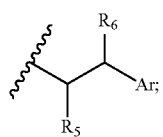

$R_5$ is H, $CO_2H$, $C_1$-$C_6$alkyl, or thiazole;
$R_6$ is OH or H;
Ar is phenyl or pyridine;
$R_1$ is H, an amino protecting group, resin, at least one amino acid, polypeptide, or polynucleotide;
$R_2$ is OH, an ester protecting group, resin, at least one amino acid, polypeptide, or polynucleotide;
$R_4$ is H, halogen, lower alkyl, or substituted lower alkyl;
$R_7$ is $C_1$-$C_6$alkyl or hydrogen;
L, $L_1$, $L_2$, $L_3$, and $L_4$ are each linkers selected from the group consisting of a bond, -alkylene-, -alkylene-C(O)—, -(alkylene-O)-alkylene-, -(alkylene-O)$_n$-alkylene-C(O)—, -(alkylene-O)—$(CH_2)_{n'}$—NHC(O)—$(CH_2)_{n''}$—$C(Me)_2$-S—S—$(CH_2)_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-J-, -alkylene'-J-(alkylene-O)$_n$-alkylene-, -(alkylene-O)$_n$-alkylene-J-alkylene', -J-(alkylene-O)$_n$-alkylene-, -(alkylene-O)$_n$-alkylene-J-(alkylene-O)$_n$-alkylene-J'—, —W—, -alkylene-W—, alkylene'-J-(alkylene- NMe)$_n$-alkylene-W—, and J-(alkylene-NMe)-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene''-W—, and -alkylene-J-alkylene'-NMe-alkylene''-NMe-alkylene'''-W—;

W has the structure of:

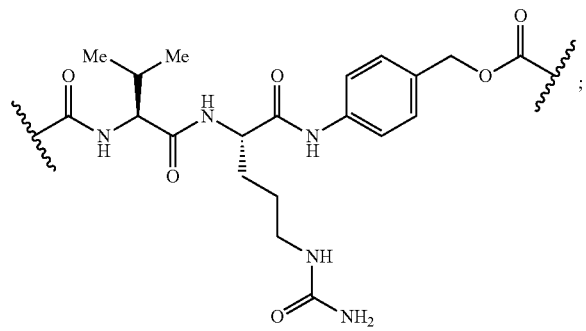 [SMILES: *C(=O)N[C@H](C(=O)N[C@@H](CCCNC(N)=O)C(=O)Nc1ccc(COC(*)=O)cc1)C(C)C]

U has the structure of:

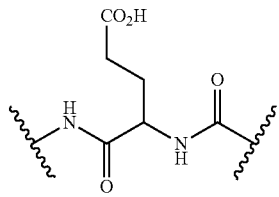 [SMILES: *NC(=O)C(CCC(=O)O)NC(*)=O]

each J and J' independently have the structure of:

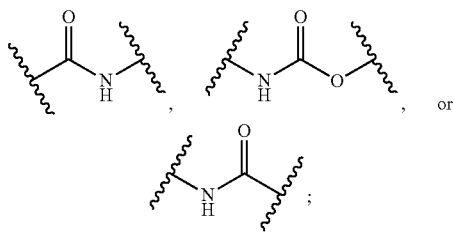

each n and n' are independently integers greater than or equal to one; and each $R_{16}$ is independently selected from the group consisting of hydrogen, halogen, alkyl, $NO_2$, CN, and substituted alkyl.

Such alkylated non-natural amino acid linked dolastatin derivatives may also be in the form of a salt, or may be incorporated into a non-natural amino acid polypeptide, polymer, polysaccharide, or a polynucleotide and optionally reductively alkylated.

In certain embodiments of compounds of Formula (XXV), (XXVI), (XXVII), (XXVIII), (XXIX), or (XXX), $R_5$ is thiazole or carboxylic acid. In certain embodiments of compounds of Formula (XXV), (XXVI), (XXVII), (XXVIII), (XXIX), or (XXX), $R_6$ is H. In certain embodiments of compounds of Formula (XXV), (XXVI), (XXVII), (XXVIII), (XXIX), or (XXX), Ar is phenyl. In certain embodiments of compounds of Formula (XXV), (XXVI), (XXVII), (XXVIII), (XXIX), or (XXX), $R_7$ is methyl. In certain embodiments of compounds of Formula (XXV), (XXVI), (XXVII), (XXVIII), (XXIX), or (XXX), n is an integer from 0 to 20. In certain embodiments of compounds of Formula (XXV), (XXVI), (XXVII), (XXVIII), (XXIX), or (XXX), n is an integer from 0 to 10. In certain embodiments of compounds of Formula (XXV), (XXVI), (XXVII), (XXVIII), (XXIX), or (XXX) or (XXIV), n is an integer from 0 to 5.

In certain embodiments of compounds of Formula (XXV), (XXVI), (XXVII), (XXVIII), (XXIX), or (XXX), $R_5$ is thiazole or carboxylic acid. In certain embodiments of compounds of Formula (XXV), (XXVI), (XXVII), (XXVIII), (XXIX), or (XXX), $R_5$ is hydrogen. In certain embodiments of compounds of Formula (XXV), (XXVI), (XXVII), (XXVIII), (XXIX), or (XXX), $R_5$ is methyl, ethyl, propyl, iso-propyl, butyl, iso-butyl, sec-butyl, tert-butyl, pentyl, or hexyl. In certain embodiments of compounds of Formula ((XXV), (XXVI), (XXVII), (XXVIII), (XXIX), or (XXX), $R_5$ is —NH-(alkylene-O)—$NH_2$, wherein alkylene is —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$—, —$CH_2CH_2CH_2CH_2CH_2CH_2CH_2CH_2CH_2CH_2$—, $CH_2CH_2CH_2CH_2CH_2CH_2CH_2CH_2CH_2CH_2CH_2$—, or —$CH_2CH_2CH_2CH_2CH_2CH_2CH_2CH_2CH_2CH_2CH_2CH_2$—.

In certain embodiments of Formula (XXV), (XXVI), (XXVII), (XXVIII), (XXIX), or (XXX), alkylene is methylene, ethylene, propylene, butylenes, pentylene, hexylene, or heptylene.

In certain embodiments of compounds of Formula (XXV), (XXVI), (XXVII), (XXVIII), (XXIX), or (XXX), $R_5$ is —NH-(alkylene-O)$_n$—$NH_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (XXV), (XXVI), (XXVII), (XXVIII), (XXIX), or (XXX), $R_6$ is H. In some embodiments of compounds of Formula (XXV), (XXVI), (XXVII), (XXVIII), (XXIX), or (XXX), $R_6$ is hydroxy.

In certain embodiments of compounds of Formula (XXV), (XXVI), (XXVII), (XXVIII), (XXIX), or (XXX), Ar is phenyl.

In certain embodiments of compounds of Formula (XXV), (XXVI), (XXVII), (XXVIII), (XXIX), or (XXX), $R_7$ is methyl, ethyl, propyl, iso-propyl, butyl, sec-butyl iso-butyl, tert-butyl, pentyl, or hexyl. In certain embodiments of compounds of Formula (XXV), (XXVI), (XXVII), (XXVIII), (XXIX), or (XXX), $R_7$ is hydrogen.

In certain embodiments of compounds of Formula (XXV), (XXVI), (XXVII), (XXVIII), (XXIX), or (XXX), each L, $L_1$, $L_2$, $L_3$, and $L_4$ is independently a cleavable linker or non-cleavable linker. In certain embodiments of compounds of Formula (XXV), (XXVI), (XXVII), (XXVIII), (XXIX), or (XXX), each L, $L_1$, $L_2$, $L_3$, and $L_4$ is independently a oligo(ethylene glycol) derivatized linker.

In certain embodiments of compounds of Formula (XXV), (XXVI), (XXVII), (XXVIII), (XXIX), or (XXX), each alkylene, alkylene', alkylene'', and alkylene''' independently is —$CH_2$—, —$CH_2CH_2$—, —$CH_2CH_2CH_2$—, —$CH_2CH_2CH_2CH_2$—, —$CH_2CH_2CH_2CH_2CH_2$—, —CH$_2$CH$_2$CH$_2$CH$_2$CH$_2$CH$_2$—,
—CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$CH$_2$—,
CH$_2$CH$_2$CH$_2$CH$_2$CH$_2$CH$_2$CH$_2$CH$_2$CH$_2$CH$_2$CH$_2$—, or
—CH$_2$CH$_2$CH$_2$CH$_2$CH$_2$CH$_2$CH$_2$CH$_2$CH$_2$CH$_2$CH$_2$CH$_2$—.

In certain embodiments of compounds of Formula (XIX), (XX), (XXI), (XXII), (XXIII) or (XXIV), alkylene is methylene, ethylene, propylene, butylenes, pentylene, hexylene, or heptylene.

In certain embodiments of compounds of Formula (XXV), (XXVI), (XXVII), (XXVIII), (XXIX), or (XXX), each n, n', n'', n''', and n'''' independently is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (XXV), (XXVI), (XXVII), (XXVIII), (XXIX), or (XXX), R$_1$ is a polypeptide. In certain embodiments of compounds of Formula (XXV), (XXVI), (XXVII), (XXVIII), (XXIX), or (XXX), R$_2$ is a polypeptide. In certain embodiments of compounds of Formula (XXV), (XXVI), (XXVII), (XXVIII), (XXIX), or (XXX), the polypeptide is an antibody. In certain embodiments of compounds of Formula (XXV), (XXVI), (XXVII), (XXVIII), (XXIX), or (XXX), the antibody is herceptin.

Compounds of Formula (XXV), (XXVI), (XXVII), (XXVIII), (XXIX), or (XXX) may be formed by the reductive alkylation of aromatic amine compounds with carbonyl containing reagents such as, by way of example, ketones, esters, thioesters, and aldehydes.

In some embodiments, the masked amine moieties of non-natural amino acids contained in polypeptides are initially reduced to give non-natural amino acids containing aromatic amine moieties incorporated into non-natural amino acid polypeptides. Such aromatic amine moieties are then reductive alkylated with carbonyl-containing reagents described above to give polypeptides containing non-natural amino acids of Formula (XXV), (XXVI), (XXVII), (XXVIII), (XXIX), or (XXX). Such reactions may also be applied to non-natural amino acids incorporated into synthetic polymers, polysaccharides, or polynucleotides. Additionally, such reactions may be applied to non-incorporated non-natural amino acids. By way of example the reducing agent used to reduce masked amine moieties includes, but is not limited to, TCEP, Na$_2$S, Na$_2$S$_2$O$_4$, LiAlH$_4$, B$_2$H$_6$, and NaBH$_4$. By way of example only, reductive alkylation may occur in aqueous buffers with a pH of about 4 to about 7 and using a mild reducing agent, such as, by way of example only, sodium cyanoborohydride (NaBCNH$_3$). In addition, other reducing agents may be used for reductive alkylation including, but not limited to, TCEP, Na$_2$S, Na$_2$S$_2$O$_4$, LiAlH$_4$, B$_2$H$_6$, and NaBH$_4$.

A non-limiting exemplary syntheses of non-natural amino acid polypeptides containing amino acids of Formula (XXV), (XXVI), (XXVII), (XXVIII), (XXIX), or (XXX) by reductive alkylation of secondary aromatic amine moieties, contained in non-natural amino acids, with carbonyl-containing reagents described above. Such reductive alkylations give polypeptides containing non-natural amino acids with tertiary aromatic amine moieties. Such reactions may also be applied to non-natural amino acids incorporated into synthetic polymers, polysaccharides, or polynucleotides. Additionally, such reactions may be applied to non-incorporated non-natural amino acids. By way of example only, reductive alkylation may occur in aqueous buffers with a pH of about 4 to about 7 and using a mild reducing agent, such as, by way of example only, sodium cyanoborohydride (NaBCNH$_3$). In addition, other reducing agents may be used for reductive alkylation including, but not limited to, TCEP, Na$_2$S, Na$_2$S$_2$O$_4$, LiAlH$_4$, B$_2$H$_6$, and NaBH$_4$.

C. Chemical Synthesis of Non-Natural Amino Acid Linked Dolastatin Derivatives: Heteroaryl-Containing Linked Dolastatin Derivatives In one aspect are non-natural amino acids for the chemical derivatization of dolastatin linked derivatives based upon the reactivity of a dicarbonyl group, including a group containing at least one ketone group, and/or at least one aldehyde groups, and/or at least one ester group, and/or at least one carboxylic acid, and/or at least one thioester group, and wherein the dicarbonyl group can be a 1,2-dicarbonyl group, a 1,3-dicarbonyl group, or a 1,4-dicarbonyl group. In further or additional aspects are non-natural amino acids for the chemical derivatization of dolastatin linked derivatives based upon the reactivity of a diamine group, including a hydrazine group, an amidine group, an imine group, a 1,1-diamine group, a 1,2-diamine group, a 1,3-diamine group, and a 1,4-diamine group. In further or additional embodiments, at least one of the aforementioned non-natural amino acids is incorporated into a dolastatin linked derivative, that is, such embodiments are non-natural amino acid linked dolastatin derivatives. In further or additional embodiments, the non-natural amino acids are functionalized on their sidechains such that their reaction with a derivatizing molecule generates a linkage, including a heterocyclic-based linkage, including a nitrogen-containing heterocycle, and/or an aldol-based linkage. In further or additional embodiments are non-natural amino acid polypeptides that can react with a derivatizing dolastatin linker to generate a non-natural amino acid linked dolastatin derivatives containing a linkage, including a heterocyclic-based linkage, including a nitrogen-containing heterocycle, and/or an aldol-based linkage. In further or additional embodiments, the non-natural amino acids are selected from amino acids having dicarbonyl and/or diamine sidechains. In further or additional embodiments, the non-natural amino acids comprise a masked sidechain, including a masked diamine group and/or a masked dicarbonyl group. In further or additional embodiments, the non-natural amino acids comprise a group selected from: keto-amine (i.e., a group containing both a ketone and an amine); keto-alkyne (i.e., a group containing both a ketone and an alkyne); and an ene-dione (i.e., a group containing a dicarbonyl group and an alkene).

In further or additional embodiments, the non-natural amino acids comprise dicarbonyl sidechains where the carbonyl is selected from a ketone, an aldehyde, a carboxylic acid, or an ester, including a thioester. In another embodiment are non-natural amino acids containing a functional group that is capable of forming a heterocycle, including a nitrogen-containing heterocycle, upon treatment with an appropriately functionalized reagent. In a further or additional embodiment, the non-natural amino acids resemble a natural amino acid in structure but contain one of the aforementioned functional groups. In another or further embodiment the non-natural amino acids resemble phenylalanine or tyrosine (aromatic amino acids); while in a separate embodiment, the non-natural amino acids resemble alanine and leucine (hydrophobic amino acids). In one embodiment, the non-natural amino acids have properties that are distinct from those of the natural amino acids. In one embodiment, such distinct properties are the chemical reactivity of the sidechain, in a further embodiment this distinct chemical reactivity permits the sidechain of the non-natural amino acid to undergo a reaction while being a unit of a polypeptide even though the sidechains of the naturally-occurring amino acid units in the same polypeptide do not undergo the aforementioned reaction. In a further embodiment, the sidechain of the non-natural amino acid has a chemistry orthogonal to those of the naturally-occurring amino acids. In a further embodiment, the sidechain of the non-natural amino acid comprises an electrophile-containing moiety; in a further embodiment, the electrophile-containing moiety on the sidechain of the non-natural amino acid can undergo nucleophilic attack to generate a heterocycle-derivatized protein, including a nitrogen-containing heterocycle-derivatized protein. In any of the aforementioned embodiments in this paragraph, the non-natural amino acid may exist as a separate molecule or may be incorporated into a polypeptide of any length; if the latter, then the polypeptide may further incorporate naturally-occurring or non-natural amino acids.

In another aspect are diamine-substituted molecules, wherein the diamine group is selected from a hydrazine, an amidine, an imine, a 1,1-diamine, a 1,2-diamine, a 1,3-diamine and a 1,4-diamine group, for the production of derivatized non-natural amino acid linked dolastatin derivatives based upon a heterocycle, including a nitrogen-containing heterocycle, linkage. In a further embodiment are diamine-substituted dolastatin derivatives used to derivatize dicarbonyl-containing non-natural amino acid polypeptides via the formation of a heterocycle, including a nitrogen-containing heterocycle, linkage between the derivatizing molecule and the dicarbonyl-containing non-natural amino acid polypeptide. In further embodiments the aforementioned dicarbonyl-containing non-natural amino acid polypeptides are diketone-containing non-natural amino acid polypeptides. In further or additional embodiments, the dicarbonyl-containing non-natural amino acids comprise sidechains where the carbonyl is selected from a ketone, an aldehyde, a carboxylic acid, or an ester, including a thioester. In further or additional embodiments, the diamine-substituted molecules comprise a group selected from a desired functionality. In a further embodiment, the sidechain of the non-natural amino acid has a chemistry orthogonal to those of the naturally-occurring amino acids that allows the non-natural amino acid to react selectively with the diamine-substituted molecules. In a further embodiment, the sidechain of the non-natural amino acid comprises an electrophile-containing moiety that reacts selectively with the diamine-containing molecule; in a further embodiment, the electrophile-containing moiety on the sidechain of the non-natural amino acid can undergo nucleophilic attack to generate a heterocycle-derivatized protein, including a nitrogen-containing heterocycle-derivatized protein. In a further aspect related to the embodiments described in this paragraph are the modified non-natural amino acid polypeptides that result from the reaction of the derivatizing molecule with the non-natural amino acid polypeptides. Further embodiments include any further modifications of the already modified non-natural amino acid polypeptides.

In another aspect are dicarbonyl-substituted molecules for the production of derivatized non-natural amino acid polypeptides based upon a heterocycle, including a nitrogen-containing heterocycle, linkage. In a further embodiment are dicarbonyl-substituted molecules used to derivatize diamine-containing non-natural amino acid polypeptides via the formation of a heterocycle, including a nitrogen-containing heterocycle group. In a further embodiment are dicarbonyl-substituted molecules that can form such heterocycle, including a nitrogen-containing heterocycle groups with a diamine-containing non-natural amino acid polypeptide in a pH range between about 4 and about 8. In a further embodiment are dicarbonyl-substituted molecules used to derivatize diamine-containing non-natural amino acid polypeptides via the formation of a heterocycle, including a nitrogen-containing heterocycle, linkage between the derivatizing molecule and the diamine-containing non-natural amino acid polypeptides. In a further embodiment the dicarbonyl-substituted molecules are diketone-substituted molecules, in other aspects ketoaldehyde-substituted molecules, in other aspects ketoacid-substituted molecules, in other aspects ketoester-substituted molecules, including ketothioester-substituted molecules. In further embodiments, the dicarbonyl-substituted molecules comprise a group selected from a desired functionality. In further or additional embodiments, the aldehyde-substituted molecules are aldehyde-substituted polyethylene glycol (PEG) molecules. In a further embodiment, the sidechain of the non-natural amino acid has a chemistry orthogonal to those of the naturally-occurring amino acids that allows the non-natural amino acid to react selectively with the carbonyl-substituted molecules. In a further embodiment, the sidechain of the non-natural amino acid comprises a moiety (e.g., diamine group) that reacts selectively with the dicarbonyl-containing molecule; in a further embodiment, the nucleophilic moiety on the sidechain of the non-natural amino acid can undergo electrophilic attack to generate a heterocyclic-derivatized protein, including a nitrogen-containing heterocycle-derivatized protein. In a further aspect related to the embodiments described in this paragraph are the modified non-natural amino acid polypeptides that result from the reaction of the derivatizing molecule with the non-natural amino acid polypeptides. Further embodiments include any further modifications of the already modified non-natural amino acid polypeptides.

In one aspect are methods to derivatize proteins via the reaction of carbonyl and hydrazine reactants to generate a heterocycle-derivatized protein, including a nitrogen-containing heterocycle-derivatized dolastatin. Included within this aspect are methods for the derivatization of dolastatin linker derivatives based upon the condensation of carbonyl- and hydrazine-containing reactants to generate a heterocycle-derivatized dolastatin, including a nitrogen-containing heterocycle-derivatized dolastatin. In additional or further embodiments are methods to derivatize ketone-containing dolastatin derivatives or aldehyde-containing dolastatin derivatives with hydrazine-functionalized non-natural amino acids. In yet additional or further aspects, the hydrazine-substituted molecule can include proteins, other polymers, and small molecules.

In another aspect are methods for the chemical synthesis of hydrazine-substituted molecules for the derivatization of carbonyl-substituted dolastatin derivatives. In one embodiment, the hydrazine-substituted molecule is a dolastatin linked derivative suitable for the derivatization of carbonyl-containing non-natural amino acid polypeptides, including by way of example only, ketone-, or aldehyde-containing non-natural amino acid polypeptides.

In one aspect are non-natural amino acids for the chemical derivatization of dolastatin analogs based upon a quinoxaline or phenazine linkage. In further or additional embodiments, the non-natural amino acids are functionalized on their sidechains such that their reaction with a derivatizing dolastatin linker generates a quinoxaline or phenazine linkage. In further or additional embodiments, the non-natural amino acids are selected from amino acids having 1,2-dicarbonyl or 1,2-aryldiamine sidechains. In further or additional embodiments, the non-natural amino acids are selected from amino acids having protected or masked 1,2-dicarbonyl or 1,2-aryldiamine sidechainis. Further included are equivalents to 1,2-dicarbonyl sidechains, or protected or masked equivalents to 1,2-dicarbonyl sidechains.

In another aspect are derivatizing molecules for the production of derivatized non-natural amino acid polypeptides based upon quinoxaline or phenazine linkages. In one embodiment are 1,2-dicarbonyl substituted dolastatin linker derivatives used to derivatize 1,2-aryldiamine containing non-natural amino acid polypeptides to form quinoxaline or phenazine linkages. In another embodiment are 1,2-aryldiamine substituted dolastatin linker derivatives used to derivatize 1,2-dicarbonyl containing non-natural amino acid polypeptides to form quinoxaline or phenazine linkages. In a further aspect related to the above embodiments are the modified non-natural amino acid polypeptides that result from the reaction of the derivatizing dolastatin linker with the non-natural amino acid polypeptides. In one embodiment are 1,2-aryldiamine containing non-natural amino acid polypeptides derivatized with 1,2-dicarbonyl substituted dolastatin linker derivative to form quinoxaline or phenazine linkages. In another embodiment are 1,2-dicarbonyl containing non-natural amino acid polypeptides derivatized with 1,2-aryldiamine substituted dolastatin linker derivatives to form quinoxaline or phenazine linkages.

Provided herein in certain embodiments are derivatizing molecules for the production of toxic compounds comprising non-natural amino acid polypeptides based upon triazole linkages. In some embodiments, the reaction between the first and second reactive groups can proceed via a dipolarophile reaction. In certain embodiments, the first reactive group can be an azide and the second reactive group can be an alkyne. In further or alternative embodiments, the first reactive group can be an alkyne and the second reactive group can be an azide. In some embodiments, the Huisgen cycloaddition reaction (see, e.g., Huisgen, in 1,3-DIPOLAR CYCLOADDITION CHEMISTRY, (ed. Padwa, A., 1984), p. 1-176) provides for the incorporation of non-naturally encoded amino acids bearing azide and alkyne-containing side chains permits the resultant polypeptides to be modified with extremely high selectivity. In certain embodiments, both the azide and the alkyne functional groups are inert toward the twenty common amino acids found in naturally-occurring polypeptides. When brought into close proximity, however, the "spring-loaded" nature of the azide and alkyne groups is revealed and they react selectively and efficiently via Huisgen [3 2]cycloaddition reaction to generate the corresponding triazole. See, e.g., Chin et al., Science 301: 964-7 (2003); Wang et al., J. Am. Chem. Soc., 125, 3192-3193 (2003); Chin et al., J. Am. Chem. Soc., 124:9026-9027 (2002). Cycloaddition reaction involving azide or alkyne-containing polypeptides can be carried out at room temperature under aqueous conditions by the addition of Cu(II) (e.g., in the form of a catalytic amount of $CuSO_4$) in the presence of a reducing agent for reducing Cu(II) to Cu(I), in situ, in catalytic amount. See, e.g., Wang et al., J. Am. Chem. Soc. 125, 3192-3193 (2003); Tornoe et al., J. Org. Chem. 67:3057-3064 (2002); Rostovtsev, Angew. Chem. Int. Ed. 41:2596-2599 (2002). Preferred reducing agents include ascorbate, metallic copper, quinine, hydroquinone, vitamin K, glutathione, cysteine, $Fe^2$, $Co^2$, and an applied electric potential.

Such non-natural amino acid heteroaryl-linked dolastatin derivatives include amino acids having the structure of Formula (XXXI), (XXXII), (XXXIII), (XXXIV), (XXXV), or (XXXVI):

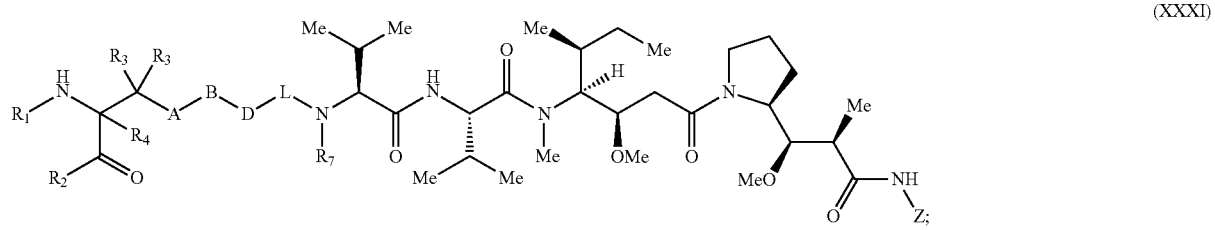

(XXXI)

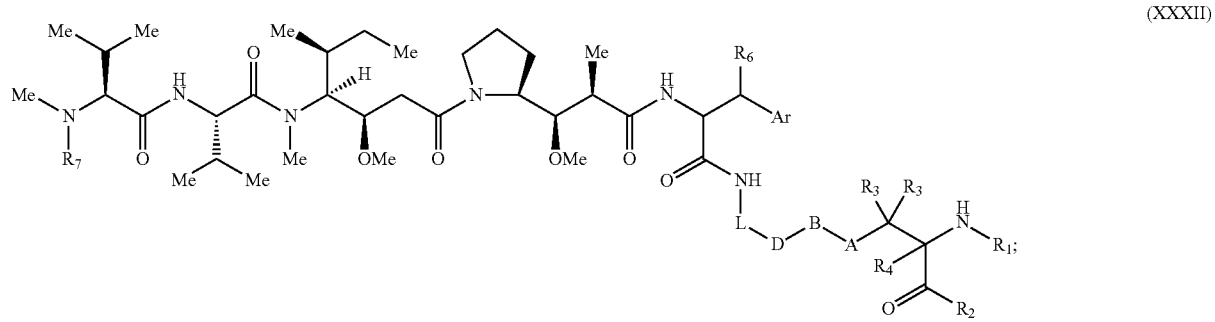

(XXXII)

(XXXIII)
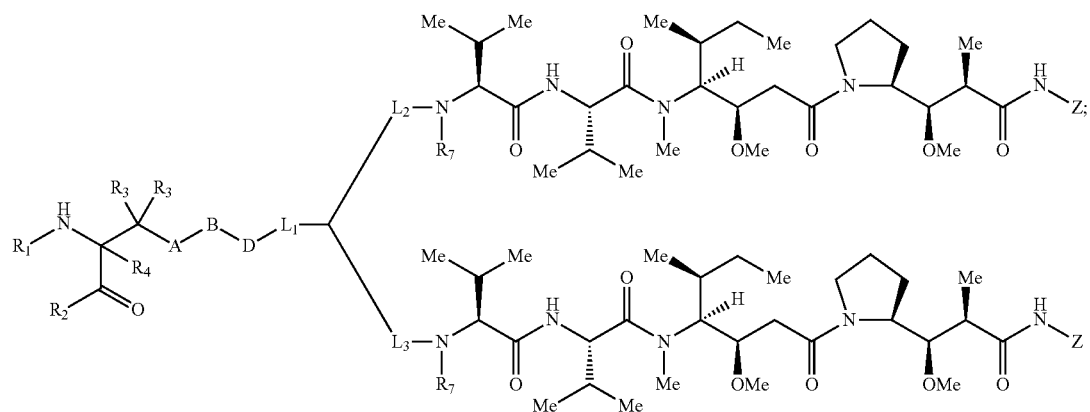
(XXXIII)
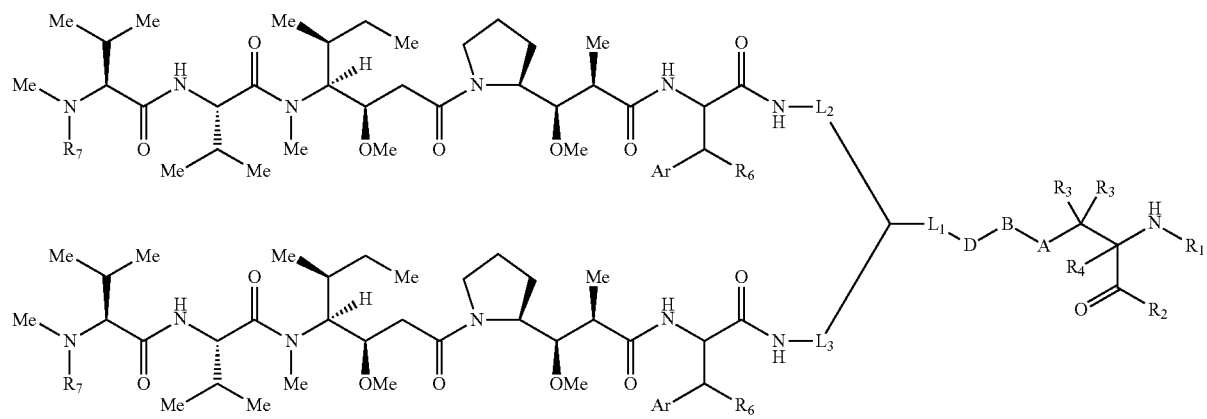
(XXXV)
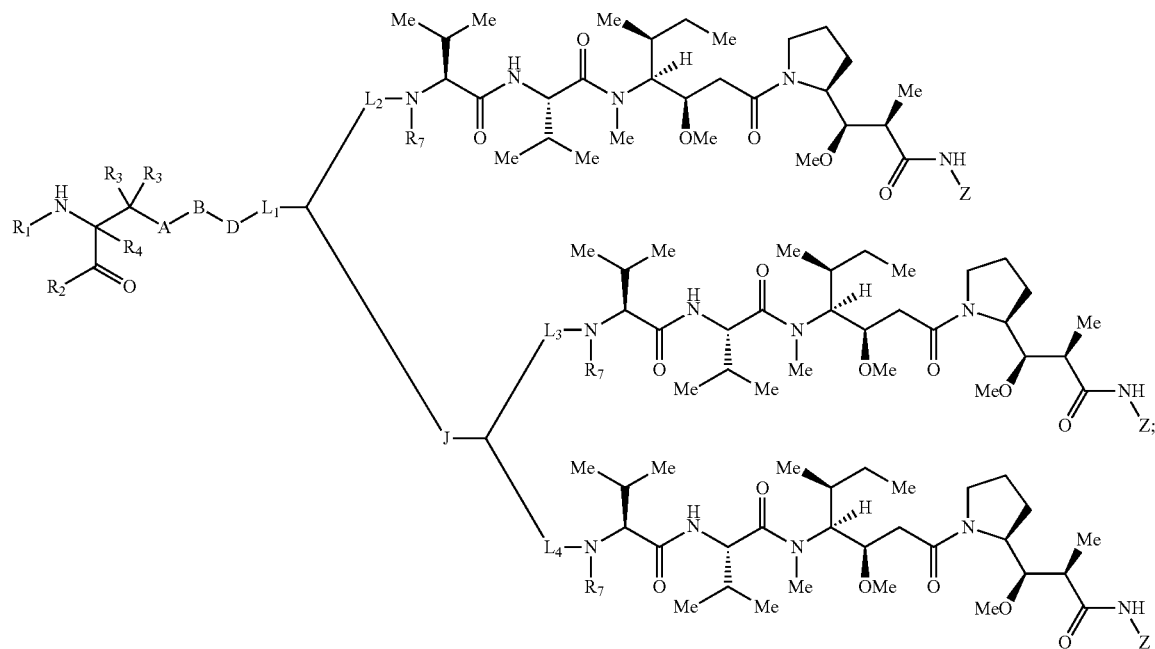

(XXXVI)

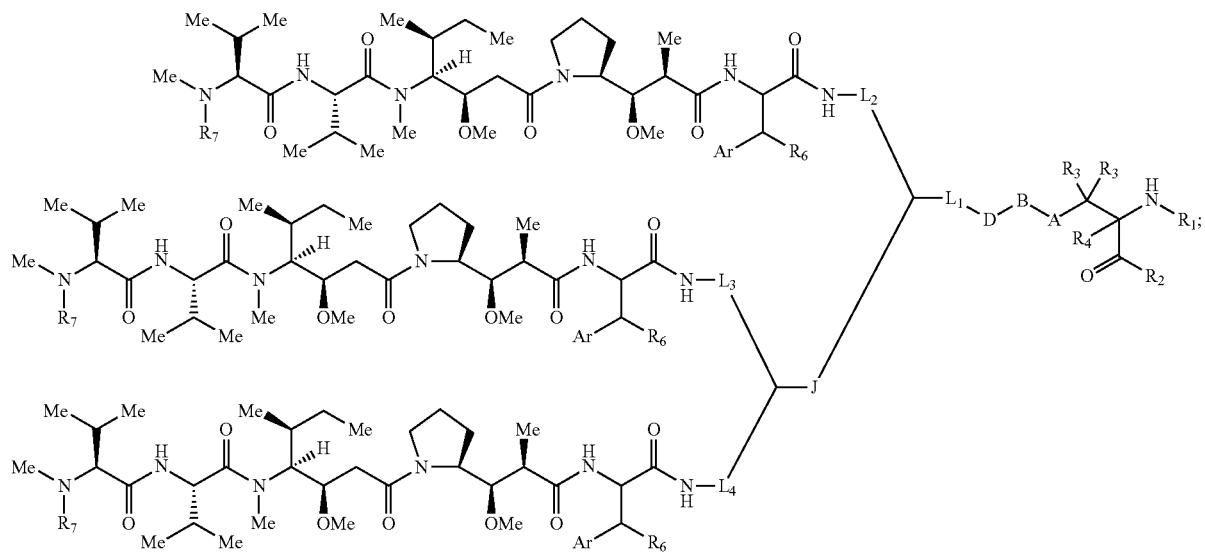

wherein:

Z has the structure of:

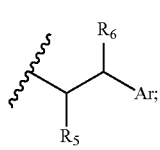

$R_5$ is H, $CO_2H$, $C_1$-$C_6$alkyl, or thiazole;

$R_6$ is OH or H;

Ar is phenyl or pyridine;

$R_1$ is H, an amino protecting group, resin, at least one amino acid, polypeptide, or polynucleotide;

$R_2$ is OH, an ester protecting group, resin, at least one amino acid, polypeptide, or polynucleotide;

$R_4$ is H, halogen, lower alkyl, or substituted lower alkyl;

$R_7$ is $C_1$-$C_6$alkyl or hydrogen;

L, $L_1$, $L_2$, $L_3$, and $L_4$ are each linkers selected from the group consisting of a bond, -alkylene-, -alkylene-C(O)—, -alkylene-J-, -(alkylene-O)$_n$-alkylene-, -(alkylene-O)$_n$-alkylene-C(O)—, -(alkylene-O)$_n$-J-, -(alkylene-O)$_n$-J-alkylene-, -(alkylene-O)$_n$—(CH$_2$)$_{n'}$—NHC(O)—CH$_2$)$_{n''}$—C(Me)$_2$-S—S—(CH$_2$)$_{n'''}$—NHC(O)-(alkylene-O)$_{n''''}$-alkylene-, -(alkylene)-O)$_n$-alkylene-W—, -alkylene-C(O)—W—, -(alkylene-O)$_n$-alkylene-J-, -alkylene'-J-(alkylene-O)$_n$-alkylene-, -(alkylene-O)$_n$-alkylene-J-alkylene', -J-(alkylene-O)$_n$-alkylene-, -(alkylene-O)$_n$-alkylene-J-(alkylene-O)$_n$-alkylene-J'-, —W—, -alkylene-W—, alkylene'-J-(alkylene-NMe)$_n$-alkylene-W—, -J-(alkylene-NMe)$_n$-alkylene-W—, -(alkylene-O)$_n$-alkylene-U-alkylene-C(O)—, -(alkylene-O)$_n$-alkylene-U-alkylene-; -J-alkylene-NMe-alkylene'-NMe-alkylene''-W—, and -alkylene-J-alkylene'-NMe-alkylene''-NMe-alkylene'''-W—;

W has the structure of:

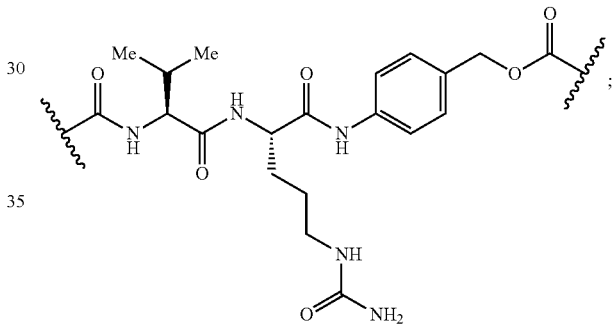

U has the structure of:

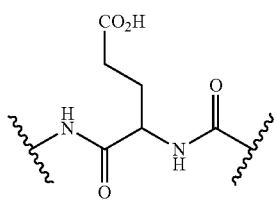 [SMILES: *NC(=O)C(CCC(=O)O)NC(*)=O]

each J and J' independently have the structure of:

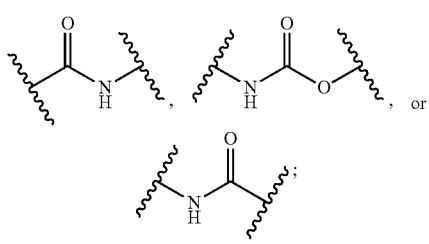

each n and n' are independently integers greater than or equal to one;

D has the structure of:

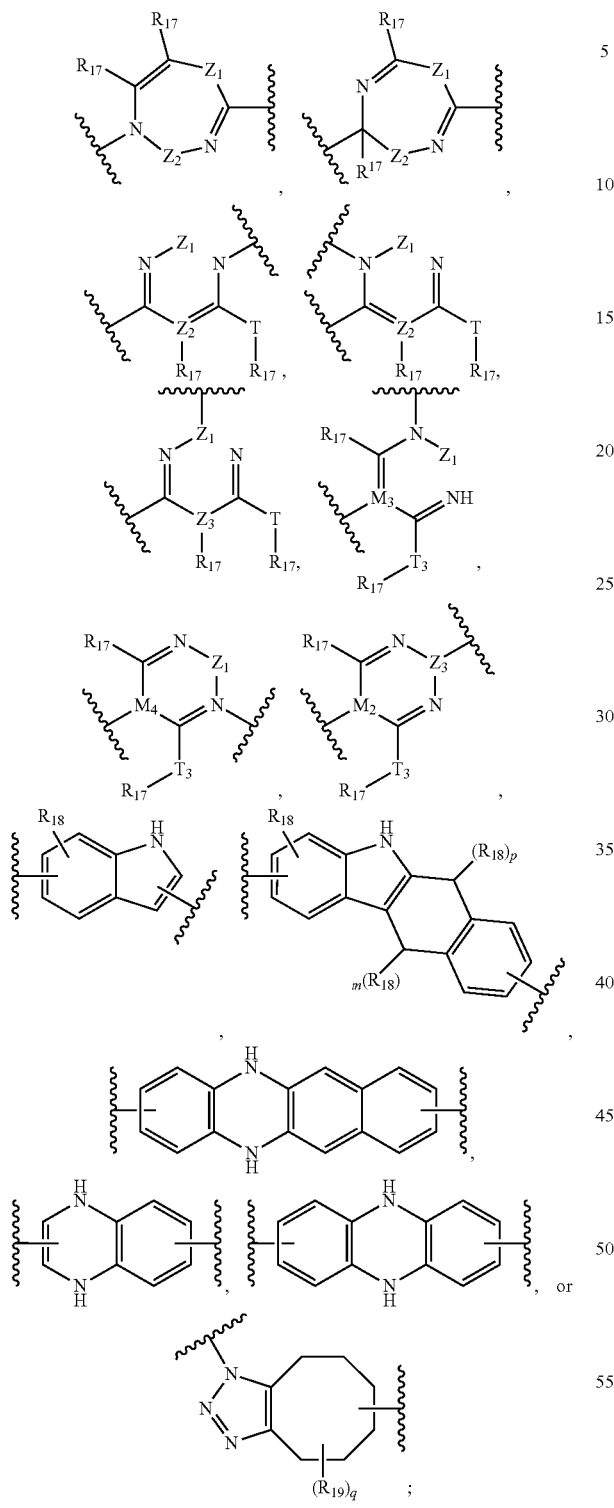

each $R_{17}$ is independently selected from the group consisting of H, alkyl, substituted alkyl, alkenyl, substituted alkenyl, alkynyl, substituted alkynyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, substituted aralkyl, -(alkylene or substituted alkylene)-ON(R")$_2$, -(alkylene or substituted alkylene)-C(O)SR", -(alkylene or substituted alkylene)-S—S-(aryl or substituted aryl), —C(O)R", —C(O)$_2$R", or —C(O)N(R")$_2$, wherein each R" is independently hydrogen, alkyl, substituted alkyl, alkenyl, substituted alkenyl, alkoxy, substituted alkoxy, aryl, substituted aryl, heteroaryl, alkaryl, substituted alkaryl, aralkyl, or substituted aralkyl;

each $Z_1$ is a bond, $CR_{17}R_{17}$, O, S, NR', $CR_{17}R_{17}$—$CR_{17}R_{17}$, $CR_{17}R_{17}$—O, O—$CR_{17}R_{17}$, $CR_{17}R_{17}$—S, S—$CR_{17}R_{17}$, $CR_{17}R_{17}$—NR', or NR'—$CR_{17}R_{17}$;

each R' is H, alkyl, or substituted alkyl;

each $Z_2$ is selected from the group consisting of a bond, —C(O)—, —C(S)—, optionally substituted $C_1$-$C_3$ alkylene, optionally substituted $C_1$-$C_3$ alkenylene, and optionally substituted heteroalkyl;

each $Z_3$ are independently selected from the group consisting of a bond, optionally substituted $C_1$-$C_4$ alkylene, optionally substituted $C_1$-$C_4$ alkenylene, optionally substituted heteroalkyl, —O—, —S—, —C(O)—, —C(S)—, and —N(R')—;

each $T_3$ is a bond, C(R")(R"), O, or S; with the proviso that when T is O or S, R" cannot be halogen;

each R" is H, halogen, alkyl, substituted alkyl, cycloalkyl, or substituted cycloalkyl;

m and p are 0, 1, 2, or 3, provided that at least one of m or p is not 0;

$M_2$ is

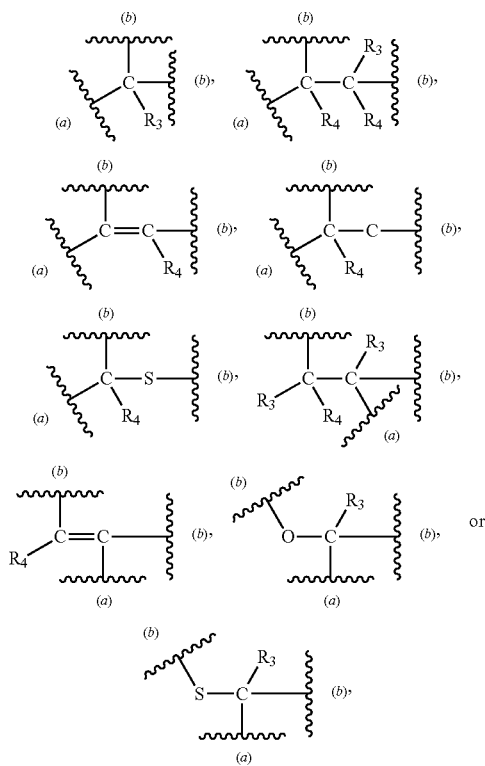

where (a) indicates bonding to the B group and (b) indicates bonding to respective positions within the heterocycle group;

$M_3$ is

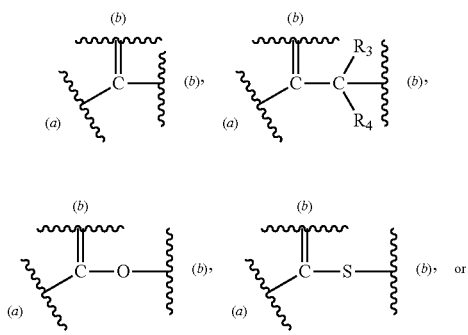

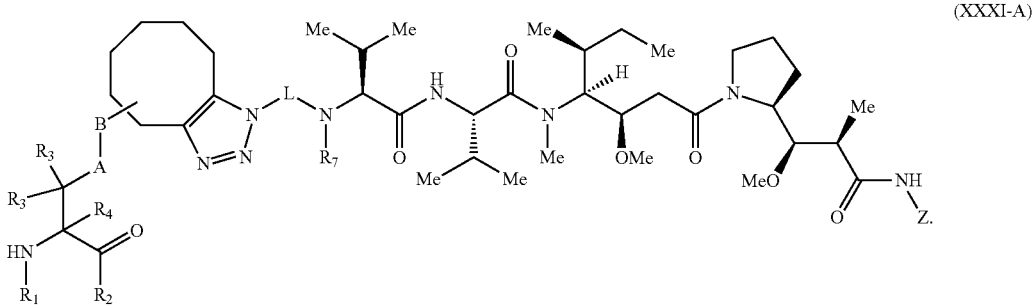

where (a) indicates bonding to the B group and (b) indicates bonding to respective positions within the heterocycle group;

each $R_{19}$ is independently selected from the group consisting of $C_1$-$C_6$ alkyl, $C_1$-$C_6$ alkoxy, ester, ether, thioether, aminoalkyl, halogen, alkyl ester, aryl ester, amide, aryl amide, alkyl halide, alkyl amine, alkyl sulfonic acid, alkyl nitro, thioester, sulfonyl ester, halosulfonyl, nitrile, alkyl nitrile, and nitro;

q is 0, 1, 2, 3, 4, 5, 6, 7, 8, 9, 10 or 11; and each $R_{16}$ is independently selected from the group consisting of hydrogen, halogen, alkyl, $NO_2$, CN, and substituted alkyl.

In some embodiments, the compound of Formula (XXXI) include compounds having the structure of Formula (XXXI-A):

(XXXI-A)

-continued

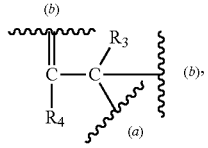

where (a) indicates bonding to the B group and (b) indicates bonding to respective positions within the heterocycle group;

$M_4$ is

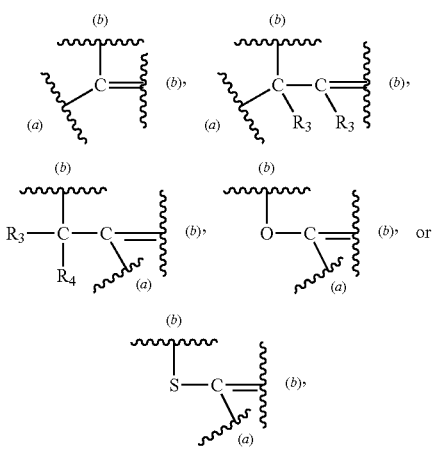

In certain embodiments of compounds of Formula (XXXI), (XXXII), (XXXIII), (XXXIV), (XXXV), or (XXXVI), $R_5$ is thiazole or carboxylic acid. In certain embodiments of compounds of Formula (XXXI), (XXXII), (XXIII), (XXXIV), (XXXV), or (XXXVI), $R_6$ is H. In certain embodiments of compounds of Formula (XXXI), (XXXII), (XXXIII), (XXXIV), (XXXV), or (XXXVI), Ar is phenyl. In certain embodiments of compounds of Formula (XXXI), (XXXII), (XXXIII), (XXXIV), (XXXV), or (XXXVI), $R_7$ is methyl. In certain embodiments of compounds of Formula (XXXI), (XXXII), (XXXIII), (XXXIV), (XXXV), or (XXXVI), n is an integer from 0 to 20. In certain embodiments of compounds of Formula (XXXI), (XXXII), (XXXIII), (XXXIV), (XXXV), or (XXXVI), n is an integer from 0 to 10. In certain embodiments of compounds of Formula (XXXI), (XXXII), (XXXIII), (XXXIV), (XXXV), or (XXXVI), n is an integer from 0 to 5.

In certain embodiments of compounds of Formula (XXXI), (XXXII), (XXXIII), (XXXIV), (XXXV), or (XXXVI), $R_5$ is thiazole or carboxylic acid. In certain embodiments of compounds of Formula (XXXI), (XXXII), (XXXIII), (XXXIV), (XXXV), or (XXXVI), $R_5$ is hydrogen. In certain embodiments of compounds of Formula (XXXI), (XXXII), (XXXIII), (XXXIV), (XXXV), or (XXXVI), $R_5$ is methyl, ethyl, propyl, iso-propyl, butyl, iso-butyl, sec-butyl, tert-butyl, pentyl, or hexyl. In certain embodiments of compounds of Formula (XXXI), (XXXII), (XXXIII), (XXXIV), (XXXV), or (XXXVI), $R_5$ is —NH-(alkylene-O)$_n$—NH$_2$, wherein alkylene is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$CH$_2$—, or
—CH$_2$CH$_2$CH$_2$CH$_2$CH$_2$CH$_2$CH$_2$CH$_2$CH$_2$CH$_2$CH$_2$—.

In certain embodiments of Formula (XXXI), (XXXII), (XXXIII), (XXXIV), (XXXV), or (XXXVI), alkylene is methylene, ethylene, propylene, butylenes, pentylene, hexylene, or heptylene.

In certain embodiments of compounds of Formula (XXXI), (XXXII), (XXXIII), (XXXIV), (XXXV), or (XXXVI), Rd$_5$ is —NH-(alkylene-O)—NH$_2$, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (XXXI), (XXXII), (XXXIII), (XXXIV), (XXXV), or (XXXVI), R$_6$ is H. In some embodiments of compounds of Formula (XXXI), (XXXII), (XXXIII), (XXXIV), (XXXV), or (XXXVI), R$_6$ is hydroxy.

In certain embodiments of compounds of Formula (XXXI), (XXXII), (XXXIII), (XXXIV), (XXXV), or (XXXVI), Ar is phenyl.

In certain embodiments of compounds of Formula (XXXI), (XXXII), (XXXIII), (XXXIV), (XXXV), or (XXXVI), R$_7$ is methyl, ethyl, propyl, iso-propyl, butyl, sec-butyl iso-butyl, tert-butyl, pentyl, or hexyl. In certain embodiments of compounds of Formula (XXXI), (XXXII), (XXXIII), (XXXIV), (XXXV), or (XXXVI), R$_7$ is hydrogen.

In certain embodiments of compounds of Formula (XXXI), (XXXII), (XXXIII), (XXXIV), (XXXV), or (XXXVI), each L, L$_1$, L$_2$, L$_3$, and L$_4$ is independently a cleavable linker or non-cleavable linker. In certain embodiments of compounds of Formula (XXXI), (XXXII), (XXXIII), (XXXIV), (XXXV), or (XXXVI), each L, L$_1$, L$_2$, L$_3$, and L$_4$ is independently a oligo(ethylene glycol) derivatized linker.

In certain embodiments of compounds of Formula (XXXI), (XXXII), (XXXIII), (XXXIV), (XXXV), or (XXXVI), each alkylene, alkylene', alkylene", and alkylene''' independently is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—,
—CH$_2$CH$_2$CH$_2$CH$_2$CH$_2$CH$_2$—,
—CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$—,
—CH$_2$CH$_2$CH$_2$CH$_2$CH$_2$CH$_2$CH$_2$CH$_2$CH$_2$CH$_2$—,
CH$_2$CH$_2$CH$_2$CH$_2$CH$_2$CH$_2$CH$_2$CH$_2$CH$_2$CH$_2$CH$_2$—, or
—CH$_2$CH$_2$CH$_2$CH$_2$CH$_2$CH$_2$CH$_2$CH$_2$CH$_2$CH$_2$CH$_2$CH$_2$—.

In certain embodiments of compounds of Formula (XXXI), (XXXII), (XXXII), (XXXIV), (XXXV), or (XXXVI), alkylene is methylene, ethylene, propylene, butylenes, pentylene, hexylene, or heptylene.

In certain embodiments of compounds of Formula (XXXI), (XXXII), (XXXIII), (XXXIV), (XXXV), or (XXXVI), each n, n', n", n''', and n'''' independently is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In certain embodiments of compounds of Formula (XXXI), (XXXII), (XXXIII), (XXXIV), (XXXV), or (XXXVI), R$_1$ is a polypeptide. In certain embodiments of compounds of Formula (XXXI), (XXXII), (XXXIII), (XXXIV), (XXXV), or (XXXVI), R$_2$ is a polypeptide. In certain embodiments of compounds of Formula (XXXI), (XXXII), (XXXIII), (XXXIV), (XXXV), or (XXXVI), the polypeptide is an antibody. In certain embodiments of compounds of Formula (XXXI), (XXXII), (XXXIII), (XXXIV), (XXXV), or (XXXVI), the antibody is αCD70.

Compounds of Formula (XXXI), (XXXII), (XXXIII), (XXXIV), (XXXV), or (XXXVI) may be formed by the reductive alkylation of aromatic amine compounds with carbonyl containing reagents such as, by way of example, ketones, esters, thioesters, and aldehydes.

The formation of such non-natural amino acid heterocycle-linked dolastatin derivatives having the structure of Formula (XXXI), (XXXII), (XXXIII), (XXXIV), (XXXV), or (XXXVI) includes, but is not limited to, (i) reactions of diamine-containing non-natural amino acids with dicarbonyl-containing dolastatin linked derivatives or reactions of diamine-containing non-natural amino acids with ketoalkyne-containing dolastatin linked derivatives, (ii) reactions of dicarbonyl-containing non-natural amino acids with either diamine-containing dolastatin linked derivatives or reactions of dicarbonyl-containing non-natural amino acids with ketoamine-containing dolastatin linked derivatives, (iii) reactions of ketoalkyne-containing non-natural amino acids with diamine-containing dolastatin linked derivatives, or (iv) reactions of ketoamine-containing non-natural amino acids with dicarbonyl-containing v.

Modification of dolastatin linked derivatives described herein with such reactions have any or all of the following advantages. First, diamines undergo condensation with dicarbonyl-containing compounds in a pH range of about 5 to about 8 (and in further embodiments in a pH range of about 4 to about 10, in other embodiments in a pH range of about 3 to about 8, in other embodiments in a pH range of about 4 to about 9, and in further embodiments a pH range of about 4 to about 9, in other embodiments a pH of about 4, and in yet another embodiment a pH of about 8) to generate heterocycle, including a nitrogen-containing heterocycle, linkages. Under these conditions, the sidechains of the naturally occurring amino acids are unreactive. Second, such selective chemistry makes possible the site-specific derivatization of recombinant proteins: derivatized proteins can now be prepared as defined homogeneous products. Third, the mild conditions needed to effect the reaction of the diamines described herein with the dicarbonyl-containing polypeptides described herein generally do not irreversibly destroy the tertiary structure of the polypeptide (excepting, of course, where the purpose of the reaction is to destroy such tertiary structure). Fourth, the reaction occurs rapidly at room temperature, which allows the use of many types of polypeptides or reagents that would be unstable at higher temperatures. Fifth, the reaction occurs readily is aqueous conditions, again allowing use of polypeptides and reagents incompatible (to any extent) with non-aqueous solutions. Six, the reaction occurs readily even when the ratio of polypeptide or amino acid to reagent is stoichiometric, near stoichiometric, or stoichiometric-like, so that it is unnecessary to add excess reagent or polypeptide to obtain a useful amount of reaction product. Seventh, the resulting heterocycle can be produced regioselectively and/or regiospecifically, depending upon the design of the diamine and dicarbonyl portions of the reactants. Finally, the condensation of diamines with dicarbonyl-containing molecules generates heterocycle, including a nitrogen-containing heterocycle, inkages which are stable under biological conditions.

VI. Location of Non-Natural Amino Acids in Dolastatin Linker Derivatives

The methods and compositions described herein include incorporation of one or more non-natural amino acids into a dolastatin linker derivative. One or more non-natural amino acids may be incorporated at one or more particular positions which do not disrupt activity of the dolastatin linker derivative. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the dolastatin linker derivative. In some embodiments, the non-natural amino acid is linked at the C-terminus of the dolastatin derivative. In other embodiments, the non-natural amino acid is linked at the N-terminus of the dolastatin derivative. Any position of the dolastatin linker derivative is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to a receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. Alternatively, the sites identified as critical to biological activity may also be good candidates for substitution with a non-natural amino acid, again depending on the desired activity sought for the polypeptide. Another alternative would be to simply make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, www.rcsb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained.

Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three dimensional crystal structure of a polypeptide with its associated ligand, receptor and/or binding proteins, a preference for conservative substitutions In one embodiment, the methods described herein include incorporating into the dolastatin linker derivative, where the dolastatin linker derivative comprises a first reactive group; and contacting the dolastatin linker derivative with a molecule (including but not limited to a second protein or polypeptide or polypeptide analog; an antibody or antibody fragment; and any combination thereof) that comprises a second reactive group. In certain embodiments, the first reactive group is a hydroxylamine moiety and the second reactive group is a carbonyl or dicarbonyl moiety, whereby an oxime linkage is formed. In certain embodiments, the first reactive group is a carbonyl or dicarbonyl moiety and the second reactive group is a hydroxylamine moiety, whereby an oxime linkage is formed. In certain embodiments, the first reactive group is a carbonyl or dicarbonyl moiety and the second reactive group is an oxime moiety, whereby an oxime exchange reaction occurs. In certain embodiments, the first reactive group is an oxime moiety and the second reactive group is carbonyl or dicarbonyl moiety, whereby an oxime exchange reaction occurs.

In some cases, the dolastatin linker derivative incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility (including but not limited to, when expressed in *E. coli* or other host cells) of the polypeptide. In some embodiments sites are selected for substitution with a naturally encoded or non-natural amino acid in addition to another site for incorporation of a non-natural amino acid for the purpose of increasing the polypeptide solubility following expression in *E. coli*, or other recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

VII. Anti-CD70 Expression and Ligand Interaction as Exemplar

The methods, compositions, strategies and techniques described herein are not limited to a particular type, class or family of polypeptides or proteins. Indeed, virtually any polypeptides may be designed or modified to include at least one "modified or unmodified" non-natural amino acids containing dolastatin linker derivative described herein. By way of example only, the polypeptide can be homologous to a therapeutic protein selected from the group consisting of: alpha-1 antitrypsin, angiostatin, antihemolytic factor, antibody, antibody fragment, monoclonal antibody (e.g., bevacizumab, cetuximab, panitumumab, infliximab, adalimumab, basiliximab, daclizumab, omalizumab, ustekinumab, etanercept, gemtuzumab, alemtuzumab, rituximab, trastuzumab, nimotuzumab, palivizumab, and abciximnab), apolipoprotein, apoprotein, atrial natriuretic factor, atrial natriuretic polypeptide, atrial peptide, C—X—C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, grf, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, pth, pyrogenic exotoxin A, pyrogenic exotoxin B, pyrogenic exotoxin C, pyy, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TOF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

Thus, the following description of an ARX-anti-CD70 ADC, anti-CD70-2H5-HA119-NCA, and CD70-2H5-HA119-NCA1 are provided for illustrative purposes and by way of non-limiting example of the scope of the methods, compositions, strategies and techniques described herein.

CD70-2H5-HA119-NCA1 is a humanized monoclonal antibody drug conjugate that interacts with the CD27 ligand which functions, by non-limiting example, by promoting cell survival and expansion of antigen primed CD8 T cells, formation of memory T cells and proliferation of B cells. CD70 receptors have been found in high densities in cancer tissue, for example 34000-189000 copies per cell (Caki-1, 786-O, L-428, UMRC3, LP-1, DBTRG-05 MG) (*Engineered anti-CD70 antibody-drug conjugate with increased therapeutic index, Molecular Cancer Therapeutics,* 2008) and in non-cancerous tissue and/or normal tissue the receptors are on 5%-15% of activated T cells and 10%-25% of activated B cells. CD70 expression has been found on ~40% of multiple myeloma isolates (*Preclinical Characterization of SGN-70, a Humanized Antibody Directed against CD70, Cancer Therapy: Preclinical,* 2008) and confirmed CD70 expression on a high percentage of, for example, Hodgkin lymphoma Reed-Steinberg cells, non-Hodgkin lymphoma, and renal cell carcinoma tumors. CD70 is a type II integral membrane protein of the TNF family. For purposes of this invention, it is possible for the αCD70 antibody to be any known CD70 antibody with one non-naturally encoded amino acid. For purposes of illustration, CD70-2H5-HA119-NCA1 antibodies are described in Table 1.

In one embodiment of the present invention, the antibody comprises an anti-CD70 constant region comprising SEQ ID NO: 3 with one non-naturally encoded amino acid. In another embodiment of the present invention, the antibody comprises an anti-CD70 constant region comprising SEQ ID NO: 4. In one embodiment of the present invention, the antibody comprises an anti-CD70 constant region comprising SEQ ID NO: 3 where one amino acid is a non-naturally encoded amino acid. In one embodiment of the present invention, the antibody comprises an anti-CD70 constant region comprising SEQ ID NO: 3 where the first amino acid is a non-naturally encoded amino acid. In one embodiment of the present invention, the antibody comprises an anti-CD70 constant region comprising SEQ ID NO: 4 where one amino acid is a non-naturally encoded amino acid. In one embodiment of the present invention, the antibody comprises an anti-CD70 constant region comprising SEQ ID NO: 4 where the first amino acid is a non-naturally encoded amino acid. In one embodiment of the present invention, the antibody comprises the αCD70 antibody with a variable heavy chain of SEQ ID NO: 1. In another embodiment of the present invention, the antibody comprises the αCD70 antibody with a variable heavy chain of SEQ ID NO: 10. In one embodiment of the present invention, the antibody comprises the αCD70 antibody with a variable light chain of SEQ ID NO: 2. In another embodiment of the present invention, the antibody comprises the αCD70 antibody with a variable light chain of SEQ ID NO: 11. In another embodiment of the present invention, the antibody comprises a heavy chain of SEQ ID NO. 1 and a light chain of SEQ ID NO. 2. In another embodiment of the present invention, the antibody comprises a heavy chain of SEQ ID NO. 10 and a light chain of SEQ ID NO. 11. In another embodiment of the present invention, the antibody comprises a heavy chain of SEQ ID NO. 1 and a light chain of SEQ ID NO. 2 and a constant region. In another embodiment of the present invention, the antibody comprises a heavy chain of SEQ ID NO. 10 and a light chain of SEQ ID NO. 11 and a constant region. In another embodiment of the present invention, the antibody comprises a heavy chain of SEQ ID NO. 10 and a light chain of SEQ ID NO. 11 and a constant region comprising SEQ ID NO.3. In another embodiment of the present invention, there is one non-naturally encoded amino acid in the anti-CD70 antibody sequence. In another embodiment of the present invention, there is more than one non-naturally encoded amino acid in the anti-CD70 antibody sequence. In another embodiment of the present invention, amino acid 119 of SEQ ID NO. 1 is substituted with a non-naturally encoded amino acid. In another embodiment of the present invention, amino acid 122 of SEQ ID NO. 10 is substituted with a non-naturally encoded amino acid. In another embodiment of the present invention, the antibody comprises a heavy chain of SEQ ID NO. 1 and a light chain of SEQ ID NO. 2 and a constant region comprising SEQ ID NO. 3. In other embodiments of the present invention, more than one non-naturally encoded amino acid is substituted into the anti-CD70 antibody. In other embodiments of the present invention, the αCD70 antibody comprises a heavy chain with 1, 2, 3, 4, 5, 6, 7, 8, 9, or 10 non-naturally encoded amino acids. In other embodiments of the present invention, the αCD70 antibody comprises SEQ ID NO. 4 and anti-CD70 variable regions provided in U.S. Published Patent Application 20100150950.

In other embodiments of the present invention, the antibody is an αCD70 antibody comprising an amino acid sequence with one or more non-naturally encoded amino acids and 90% homology to SEQ ID NO: 1. In other embodiments of the present invention, the antibody is an αCD70 antibody comprising an amino acid sequence with one or more non-naturally encoded amino acids and 90% homology to SEQ ID NO: 2. In other embodiments of the present invention, the antibody is an αCD70 antibody comprising an amino acid sequence with one or more non-naturally encoded amino acids and 90% homology to SEQ ID NO: 3. In other embodiments of the present invention, the antibody is an αCD70 antibody comprising an amino acid sequence with one or more non-naturally encoded amino acids and 95% homology to SEQ ID NO: 1. In other embodiments of the present invention, the antibody is an αCD70 antibody comprising an amino acid sequence with one or more non-naturally encoded amino acids and 95% homology to SEQ ID NO: 2. In other embodiments of the present invention, the antibody is an αCD70 antibody comprising an amino acid sequence with one or more non-naturally encoded amino acids and 95% homology to SEQ ID NO: 3. In other embodiments of the present invention, the antibody is an αCD70 antibody comprising an amino acid sequence with one or more non-naturally encoded amino acids and 96% homology to SEQ ID NO: 1. In other embodiments of the present invention, the antibody is an αCD70 antibody comprising an amino acid sequence with one or more non-naturally encoded amino acids and 96% homology to SEQ ID NO: 2. In other embodiments of the present invention, the antibody is an αCD70 antibody comprising an amino acid sequence with one or more non-naturally encoded amino acids and 96% homology to SEQ ID NO: 3. In other embodiments of the present invention, the antibody is an αCD70 antibody comprising an amino acid sequence with one or more non-naturally encoded amino acids and 97% homology to SEQ ID NO: 1. In other embodiments of the present invention, the antibody is an αCD70 antibody comprising an amino acid sequence with one or more non-naturally encoded amino acids and 97% homology to SEQ ID NO: 2. In other embodiments of the present invention, the antibody is an αCD70 antibody comprising an amino acid sequence with one or more non-naturally encoded amino acids and 97% homology to SEQ ID NO: 3. In other embodiments of the present invention, the antibody is an αCD70 antibody comprising an amino acid sequence with one or more non-naturally encoded amino acids and 98% homology to SEQ ID NO: 1. In other embodiments of the present invention, the antibody is an αCD70 antibody comprising an amino acid sequence with one or more non-naturally encoded amino acids and 98% homology to SEQ ID NO: 2. In other embodiments of the present invention, the antibody is an αCD70 antibody comprising an amino acid sequence with one or more non-naturally encoded amino acids and 98% homology to SEQ ID NO: 3. In other embodiments of the present invention, the antibody is an αCD70 antibody comprising an amino acid sequence a non-naturally encoded amino acids and 99% homology to SEQ ID NO: 1. In other embodiments of the present invention, the antibody is an αCD70 antibody comprising an amino acid sequence a non-naturally encoded amino acids and 99% homology to SEQ ID NO: 2. In other embodiments of the present invention, the antibody is an αCD70 antibody comprising an amino acid sequence a non-naturally encoded amino acids and 99% homology to SEQ ID NO: 3. Non-naturally encoded amino acid site selection is described within this specification, and as it specifically pertains to α-CD70 antibodies, sites were selected based on surface exposure/site accessibility within the antibody and hydrophobic/neutral amino acid sites were selected to maintain the charge on the antibody.

TABLE 1

ANTIBODY AMINO ACID AND NUCLEOTIDE SEQUENCES

| SEQ ID NO. | IDENTIFIER | SEQUENCE |
|---|---|---|
| 1 | Humanized 7F2 VH amino acid | EVQLVQSGAEVKKPGATVKISCKVSGYTFTDYYMNWVQQA PGKGLEWMGIINPYNGGTHYNQKFKGRVTITADTSTDTAYM ELSSLRSEDTAVYYCATSGYDLYFDYWGQGTLVTVSS* (Amber substitution at A119) |
| 2 | Humanized 7F2 VL amino acid | EIVMTQSPATLSVSPGERATLSCKASQNVGTAVAWYQQKPG QAPRLLIYSAFNRYNGIPARFSGSGPGTDFTLTISSLQSED FAVYYCQQYSTYPLTFGGGTKVEIK |

TABLE 1-continued

ANTIBODY AMINO ACID AND NUCLEOTIDE SEQUENCES

| SEQ ID NO. | IDENTIFIER | SEQUENCE |
|---|---|---|
| 3 | Constant Region, 234-236 mutations amino acid | STKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPPVAGGPSVFLFPP KPKDTLMISRTPEVTCVVVDVSHEDPEVKFNWYVDGVEVHN AKTKPREEQYNSTYRVVSVLTVLHQDWLNGKEYKCKVSNK ALPAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPG* |
| 4 | Constant Region, Wild Type amino acid | STKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPG |
| 5 | Humanized 7F2 Kappa amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC* |
| 6 | Humanized 7F2 VH nucleotide | GAGGTGCAGCTGGTTCAGTCTGGGGCCGAGGTGAAAAAGC CTGGGGCCACCGTGAAAATTTCTTGTAAAGTTTCTGGATAT ACCTTCACCGATTACTATATGAACTGGGTTCAGCAAGCCC CTGGAAAGGGACTGGAGTGGATGGGGATAATTAACCCATA TAACGGCGGCACCCACTATAACCAAAAGTTCAAGGGGAG GGTTACCATCACTGCAGACACCAGCACCGACACCGCTTAT ATGGAGCTGAGTAGCCTGAGGTCCGAGGATACTGCAGTTT ACTATTGTGCGACTTCCGGCTACGATCTGTACTTTGACTAC TGGGGCCAGGGAACCCTCGTTACCGTCTCCTCA |
| 7 | Humanized 7F2 VL nucleotide | GAAATTGTGATGACACAGTCTCCGGCCACCCTGTCTGTTTC TCCGGGGGAAAGAGCTACCCTGAGTTGCAAAGCCAGTCAG AACGTTGGGACCGCCGTTGCCTGGTACCAACAGAAACCTG GCCAGGCCCCCCGTCTCCTCATCTATTCCGCATTCAACAGG TATAACGGCATCCCAGCAAGGTTCTCCGGCAGTGGGCCAG GGACAGACTTCACTCTCACCATCAGCAGCCTGCAGAGCGA GGACTTCGCAGTTTATTATTGTCAGCAGTACAGTACCTACC CTCTCACTTTCGGAGGAGGCACTAAAGTTGAGATCAAA |
| 8 | 7F2 Constant Region, 234-236 mutations nucleotide | GCACCTCCCGTCGCCGGGGACCGTCAGTCTTCCTCTTCCC CCCAAAACCCAAGGACACCCTCATGATCTCCCGGACCCCT GAGGTCACATGCGTGGTGGTGGACGTGAGCCACGAAGACC CTGAGGTCAAGTTCAACTGGTACGTGGACGGCGTGGAGGT GCATAATGCCAAGACAAAGCCGCGGGAGGAGCAGTACAA CAGCACGTACCGTGTGGTCAGCGTCCTCACCGTCCTGCAC CAGGACTGGCTGAATGGCAAGGAGTACAAGTGCAAGGTCT CCAACAAAGCCCTCCCAGCCCCCATCGAGAAAACCATCTC CAAAGCCAAAGGGCAGCCCCGAGAACCACAGGTGTACAC CCTGCCCCCATCCCGGGATGAGCTGACCAAGAACCAGGTC AGCCTGACCTGCCTGGTCAAAGGCTTCTATCCCAGCGACA TCGCCGTGGAGTGGGAGAGCAATGGGCAGCCGGAGAACA ACTACAAGACCACGCCTCCCGTGCTGGACTCCGACGGCTC CTTCTTCCTCTACAGCAAGCTCACCGTGGACAAGAGCAGG TGGCAGCAGGGGAACGTCTTCTCATGCTCCGTGATGCATG AGGCTCTGCACAACCACTACACGCAGAAGAGCCTCTCCCT GTCTCCGGGTTGA |
| 9 | Humanized 7F2 Kappa nucleotide | CGTACGGTGGCTGCACCATCTGTCTTCATCTTCCCGCCATC TGATGAGCAGTTGAAATCTGGAACTGCCTCTGTTGTGTGCC TGCTGAATAACTTCTATCCCAGAGAGGCCAAAGTACAGTG GAAGGTGGATAACGCCCTCCAATCGGGTAACTCCCAGGAG AGTGTCACAGAGCAGGACAGCAAGGACAGCACCTACAGC CTCAGCAGCACCCTGACGCTGAGCAAAGCAGACTACGAGA AACACAAAGTCTACGCCTGCGAAGTCACCCATCAGGGCCT GAGCTCGCCCGTCACAAAGAGCTTCAACAGGGGAGAGTGT TGA |
| 10 | Humanized 8A1 VH amino acid | QVQLVQSGAEVKKPGSSVKVSCKASGYSFSDYYMNWVRQA PGQGLEWMGEINPTTGGATYNQKFKARVTITADESTSTAYM ELSSLRSEDTAVYYCARSLFPANYAGFVYWGQGTLVTVSS* (Amber substitution at A122) |

TABLE 1-continued

ANTIBODY AMINO ACID AND NUCLEOTIDE SEQUENCES

| SEQ ID NO. | IDENTIFIER | SEQUENCE |
|---|---|---|
| 11 | Humanized 8A1 VL amino acid | DIQMTQSPSSLSASVGDRVTITCSASSSVSYMYWYQQKPGKA PKLLIYDTSKLASGVPSRFSGSGSGTDYTFTISSLQPEDIAT YYCQQWSSYPWTFGQGTKVEIK |
| 12 | Humanized 8A1 Kappa amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC* |
| 13 | Humanized 8A1 VH nucleotide | CAGGTGCAGCTGGTTCAGTCTGGGGCCGAGGTGAAAAAGC CTGGGTCTTCTGTGAAAGTTTCTTGTAAAGCAAGTGGATAT TCTTTCAGTGATTACTATATGAACTGGGTTAGGCAGGCCCC TGGCCAAGGACTCGAGTGGATGGGGGAGATTAACCCAACC ACCGGCGGGGCAACCTATAACCAAAAGTTCAAAGCAAGG GTTACCATCACTGCTGACGAGAGCACTTCAACTGCTTATAT GGAGCTGAGCAGCCTGAGGTCCGAGGATACCGCAGTTTAC TATTGTGCGAGATCCCTCTTCCCTGCAAACTACGCAGGCTT CGTTTACTGGGGACAGGGAACCCTGGTCACCGTCTCCTCA |
| 14 | Humanized 8A1 VL nucleotide | GATATTCAGATGACACAGTCTCCGTCTTCTCTGTCTGCCAG TGTTGGGGATAGAGTTACCATTACCTGCAGTGCCAGTTCTA GTGTTTCCTACATGTACTGGTACCAACAGAAACCTGGCAA GGCCCCCAAACTCCTCATCTATGACACCTCCAAACTCGCA AGTGGCGTTCCATCCAGGTTCTCCGGCAGTGGGAGTGGGA CAGACTATACTTTCACCATCAGCAGCCTCCAGCCTGAGGA CATCGCAACCTATTATTGTCAGCAGTGGAGTAGCTACCCTT GGACTTTCGGACAGGGAACGAAAGTTGAGATCAAACGTAC GGTGGCTGCACCATCTGT |
| 15 | 8A1 Constant Region, 234-236 mutations nucleotide | TAGAGCACCAAGGGCCCATCGGTCTTCCCCCTGGCACCCT CCTCCAAGAGCACCTCTGGGGGCACAGCGGCCCTGGGCTG CCTGGTCAAGGACTACTTCCCCGAACCGGTGACGGTGTCG TGGAACTCAGGCGCCCTGACCAGCGGCGTGCACACCTTCC CGGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGGT GGACAAGAAAGTTGAGCCCAAATCTTGTGACAAAACTCAC ACATGCCCACCGTGCCCAGCACCTCCCGTCGCCGGGGAC CGTCAGTCTTCCTCTTCCCCCCAAAACCCAAGGACACCCTC ATGATCTCCCGGACCCCTGAGGTCACATGCGTGGTGGTGG ACGTGAGCCACGAAGACCCTGAGGTCAAGTTCAACTGGTA CGTGGACGGCGTGGAGGTGCATAATGCCAAGACAAAGCC GCGGGAGGAGCAGTACAACAGCACGTACCGTGTGGTCAG CGTCCTCACCGTCCTGCACCAGGACTGGCTGAATGGCAAG GAGTACAAGTGCAAGGTCTCCAACAAAGCCCTCCCAGCCC CCATCGAGAAAACCATCTCCAAAGCCAAAGGGCAGCCCCG AGAACCACAGGTGTACACCCTGCCCCCATCCCGGGATGAG CTGACCAAGAACCAGGTCAGCCTGACCTGCCTGGTCAAAG GCTTCTATCCCAGCGACATCGCCGTGGAGTGGGAGAGCAA TGGGCAGCCGGAGAACAACTACAAGACCACGCCTCCCGTG CTGGACTCCGACGGCTCCTTCTTCCTCTACAGCAAGCTCAC CGTGGACAAGAGCAGGTGGCAGCAGGGGAACGTCTTCTCA TGCTCCGTGATGCATGAGGCTCTGCACAACCACTACACGC AGAAGAGCCTCTCCCTGTCTCCGGGTTGA |
| 16 | Humanized 8A1 Kappa nucleotide | CTTCATCTTCCCGCCATCTGATGAGCAGTTGAAATCTGGAA CTGCCTCTGTTGTGTGCCTGCTGAATAACTTCTATCCCAGA GAGGCCAAAGTACAGTGGAAGGTGGATAACGCCCTCCAAT CGGGTAACTCCCAGGAGAGTGTCACAGAGCAGGACAGCA AGGACAGCACCTACAGCCTCAGCAGCACCCTGACGCTGAG CAAAGCAGACTACGAGAAACACAAAGTCTACGCCTGCGA AGTCACCCATCAGGGCCTGAGCTCGCCCGTCACAAAGAGC TTCAACAGGGGAGAGTGTTGA |
| 17 | ARX-anti-CD70 2H5 VH | QVQLVESGGGVVQPGRSLRLSCAASGFTFSSYIMHWVRQAP GKGLEWVAVISYDGRNKYYADSVKGRFTISRDNSKNTLYLQ MNSLRAEDTAVYYCARDTDGYDFDYWGQGTLVTVSS |
| 18 | ARX-anti-CD70 2H5 VL | EIVLTQSPATLSLSPGERATLSCRASQSVSSYLAWYQQKPGQ APRLLIYDASNRATGIPARFSGSGSGTDFTLTISSLEPEDFA VYYCQQRTNWPLTFGGGTKVEIK |

In one embodiment, the present invention provides an αCD70 antibody drug conjugate (ADC or an αCD70-ADC) wherein the antibody is an αCD70 comprising a light and heavy chain. In another embodiment of the present invention is provided an αCD70-ADC comprising a heavy chain (SEQ. ID. NO.: 1). In another embodiment of the present invention is provided an αCD70-ADC comprising a light (SEQ. ID. NO.: 2). In another embodiment of the present invention is provided an αCD70-ADC comprising a heavy chain (SEQ. ID. NO.: 10). In another embodiment of the present invention is provided an αCD70-ADC comprising a light (SEQ. ID. NO.: 11). In another embodiment of the present invention is provided an αCD70-ADC comprising a light (SEQ. ID. NO.: 2) and heavy chain (SEQ. ID. NO.: 1). In another embodiment of the present invention is provided an αCD70-ADC comprising a light (SEQ. ID. NO.: 11) and heavy chain (SEQ. ID. NO.: 10). In some embodiments of the present invention the constant region, SEQ ID NO. 3 or 4, has mutated any of the amino acid positions selected from the group 115, 116, 117. In some embodiments of the present invention, mutations are made to the antibody to inhibit ADCC function. In some embodiments of the present invention, the antibody comprises an αCD70 antibody with one or more non-naturally encoded amino acids. In another embodiment of the present invention, the antibody comprises an αCD70 antibody with one or more non-naturally encoded amino acids substituted at one or more positions of SEQ ID NO: 1. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 1. In another embodiment of the present invention, the antibody comprises an αCD70 antibody with one non-naturally encoded amino acid substituted at a position in SEQ ID NO: 1. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 1. In another embodiment of the present invention, the antibody comprises an αCD70 antibody with one or more non-naturally encoded amino acids substituted at one or more positions of SEQ ID NO: 2. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 2. In another embodiment of the present invention, the antibody comprises an αCD70 antibody with one non-naturally encoded amino acid substituted at a position in SEQ ID NO: 2. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 2.

In another embodiment of the present invention, the antibody comprises an αCD70 antibody with one or more non-naturally encoded amino acids substituted at one or more positions of SEQ ID NO: 3. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 3. In another embodiment of the present invention, the antibody comprises an αCD70 antibody with one non-naturally encoded amino acid substituted at a position in SEQ ID NO: 3. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 3.

In another embodiment of the present invention, the antibody comprises an αCD70 antibody with one or more non-naturally encoded amino acids substituted at one or more positions of SEQ ID NO: 10. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 10. In another embodiment of the present invention, the antibody comprises an αCD70 antibody with one non-naturally encoded amino acid substituted at a position in SEQ ID NO: 10. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 10.

In another embodiment of the present invention, the antibody comprises an αCD70 antibody with one or more non-naturally encoded amino acids substituted at one or more positions of SEQ ID NO: 11. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 11. In another embodiment of the present invention, the antibody comprises an αCD70 antibody with one non-naturally encoded amino acid substituted at a position in SEQ ID NO: 11. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 11.

In another embodiment of the present invention, the antibody comprises an αCD70 antibody with one or more non-naturally encoded amino acids substituted at one or more positions of SEQ ID NO: 4. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 4. In another embodiment of the present invention, the antibody comprises an αCD70 antibody with one non-naturally encoded amino acid substituted at a position in SEQ ID NO: 4. In another embodiment of the present invention, the antibody comprises an αCD70 antibody with one non-naturally encoded amino acids substituted at 1, 2, 3, 4, 5, 6, 7, 8, 9, or 10 positions of SEQ ID NO: 4.

In another embodiment of the present invention, the antibody comprises an αCD70 antibody with one or more non-naturally encoded amino acids substituted at 1, 2, 3, 4, or 5 positions of SEQ ID NO: 1. In another embodiment of the present invention, the antibody comprises an αCD70 antibody with one or more non-naturally encoded amino acids substituted at 1, 2, or 3 positions of SEQ ID NO: 1. In another embodiment of the present invention, the antibody comprises an αCD70 antibody with one or more non-naturally encoded amino acids substituted at 1 or 2 positions of SEQ ID NO: 1. In another embodiment of the present invention, the antibody comprises an αCD70 antibody with two non-naturally encoded amino acids substituted at 2 positions of SEQ ID NO: 1. In another embodiment of the present invention, the antibody comprises an αCD70 antibody with one non-naturally encoded amino acids substituted at one positions of SEQ ID NO: 1. In another embodiment of the present invention, the antibody comprises the αCD70 antibody of SEQ ID NO: 3. In another embodiment of the present invention, the antibody comprises the αCD70 antibody of SEQ ID NO: 4. In another embodiment of the present invention, the antibody comprises the αCD70 antibody of SEQ ID NO: 5. In another embodiment of the present invention, the antibody comprises the αCD70 antibody of SEQ ID NO: 6. In another embodiment of the present invention, the antibody comprises the αCD70 antibody of SEQ ID NO: 7. In another embodiment of the present invention, the antibody comprises the αCD70 antibody of SEQ ID NO: 8. In another embodiment of the present invention, the antibody comprises the αCD70 antibody of SEQ ID NO: 1 and an αCD70 antibody heavy chain. In another embodiment of the present invention, the antibody comprises the αCD70 antibody of SEQ ID NO: 1 and an αCD70 antibody heavy chain of SEQ ID NO. 2 wherein the heavy chain comprises one or more non-naturally encoded amino acids. In another embodiment of the present invention, the antibody comprises the αCD70 antibody of SEQ ID NO: 1 and an αCD70 antibody heavy chain of SEQ ID NO. 2 wherein the heavy chain comprises 1, 2, 3, 4, 5, 6, 7, 8, 9, or 10 non-naturally encoded amino acids. In another embodiment of the present invention, the antibody comprises the αCD70 antibody of SEQ ID NO: 1 and an αCD70 antibody heavy chain of SEQ ID NO. 2 wherein the heavy chain comprises 1, 2, 3, 4, or 5 non-naturally encoded amino acids. In another embodiment of the present invention, the antibody comprises the αCD70 antibody of SEQ ID NO: 1 and an αCD70 antibody heavy chain of SEQ ID NO. 2 wherein the heavy chain comprises 1, 2, or 3 non-naturally encoded amino acids. In another embodiment of the present invention, the antibody comprises the αCD70 antibody of SEQ ID NO: 1 and an αCD70 antibody heavy chain of SEQ ID NO. 2 wherein the heavy chain comprises two non-naturally encoded amino acids. In another embodiment of the present invention, the antibody comprises the αCD70 antibody of SEQ ID NO: 1 and an αCD70 antibody heavy chain of SEQ ID NO. 2 wherein the heavy chain comprises one non-naturally encoded amino acid. In another embodiment, the present invention provides an αCD70-ADC comprising SEQ ID NO: 1 and SEQ ID NO: 9. In another embodiment, the present invention provides an αCD70-ADC comprising SEQ ID NO: 1 and SEQ ID NO: 10. In another embodiment, the present invention provides an αCD70-ADC comprising SEQ ID NO: 1 and SEQ ID NO: 11. In another embodiment, the present invention provides an αCD70-ADC comprising SEQ ID NO: 1 and SEQ ID NO: 12. In another embodiment, the present invention provides an αCD70-ADC comprising SEQ ID NO: 1 and SEQ ID NO: 13. In another embodiment, the present invention provides an αCD70-ADC comprising SEQ ID NO: 1 and SEQ ID NO: 14.

In another embodiment of the present invention, the antibody comprises an αCD70 antibody with one or more non-naturally encoded amino acids substituted at one or more positions of SEQ ID NO: 2. In another embodiment of the present invention, the antibody comprises an αCD70 antibody with one or more non-naturally encoded amino acids substituted at 1, 2, 3, 4, 5, 6, 7, 8, 9, or 10 positions of SEQ ID NO: 2. In another embodiment of the present invention, the antibody comprises an αCD70 antibody with one or more non-naturally encoded amino acids substituted at 1, 2, 3, 4, or 5 positions of SEQ ID NO: 2. In another embodiment of the present invention, the antibody comprises an αCD70 antibody with one or more non-naturally encoded amino acids substituted at 1, 2, or 3 positions of SEQ ID NO: 2. In another embodiment of the present invention, the antibody comprises an αCD70 antibody with one or more non-naturally encoded amino acids substituted at 1 or 2 positions of SEQ ID NO: 2. In another embodiment of the present invention, the antibody comprises an αCD70 antibody with two non-naturally encoded amino acids substituted at 2 positions of SEQ ID NO: 2. In another embodiment of the present invention, the antibody comprises an αCD70 antibody with one non-naturally encoded amino acids substituted at one positions of SEQ ID NO: 2. In another embodiment of the present invention, the antibody comprises the αCD70 antibody of SEQ ID NO: 9. In another embodiment of the present invention, the antibody comprises the αCD70 antibody of SEQ ID NO: 10. In another embodiment of the present invention, the antibody comprises the αCD70 antibody of SEQ ID NO: 11. In another embodiment of the present invention, the antibody comprises the αCD70 antibody of SEQ ID NO: 12. In another embodiment of the present invention, the antibody comprises the αCD70 antibody of SEQ ID NO: 13. In another embodiment of the present invention, the antibody comprises the αCD70 antibody of SEQ ID NO: 14. In another embodiment of the present invention, the antibody comprises the αCD70 antibody of SEQ ID NO: 2 and an αCD70 antibody light chain. In another embodiment of the present invention, the antibody comprises the αCD70 antibody of SEQ ID NO: 9 and an αCD70 antibody light chain. In another embodiment of the present invention, the antibody comprises the αCD70 antibody of SEQ ID NO: 10 and an αCD70 antibody light chain. In another embodiment of the present invention, the antibody comprises the αCD70 antibody of SEQ ID NO: 11 and an αCD70 antibody light chain. In another embodiment of the present invention, the antibody comprises the αCD70 antibody of SEQ ID NO: 12 and an αCD70 antibody light chain. In another embodiment of the present invention, the antibody comprises the αCD70 antibody of SEQ ID NO: 13 and an αCD70 antibody light chain. In another embodiment of the present invention, the antibody comprises the αCD70 antibody of SEQ ID NO: 14 and an αCD70 antibody light chain.

As an additional, non-limiting example, the following description of HER2 antibody trastuzumab is provided for illustrative purposes and by way of example only, and not as a limit on the scope of the methods, compositions, strategies and techniques described herein. Further, reference to trastuzumab in this application is intended to use the generic term as an example of any antibody. Thus, it is understood that the modifications and chemistries described herein with reference to trastuzumab can be equally applied to any antibody or monoclonal antibody, including those specifically listed herein.

Trastuzumab is a humanized monoclonal antibody that binds to the domain IV of the extracellular segment of the HER2/neu receptor. The HER2 gene (also known as HER2/neu and ErbB2 gene) is amplified in 20-30% of early-stage breast cancers, which makes it overexpressed. Also, in cancer, HER2 may send signals without mitogens arriving and binding to any receptor, making it overactive.

HER2 extends through the cell membrane, and carries signals from outside the cell to the inside. In healthy people, signaling compounds called mitogens arrive at the cell membrane, and bind to the outside part of other members of the HER family of receptors. Those bound receptors then link (dimerize) with HER2, activating it. HER2 then sends a signal to the inside of the cell. The signal passes through different biochemical pathways. This includes the PI3K/Akt pathway and the MAPK pathway. These signals promote invasion, survival and growth of blood vessels (angiogenesis) of cells.

Cells treated with trastuzumab undergo arrest during the G1 phase of the cell cycle so there is reduced proliferation. It has been suggested that trastuzumab induces some of its effect by downregulation of HER2/neu leading to disruption of receptor dimerization and signaling through the downstream PI3K cascade. P27Kip1 is then not phosphorylated and is able to enter the nucleus and inhibit cdk2 activity, causing cell cycle arrest. Also, trastuzumab suppresses angiogenesis by both induction of antiangiogenic factors and repression of proangiogenic factors. It is thought that a contribution to the unregulated growth observed in cancer could be due to proteolytic cleavage of HER2/neu that results in the release of the extracellular domain. Trastuzumab has been shown to inhibit HER2/neu ectodomain cleavage in breast cancer cells.

VIII. Cellular Uptake of Non-Natural Amino Acids

Non-natural amino acid uptake by a eukaryotic cell is one issue that is typically considered when designing and selecting non-natural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which non-natural amino acids, if any, are taken up by cells (examples 15 & 16 herein illustrate non-limiting examples of tests which can be done on non-natural amino acids). See, e.g., the toxicity assays in, e.g., the U.S. Patent Publication No. 2004/198637 entitled "Protein Arrays," which is herein incorporated by reference in its entirety, and Liu, D. R. & Schultz, P. G. (1999) *Progress toward the evolution of an organism with an expanded genetic code. PNAS United States* 96:4780-4785. Although uptake is easily analyzed with various assays, an alternative to designing non-natural amino acids that are amenable to cellular uptake pathways is to provide biosynthetic pathways to create amino acids in vivo.

Typically, the non-natural amino acid produced via cellular uptake as described herein is produced in a concentration sufficient for efficient protein biosynthesis, including but not limited to, a natural cellular amount, but not to such a degree as to affect the concentration of the other amino acids or exhaust cellular resources. Typical concentrations produced in this manner are about 10 mM to about 0.05 mM.

IX. Biosynthesis of Non-Natural Amino Acids

Many biosynthetic pathways already exist in cells for the production of amino acids and other compounds. While a biosynthetic method for a particular non-natural amino acid may not exist in nature, including but not limited to, in a cell, the methods and compositions described herein provide such methods. For example, biosynthetic pathways for non-natural amino acids can be generated in host cell by adding new enzymes or modifying existing host cell pathways. Additional new enzymes include naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided herein. Additional enzymes sequences are found, for example, in Genbank. Artificially evolved enzymes can be added into a cell in the same manner. In this manner, the cellular machinery and resources of a cell are manipulated to produce non-natural amino acids.

A variety of methods are available for producing novel enzymes for use in biosynthetic pathways or for evolution of existing pathways. For example, recursive recombination, including but not limited to, as developed by Maxygen, Inc. (available on the world wide web at www.maxygen.com), can be used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly DesignPath™, developed by Genencor (available on the world wide web at genencor.com) is optionally used for metabolic pathway engineering, including but not limited to, to engineer a pathway to create a non-natural amino acid in a cell. This technology reconstructs existing pathways in host organisms using a combination of new genes, including but not limited to those identified through functional genomics, molecular evolution and design. Diversa Corporation (available on the world wide web at diversa.com) also provides technology for rapidly screening libraries of genes and gene pathways, including but not limited to, to create new pathways for biosynthetically producing non-natural amino acids.

Typically, the non-natural amino acid produced with an engineered biosynthetic pathway as described herein is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and a non-natural amino acid is generated, in vivo selections are optionally used to further optimize the production of the non-natural amino acid for both ribosomal protein synthesis and cell growth.

X. Additional Synthetic Methodology

The non-natural amino acids described herein may be synthesized using methodologies described in the art or using the techniques described herein or by a combination thereof. As an aid, the following table provides various starting electrophiles and nucleophiles which may be combined to create a desired functional group. The information provided is meant to be illustrative and not limiting to the synthetic techniques described herein.

TABLE 2

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |

TABLE 2-continued

Examples of Covalent Linkages and Precursors Thereof

| Covalent Linkage Product | Electrophile | Nucleophile |
|---|---|---|
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Non-limiting examples of carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage to of being kinetically stable in water or polar organic solvents. Other non-limiting examples of carbon nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon-carbon bonds between the carbon nucleophile and carbon electrophile.

Non-limiting examples of non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a hetereoatom, including, but not limited to, oxygen, sulfur, or nitrogen.

EXAMPLES

Example 1: Synthesis of Compound 1

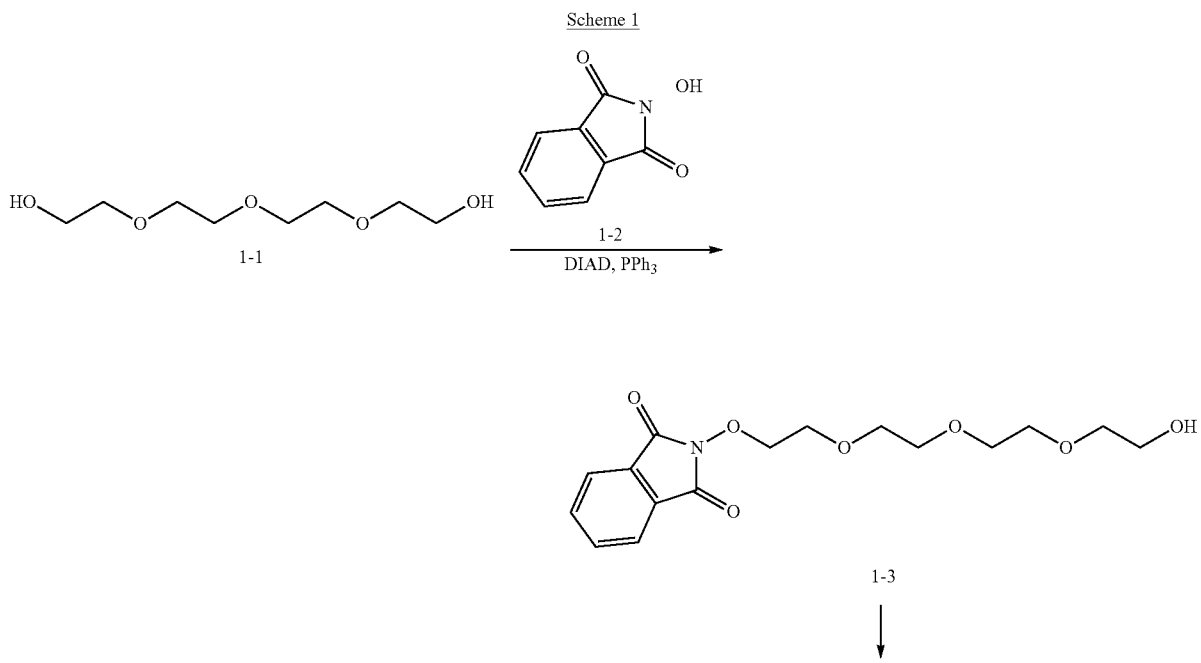

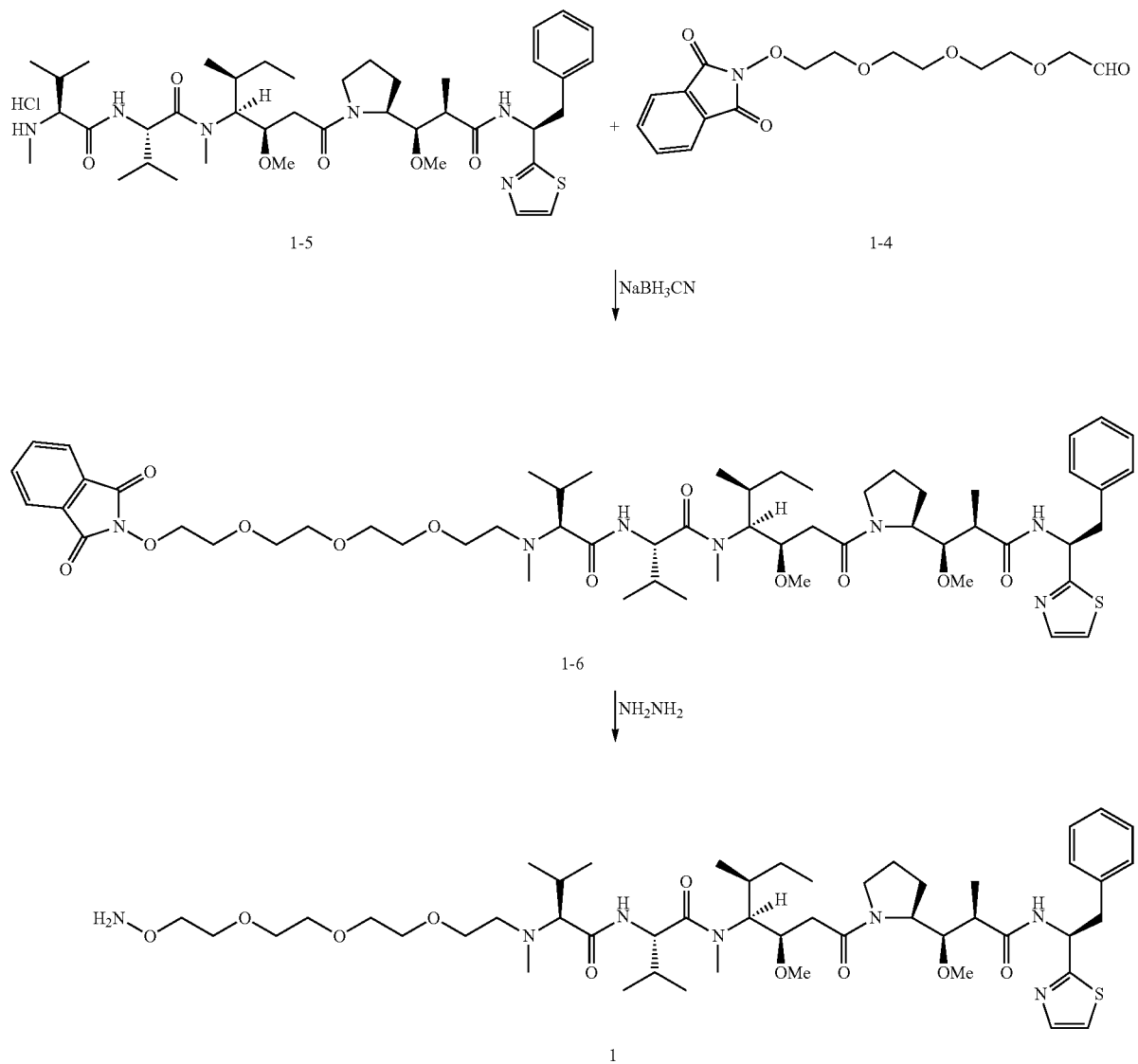

Compound 1-3: Tetra (ethylene glycol) 1-1 (10 g, 51.5 mmol), N-hydroxyphthalimide 1-2 (8.4 g, 51.15 mmol) and triphenylphosphine (17.6 g, 67 mmol) were dissolved in 300 mL of tetrahydrofuran followed by addition of DIAD (12.8 mL, 61.78 mmol) at 0° C. The resulting solution was stirred at room temperature overnight, and then concentrated to dryness. The residue was purified by flash column chromatography to give 5.47 g (31%) of compound 1-3.

Compound 1-4: To a solution of compound 1-3 (200 mg, 0.59 mmol) in 15 mL dichloromethane was added Dess-Martin Periodinane (300 mg, 0.71 mmol). The reaction mixture was stirred at ambient temperature overnight. The reaction was quenched with the solution of sodium bisulfite in 15 mL of saturated sodium bicarbonate. The mixture was separated. The organic layer was washed with saturated sodium bicarbonate, brine, dried over sodium sulfate, filtered and concentrated in vacuo. The residue was purified by flash column chromatography to give 150 mg (75%) of compound 1-4.

Compound 1-6: To a solution of monomethyldolastatin hydrochloride salt 1-5 (50 mg, 0.062 mmol) in 1 mL of DMF was added compound 1-4 (63 mg, 0.186 mmol) and 70 μL of acetic acid, followed by addition of 8 mg of sodium cyanoborohydride. The resulting mixture was stirred at ambient temperature for 2 hours. The reaction mixture was diluted with water and purified by HPLC to give 60 mg (80%) of compound 1-6. MS (ESI) m/z 547 [M+2H], 1092 [M+H].

1d.

Compound 1: Compound 1-6 (60 mg, 0.05 mmol) was dissolved in 1 mL of DMF. 32 μL of hydrazine was added. The resulting solution was stirred at ambient temperature for 1 hour. The reaction was quenched with 1N hydrochloride solution. The reaction mixture was purified by HPLC to give 33 mg (55%) of compound 1. MS (ESI) m/z 482 [M+2H], 962 [M+H].

Example 2: Synthesis of Compound 2
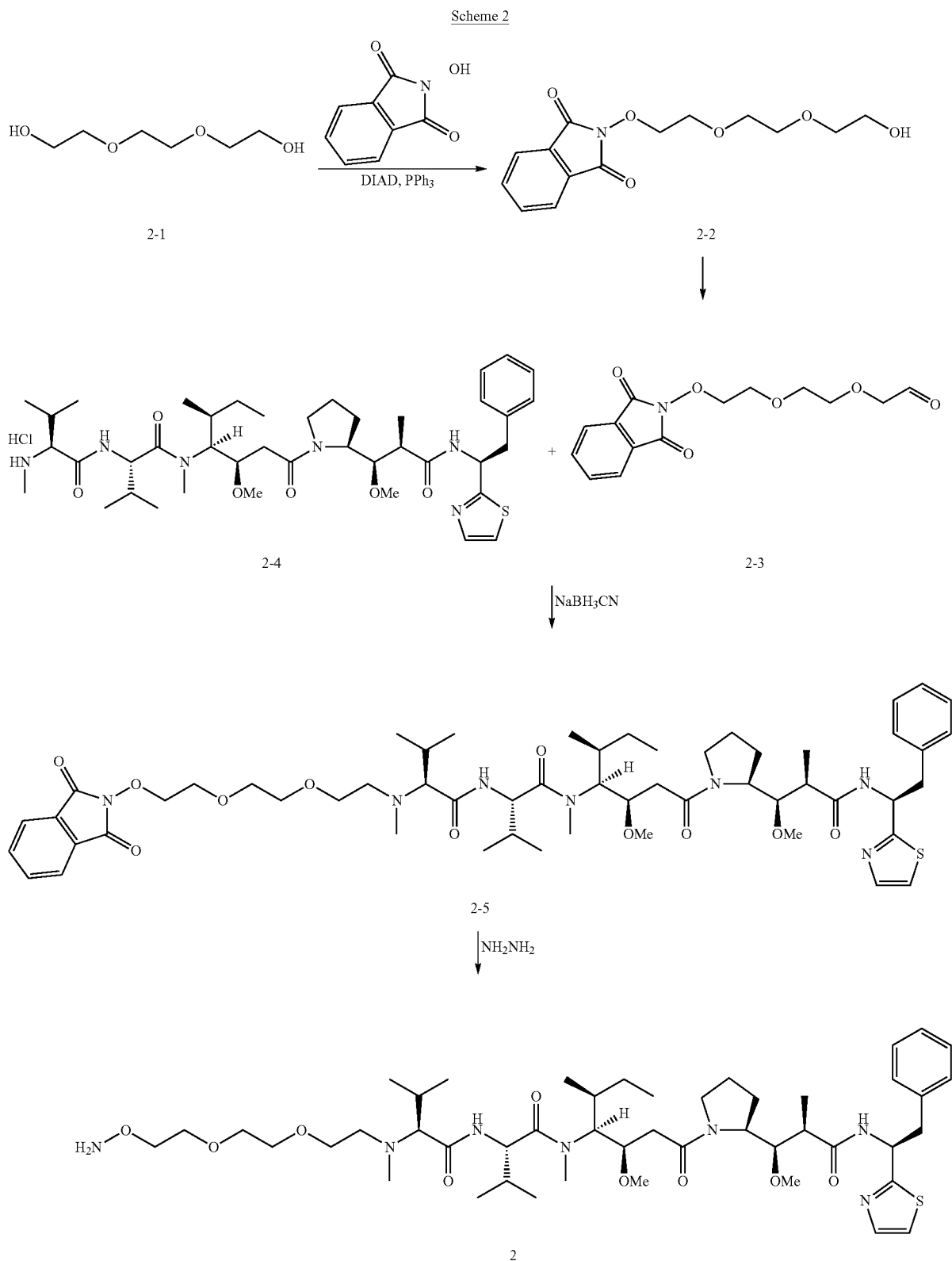

Compound 2 was synthesized via a similar synthetic route as described in Example 1. MS (ESI) m/z 460 [M+2H], 918 [M+H].

Example 3: Synthesis of Compound 3

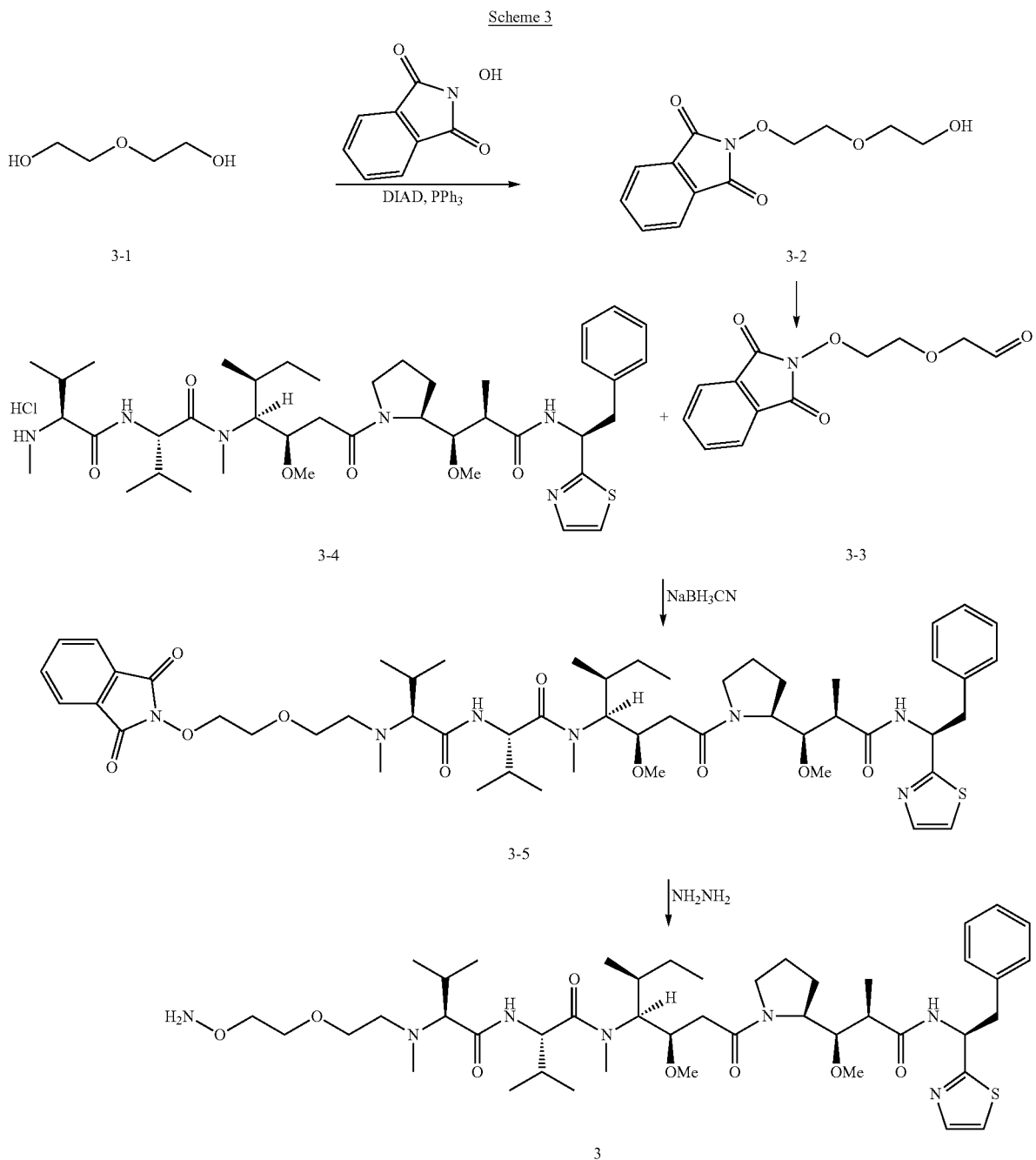

Compound 3 was synthesized via similar synthetic route to Example 1. MS (ESI) m/z 438 [M+2H], 974 [M+H].

Example 4: Synthesis of Compound 4

Compound 4-2: To a solution of Val (OtBu)-OH.HCl 4-1 (1 g, 4.77 mmol) and bromoethanol (304.7 µL, 4.3 mmol) in 10 mL of DMF was added 1.68 ml of DIEA. The reaction mixture was stirred at room temperature for 2 days. 4.8 mmol of Boc₂OO was added to the reaction mixture, followed by 0.84 mL of DIEA. The reaction mixture was stirred at room temperature for 2 days. The reaction mixture was concentrated in vacuo and extracted with ethyl acetate, and washed with water, brine, dried over sodium sulfate and concentrated in vacuo. The residue was purified by flash column chromatography to give 0.66 g of compound 4-2.

Scheme 4
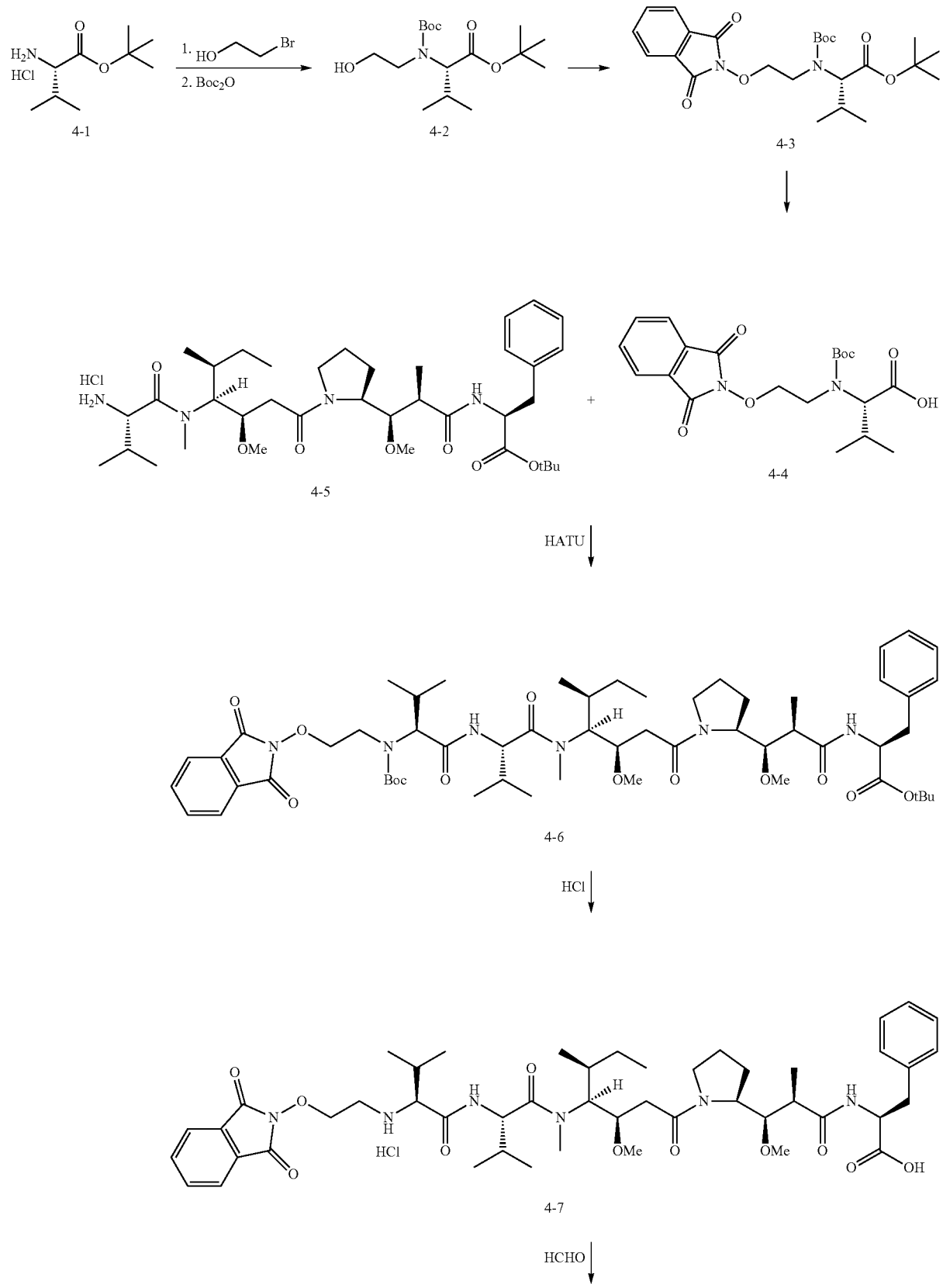

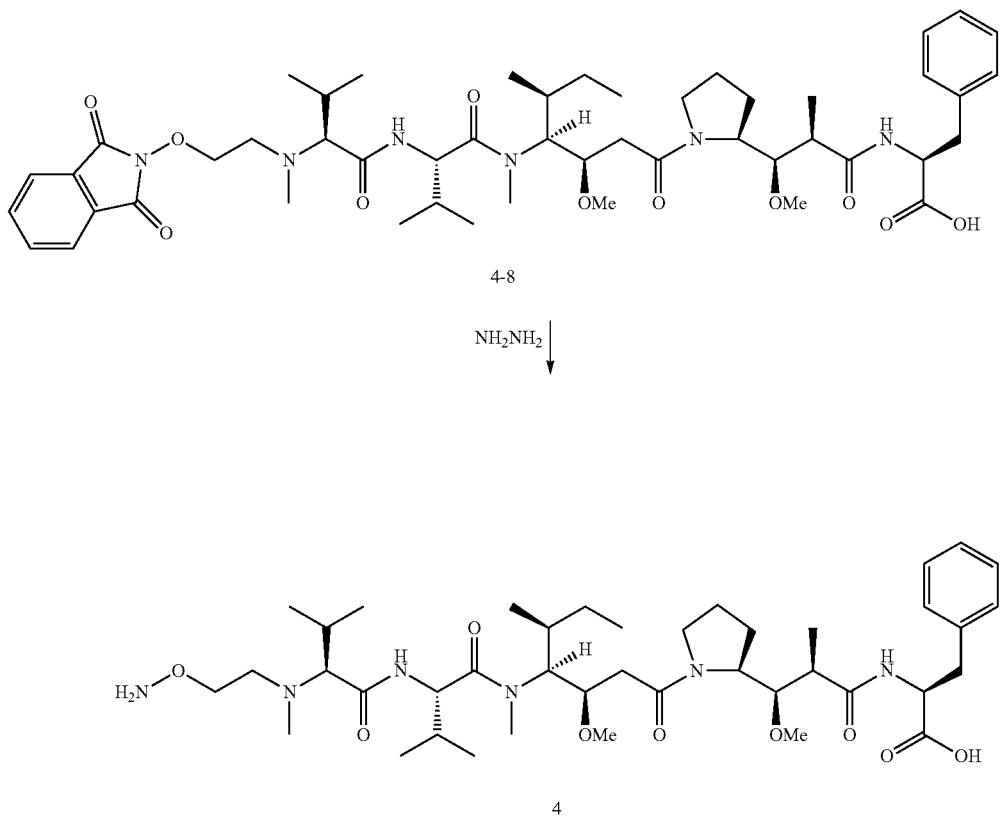

4-8

NH₂NH₂ ↓

4

Compound 4-3: To a solution of compound 4-2 (500 mg, 1.58 mmol), N-hydroxyphthalimide (261 mg, 1.6 mmol) and triphenylphosphine (538 mg, 2.05 mmol) in 15 mL THF was added DIAD (394 μL, 1.9 mmol) at at 0° C. The resulting solution was stirred at room temperature overnight, and then concentrated in vacuo. The residue was purified by flash column chromatography to give 0.68 g of compound 4-3.

Compound 4-4: Compound 4-3 was dissolved in 15 mL 4N HCl/Dioxane. The reaction mixture was stirred at room temperature for 2 days and concentrated in vacuo. The residue was dissolved in DMF and treated with Boc₂O (230 μL, 1 mmol) and DIEA (352 μL, 2 mmol). The reaction mixture was stirred at room temperature for 2 days. The reaction mixture was purified by HPLC to give 100 mg of compound 4-4.

Compound 4-5: To a solution of compound Boc-Val-Dil-methylDap-OH in DMF is added phe(OtBu)-OH.HCl, HATU and N-methylmorpholine. The reaction mixture is stirred at room temperature for 4 hours. The reaction mixture is concentrated in vacuo and extracted with ethyl acetate (100 mL×1, 50 mL×2). The organic layer is combined and washed with brine, dried over sodium sulfate and concentrated in vacuo. The residue is purified by flash chromatography. The resulting compound is treated with HCl/EtOAC to give compound 4-5.

Compound 4-6: To a solution of compound 4-5 in DMF is added compound 4-4, HATU and DIEA. The reaction mixture is stirred at room temperature for 4 hours. The reaction mixture is concentrated in vacuo and extracted with ethyl acetate (100 mL×1, 50 mL×2). The organic layer is combined and washed with brine, dried over sodium sulfate and concentrated in vacuo. The residue is purified by flash chromatography to give compound 4-6.

Compound 4-7: Compound 4-6 is dissolved in 15 mL 4N HCl/Dioxane. The reaction mixture is stirred at room temperature for 2 hours and concentrated in vacuo to give compound 4-7.

Compound 4-8: To a solution of compound 4-7 in 1 mL of DMF is added formylaldehyde and acetic acid, followed by addition of sodium cyanoborohydride. The resulting mixture is stirred at ambient temperature for 2 hours. The reaction mixture is diluted with water and purified by HPLC to give compound 4-8.

Compound 4: Compound 4-8 is dissolved in 1 mL of DMF. Hydrazine is added. The resulting solution is stirred at ambient temperature for 1 hour. The reaction is quenched with 1N hydrochloride solution. The reaction mixture is purified by HPLC to give Compound 4.

Example 5: Synthesis of Compound 5

Compound 4-7 is dissolved in 1 mL of DMF. Hydrazine is added. The resulting solution is stirred at ambient temperature for 1 hour. The reaction is quenched with 1N hydrochloride solution. The reaction mixture is purified by HPLC to give Compound 5.

Example 6: Synthesis of Compound 6
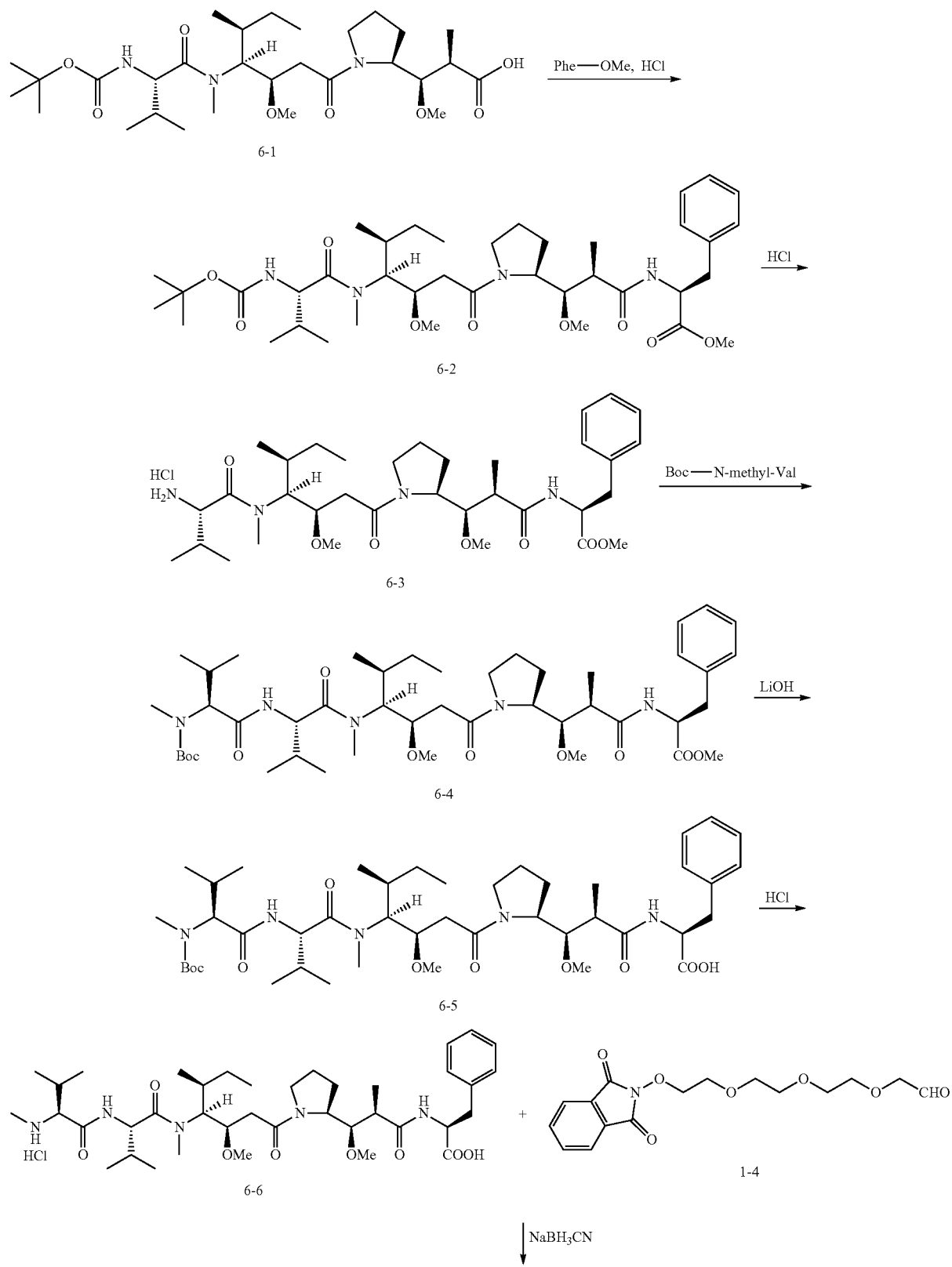

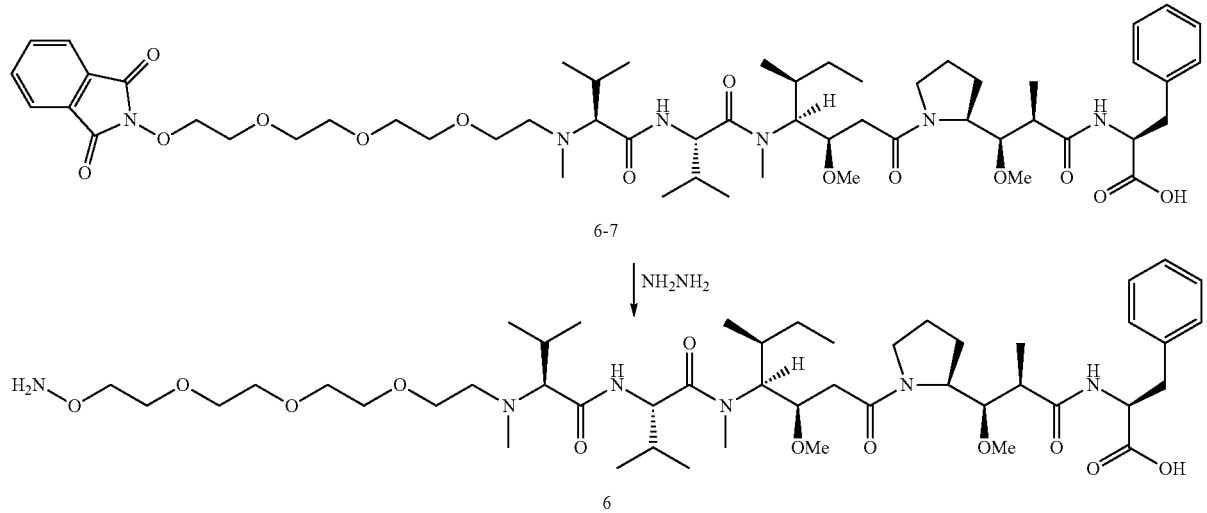

6-7

↓ NH₂NH₂

6

Compound 6-2: To a solution of compound 6-1 (500 mg, 0.875 mmol) in 3 mL of DMF was added 283 mg of phenylalanine hydrochloride, 433 mg of HATU and 581 μL of N-methylmorpholine. The reaction mixture was stirred at room temperature for 4 hours. The reaction mixture was concentrated in vacuo and extracted with ethyl acetate (100 mL×1, 50 mL×2). The organic layer was combined and washed with brine, dried over sodium sulfate and concentrated in vacuo. The residue was purified by flash chromatography to give 560 mg (76%) of compound 6-2.

Compound 6-3: Compound 6-2 was dissolved in 15 mL 4N HCl/Dioxane. The reaction mixture was stirred at room temperature for 2 hours and concentrated in vacuo to give 511 mg of compound 6-3.

Compound 6-4: To a solution of compound 6-3 (368 mg, 0.55 mmol) in 3 mL of DMF was added 255 mg of Boc-N-methyl valine, 314 mg of HATU and 303 μL of N-methylmorpholine. The reaction mixture was stirred at room temperature for 4 hours. The reaction mixture was concentrated in vacuo and extracted with ethyl acetate (100 mL×1, 50 mL×2). The organic layer was combined and washed with brine, dried over sodium sulfate and concentrated in vacuo. The residue was purified by flash chromatography to give 370 mg (79%) of compound 6-4.

Compound 6-5: To a solution of compound 6-4 (170 mg) in 10 mL MeOH was added Seq of 1N LiOH. The reaction mixture was stirred at room temperature for 2 hours. The reaction mixture was acidified by 1NHCl and extracted with ethyl acetate washed with brine, dried over sodium sulfate and concentrated in vacuo to give 150 mg (90%) of compound 6-5.

Compound 6-6: Compound 6-5 was dissolved in 4N HCl/Dioxane. The reaction mixture was stirred at room temperature for 2 hours and concentrated in vacuo and purified by HPLC to give 150 mg of compound 6-6.

Compound 6-7: To a solution of compound 6-6 (50 mg, 0.062 mmol) in 1 mL of DMF was added compound 1-4 (63 mg, 0.186 mmol) and 70 μL of acetic acid, followed by addition of 8 mg of sodium cyanoborohydride. The resulting mixture was stirred at ambient temperature for 2 hours. The reaction mixture was diluted with water and purified by HPLC to give 60 mg (80%) of compound 6-7.

Compound 6: Compound 6-7 (60 mg, 0.05 mmol) was dissolved in 1 mL of DMF. 32 μL of hydrazine was added. The resulting solution was stirred at ambient temperature for 1 hour. The reaction was quenched with 1N hydrochloride solution. The reaction mixture was purified by HPLC to give 33 mg (55%) of Compound 6.

Example 7: Synthesis of Compound 7

Scheme 7

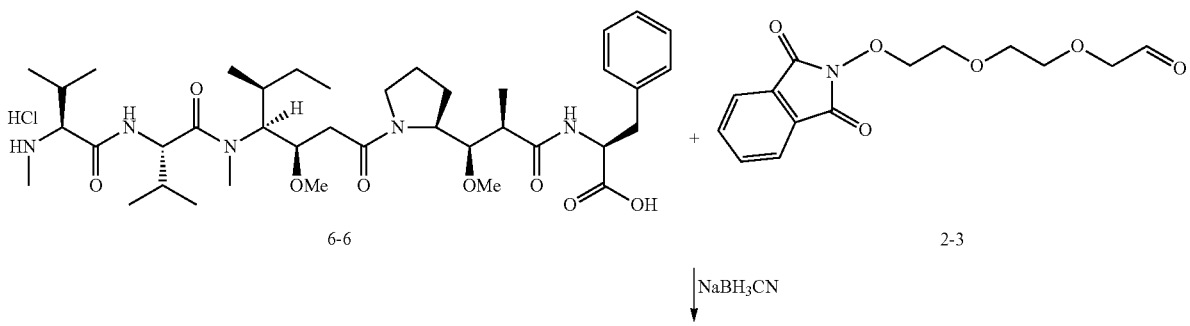

6-6 + 2-3

↓ NaBH₃CN

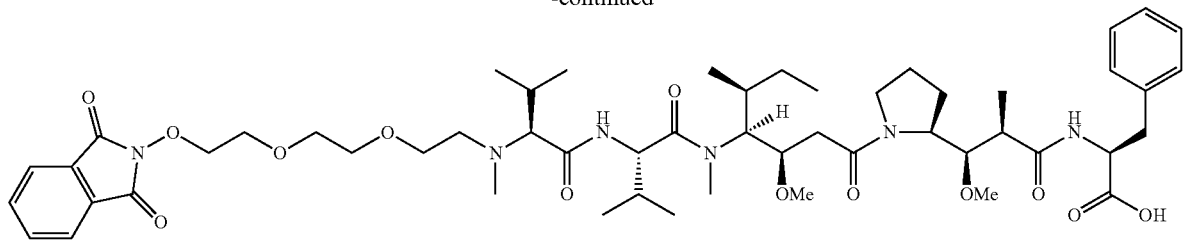
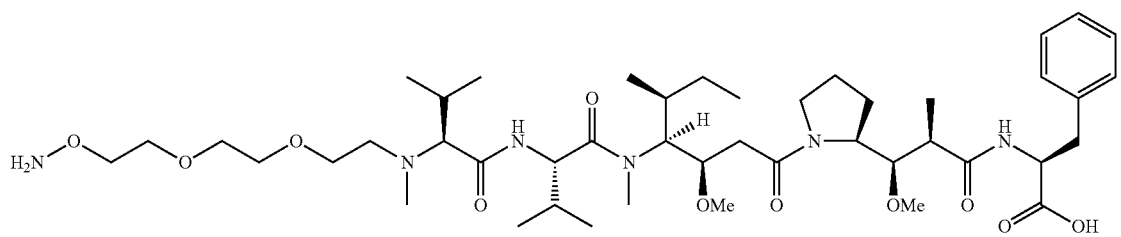
Compound 7 was synthesized via similar synthetic route to Compound 1. MS (ESI) m/z 440 [M+2H], 879 [M+H].
Example 8: Synthesis of Compound 8
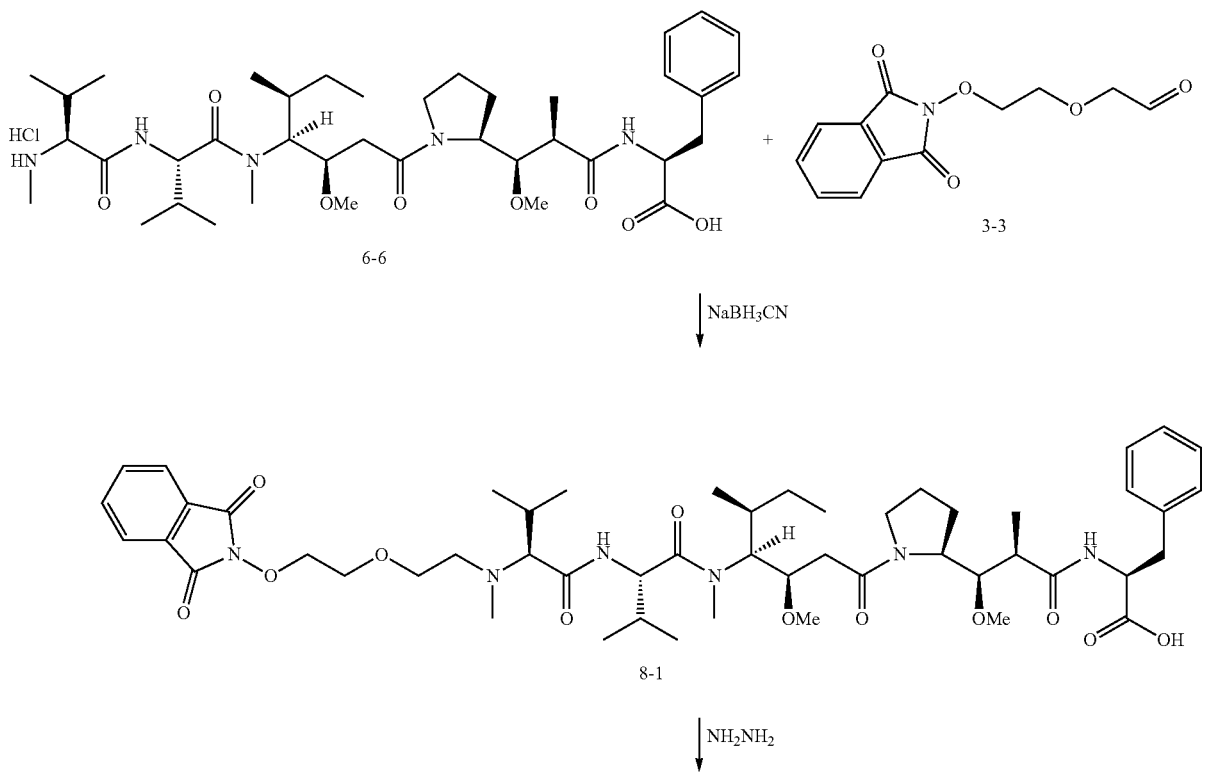

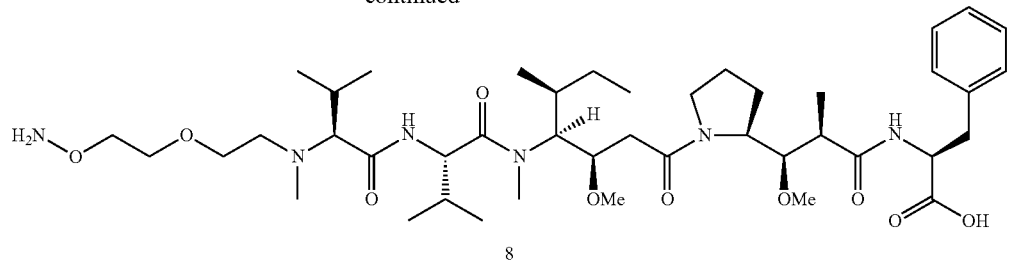
8
Compound 8 was synthesized via similar synthetic route to Compound 1. MS (ESI) m/z 418 [M+2H], 835 [M+H].
Example 9: Synthesis of Compound 9
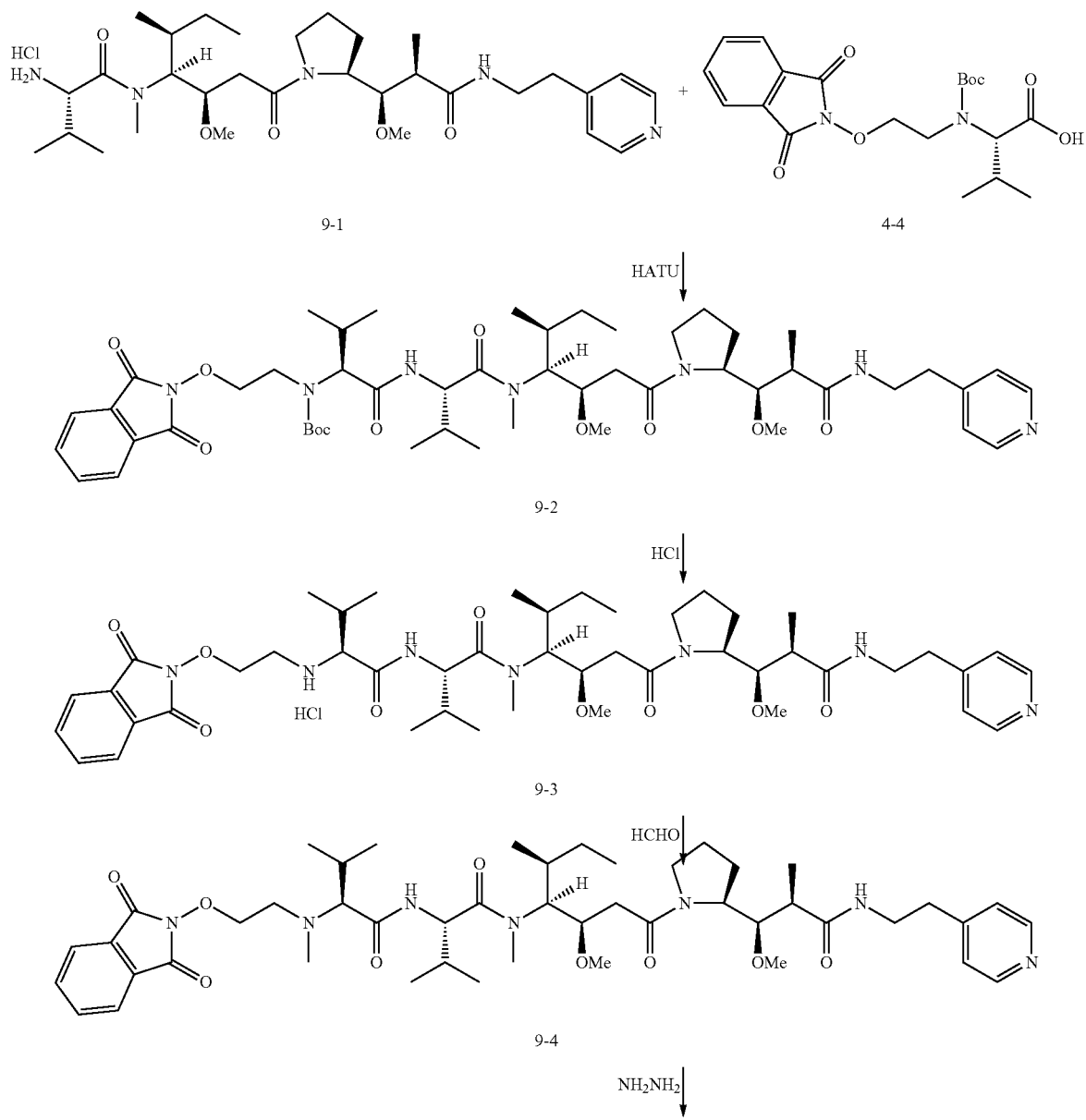

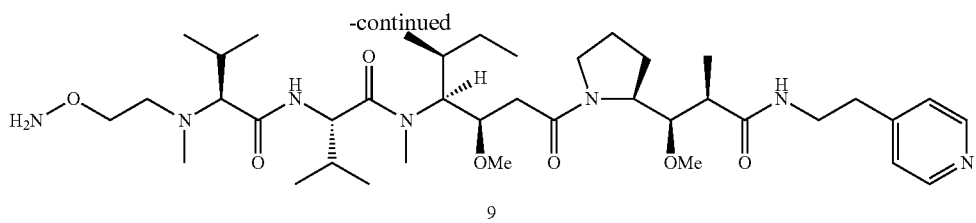

9

Compound 9-1: To a solution of compound Boc-Val-Dil-methylDap-OH in DMF is added 4-(2-Aminoethyl)pyridine, HATU and N-methylmorpholine. The reaction mixture is stirred at room temperature for 4 hours. The reaction mixture is concentrated in vacuo and extracted with ethyl acetate (100 mL×1, 50 mL×2). The organic layer is combined and washed with brine, dried over sodium sulfate and concentrated in vacuo. The residue is purified by flash chromatography. The resulting compound is treated with HCl/EtOAC to give compound 9-1.

Compound 9-2: To a solution of compound 9-1 in DMF is added compound 4-4, HATU and DIEA. The reaction mixture is stirred at room temperature for 4 hours. The reaction mixture is concentrated in vacuo and extracted with ethyl acetate (100 mL×1, 50 mL×2). The organic layer is combined and washed with brine, dried over sodium sulfate and concentrated in vacuo. The residue is purified by flash chromatography to give compound 9-2.

Compound 9-3: Compound 9-2 is dissolved in 15 mL 4N HCl/Dioxane. The reaction mixture is stirred at room temperature for 2 hours and concentrated in vacuo to give compound 9-3.

Compound 9-4: To a solution of compound 9-3 in 1 mL of DMF is added formylaldehyde and acetic acid, followed by addition of sodium cyanoborohydride. The resulting mixture is stirred at ambient temperature for 2 hours. The reaction mixture is diluted with water and purified by HPLC to give compound 9-4.

Compound 9: Compound 9-4 is dissolved in 1 mL of DMF. Hydrazine is added. The resulting solution is stirred at ambient temperature for 1 hour. The reaction is quenched with 1N hydrochloride solution. The reaction mixture is purified by HPLC to give compound 9.

Example 10: Synthesis of Compound 10

Scheme 10

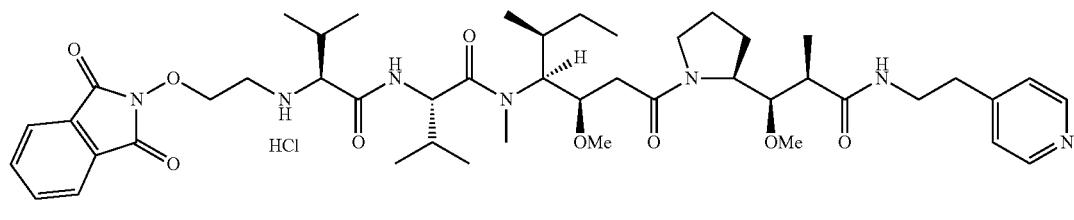

9-3

NH₂NH₂ ↓

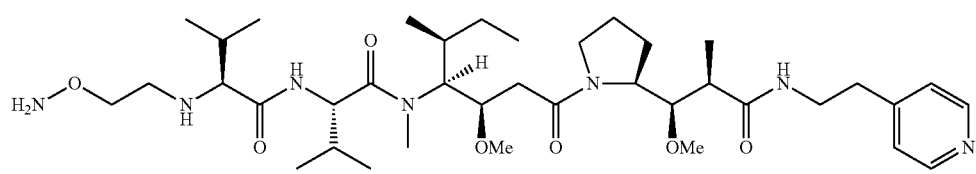

10

Compound 10: Compound 9-3 is dissolved in 1 mL of DMF. Hydrazine is added. The resulting solution is stirred at ambient temperature for 1 hour. The reaction is quenched with 1N hydrochloride solution. The reaction mixture is purified by HPLC to give Example 10.
Example 11: Synthesis of Compound 11
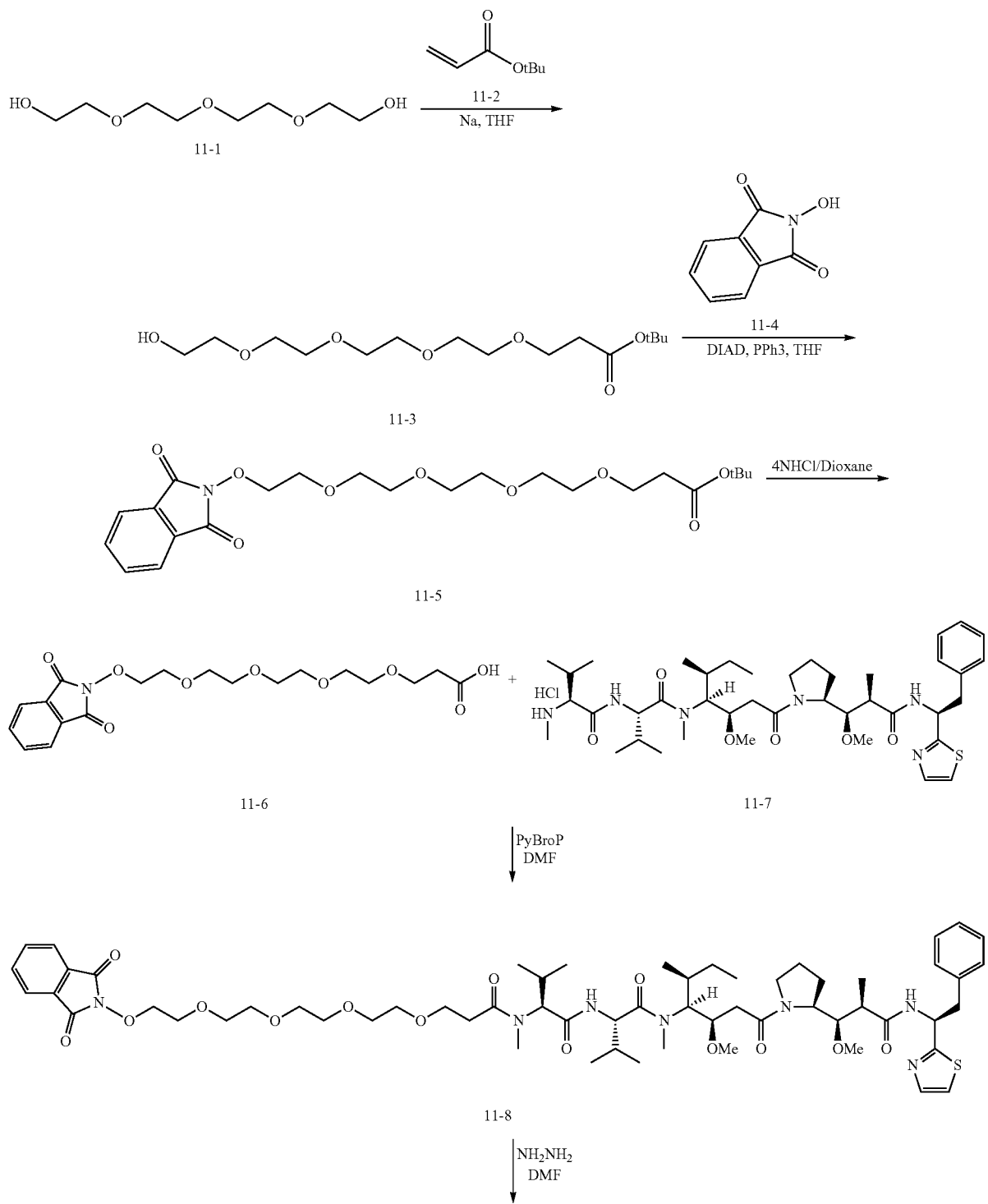

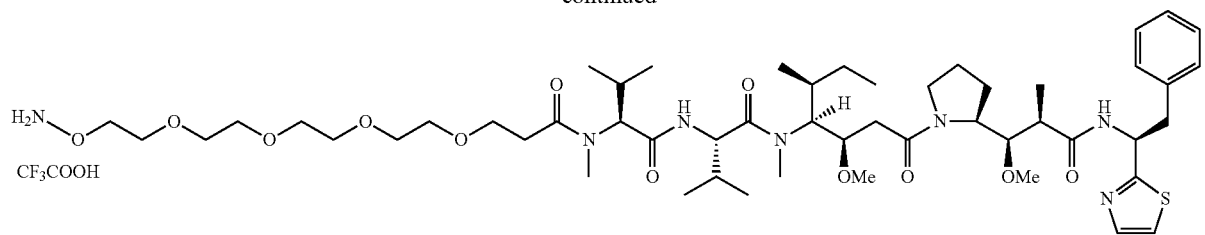

11

Compound 11-3: To a solution of tetra (ethylene glycol) 11-1 (40.6 mL, 235 mmol) in 100 mL of tetrahedrofuran was added 47 mg of sodium. 12 mL of tert-butylacrylate was added after sodium was dissolved. The reaction mixture was stirred at room temperature for 24 hours. The reaction mixture was concentrated in vacuo and quenched with 2 mL of 1 N HCl. The residue was suspended in brine and extracted with ethyl acetate (100 mL×1, 50 mL×2). The organic layer was combined and washed with brine, dried over sodium sulfate and concentrated in vacuo to give 6.4 g (23%) of compound 11-3.

Compound 11-5: Compound 11-3 (1.0 g, 3.12 mmol), N-hydroxyphthalimide 11-4 (611 mg, 3.744 mmol) and triphenylphosphine (1.23 g, 4.68 mmol) were dissolved in 20 mL of tetrahydrofuran followed by addition of DIAD (0.84 mL, 4.06 mmol) at 0° C. The resulting solution was stirred at room temperature overnight, and then concentrated to dryness. The residue was purified by flash column chromatography using SiliaSep Cartridges (80 g), eluting with 0-100% ethyl acetate/hexanes, to give 1.0 g (100%) of compound 11-5.

Compound 11-6: Compound 11-5 was dissolved in 15 mL 4N HCl/Dioxane. The reaction mixture was stirred at room temperature for 2 hours and concentrated in vacuo to give 1.0 g of compound 11-6.

Compound 11-8: To a solution of 30 mg (0.0372 mmol) of monomethyldolastatin hydrochloride, 31 mg (0.0744 mmol) of compound 11-6 and 38.2 mg (0.082 mmol) of PyBroP in 1 mL of DMF was added 33 µL (0.186 mmol) of diisopropylethylamine. The reaction mixture was stirred at room temperature for 5 hours. The reaction mixture was purified by HPLC to give 28 mg (65%) of compound 11-8. MS (ESI) m/z 785 [M+2H], 1164[M+H].

Compound 11: Compound 11-8 (28 mg, 0.024 mmol) was dissolved in 1 mL of DMF. 23 µL (0.72 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 20 mg (66%) of Compound 11. MS (ESI) m/z 518 [M+2H], 1034[M+H].

Example 12: Synthesis of Compound 12

Scheme 12

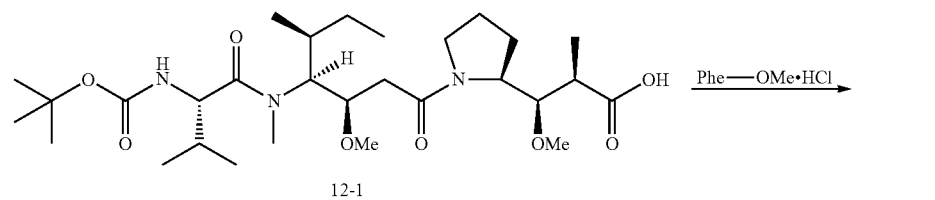

12-1

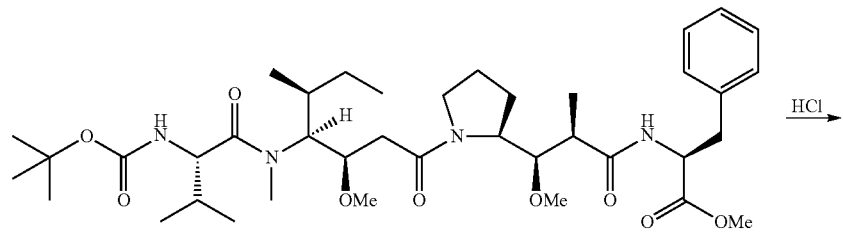

12-2

-continued
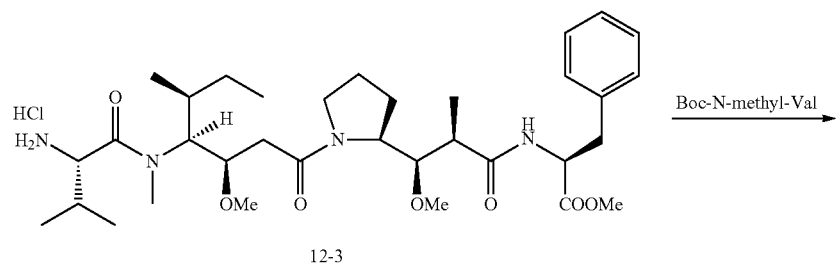
12-3
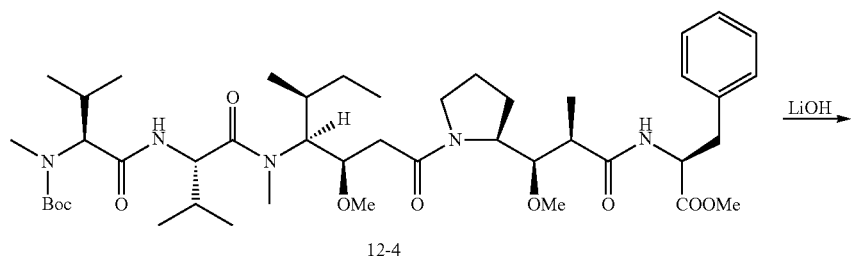
12-4
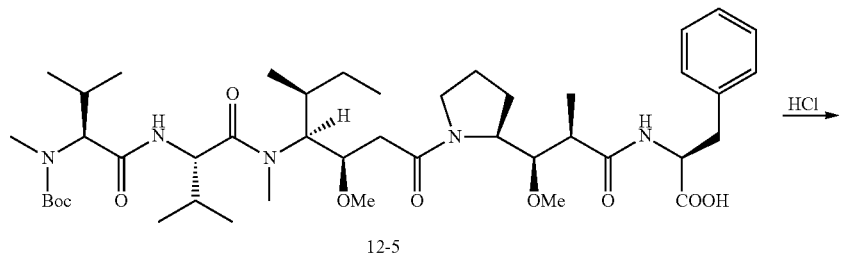
12-5
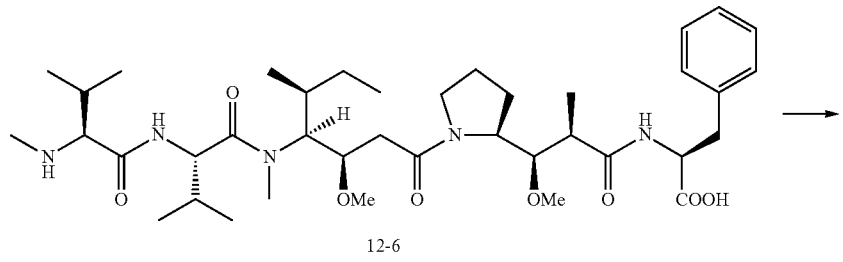
12-6
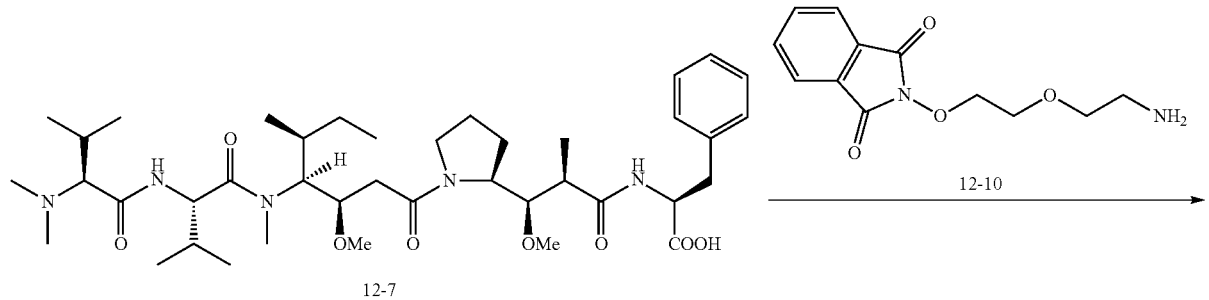
12-7
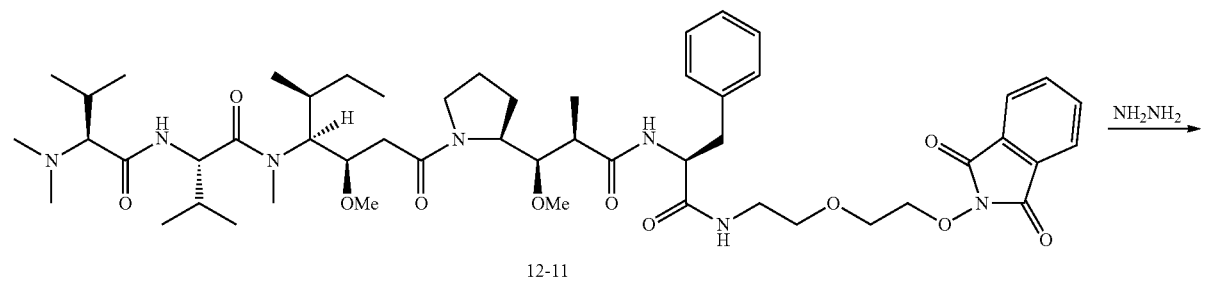
12-11

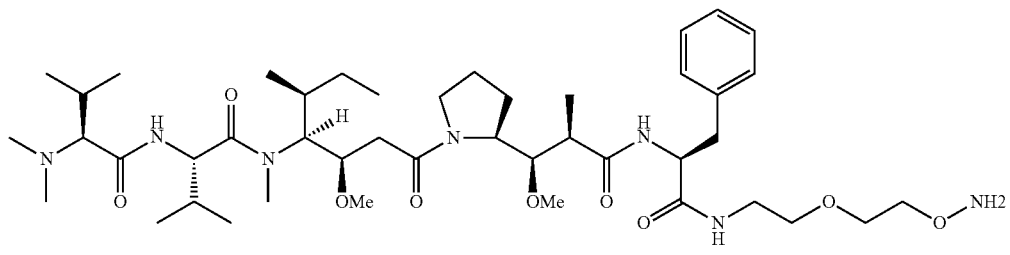

12

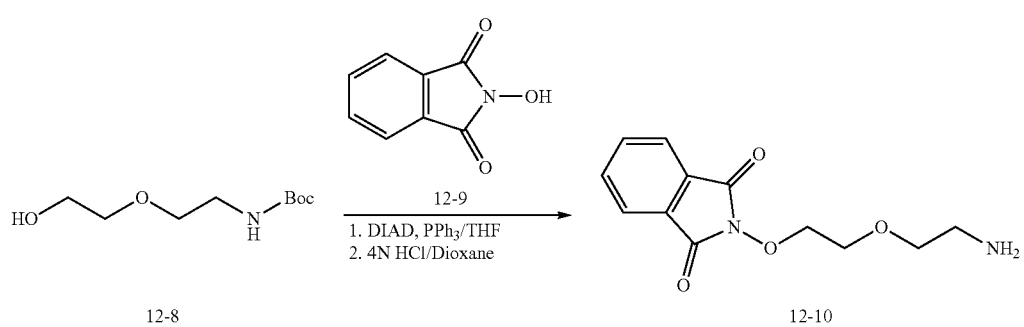

Compound 12-2: To a solution of compound 12-1 (500 mg, 0.875 mmol) in 3 mL of DMF was added 283 mg of phenylalanine hydrochloride, 433 mg of HATU and 581 µL of N-methylmorpholine. The reaction mixture was stirred at room temperature for 4 hours. The reaction mixture was concentrated in vacuo and extracted with ethyl acetate (100 mL×1, 50 mL×2). The organic layer was combined and washed with brine, dried over sodium sulfate and concentrated in vacuo. The residue was purified by flash chromatography to give 560 mg (76%) of compound 12-2.

Compound 12-3: Compound 12-2 was dissolved in 15 mL 4N HCl/Dioxane. The reaction mixture was stirred at room temperature for 2 hours and concentrated in vacuo to give 511 mg of compound 12-3.

Compound 12-4: To a solution of compound 12-3 (368 mg, 0.55 mmol) in 3 mL of DMF was added 255 mg of Boc-N-methyl valine, 314 mg of HATU and 303 µL of N-methylmorpholine. The reaction mixture was stirred at room temperature for 4 hours. The reaction mixture was concentrated in vacuo and extracted with ethyl acetate (100 mL×1, 50 mL×2). The organic layer was combined and washed with brine, dried over sodium sulfate and concentrated in vacuo. The residue was purified by flash chromatography to give 370 mg (79%) of compound 12-4.

Compound 12-5: To a solution of compound 12-4 (170 mg) in 10 mL MeOH was added 5 eq of 1N LiOH. The reaction mixture was stirred at room temperature for 2 hours. The reaction mixture was acidified by 1NHCl and extracted with ethyl acetate washed with brine, dried over sodium sulfate and concentrated in vacuo to give 150 mg (90%) of compound 12-5.

Compound 12-6: Compound 12-5 was dissolved in 4N HCl/Dioxane. The reaction mixture was stirred at room temperature for 2 hours and concentrated in vacuo and purified by HPLC to give 150 mg of compound 12-6.

Compound 12-7: To a solution of compound 12-6 in DMF was added formylaldehyde (3 eq) and 20 eq of acetic acid, followed by addition of 2 eq of sodium cyanoborohydride. The resulting mixture was stirred at ambient temperature for 2 hours. The reaction mixture was diluted with water and purified by HPLC to give compound 12-7.

Compound 12-10: tert-Butyl 2-(2-hydroxyethoxy)ethyl-carbamate (2.05 g, 10 mmol), N-hydroxyphthalimide (1.8 g, 11 mmol) and triphenylphosphine (3.67 g, 14 mmol) were dissolved in 100 mL of tetrahydrofuran followed by addition of DIAD (2.48 mL, 12 mmol) at 0° C. The resulting solution was stirred at room temperature overnight, and then concentrated to dryness. The residue was treated with 50 mL of 4N HCl/dioxane. The mixture was stirred at room temperature for 2 hours. The solvent was removed in vacuo. The residue was treated with ether, filtered, washed with ether and dried in vacuo to get 2.6 g (91%) of compound 12-10. MS (ESI) m/z 251 [M+H].

Compound 12-11: To a solution of compound 12-10 (20 mg, 0.026 mmol) in 1 mL of DMF was added 11.2 mg of compound 12-10, 15 mg of HATU and 23 µL of DIEA. The reaction mixture was stirred at room temperature for 2 hours. The reaction mixture was purified by HPLC to give 20 mg (70%) of compound 12-4. MS (ESI) m/z 490 [M+2H], 978[M+H].

Compound 12: Compound 12-11 (20 mg, 0.0183 mmol) was dissolved in 1 mL of DMF. 18 µL (0.56 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 14 mg (72%) of Compound 12. MS (ESI) m/z 425 [M+2H], 848[M+H].

Example 13: Synthesis of Compound 13
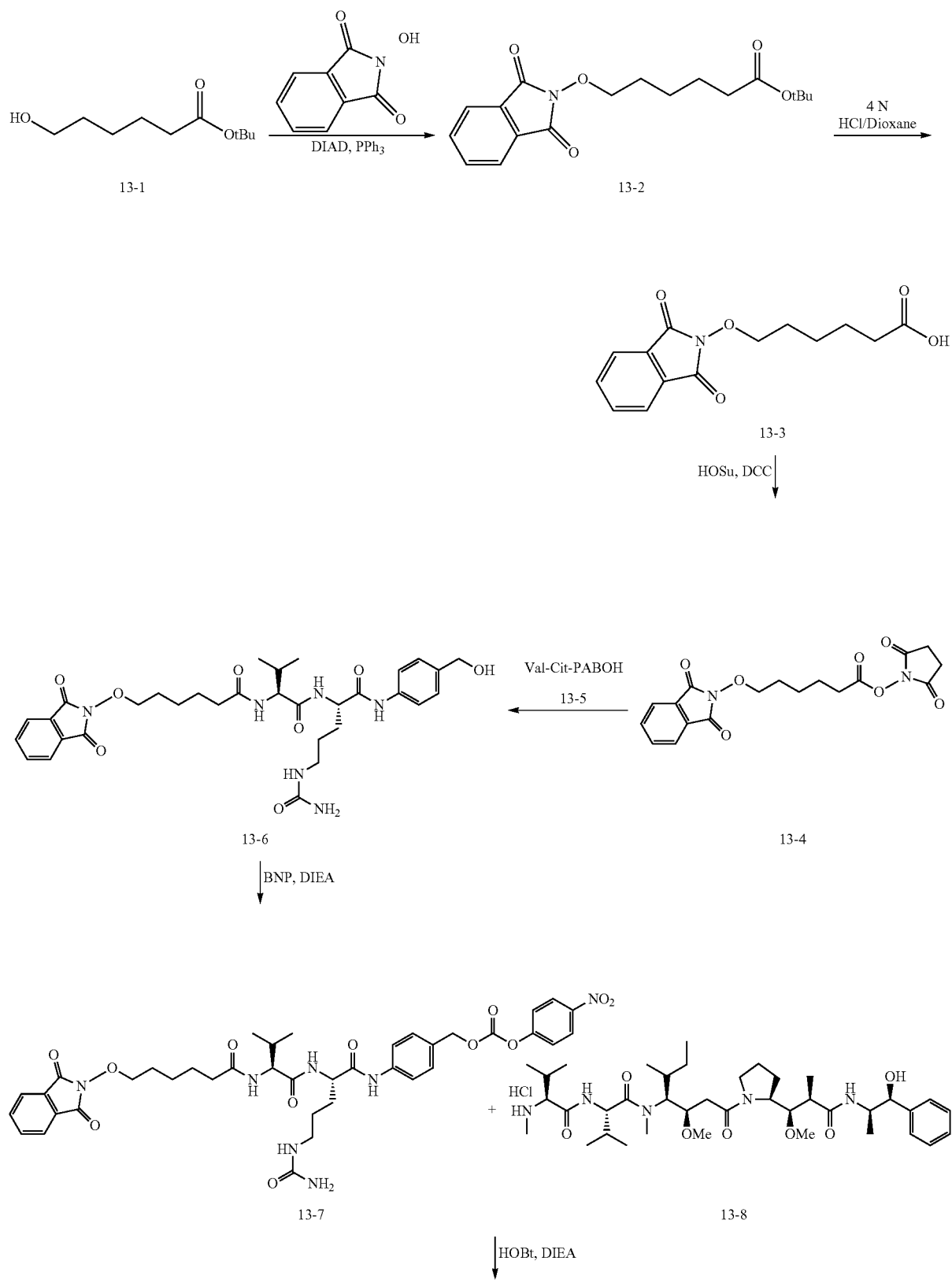

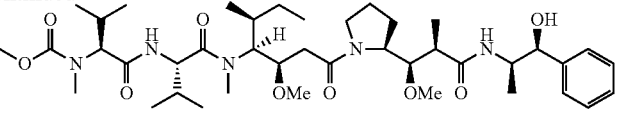
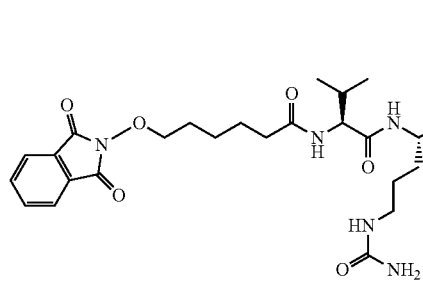

13-9

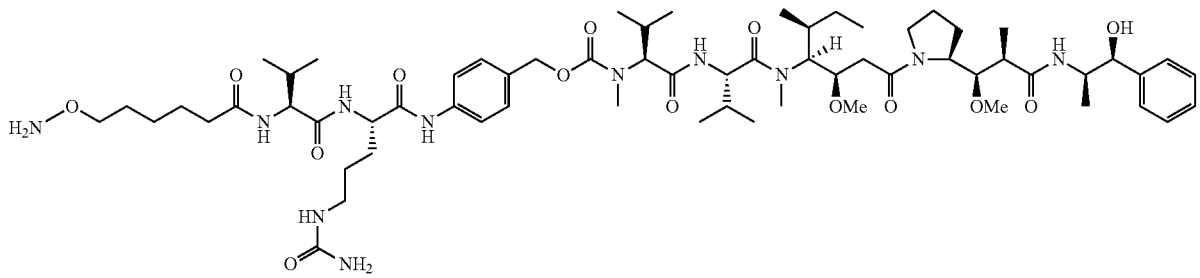

13

Compound 13-2: Tert-butyl 6-hydroxyhexanoate 13-1 (1.5 g, 1.97 mmol), N-hydroxyphthalimide (1.42 g, 8.76 mmol) and triphenylphosphine (2.82 g, 10.76 mmol) were dissolved in 50 mL of tetrahydrofuran followed by addition of DIAD (2 mL, 9.564 mmol) at 0° C. The resulting solution was stirred at room temperature overnight, and then concentrated to dryness. The residue was purified by flash column chromatography to give 2.5 g (95%) of compound 13-2.

Compound 13-3: The compound 13-2 was treated with 15 mL 4N HCl in dioxane. The reaction mixture was stirred at ambient temperature for 12 hours and concentrated to dryness in vacuo to give 900 mg (100%) of compound 13-3.

Compound 13-4: To a solution of compound 13-3 (900 mg, 3.0 mmol) in 10 mL of THF was added 397 mg of N-hydroxysuccinimide, followed by adding 669 mg of DCC. The reaction mixture was stirred at ambient temperature overnight and filtered. The filtration was concentrated and treated with 10 mL of DCM. The DCM solution was stayed at ambient temperature for 1 hour and filtered. The filtration was concentrated and purified by flash column chromatography to give 800 mg (71%) of compound 13-4.

Compound 13-6: The mixture of compound 13-4 (435 mg, 1.16 mmol) and Val-Cit-PABOH 13-5[1] (400 mg, 1.054 mmol) in 12 mL of DMF was stirred at ambient temperature for 24 hours. The solvent was removed in vacuo. The residue was treated with ether, filtered and washed with ether. The solid was dried in vacuo to give 660 mg (98%) of compound 13-6.

Compound 13-7: To the solution of compound 13-6 (200 mg, 0.313 mmol) in 6 mL of DMF was added bis(p-nitrophenyl)carbonate (286 mg, 0.94 mmol), followed by addition of 110.2 µL of DIEA. The reaction mixture was stirred at ambient temperature for 5 hours and concentrated. The residue was treated with ether and filtered. The collected solid was washed with ether, 5% citric acid, water, ether and dried in vacuo to give 210 mg (83%) compound 13-7.

Compound 13-9: To a solution of monomethylauristatin hydrochloride salt 13-8 (100 mg, 0.1325 mmol) in 2 mL of DMF was added compound 13-7 (159 mg, 0.2 mmol) and 10 mg of HOBt, followed by addition of 35.2 µL of DIEA. The resulting mixture was stirred at ambient temperature for 2 days. The reaction mixture was diluted with water and purified by HPLC to give 93 mg (51%) of compound 13-9. MS (ESI) m/z 692 [M+2H], 1382 [M+H].

Compound 13: The compound 13-9 (50 mg, 0.036 mmol) was dissolved in 1 mL of DMF. 23 µL of hydrazine was added. The resulting solution was stirred at ambient temperature for 3 hours. The reaction was quenched with 1N hydrochloride solution. The reaction mixture was purified by HPLC to give 32 mg (65%) of Compound 13. MS (ESI) m/z 638.5 [M+Na+2H], 1253.3 [M+H], 1275.8 [M+Na].

Example 14: Synthesis of Compound 14

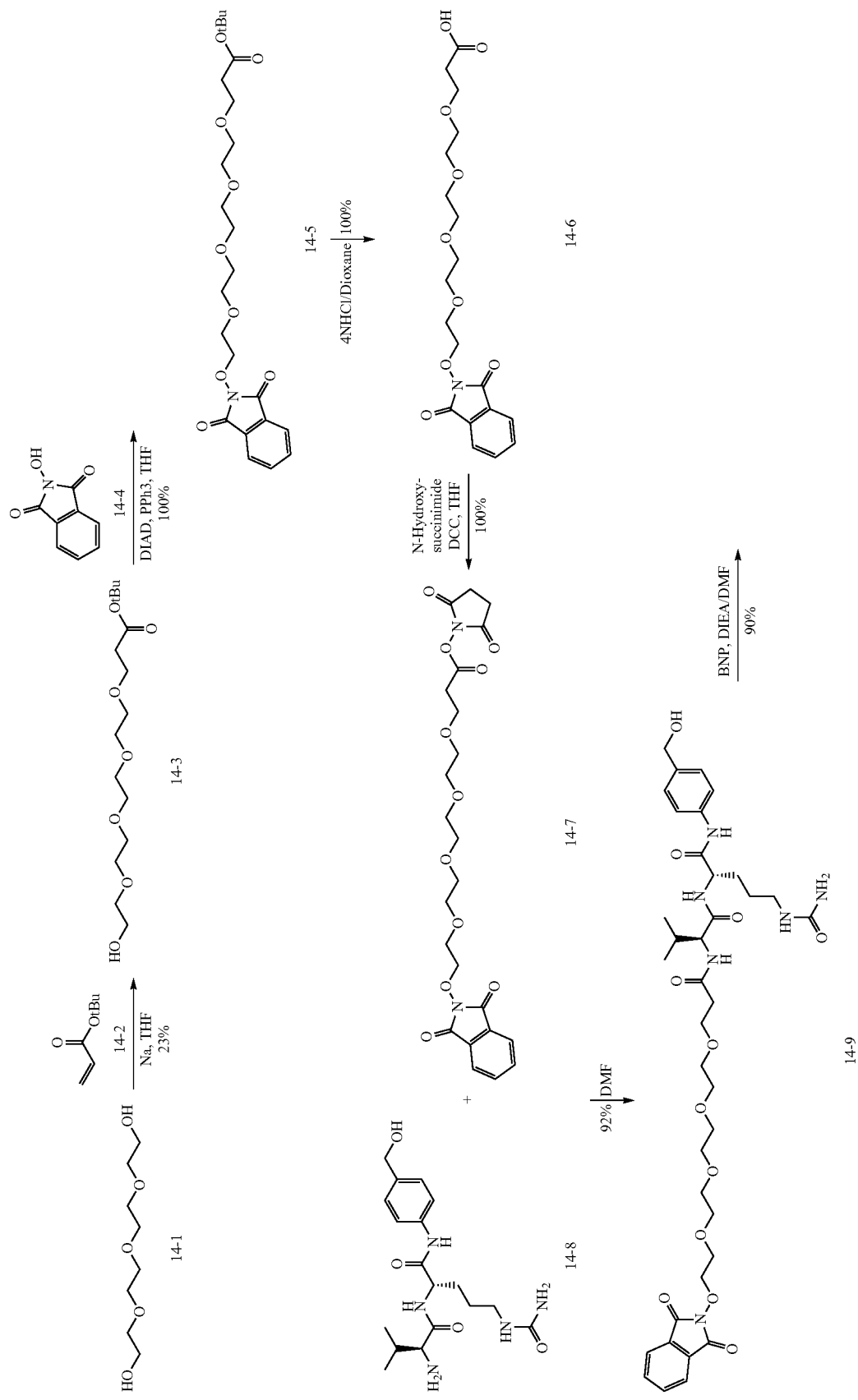
Scheme 14

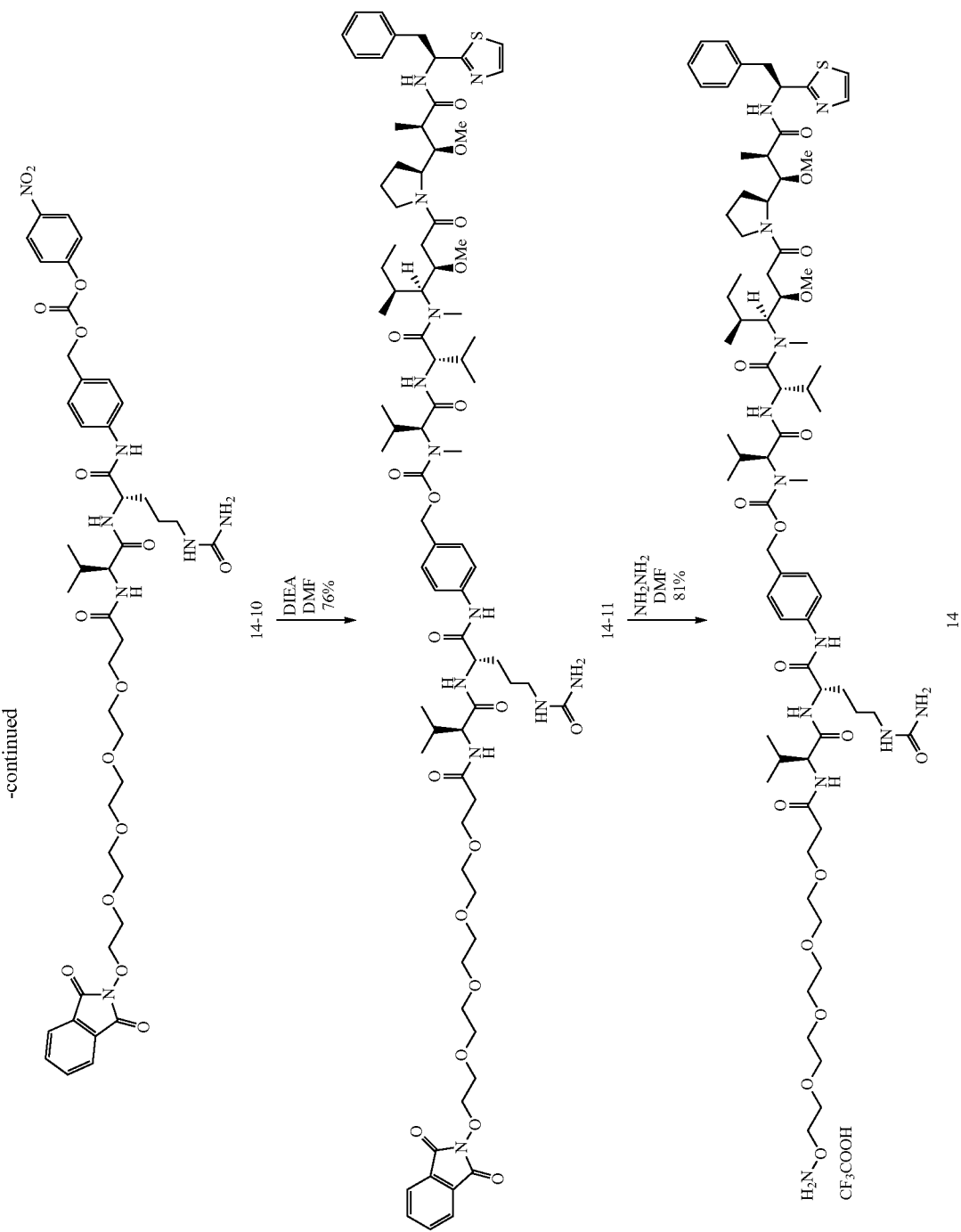

Compound 14-3: To a solution of tetra (ethylene glycol) 14-1 (40.6 mL, 235 mmol) in 100 mL of tetrahedrofuran was added 47 mg of sodium. 12 mL of tert-butylacrylate was added after sodium was dissolved. The reaction mixture was stirred at room temperature for 24 hours. The reaction mixture was concentrated in vacuo and quenched with 2 mL of 1 N HCl. The residue was suspended in brine and extracted with ethyl acetate (100 mL×1, 50 mL×2). The organic layer was combined and washed with brine, dried over sodium sulfate and concentrated in vacuo to give 6.4 g (23%) of compound 14-3.

Compound 14-5: Compound 14-3 (1.0 g, 3.12 mmol), N-hydroxyphthalimide 14-4 (611 mg, 3.744 mmol) and triphenylphosphine (1.23 g, 4.68 mmol) were dissolved in 20 mL of tetrahydrofuran followed by addition of DIAD (0.84 mL, 4.06 mmol) at 0° C. The resulting solution was stirred at room temperature overnight, and then concentrated to dryness. The residue was purified by flash column chromatography using SiliaSep Cartridges s15 (80 g), eluting with 0-100% ethyl acetate/hexanes, to give 1.0 g (100%) of compound 14-5.

Compound 14-6: Compound 14-5 was dissolved in 15 mL 4N HCl/Dioxane. The reaction mixture was stirred at room temperature for 2 hours and concentrated in vacuo to give 1.0 g of compound 14-6.

Compound 14-7: To a solution of compound 6 (1.93 g, 4.68 mmol) and N-hydroxysuccinimide (646 mg, 5.616 mmol) in 20 mL of tetrahedrofuran was added 1.062 g (5.148 mmol) of DCC. The reaction mixture was stirred at room temperature overnight and filtered. The filtration was concentrated and purified by flash column chromatography using SiliaSep Cartridges (80 g), eluting with 0-100% ethyl acetate/hexanes to give 2.37 g (100%) of compound 14-7.

Compound 14-8: Compound 14-8 was made according to the literature (Bioconjugat Chem. 2002, 13 (4), 855-869.)

Compound 14-9: To a solution of compound 14-8 (200 mg, 0.527 mmol) in 2 mL of DMF was added 295 mg (0.58 mmol) of compound 14-7. The reaction mixture was stirred at room temperature overnight and concentrated in vacuo. The residue was treated with ether, filtered, washed with ether and dried in vacuo to give 402 mg (98%) of compound 14-9.

Compound 14-10: To a solution of compound 14-9 (406 mg, 0.527 mmol) and bis(p-nitrophenol) carbonate (481 mg, 1.58 mmol) in 10 mL of DMF was added 0.186 mL (1.054 mmol) of diisopropylethylamine. The reaction mixture was stirred at room temperature for 5 hours. The solvent was removed in vacuo. The residue was treated with ether, filtered, washed with ether, 5% citic acid, water, ether and dried in vacuo to give 350 mg (72%) of compound 14-10.

Compound 14-11: To a solution of 50 mg (0.062 mmol) of monomethyldolastatin hydrochloride, 87.2 mg (0.093 mmol) of compound 14-10 and 4.7 mg (0.031 mmol) of HOBt in 1 mL of DMF was added 22 µL (0.124 mmol) of diisopropylethylamine. The reaction mixture was stirred at room temperature for 16 hours. The reaction mixture was purified by HPLC to give 41 mg (42%) of compound 14-11. MS (ESI) m/z 785 [M+2H].

Compound 14: Compound 14-11 (41 mg, 0.026 mmol) was dissolved in 1 mL of DMF. 17 µL (0.52 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 22 mg (58%) of compound 14. MS (ESI) m/z 720 [M+2H].

Example 15: Synthesis of Compound 15

Scheme 15
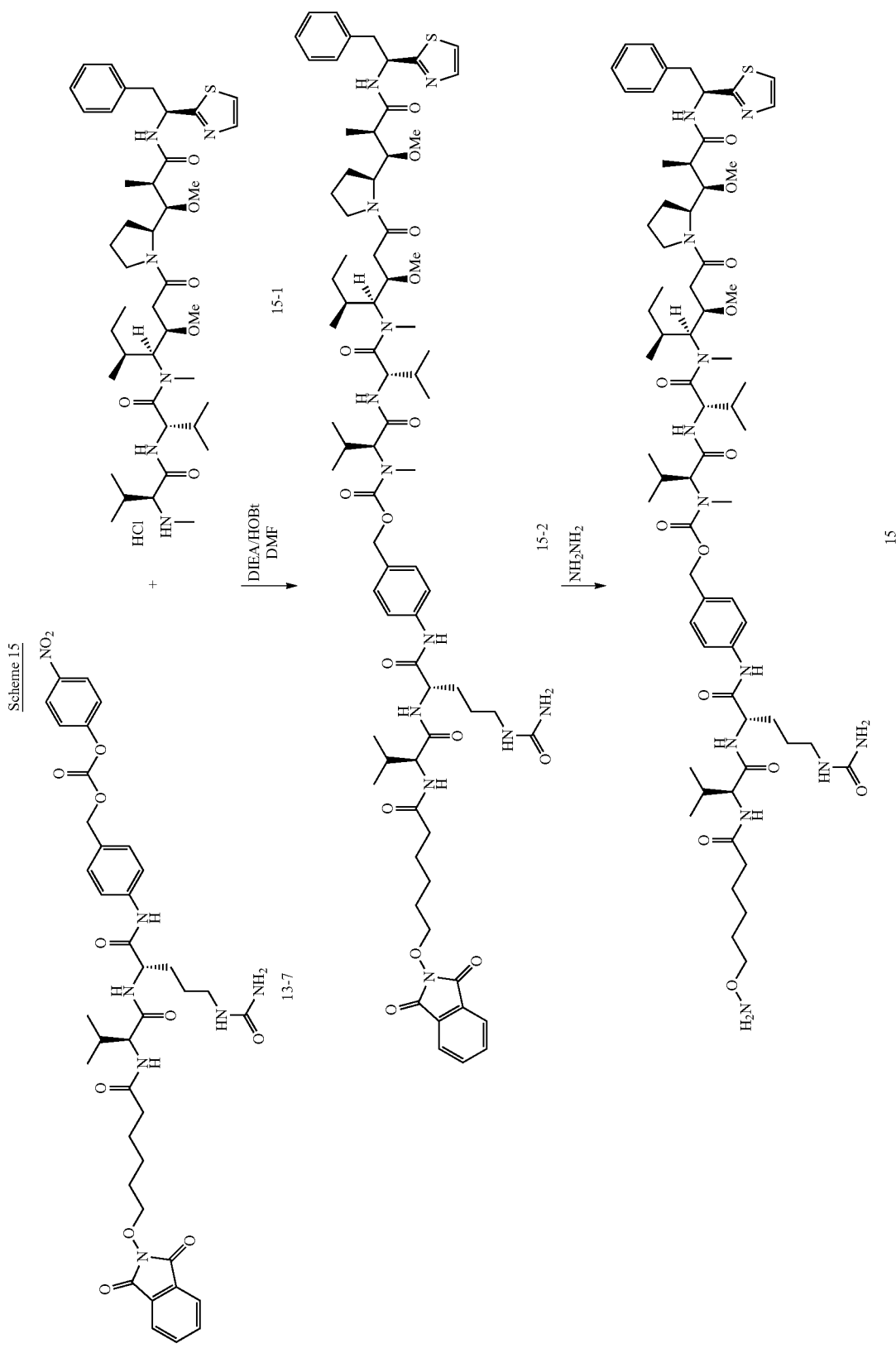

Compound 15-2: To a solution of 50 mg (0.062 mmol) of monomethyldolastatin hydrochloride, 75 mg (0.093 mmol) of compound 13-7 and 4.7 mg (0.031 mmol) of HOBt in 1 mL of DMF was added 22 µL (0.124 mmol) of diisopropylethylamine. The reaction mixture was stirred at room temperature for 16 hours. The reaction mixture was purified by HPLC to give 41 mg (42%) of compound 15-2. MS (ESI) m/z 718 [M+2H], 1435 [M+H].

Compound 15-2: Compound 15-2 (41 mg, 0.026 mmol) was dissolved in 1 mL of DMF. 17 µL (0.52 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 22 mg (58%) of example 15. MS (ESI) m/z 653 [M+2H], 1305 [M+H].

Example 16: Synthesis of Compound 16

Scheme 16
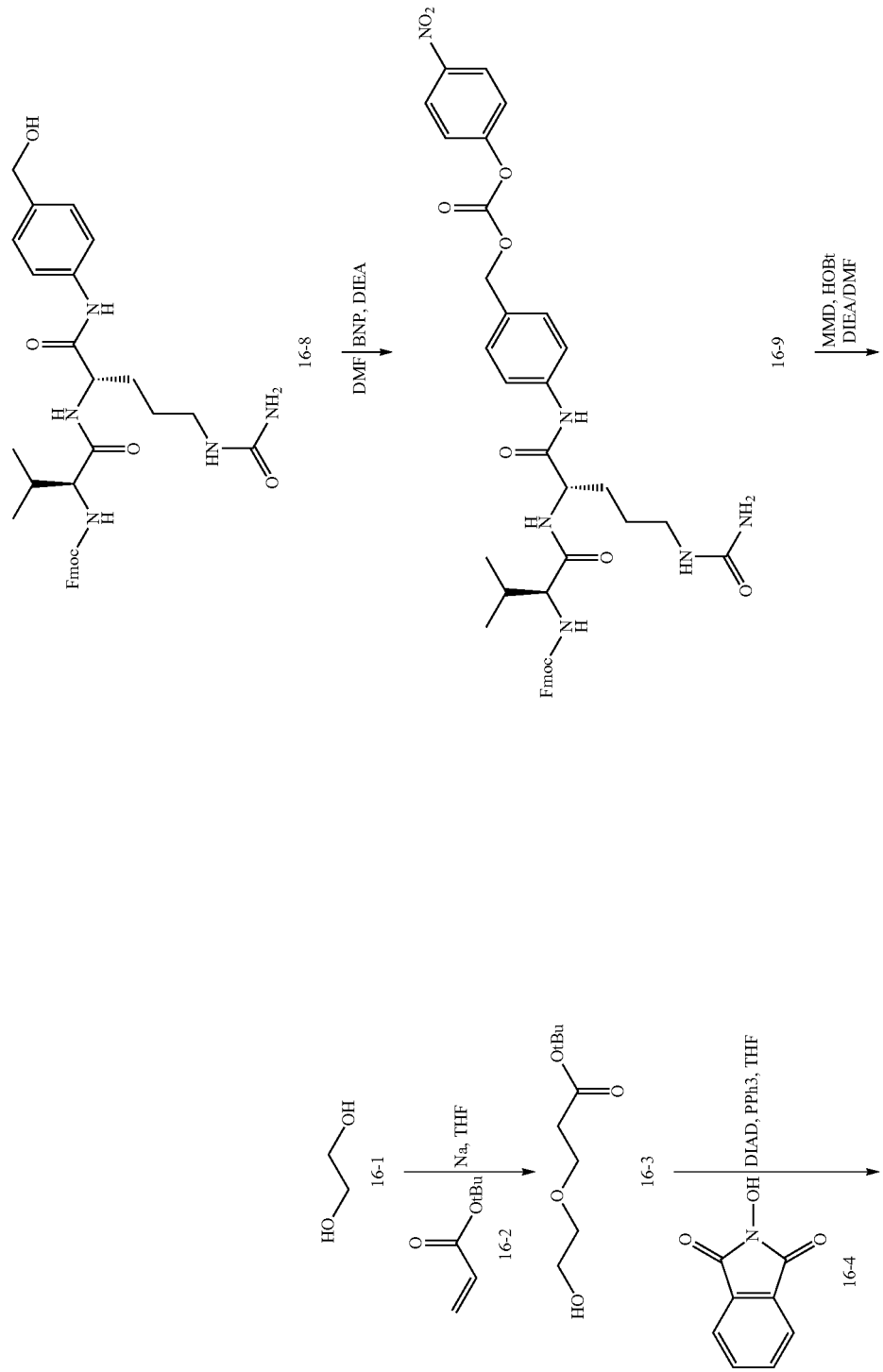

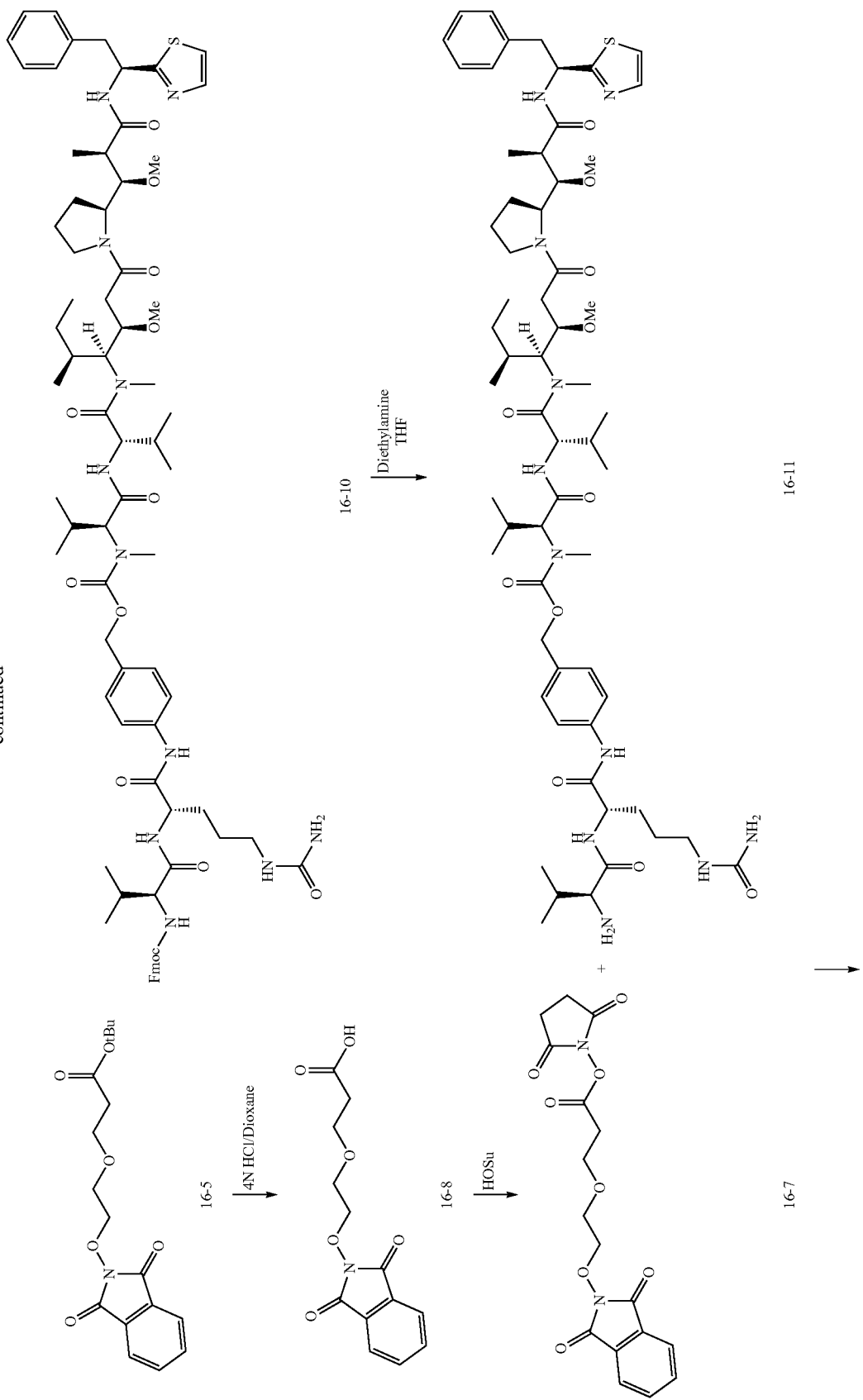

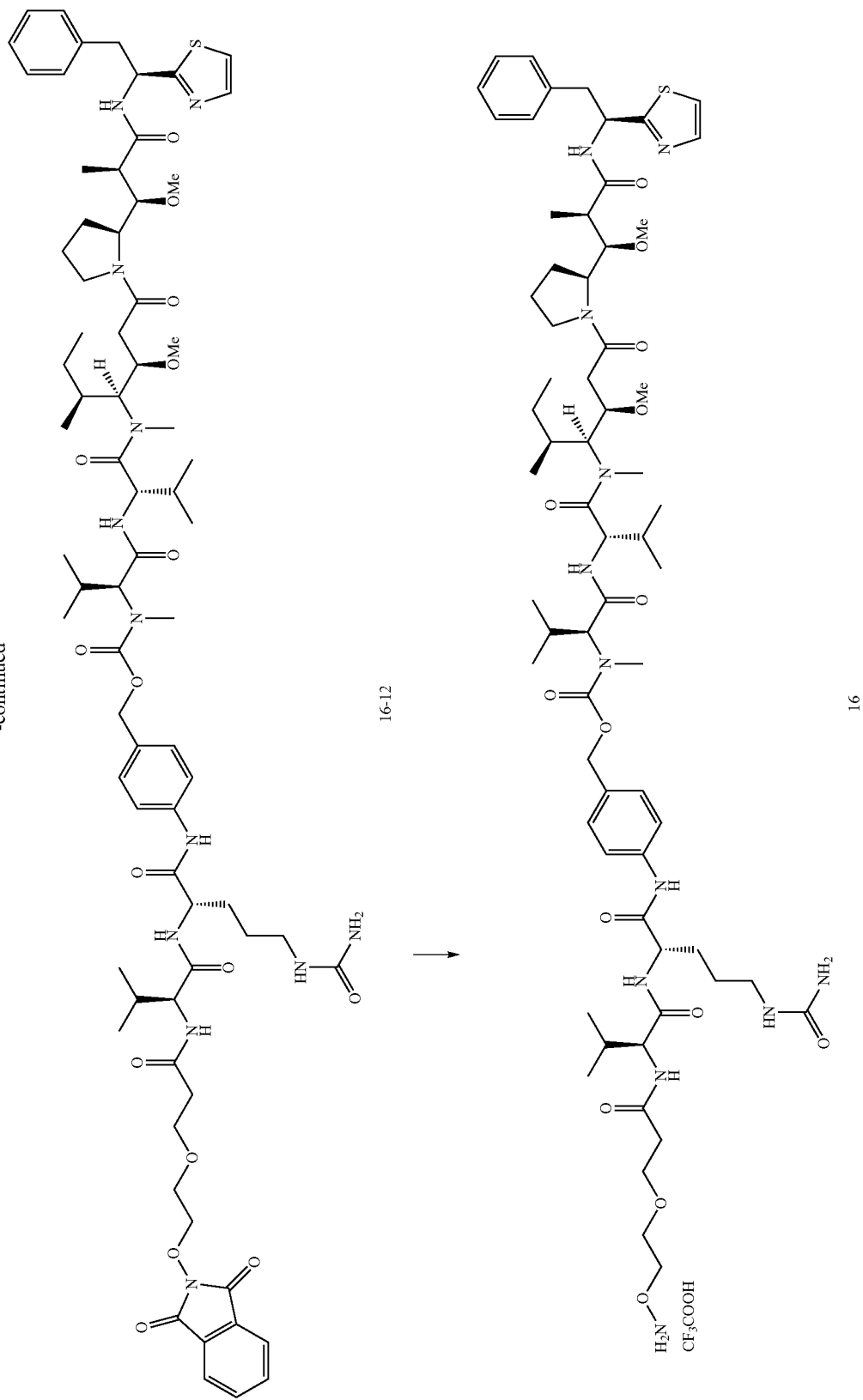

Compound 16-3: To a solution of ethylene glycol 16-1 (13.1 mL, 235 mmol) 100 mL of tetrahedrofuran was added 47 mg of sodium. 12 mL of tert-butylacrylate was added after sodium was dissolved. The reaction mixture was stirred at room temperature for 24 hours. The reaction mixture was concentrated in vacuo and quenched with 2 mL of 1 N HCl. The residue was suspended in brine and extracted with ethyl acetate (100 mL×1, 50 mL×2). The organic layer was combined and washed with brine, dried over sodium sulfate and concentrated in vacuo. The residue was purified by flash column chromatography to give 5.2 g (24%) of compound 16-3.

Compound 16-5: Compound 16-3 (2.0 g, 10.5 mmol), N-hydroxyphthalimide (2.05 g, 12.6 mmol) and triphenylphosphine (3.58 g, 13.65 mmol) were dissolved in 50 mL of tetrahedrofuran followed by addition of DIAD (3.26 mL, 15.75 mmol) at 0° C. The resulting solution was stirred at room temperature overnight, and then concentrated to dryness. The residue was purified by flash column chromatography to give compound 16-5.

Compound 16-6: Compound 16-5 was dissolved in 15 mL 4N HCl/Dioxane. The reaction mixture was stirred at room temperature for 2 hours and concentrated in vacuo to give compound 16-6.

Compound 16-7: To a solution of compound 16-6 (5.16 mmol) and N-hydroxysuccinimide (722 mg, 6.7 mmol) in 20 mL of tetrahedrofuran was added 1.28 g (6.2 mmol) of DCC. The reaction mixture was stirred at room temperature overnight and filtered. The filtration was concentrated and purified by flash column chromatography to give 500 mg of compound 16-7.

Compound 16-8: Compound 16-8 was made according to the literature (Bioconjugat Chem. 2002, 13 (4), 855-869.)

Compound 16-9: To a solution of compound 16-8 (5.0 g, 8.3 mmol) and bis(p-nitrophenol) carbonate (7.6 g, 25 mmol) in 100 mL of DMF was added 2.92 mL (16.6 mmol) of diisopropylethylamine. The reaction mixture was stirred at room temperature for 16 hours. The solvent was removed in vacuo. The residue was treated with ether, filtered, washed with ether, 5% citic acid, water, ether and dried in vacuo to give 5.0 g (81%) of compound 16-9.

Compound 16-10: To a solution of 1.0 g (1.24 mmol) of monomethyldolastatin hydrochloride, 1.42 g (1.8575 mmol) of compound 16-9 and 95 mg (0.62 mmol) of HOBt in 10 mL of DMF was added 437 µL (2.48 mmol) of diisopropylethylamine. The reaction mixture was stirred at room temperature for 16 hours. The reaction mixture was purified by HPLC to give 1.0 g (58%) of compound 16-10. MS (ESI) m/z 700 [M+2H], 1398 [M+H].

Compound 16-11: To a solution of compound 16-10 (1.0 g, 0.715 mmol) in 15 mL of tetrahedrofuran was added 5 mL (48 mmol) of diethylamine. The reaction mixture was stirred at room temperature for 1.5 hours and concentrated in vacuo. The residue was dissolved in 20 mL of DCM, treated with 200 mL of ether and filtered, wshed with ether and dried in vacuo to give 860 mg of compound 16-11. MS (ESI) m/z 589 [M+2H], 1176 [M+H].

Compound 16: To a solution of 50 mg (0.0425 mmol) of compound 16-11 in 1 mL of DMF was added 32 mg (0.085 mmol) of compound 16-7. The reaction mixture was stirred at room temperature for 16 hours. The HPLC and MS showed reaction done. 27.2 L (0.85 mmol) of anhydrous hydrazine was added to the reaction mixture. The reaction was done in 2 hours. The reaction mixture was acidified with 1N HCl and purified by HPLC to give 40 mg (66%) of compound 16. MS (ESI) m/z 654 [M+2H], 1307[M+H].

Example 17

Scheme 17

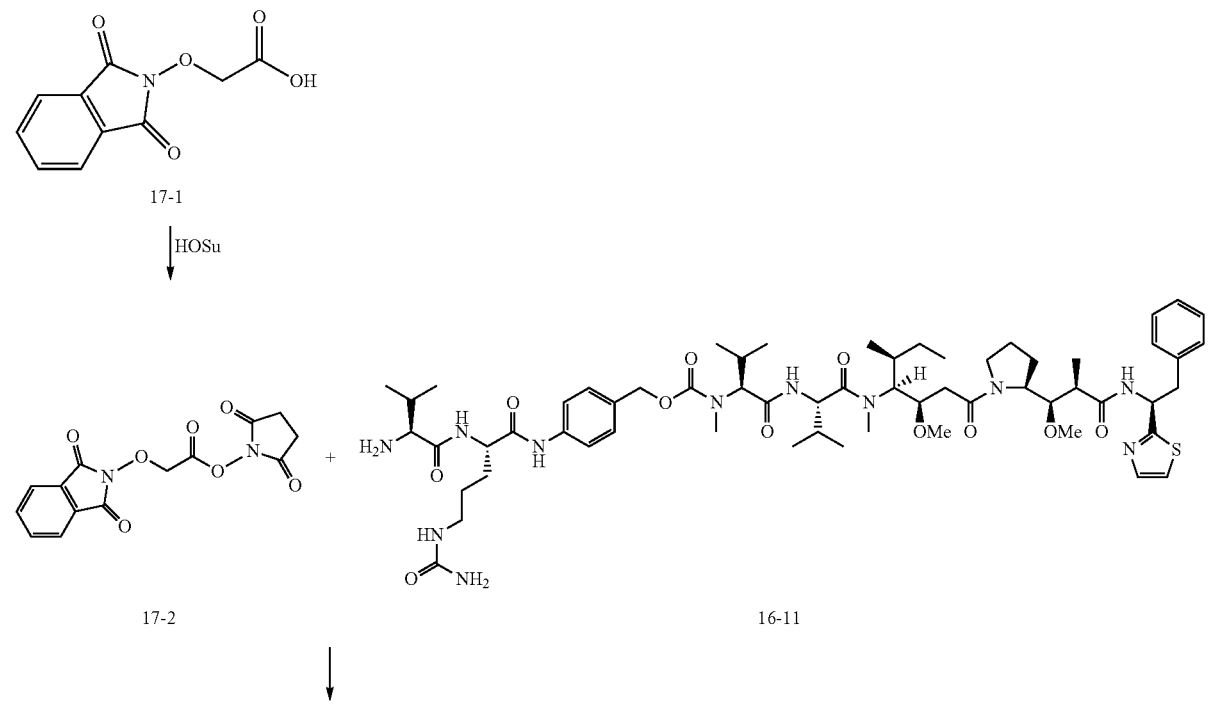

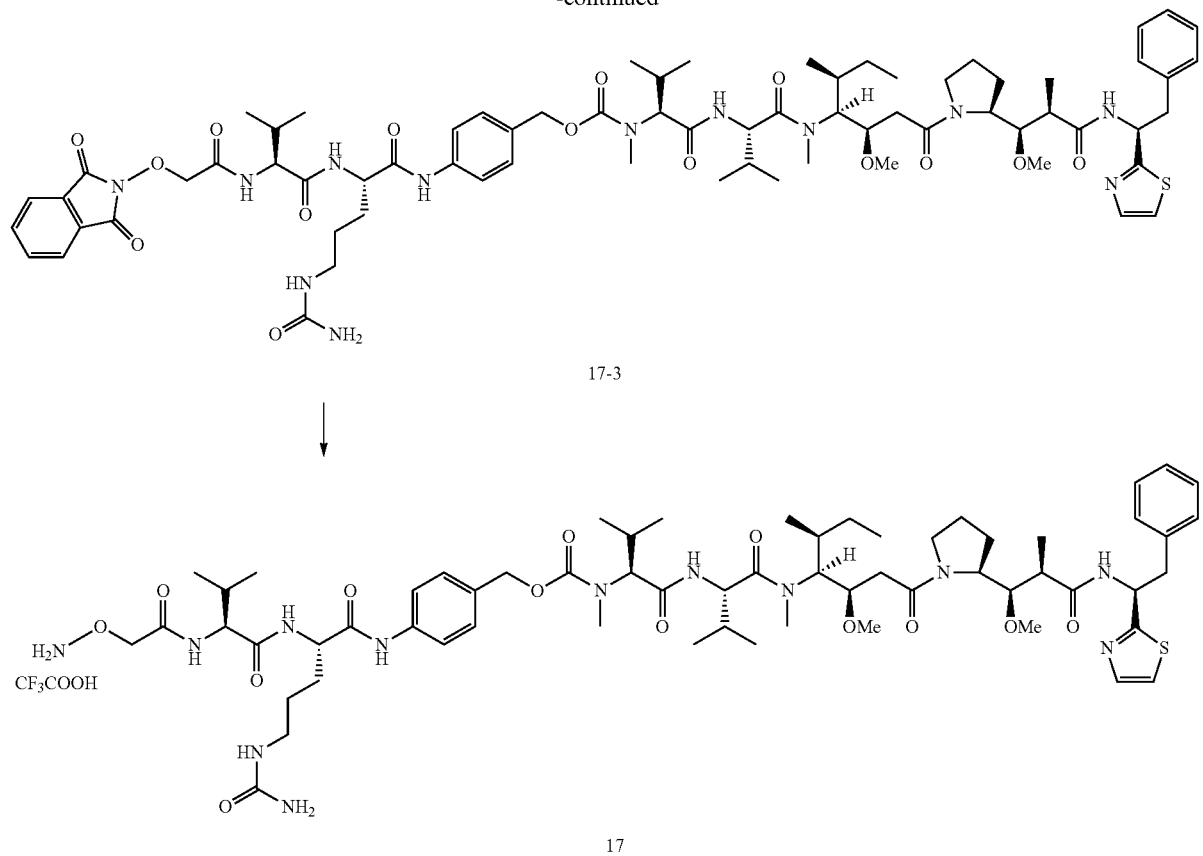

17-3

17

Compound 17-2: To a solution of compound 17-1 (1.0 g, 4.52 mmol) and N-hydroxysuccinimide (572 mg, 4.97 mmol) in 20 mL of tetrahedrofuran was added 1.12 g (5.424 mmol) of DCC. The reaction mixture was stirred at room temperature overnight and filtered. The filtration was concentrated to give compound 17-2.

Compound 17: To a solution of 50 mg (0.0425 mmol) of compound 16-11 in 1 mL of DMF was added 41 mg (0.1275 mmol) of compound 17-2. The reaction mixture was stirred at room temperature for 16 hours. The HPLC and MS showed reaction done. 20 μL (0.625 mmol) of anhydrous hydrazine was added to the reaction mixture. The reaction was done in 2 hours. The reaction mixture was acidified with 1N HCl and purified by HPLC to give 35 mg (60%) of compound 17. MS (ESI) m/z 625 [M+2H], 1249 [M+H].

Example 18: Synthesis of Compound 18

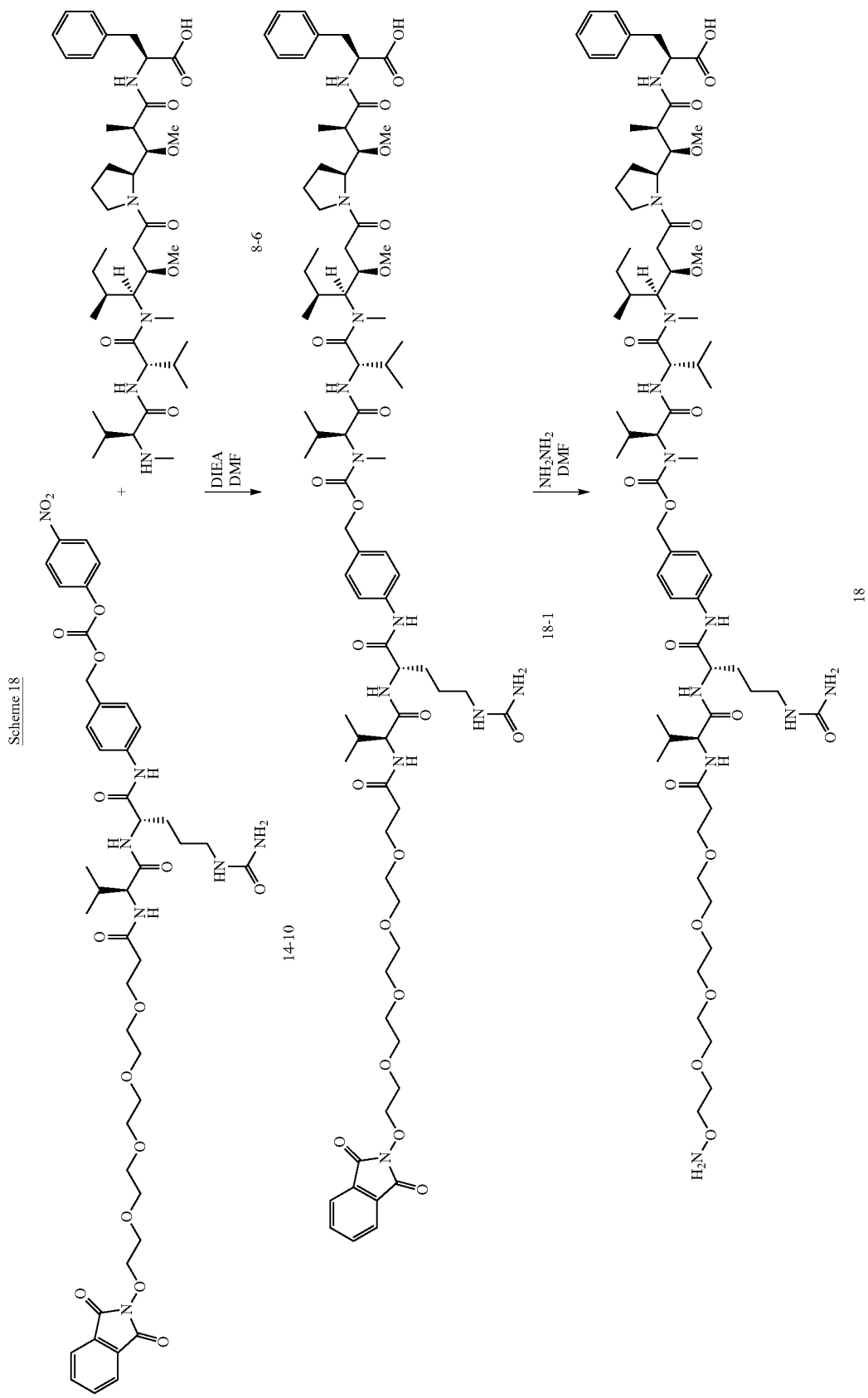

Compound 18: Compound 18-1 was dissolved in 1 mL of DMF. Anhydrous

Compound 18-1: To a solution of compound 6-6, mg (0.062 mmol) of compound 14-10 and HOBt in 1 mL of DMF was added diisopropylethylamine. The reaction mixture was stirred at room temperature for 16 hours. The reaction mixture was purified by HPLC to give compound 18-1.

Compound 18: Compound 18-1 was dissolved in 1 mL of DMF. Anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give compound 18.

Example 19: Synthesis of Compound 19

Scheme 19
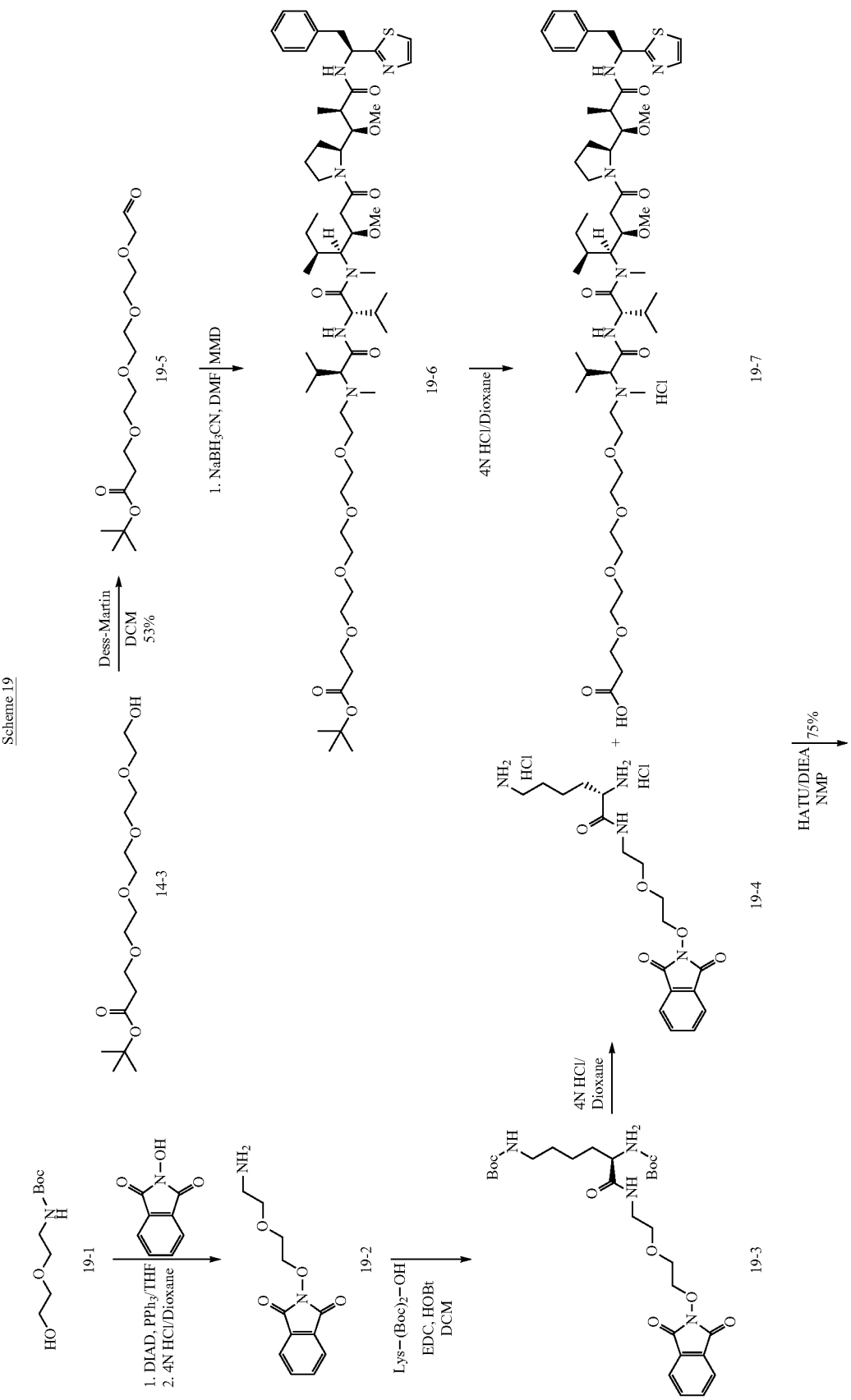

-continued
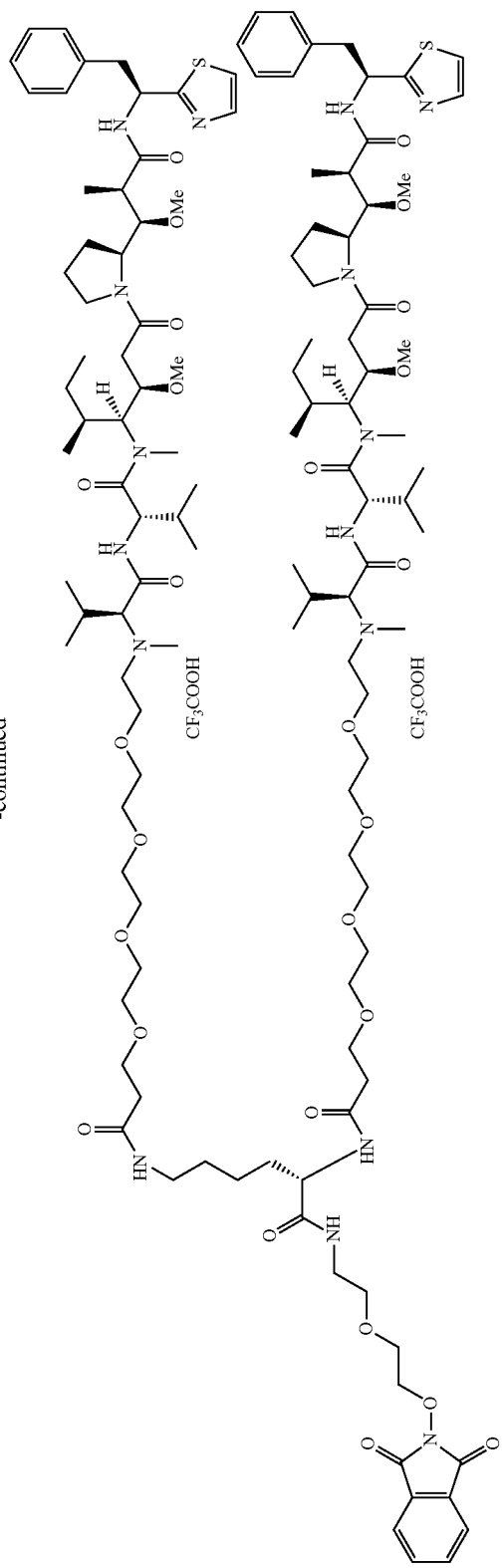
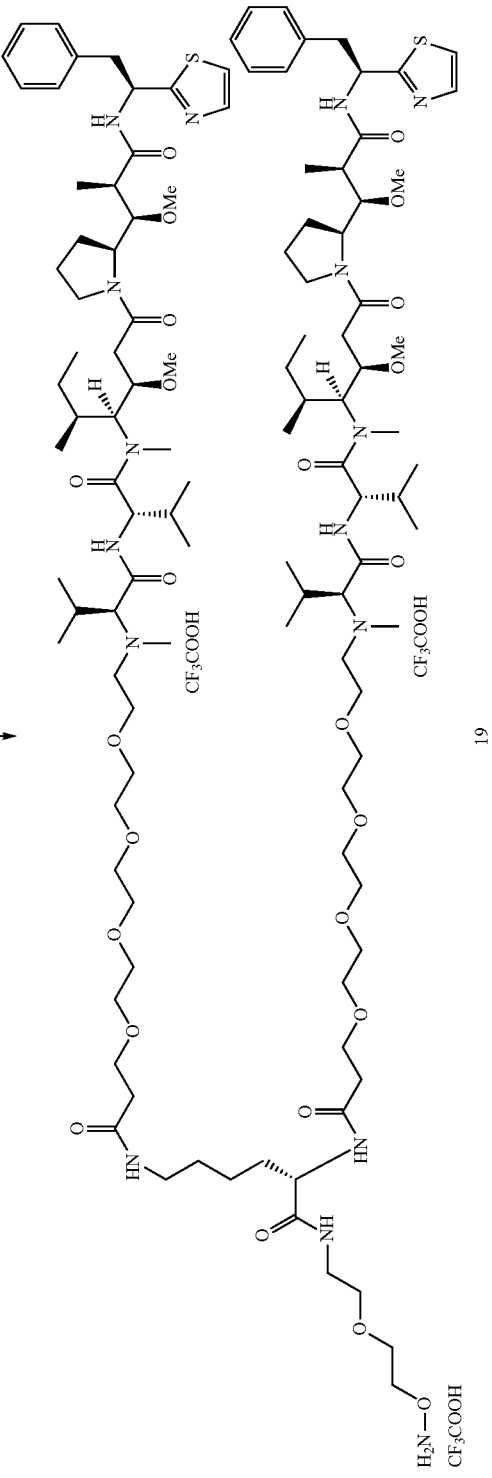

Compound 19-2: tert-Butyl 2-(2-hydroxyethoxy)ethylcarbamate 13 (2.05 g, 10 mmol), N-hydroxyphthalimide (1.8 g, 11 mmol) and triphenylphosphine (3.67 g, 14 mmol) were dissolved in 100 mL of tetrahydrofuran followed by addition of DIAD (2.48 mL, 12 mmol) at 0° C. The resulting solution was stirred at room temperature overnight, and then concentrated to dryness. The residue was treated with 50 mL of 4N HCl/dioxane. The mixture was stirred at room temperature for 2 hours. The solvent was removed in vacuo. The residue was treated with ether, filtered, washed with ether and dried in vacuo to get 2.6 g (91%) of compound 19-2. MS (ESI) m/z 251 [M+H].

Compound 19-3: To the mixture of compound 19-2 (315 mg, 1.1 mmol), Boc-Lys(Boc)-OH (365 mg, 1 mmol), EDC (382 mg, 2 mmol) and HOBt (306 mg, 2 mmol) in 10 mL of DCM was added 1.056 mL (6 mmol) of diisopropylethylamine. The reaction mixture was stirred at room temperature for 3 hours and extracted with ethyl acetate, washed with 5% citric acid, saturate sodium bicarbonate, brine, dried over sodium sulfate, filtered and concentrated in vacuo. The residue was purified flash column chromatography using SiliaSep Cartridges (40 g), eluting with 0-100% ethyl acetate/hexanes, to give 405 mg (70%) of compound 19-3.

Compound 19-4: Compound 19-3 was dissolved in 15 mL 4N HCl/Dioxane. The reaction mixture was stirred at room temperature for 2 hours and concentrated in vacuo to give 315 mg (98%) of compound 19-4. MS (ESI) m/z 379 [M+H].

Compound 19-5: To a solution of compound 14-3 (322 mg, 1 mmol) in 20 mL dichloromethane was added Dess-Martin Periodinane (636 mg, 1.5 mmol). The reaction mixture was stirred at room temperature for 3 hours. The reaction was quenched with a solution of sodium thiosulfate (1.4 g, 8.85 mmol) in 15 mL of saturated sodium bicarbonate. The mixture was separated. The organic layer was washed with saturated sodium bicarbonate, brine, dried over sodium sulfate, filtered and concentrated in vacuo. The residue was purified by flash column chromatography using SiliaSep Cartridges (40 g), eluting with 0-100% ethyl acetate/hexanes to give 170 mg (53%) of compound 19-5.

Compound 19-6: To a solution of monomethyldolastatin hydrochloride 1.0 g (1.24 mmol) in 20 mL of DMF was added 1.19 g (3.72 mmol) of compound 17 followed by 1.4 mL (24.8 mmol) of acetic acid and 156 mg (2.48 mmol) of sodium cyanoborohydride. The resulting mixture was stirred at room temperature for 2 hours. The solvent was removed in vacuo. The residue was adjusted to pH 8 by sodium bicarbonate and extracted with DCM, washed with brine, dried over sodium sulfate, filtered and concentrated in vacuo. The residue was purified by flash column chromatography using SiliaSep Cartridges (40 g), eluting with 0-5% methanol/DCM to give 680 mg (51%) of compound 19-6. MS (ESI) m/z 538 [M+2H], 1075 [M+H].

Compound 19-7: To a solution of compound 19-6 (680 mg, 0.632 mmol) in 5 mL of DCM was added 20 mL of 4N HCl/dioxane. The reaction mixture was stirred at room temperature for 2 hours and concentrated in vacuo. The residue was treated with ether, filtered, washed with ether and dried in vacuo to give 660 mg (98%) of compound 19-7. MS (ESI) m/z 510 [M+2H], 1019 [M+H].

Compound 19-8: To a solution of compound 19-7 (280 mg, 0.257 mmol), compound 19-4 (38 mg, 0.0857 mmol) and N-methylmorpholine (0.283 mL, 2.57 mmol) in 5 mL of N-methylmpyrrolidinone was added 98 mg (0.257 mmol) of HATU. The reaction mixture was stirred at room temperature for 1 hour. The reaction mixture was purified by HPLC to give 160 mg (71%) of compound 19-8. MS (ESI) m/z 596 [M+4H], 794[M+3H], 1191 [M+2H].

Compound 19: Compound 19-8 (160 mg, 0.0613 mmol) was dissolved in 1.5 mL of DMF. 20 µL (0.613 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 120 mg (75%) of compound 19. MS (ESI) m/z 451[M+5H], 563 [M+4H], 751 [M+3H], 1126 [M+2H].

Example 20: Synthesis of Compound 20

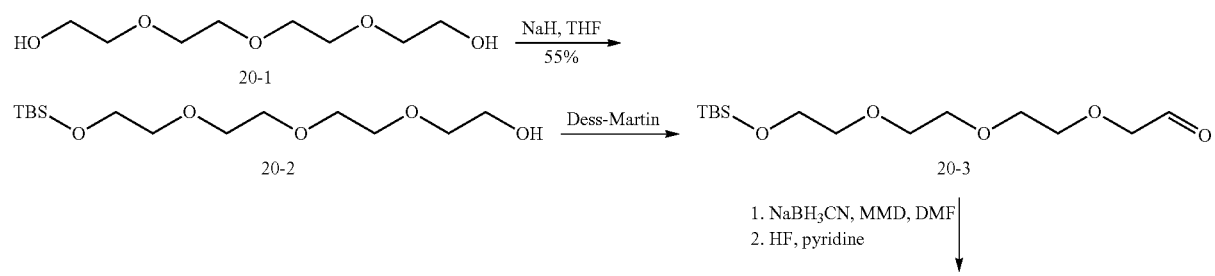

-continued
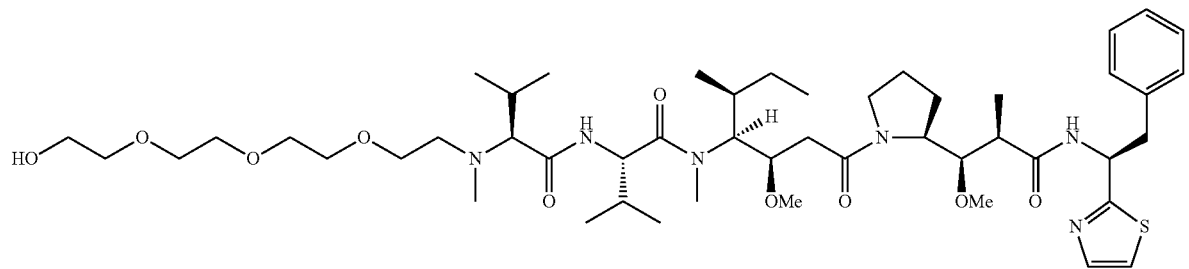
20-4
↓ COCl₂
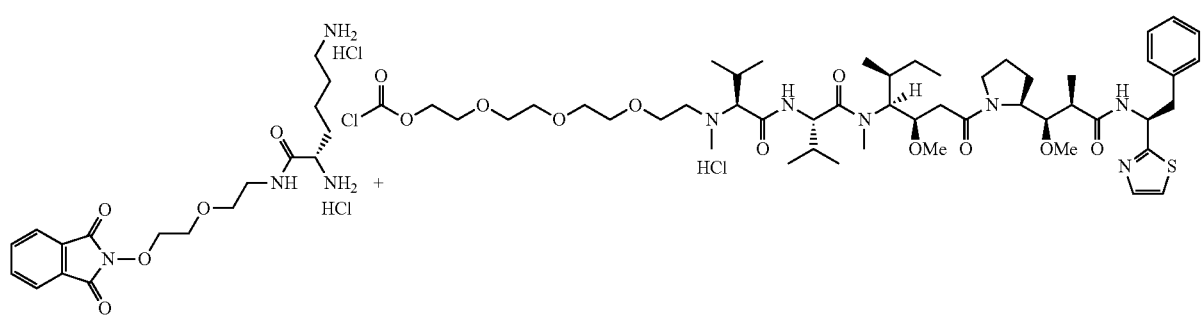
19-4   20-5
↓ DCM, DIEA
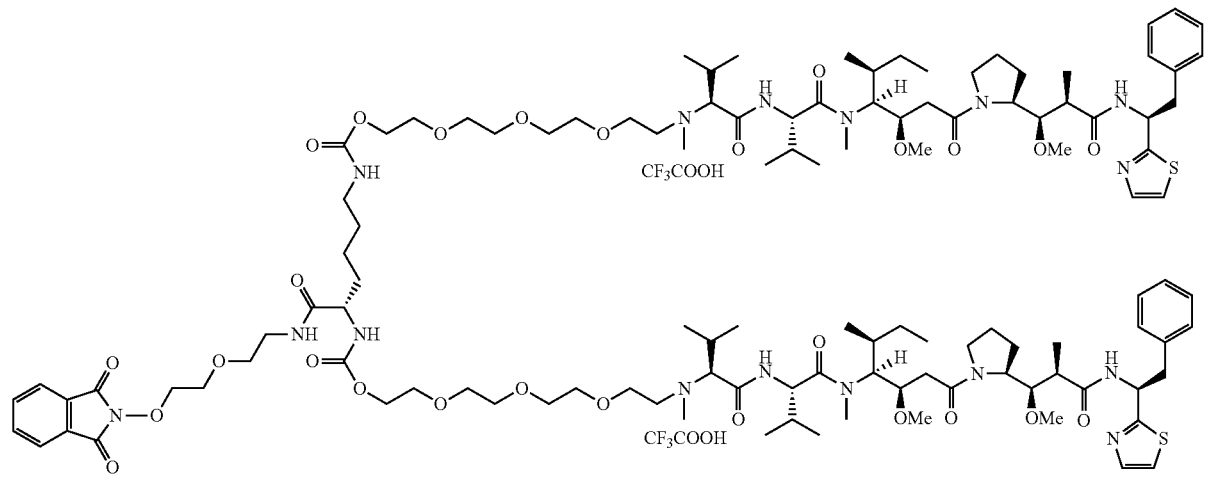
38
↓ NH₂NH₂

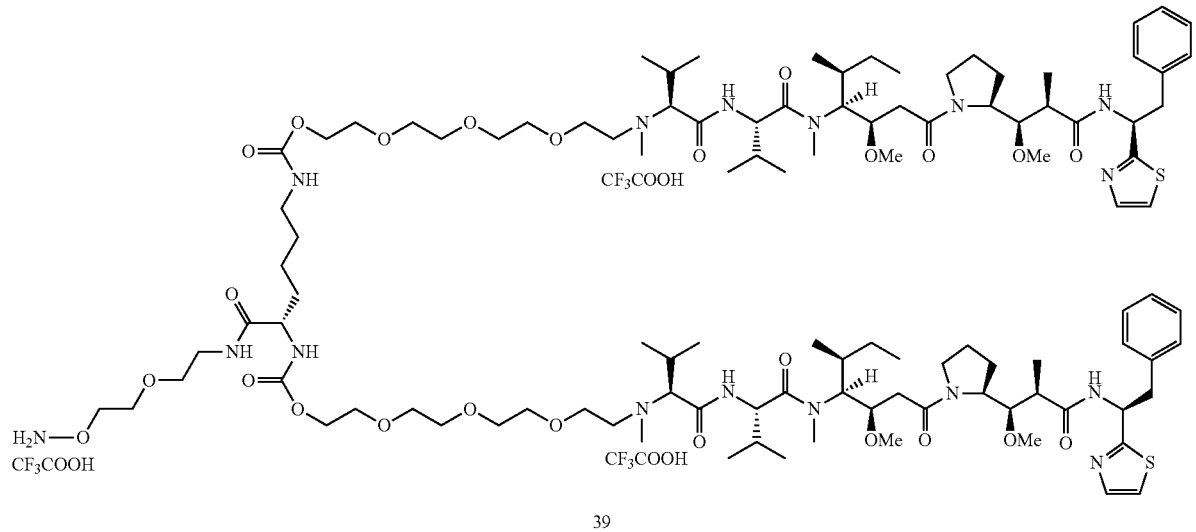

39

Compound 20-2: To a solution of tetra (ethylene glycol) 20-1 (8.0 g, 41.2 mmol) in 100 mL of tetrahedrofuran was added 1.65 g of sodium hydride at 0° C. The reaction mixture was stirred at room temperature for 30 min. 6.21 g of TBS-Cl was added to this solution. The reaction mixture was stirred at room temperature overnight. The reaction mixture was concentrated in vacuo and quenched with 2 mL of 1 N HCl. The residue was suspended in brine and extracted with ethyl acetate (100 mL×1, 50 mL×2). The organic layer was combined and washed with brine, dried over sodium sulfate and concentrated in vacuo. The residue was purified by flash column chromatography to give 5.7 g of compound 20-2.

Compound 20-3: To a solution of compound 20-2 (500 mg, 1.62 mmol) in 30 mL dichloromethane was added Dess-Martin Periodinane (1.03 g, 2.43 mmol). The reaction mixture was stirred at room temperature for 3 hours. The reaction was quenched with a solution of sodium thiosulfate (1.4 g, 8.85 mmol) in 15 mL of saturated sodium bicarbonate. The mixture was separated. The organic layer was washed with saturated sodium bicarbonate, brine, dried over sodium sulfate, filtered and concentrated in vacuo. The residue was purified by flash column chromatography to give 400 mg of compound 20-3.

Compound 20-4: To a solution of monomethyldolastatin hydrochloride 213 mg (0.263 mmol) in 4 mL of DMF was added 245 mg (0.75 mmol) of compound 20-3 followed by 0.303 mL (5 mmol) of acetic acid and 34 mg (0.5 mmol) of sodium cyanoborohydride. The resulting mixture was stirred at room temperature for 2 hours. The solvent was removed in vacuo. 3 mL of 60% acetonitrile was added, followed by 0.2 mL of HF.Pyridine at 0° C. The resulting solution was stirred at room temperature for 2 hours. The organic solvent was removed in vacuo. The residue was adjusted to pH 8 by sodium bicarbonate and extracted with DCM, washed with brine, dried over sodium sulfate, filtered and concentrated in vacuo. The residue was purified by flash column chromatography to give 160 mg of compound 20-4. MS (ESI) m/z 474 [M+2H], 947[M+H].

Compound 20-5: To a solution of compound 20-4 (50 mg, 0.062 mmol) in 4 mL of DCM was added 0.3 mL of phosgene/toluene at 0° C. The reaction mixture was stirred at 0° C. for 3 hours and concentrated in vacuo for next step without purification.

Compound 20-6: To a solution of compound 19-4 (7.6 mg, 0.017 mmol) and compound 20-5 (0.062 mmol) was added 25 µL of diisopropylethylamine. The reaction mixture was stirred at room temperature for 1 hour. The reaction mixture was purified by HPLC, eluting with 20-70% CH3CN/H2O in 20 min at 254 nm, to give 33 mg of compound 20-6. MS (ESI) m/z 582[M+4H], 775[M+3H], 1163[M+2H].

Compound 20: Compound 20-6 (33 mg, 0.014 mmol) was dissolved in 1 mL of DMF. 14 µL (0.43 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 10 mg of compound 20. MS (ESI) m/z 549 [M+4H], 732[M+3H], 1098[M+2H].

Example 21: Synthesis of Compound 21
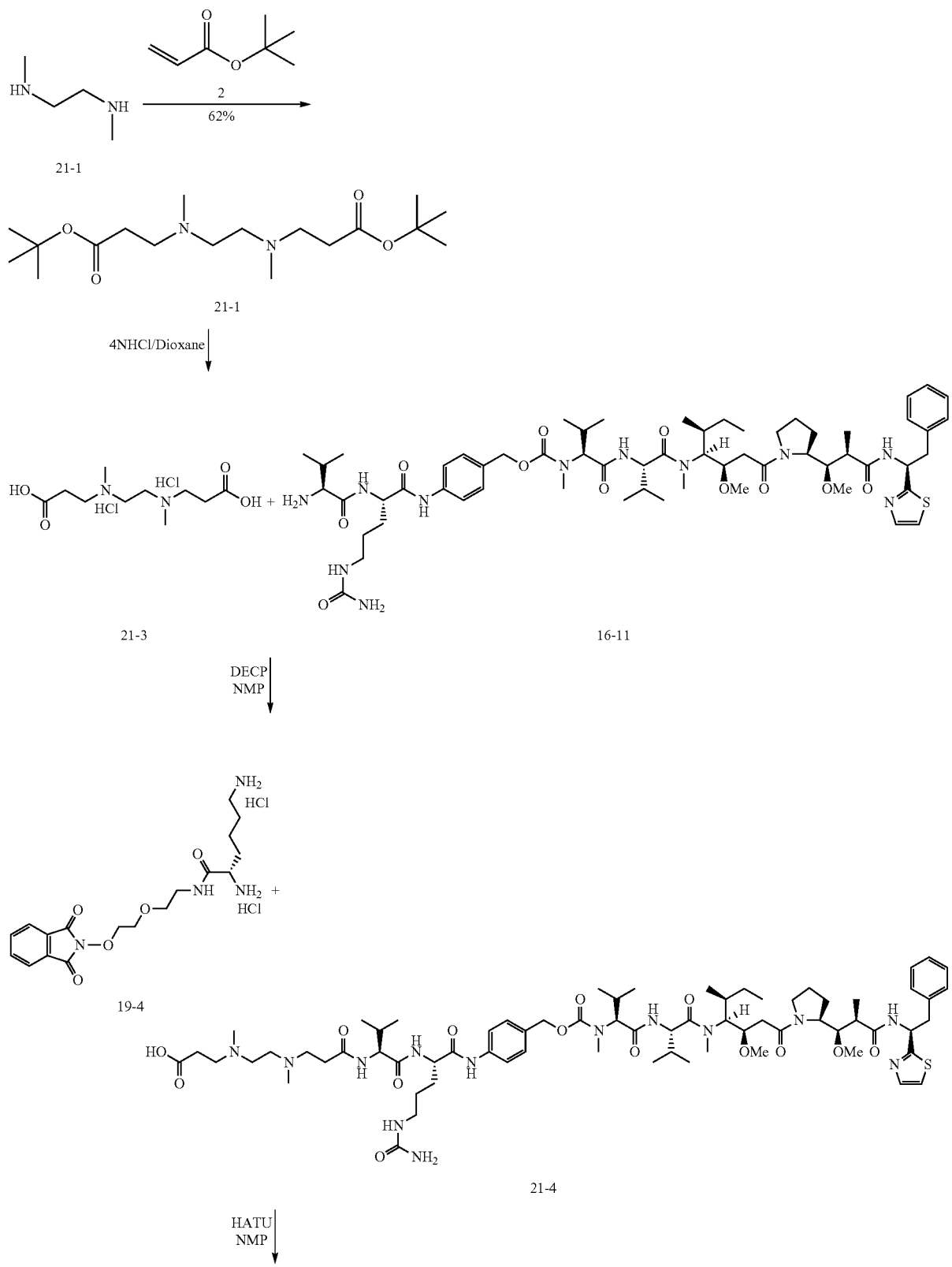

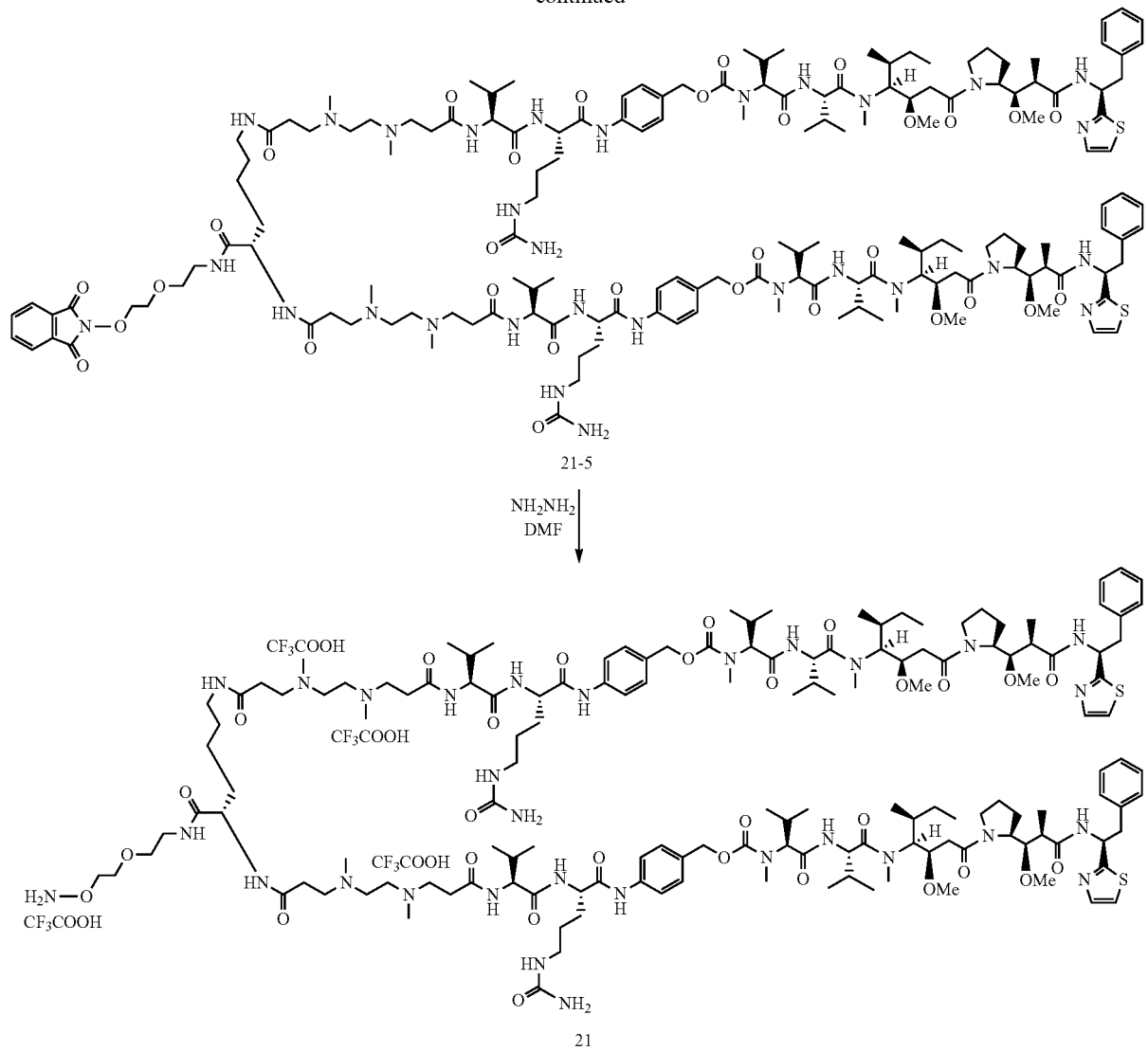

Compound 21-2: The mixture of N,N'-Dimethylene diamine 21-1 (5 mL, 46.5 mmol) and tert-butyl acrylate 13 mL (116 mmol) was heated at 85° C. for 1 hour. Another 13 mL (116 mmol) of tert-butyl acrylate was added. The reaction mixture was continuely heated at 85° C. for 1 hour and stirred at room temperature overnight. The reaction mixture was concentrated in vacuo. The residue wasdiluted with hexanes and purified by flash column chromatography using SiliaSep Cartridges (120 g), eluting with 0-5% methanol/DCM to give 10.1 g (62%) of compound 21-2. MS (ESI) m/z 345 [M+H].

Compound 21-3: To a solution of compound 21-2 (5.0 g, 14.5 mmol) in 50 mL of DCM was added 40 mL of 4N HCl/dioxane. The reaction mixture was stirred at room temperature for 2 days and concentrated in vacuo. The residue was treated with ether, filtered, washed with ether and dried in vacuo to give 4.3 g (97%) of compound 21-3.

Compound 21-4: To a solution of 166 mg (0.544 mmol) of compound 21-3 and 0.15 mL of N-methylmorpholine in 10 mL of N-methylpyrrolidinone was added 160 mg of compound 16-11, followed by 0.068 mL (0.408 mmol) of DECP. The reaction mixture was stirred at room temperature for 1 hour. The reaction mixture was purified by preparative HPLC, eluting with 35-70% CH3CN/H2O in 20 min at 254 nm, to give 100 mg (50%) of compound 21-4. MS (ESI) m/z 464[M+3H], 696 [M+2H], 1391 [M+H].

Compound 21-5: To a solution of compound 19-4 (11 mg, 0.025 mmol), compound 21-4 (115 mg, 0.077 mmol) and N-methylmorpholine (0.028 mL, 0.25 mmol) in 1.5 mL of N-methylmpyrrolidinone was added 29.3 mg (0.077 mmol) of HATU. The reaction mixture was stirred at room temperature for 1 hour. The reaction mixture was purified by HPLC, eluting with 20-70% CH3CN/H2O in 20 min at 254 nm, to give 60 mg (67%) of compound 21-5. MS (ESI) m/z 625 [M+5H], 781 [M+4H], 1041[M+3H].

Compound 21: Compound 21-5 (60 mg, 0.014 mmol) was dissolved in 1 mL of DMF. 7 µL (0.21 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 29 mg (58%) of compound 21. MS (ESI) m/z 599 [M+5H], 749 [M+4H], 998 [M+3H].

Example 22: Synthesis of Compound 22
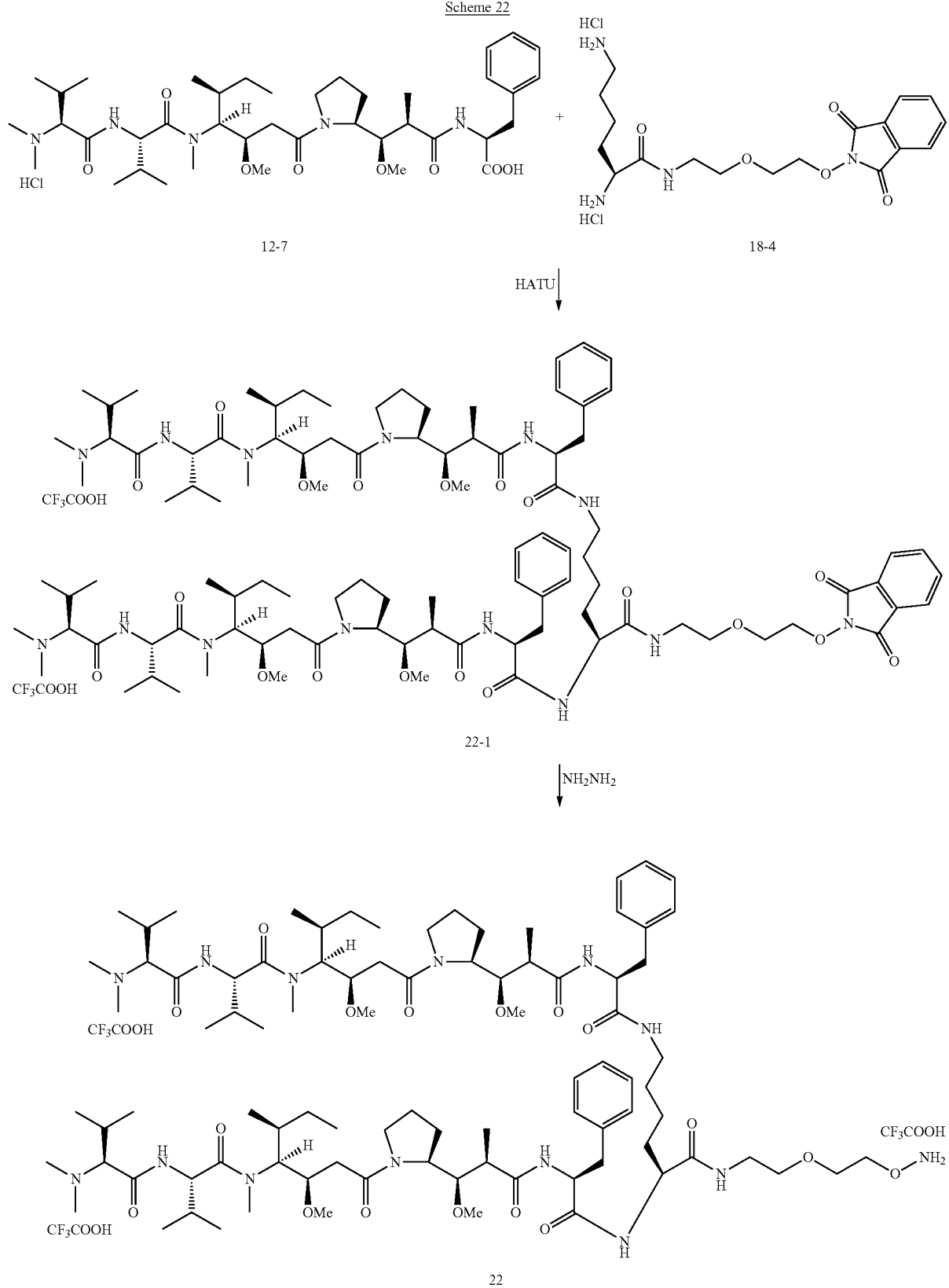

Compound 22-1: To a solution of compound 19-4 (7.6 mg, 0.017 mmol), compound 12-7 (40 mg, 0.051 mmol) and DIEA (0.030 mL, 0.17 mmol) in 2 mL of DMF was added 32 mg (0.085 mmol) of HATU. The reaction mixture was stirred at room temperature for 2 hour. The reaction mixture was purified by HPLC, eluting with 20-70% CH3CN/H2O in 20 min at 254 nm, to give 24 mg (68%) of compound 22-1. MS (ESI) m/z 612 [M+3H], 917 [M+2H], 1834[M+H].

Compound 22: Compound 22-1 (24 mg, 0.012 mmol) was dissolved in 1 mL of DMF. 12 µL (0.36 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 15 mg (58%) of Example 21. MS (ESI) m/z 569 [M+3H], 852[M+2H], 1726[M+2H].

Example 23: Synthesis of Compound 23

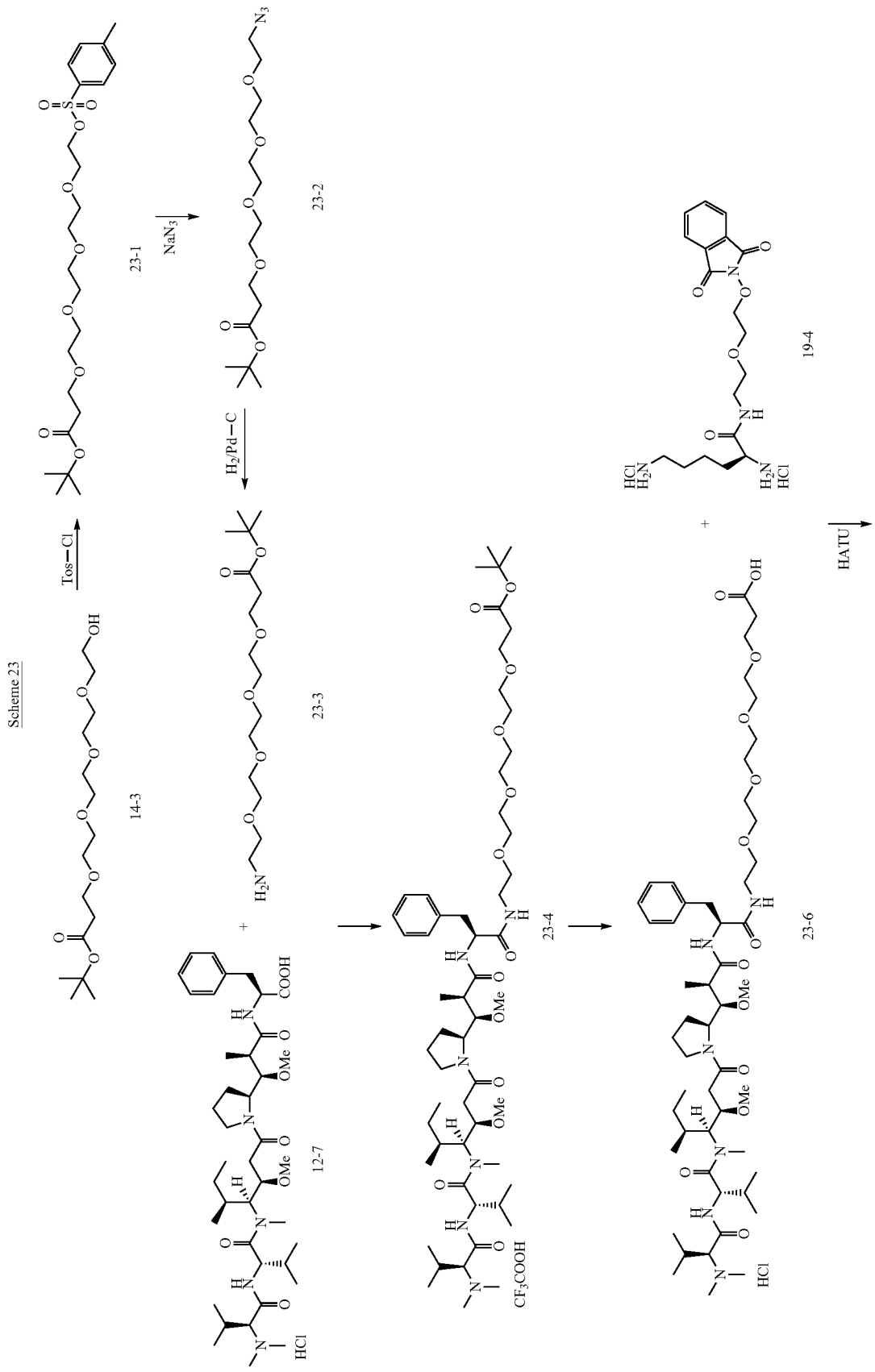

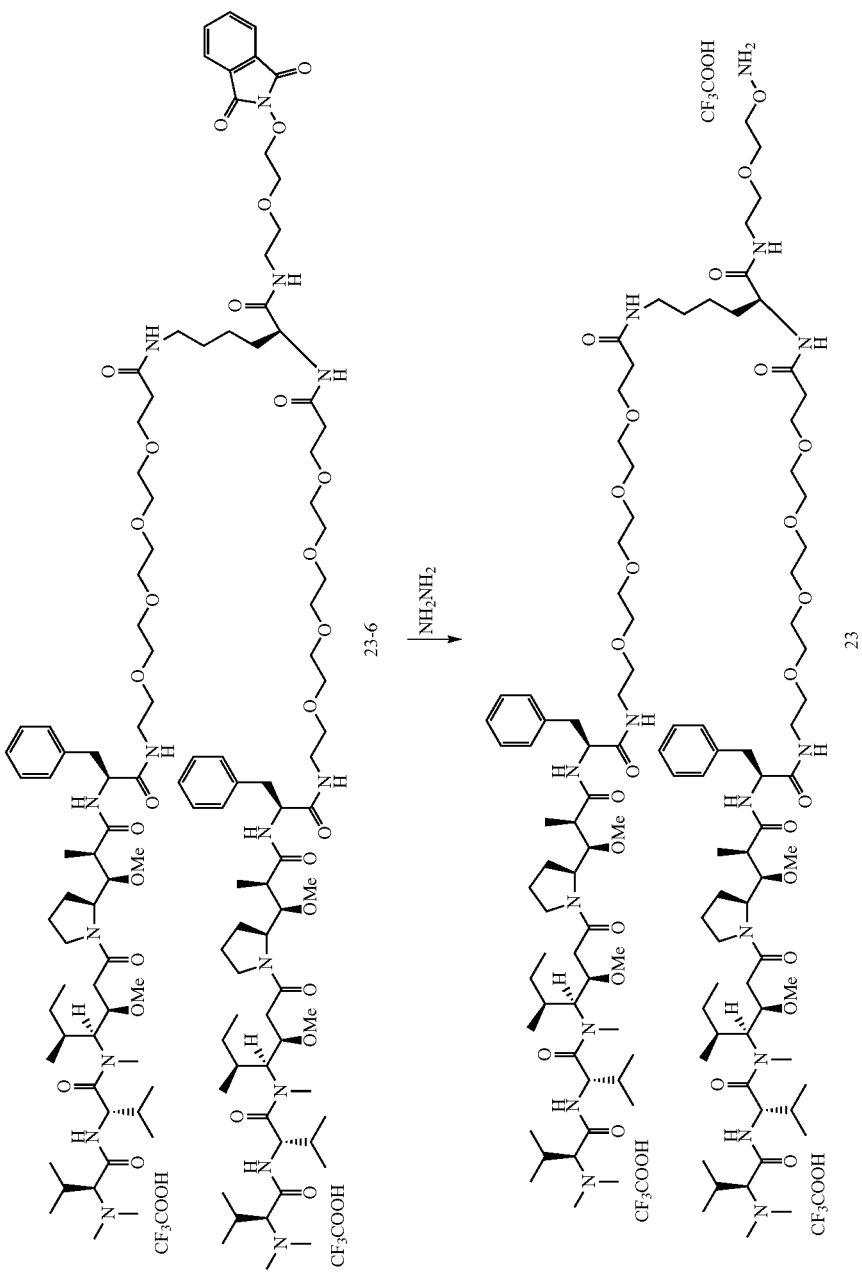

Compound 23-1: To a solution of compound 14-3 (4.0 g, 12.4 mmol) and 6.6 mL (37.2 mmol) of DIEA in 50 mL of DCM was added 3.31 g of toluenenesulfonyl chloride at 0° C. The reaction mixture was stirred at room temperature for 2 days. The reaction mixture was extracted with ethyl acetate. The organic layer was combined and washed with 5% citric acid, water, brine, dried over sodium sulfate and concentrated in vacuo. The residue was purified by flash column chromatography to give 3.5 g of compound 23-1.

Compound 23-2: To a solution of compound 23-1 (3.5 g, 7.34 mmol) in 20 mL DMF was added solium azide (1.44 g, 22.02 mmol). The reaction mixture was stirred at 50° C. for 2 days. The reaction mixture was extracted with ethyl acetate. The organic layer was washed with water, brine, dried over sodium sulfate, filtered and concentrated in vacuo. The residue was purified by flash column chromatography to give 2.1 g of compound 23-2.

Compound 23-3: To a solution of compound 23-2 (2.1 g, 6.05 mmol) in 50 mL MeOH was added 400 mg (10%) of Pd—C. The resulting mixture was stirred at room temperature under 1 atm $H_2$ for 24 hours. The reaction mixture was filtered and concentrated in vacuo to give 2.1 g of compound 23-3. MS (ESI) m/z 322[M+H].

Compound 23-4: To a solution of compound 23-3 (33 mg, 0.102 mmol), compound 12-7 (40 mg, 0.051 mmol) and 54 μL of diisopropylethylamine in 1 mL of DMF was added 38 mg of HATU. The reaction mixture was stirred at room temperature for 4 hours. The reaction mixture was purified by HPLC to give 52 mg of compound 23-4. MS (ESI) m/z 525[M+2H], 1049 [M+H].

Compound 23-5: Compound 23-4 (52 mg, 0.045 mmol) was dissolved in 5 mL 4N HCl/Dioxane. The reaction mixture was stirred at room temperature for 2 hours and concentrated in vacuo to give 52 mg (100%) of compound 23-5. MS (ESI) m/z 497[M+2H], 993 [M+H].

Compound 23-6: To a solution of compound 19-4 (7.6 mg, 0.017 mmol), compound 23-6 (52 mg, 0.051 mmol) and DIEA (0.030 mL, 0.17 mmol) in 2 mL of DMF was added 32 mg (0.085 mmol) of HATU. The reaction mixture was stirred at room temperature for 2 hour. The reaction mixture was purified by HPLC, eluting with 20-70% CH3CN/H2O in 20 min at 254 nm, to give 26 mg (61%) of compound 23-6. MS (ESI) m/z 583[M+4H], 777[M+3H], 1165[M+2H].

Compound 23: Compound 23-6 (26 mg, 0.01 mmol) was dissolved in 1 mL of DMF. 10 μL (0.31 mmol) of anhydrous hydrazine was added. The resulting solution was stirred at room temperature for 1 hour. The reaction was quenched with 1N hydrochloride solution. The reaction mixture was purified by preparative HPLC, eluting with 20-70% CH3CN/H2O in 20 min at 254 nm, to give 10 mg (40%) of Example 23. MS (ESI) m/z 550[M+4H], 733[M+3H], 1100 [M+2H].

TABLE 3

Structures of Compounds 1-23

| Example | Structure |
|---|---|
| 1 | 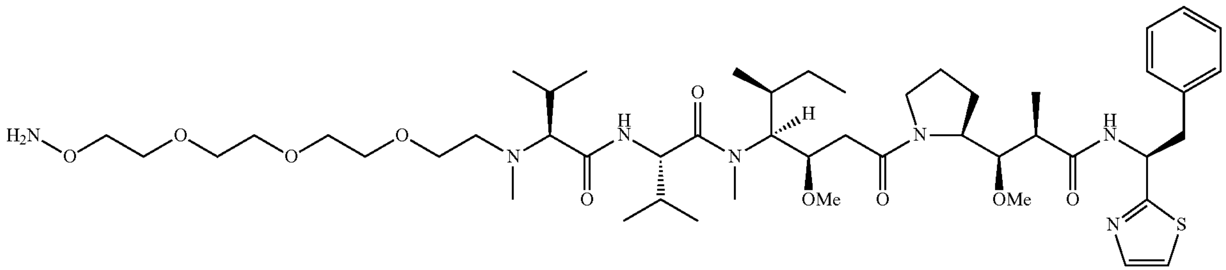 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCOCCOCCON)C(C)C] |
| 2 | 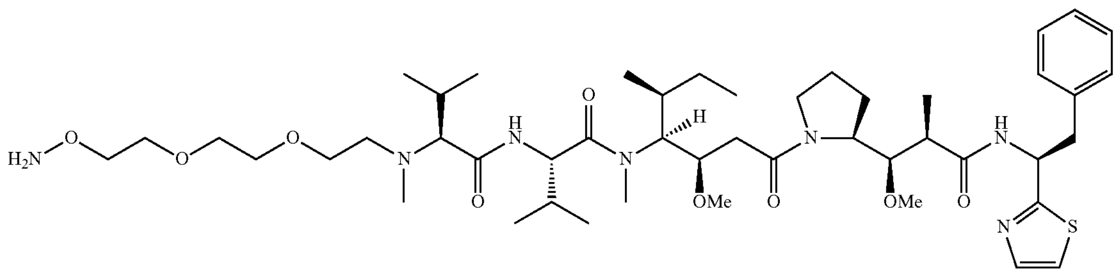 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCOCCON)C(C)C] |
| 3 | 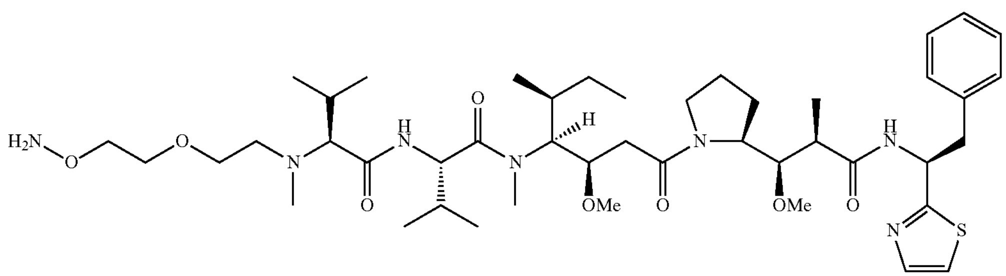 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCON)C(C)C] |

TABLE 3-continued

Structures of Compounds 1-23

| Example | Structure |
|---|---|
| 4 | 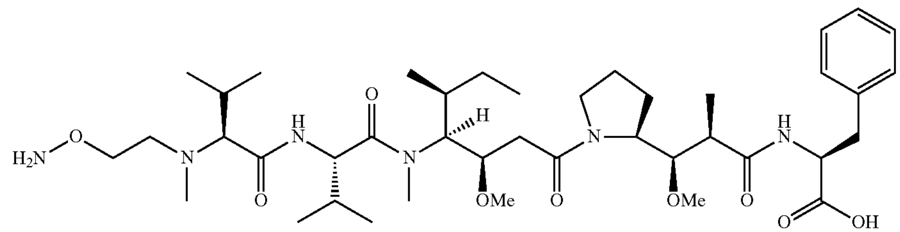 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCON)C(C)C] |
| 5 | 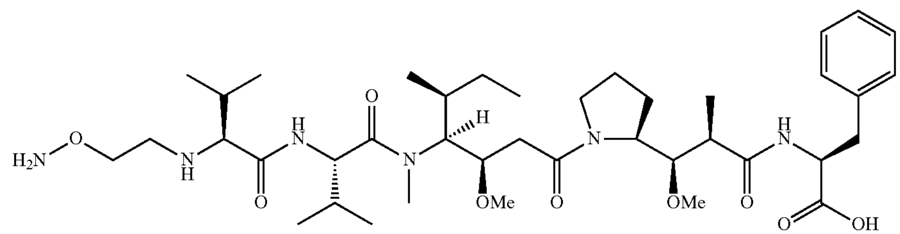 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NCCON)C(C)C)C(C)C] |
| 6 | 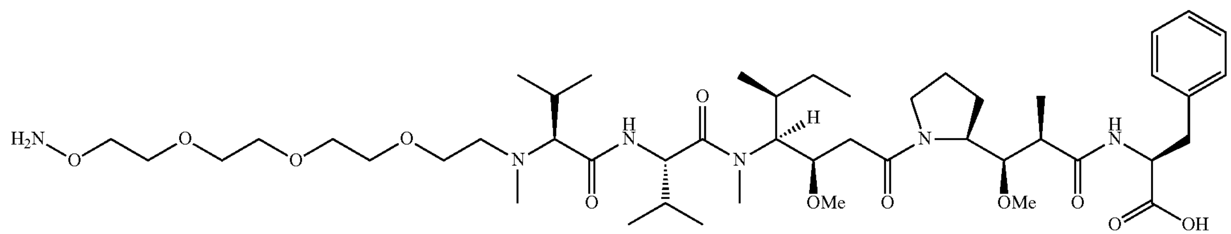 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCOCCON)C(C)C] |
| 7 | 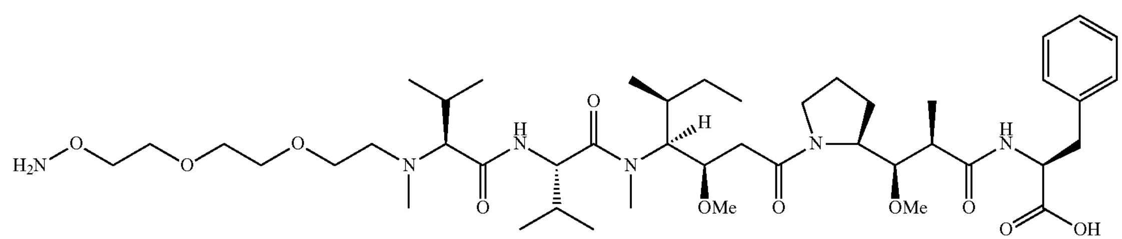 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCON)C(C)C] |

TABLE 3-continued

Structures of Compounds 1-23

| Example | Structure |
|---------|-----------|
| 8 | 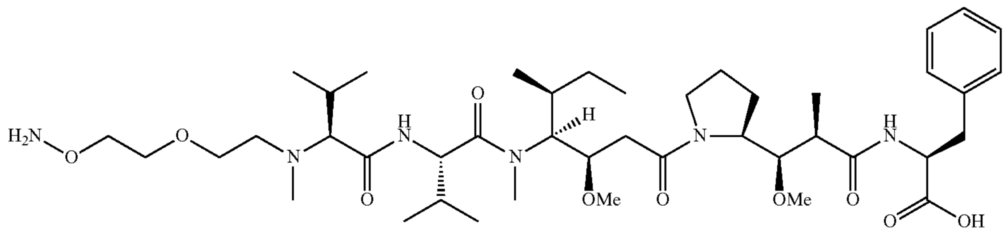 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCON)C(C)C] |
| 9 | 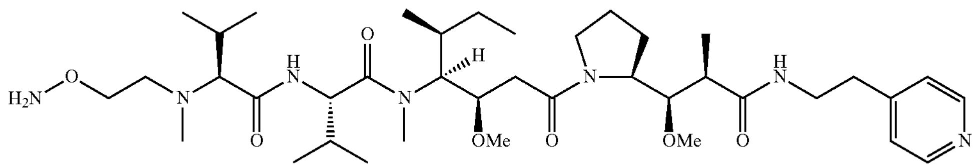 [SMILES: CC[C@H](C)[C@@H]([C@@H](CC(=O)N1CCC[C@H]1[C@H](OC)[C@@H](C)C(=O)NCCc1ccncc1)OC)N(C)C(=O)[C@@H](NC(=O)[C@H](C(C)C)N(C)CCON)C(C)C] |
| 10 | 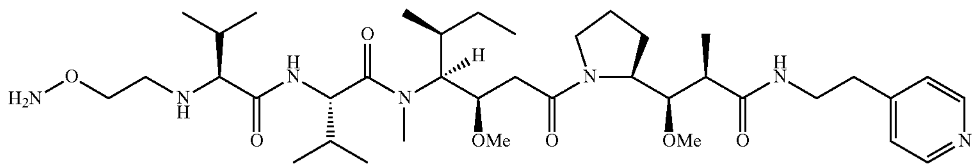 [SMILES: CC[C@H](C)[C@@H]([C@@H](CC(=O)N1CCC[C@H]1[C@H](OC)[C@@H](C)C(=O)NCCc1ccncc1)OC)N(C)C(=O)[C@@H](NC(=O)[C@@H](NCCON)C(C)C)C(C)C] |
| 11 | 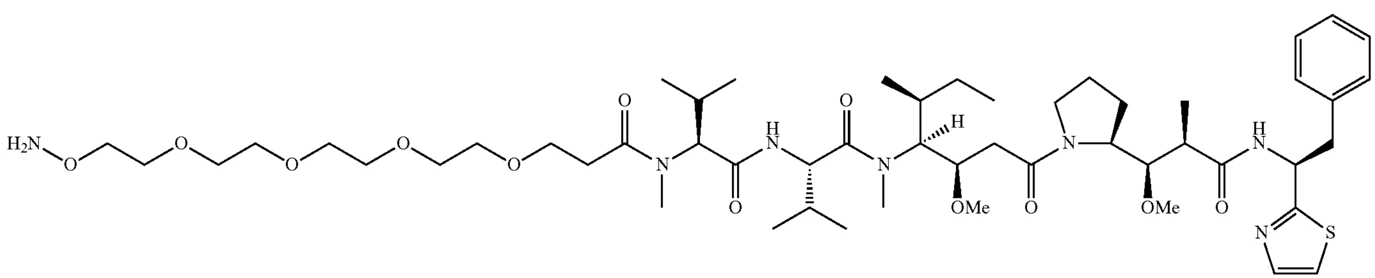 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)CCOCCOCCOCCOCCON)C(C)C] |

TABLE 3-continued

Structures of Compounds 1-23

| Example | Structure |
|---|---|
| 12 | 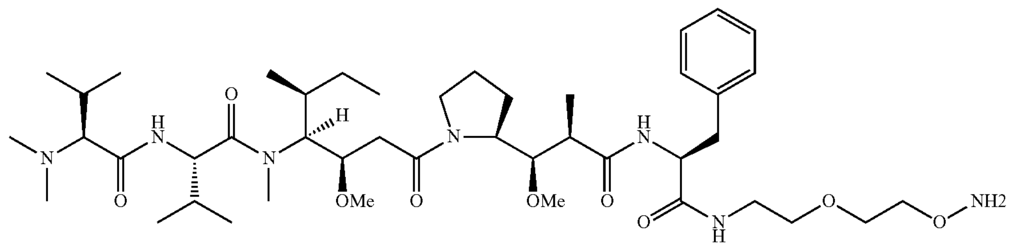 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCON)OC)N(C)C(=O)[C@@H](NC(=O)[C@H](C(C)C)N(C)C)C(C)C] |
| 13 | 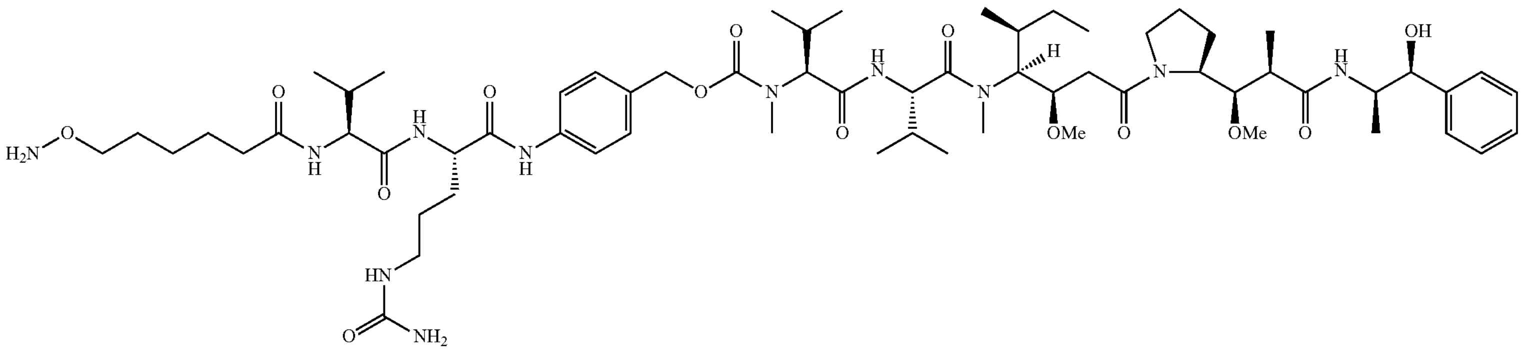 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCON)C(C)C)cc1)C(C)C] |
| 14 | 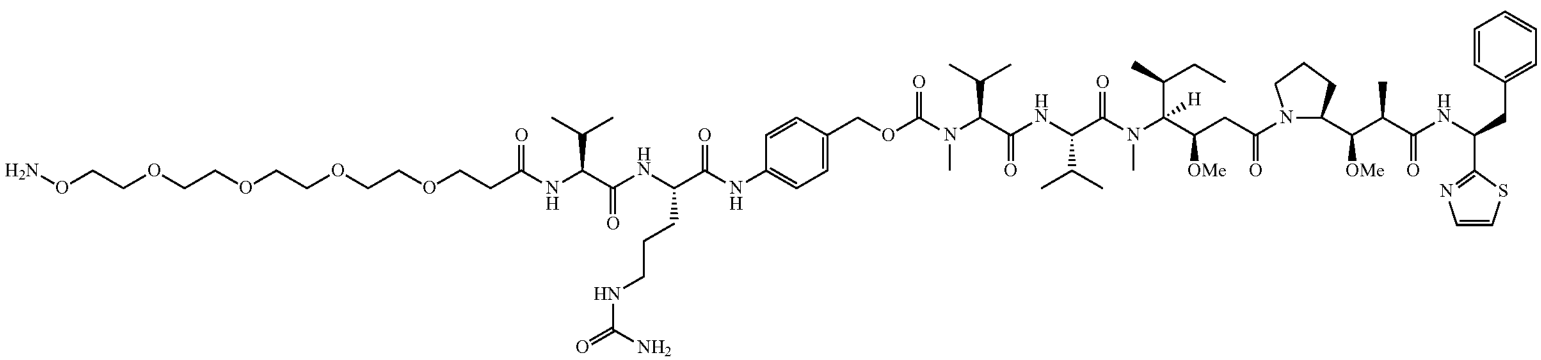 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCON)C(C)C)cc1)C(C)C] |

TABLE 3-continued

Structures of Compounds 1-23

| Example | Structure |
|---|---|
| 15 | 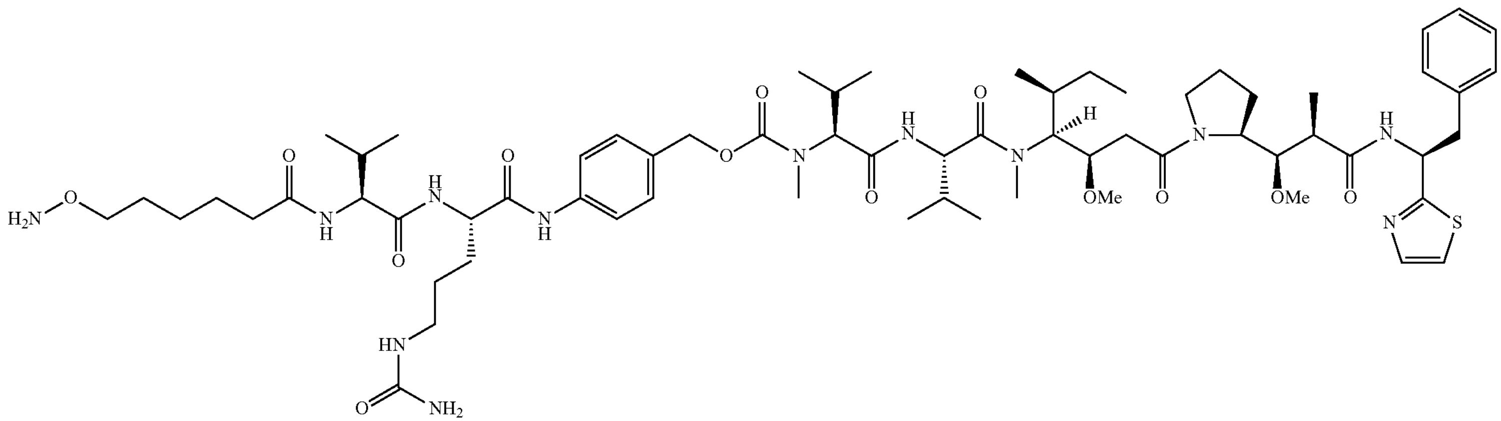 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCON)C(C)C)cc1)C(C)C] |
| 16 | 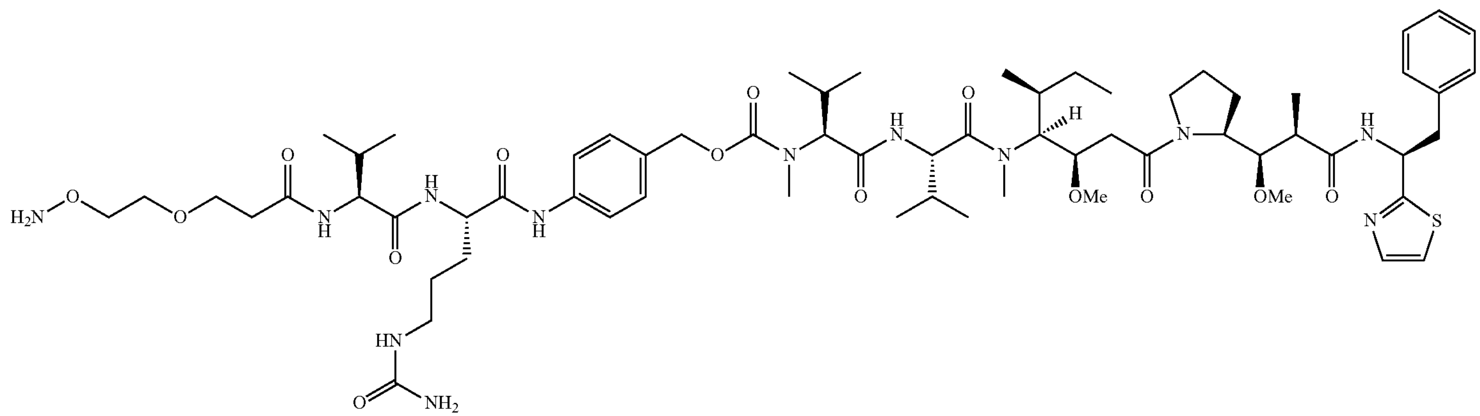 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCON)C(C)C)cc1)C(C)C] |

TABLE 3-continued
Structures of Compounds 1-23
| Example | Structure |
|---|---|
| 17 | 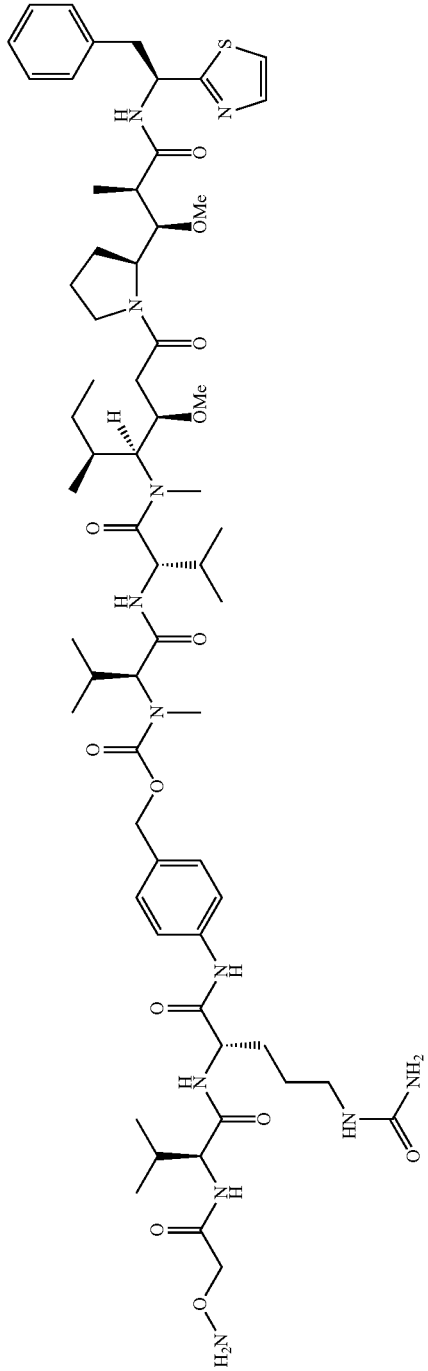 |
| 18 | 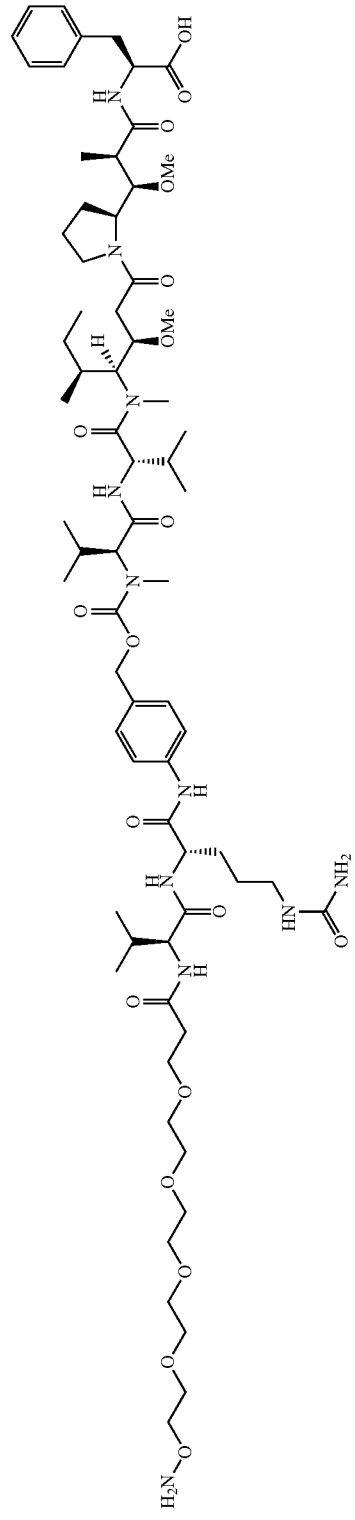 |

TABLE 3-continued
Structures of Compounds 1-23
| Example | Structure |
|---|---|
| 19 | 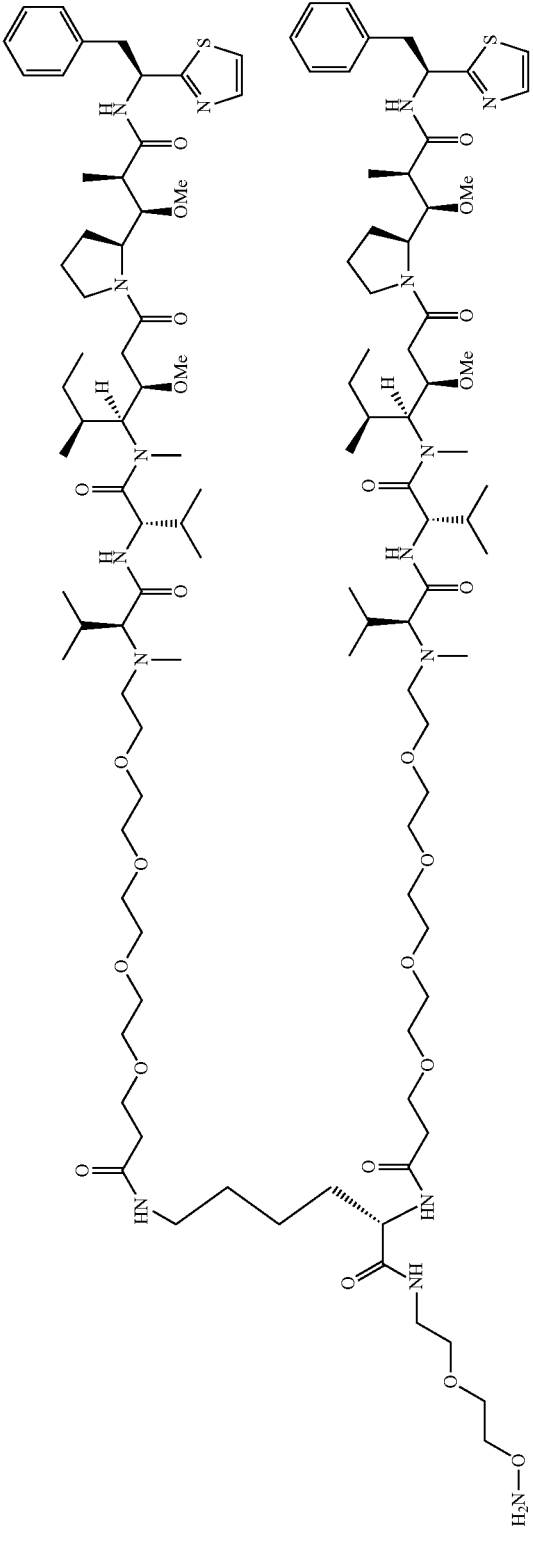 |

TABLE 3-continued
Structures of Compounds 1-23
| Example | Structure |
|---|---|
| 20 | 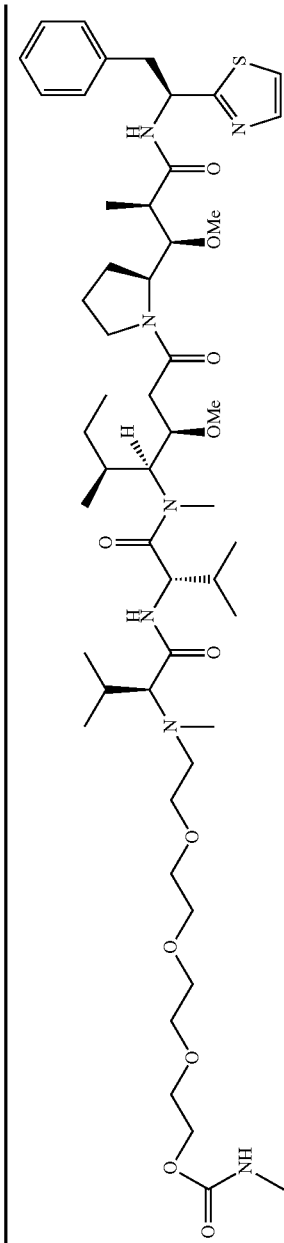 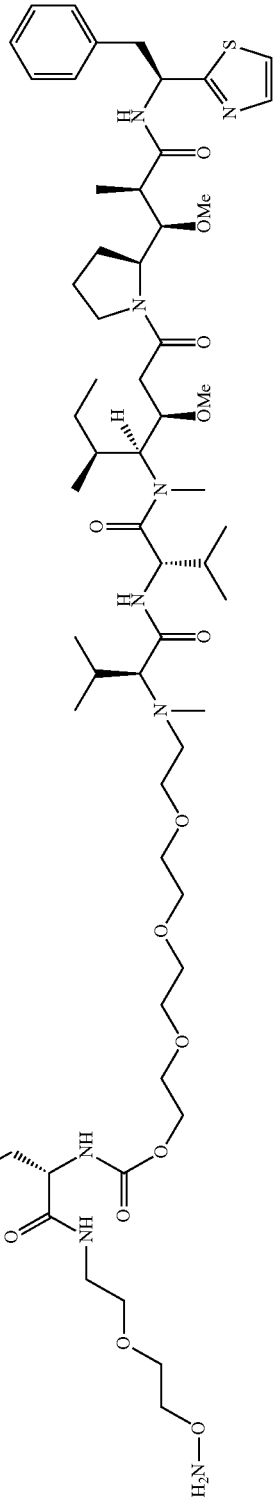 |

TABLE 3-continued
Structures of Compounds 1-23
| Example | Structure |
|---|---|
| 21 | 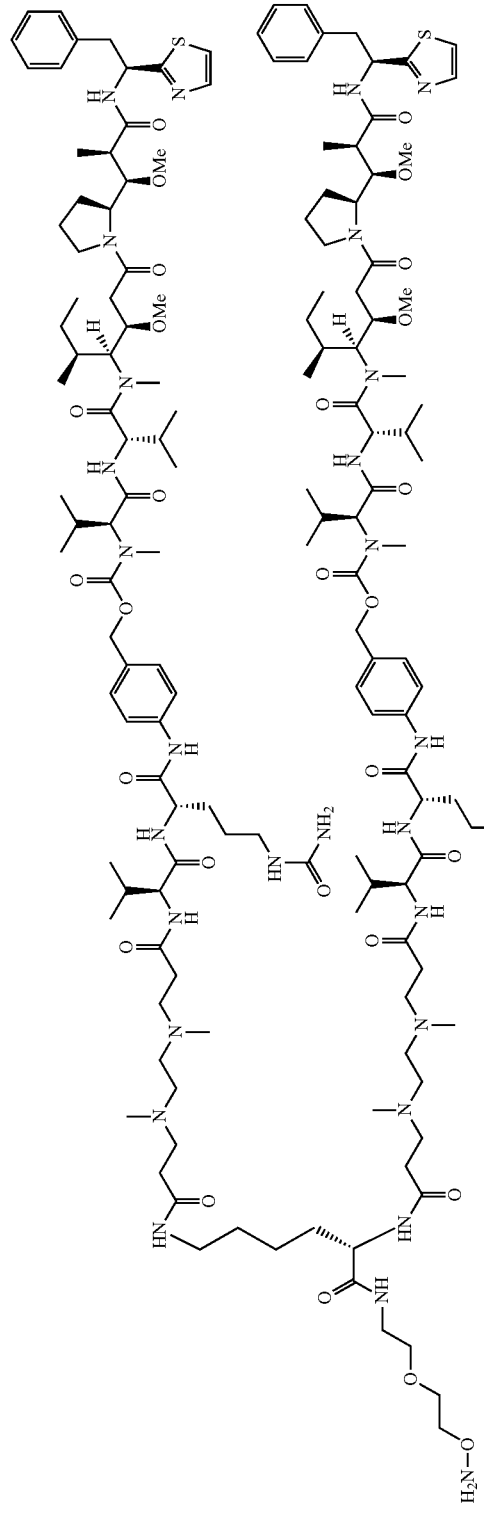 |

TABLE 3-continued
Structures of Compounds 1-23
| Example | Structure |
|---|---|
| 22 | 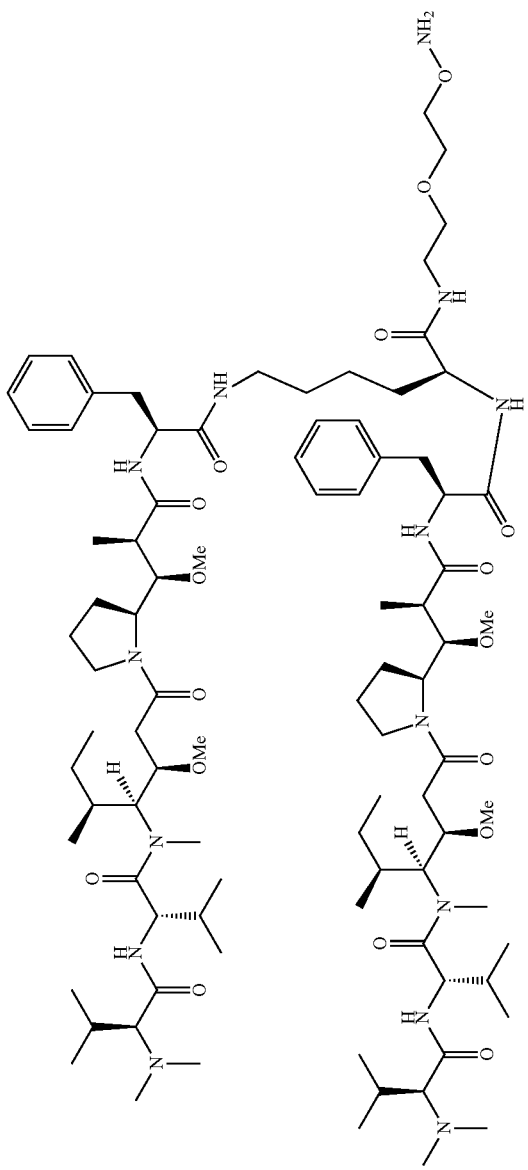 |

TABLE 3-continued
Structures of Compounds 1-23
| Example | Structure |
|---|---|
| 23 | 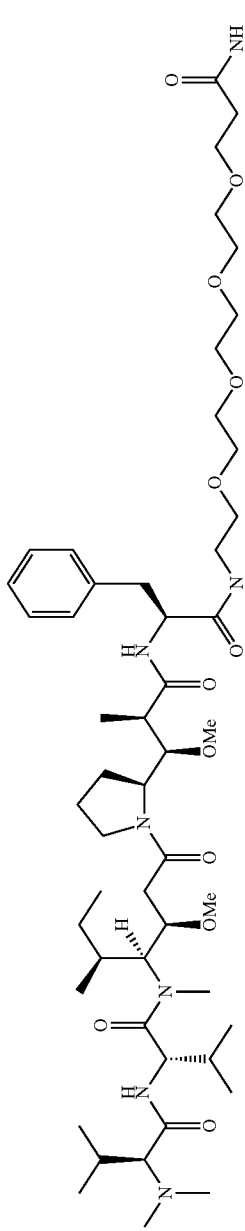 |

Example 24: Transient Transfection

CHO—S culture is seeded at 0.75×10^6/mL approximately 16 hours pre-transfection in FreeStyle Cho medium. Cells are ready to transfect the next day when the cell count has reached 1.4-1.6×10^6/mL. When cells reach target count, 400 mM pAF stock is added to a 1.4 mM final culture concentration. PEI/DNA complex is prepared as described: DNA (1.42 ug/1×10^6 cells) is dissolved in RPMI (5% (v/v) of total culture volume), DNA/RPMI mixture is incubated at room temperature for 2 minutes, PEI stock (1 mg/mL) is added to DNA solution at a 3:1 ratio (mL PEI/ug DNA), and the mixture is incubated at room temperature for 5 min. The culture is gently added to the mixture and swirled. The flasks are transferred to a 32° C. incubator. At day 6 post-transfection, a western blot analysis is performed. At day 7 post-transfection, the supernatant is harvested.

Example 25: CD70-ADC In Vivo Efficacy Study

Figure 2:
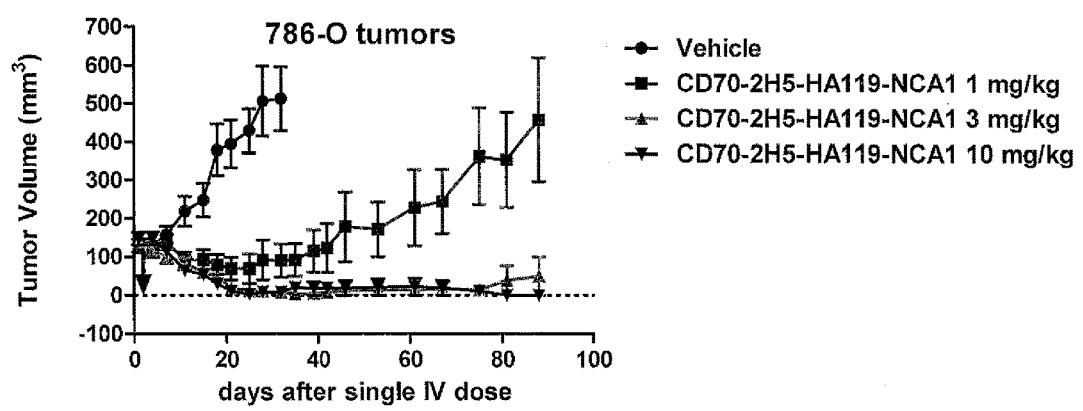
FIG. 2 presents a graphical illustration of tumor volume in female nude mice test subject groups treated with 1 mg/kg, 3 mg/kg, and 10 mg/kg doses of the antibody drug conjugate CD70-2H5-HA119-NCA1 in the renal cell carcinoma xenograft model, same conditions from FIG. 1.

Anti-tumor efficacy of CD70-2H5-HA119-NCA1 conjugated to NCA1 was tested in a renal cell carcinoma xenograft mouse model. 786-O, human renal cell carcinoma cells, were transferred as tumor fragment for 2 in vivo passages into nude, female, 5 weeks old mice. The mice, ten per test group, were treated with different doses of CD70-2H5-HA119-NCA1 in a formulation of 50 mM histidine, 100 mM NaCl, 5% trehalose, pH 6.0 and measured against formulation test vehicle without ADC by IV tail injection once on day one of the study. Mice were weighed and measured for tumor three dimensionally using an electronic caliper. Individual tumor volume was calculated as height× width×length. Mice with vascularized tumors (determined by appearance of the tumors) of appropriate sizes were randomized into treatment groups and were dosed per individual body weight on Day 33 (three (3) weeks following injection with cells). Results from this experiment are shown in FIG. 2.

TABLE 4

Test Groups for CD70 In Vivo Efficacy Study

| Grp | Treatment | Dose | Concentration | Dose Volume | Route | Schedule |
|---|---|---|---|---|---|---|
| 1 | Vehicle | N/A | N/A | 5 mL/kg | IV | Once, day 1 |
| 2 | CD70-2H5-HA119-NCA1 | 1 mg/kg | 0.2 mg/mL | 5 mL/kg | IV | Once, day 1 |
| 3 | CD70-2H5-HA119-NCA1 | 3 mg/kg | 0.6 mg/mL | 5 mL/kg | IV | Once, day 1 |
| 4 | CD70-2H5-HA119-NCA1 | 10 mg/kg | 2 mg/mL | 5 mL/kg | IV | Once, day 1 |

*Ten (10) nude mice per group

Example 26: CD70-ADC in Burkitt Lymphoma Model

Anti-tumor efficacy of ARX-αCD70 unconjugated and ARX-αCD70 conjugated ADC was measured in the Daudi (Burkitt lymphoma) tumor model. Nude female mice were used as test subjects, ten per group, and to start, a single IV injection was given on day 1 to all groups (N=20). There were five groups, 10 test article and 10 vehicle per group, randomized after a week.

| Treatment | Dose | route | schedule | N | Second IV injection | N |
|---|---|---|---|---|---|---|
| Vehicle | N/A | IV | once, day 1 | 20 | none | N/A |
| CD70-2H5-HA119-NCA1 | 1 mg/kg | IV | once, day 1 | 20 | once, approx Day 21 | 10 = vehicle<br>10 = test article |
| CD70-2H5-HA119-NCA1 | 3 mg/kg | IV | once, day 1 | 20 | once, approx Day 21 | 10 = vehicle<br>10 = test article |
| CD70-2H5-HA119-NCA1 | 10 mg/kg | IV | once, day 1 | 20 | once, approx Day 21 | 10 = vehicle<br>10 = test article |
| CD70-2H5-HA119-unconjugated | 10 mg/kg | IV | once, day 1 | 20 | once, approx Day 21 | 10 = vehicle<br>10 = test article |

A second injection is administered after 21 days (or when tumors start to re-grow), and non-vehicle groups are split into equal groups of 10 each and given a second IV injection.

Mice are weighed and measured for tumor three dimensionally using an electronic caliper. Individual tumor volume is calculated as height×width×length. Mice with vascularized tumors (determined by appearance of the tumors) of appropriate sizes are randomized into treatment groups and are dosed per individual body weight on Day 33 (three (3) weeks following injection with cells).

Example 27: CD70-2H5-HA119-NCA1 786-O 96h Cytotoxicity Study

Figure 3A:
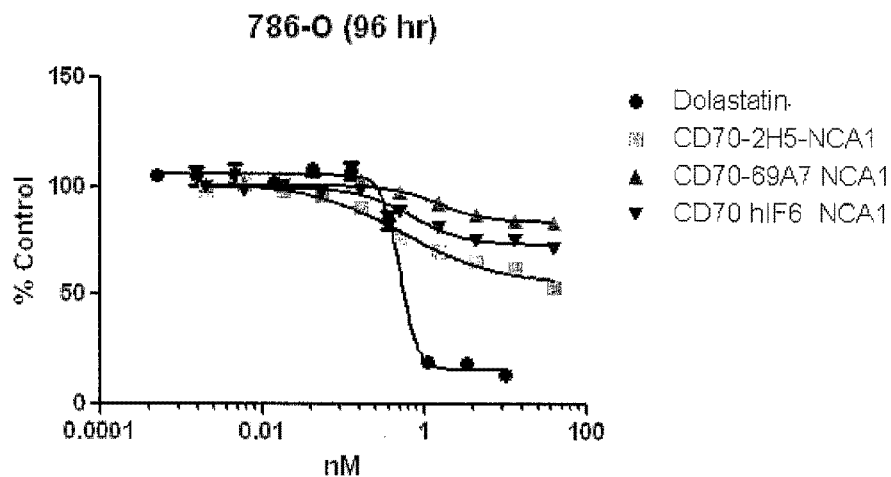
FIG. 3A presents a graphical illustration of the results from a cytotoxicity assay of three ARX-antibody drug conjugates; CD70-2H5-NCA1, CD70-69A7-NCA1, and CD70hIF6-NCA1 in 786-O cells.

Cytotoxicity of ARX-αCD70 antibody drug conjugates was compared to dolastatin in 786-O cells. IC50 was measured and the results from this experiment are shown in FIG. 3A.

Example 28: CD70-2H5-HA119-NCA1 Caki-1 96h Cytotoxictty Study

Figure 3B:
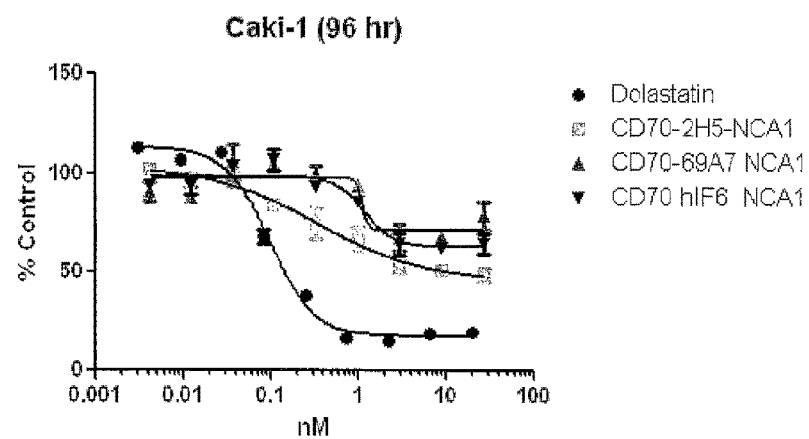
FIG. 3B presents a graphical illustration of the results from a cytotoxicity assay of three ARX-antibody drug conjugates; CD70-2H5-NCA1, CD70-69A7-NCA1, and CD70hIF6-NCA1 in Caki-1 cells.

Cytotoxicity of ARX-αCD70 antibody drug conjugates was compared to dolastatin in Caki-1 cells. IC50 was measured and the results from this experiment are shown in FIG. 3B.

Figure 4A:
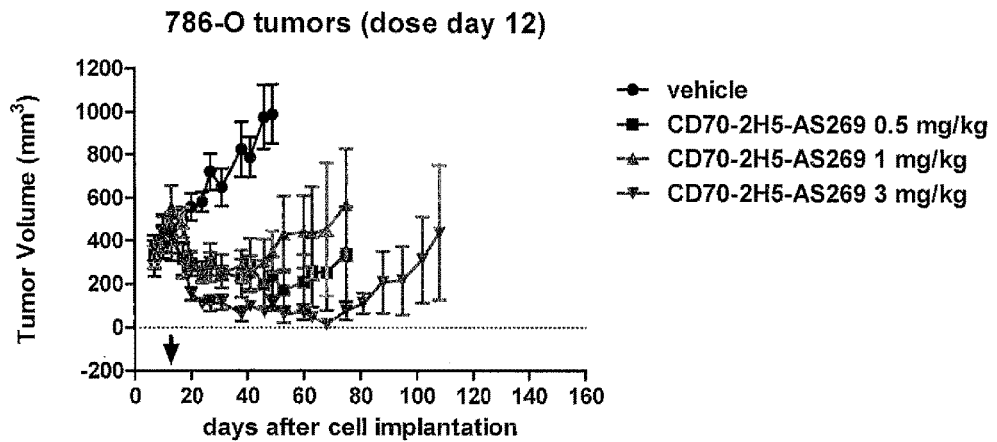
FIG. 4 presents a graphical illustration of tumor volume over time following a single injection at day 12 of FIG. 4(A) αCD70 antibody CD70-2H5-HA119 conjugated to AS269 (also referred to as NCA1 within the present application)
FIG. 4(B) αCD70 antibody CD70-8A1-HA122 conjugated to AS269.
FIG. 4(C) αCD70 antibody CD70-7F2-HA119 conjugated. The antibody drug conjugates were given in doses of 0.5 mg/kg; 1 mg/kg; and 3 mg/kg and compared to vehicle.
Figure 4B:
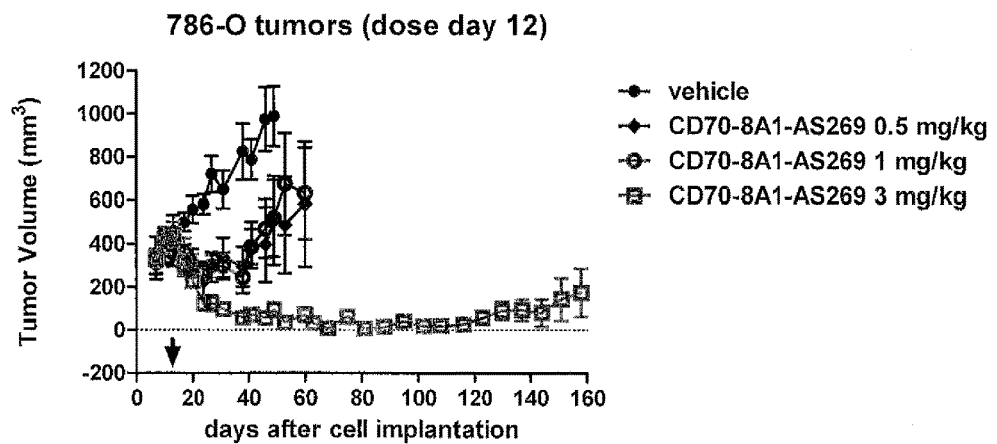
Figure 4C:
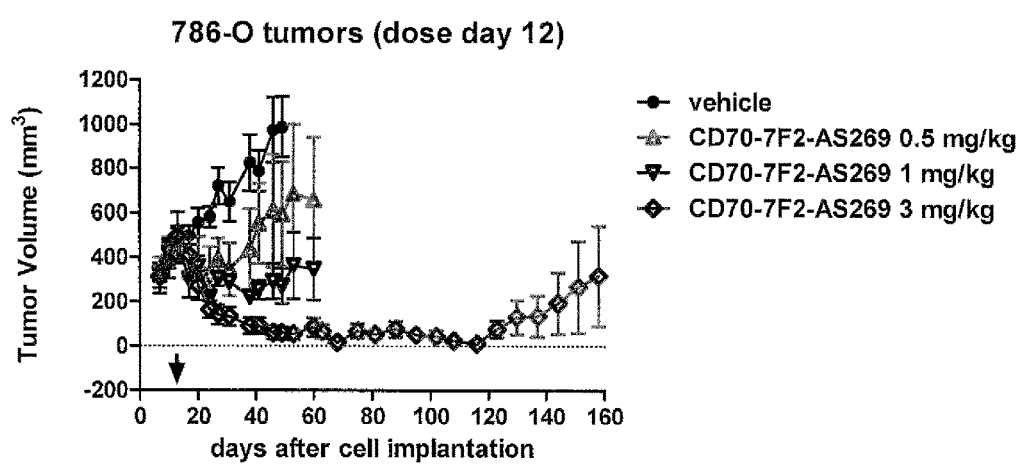
Figure 5:
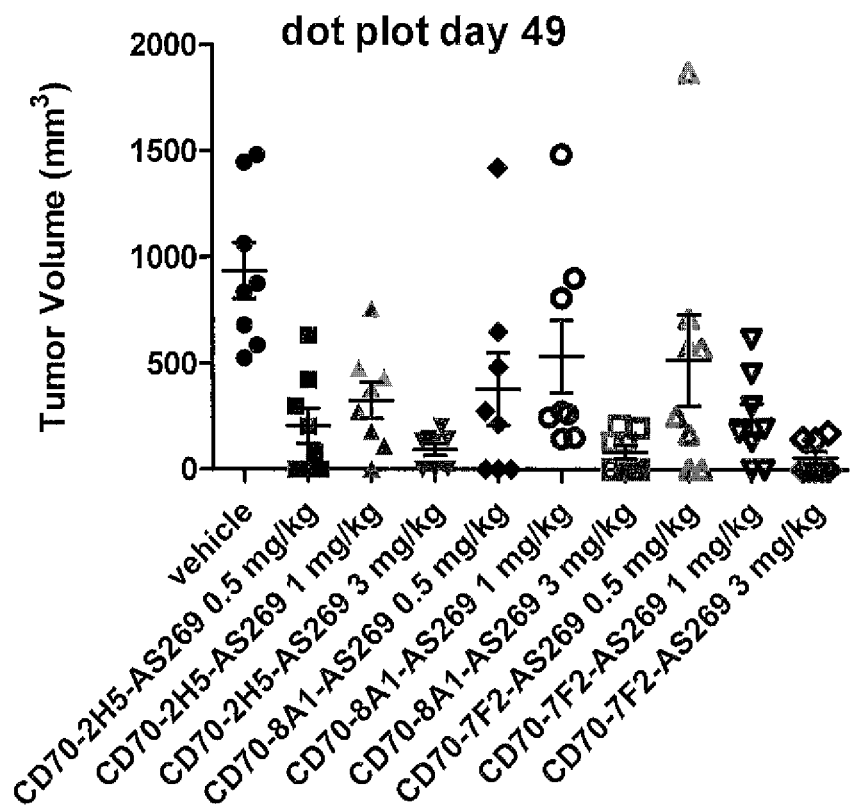
FIG. 5 presents a dot plot of the tumor volumes from the different test groups as measured on day 49 following transplantation of 786-O tumor fragment.
Figure 6A:
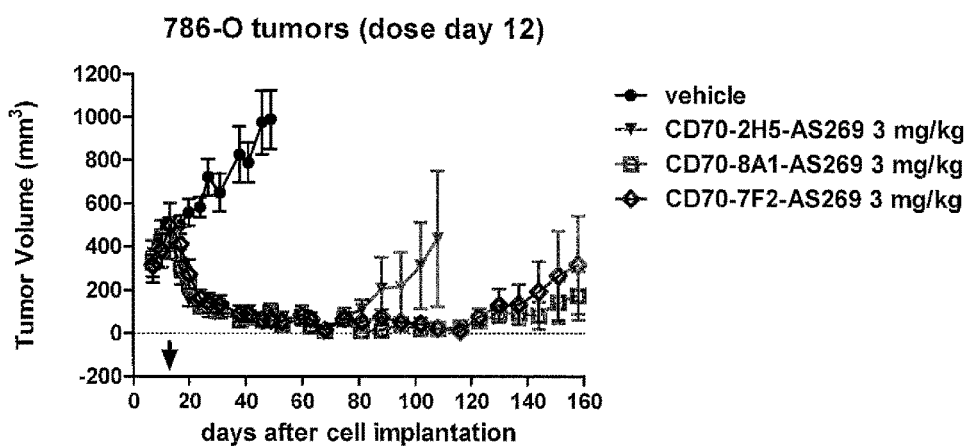
FIG. 6A presents a graphical illustration of tumor volume in female nude mice test subject groups treated with CD70-2H5-AS269 3 mg/kg; CD70-8A1-AS269 3 mg/kg; and CD70-7F2-AS269 3 mg/kg; administered 12 days following transplantation of a 786-O tumor fragment.
Figure 6B:
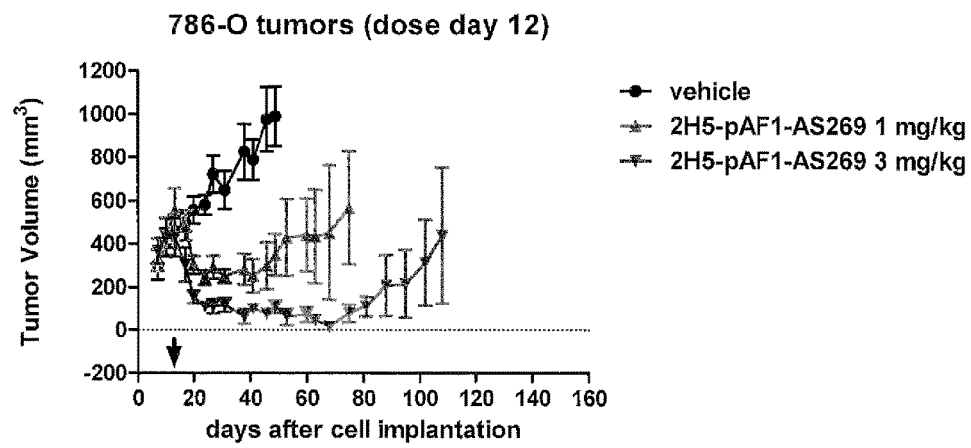
FIG. 6B presents a graphical illustration of tumor volume in female nude mice test subject groups treated with CD70-2H5-AS269 in 1 mg/kg and 3 mg/kg as compared to vehicle; antibody drug conjugates were administered 12 days following transplantation of a 786-O tumor fragment.
Figure 6C:
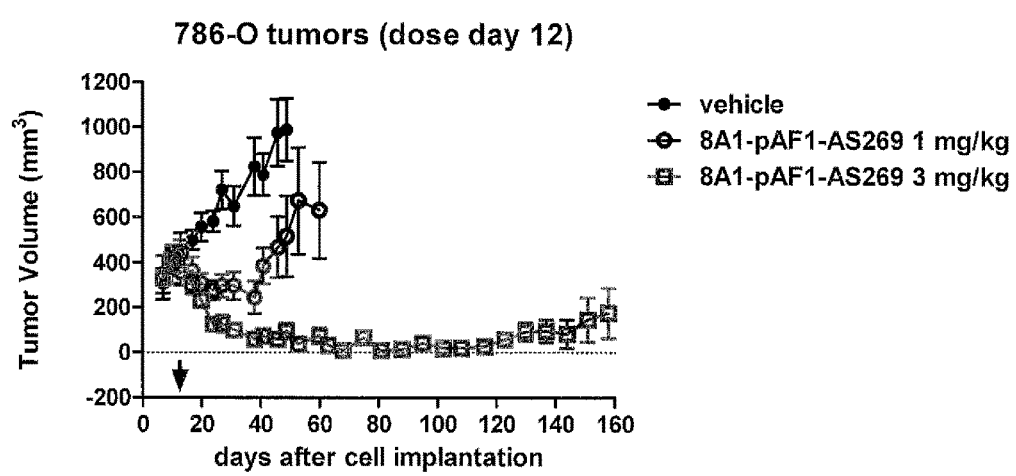
FIG. 6C presents a graphical illustration of tumor volume in female nude mice test subject groups treated with 8A1-pAF1-AS269 in 1 mg/kg and 3 mg/kg as compared to vehicle; antibody drug conjugates were administered 12 days following transplantation of a 786-O tumor fragment.

Example 29: Anti-Tumor Activity of Three CD70-AS269 in the 786-O Xenograft Model of Kidney Cancer The 786-O renal cell carcinoma tumor model was used in nude female mice. Ten groups of ten mice each were given 786-O tumor fragments and later randomized after a week and a half when tumors grew to between 100-300 mm$^3$. The groups, one for each dose level and one for vehicle, were treated as follows:
Vehicle,
CD70-2H5-HA119-NCA1-IgG1v1 at 0.5, 1 and 3 mg/kg
CD70-7F2-HA119-NCA1-IgG1v1 at 0.5, 1 and 3 mg/kg
CD70-8A1-HA122-NCA1-IgG1v1 at 0.5, 1 and 3 mg/kg
A single dose injection was given intravenously to all 100 mice on day 12 following transplantation, and the results from these experiments include data given in FIGS. 4-6.

Example 30: Human Clinical Trial of CD70-2H5-HA119-NCA1 for Oncology

Human Clinical Trial of the Safety and/or Efficacy of CD70-2H5-HA119-NCA1 for Oncology Objective: To compare the safety and pharmacokinetics of administered composition comprising ARX-αCD70-linked dolastatin derivative.

Study Design: This study will be a Phase I, single-center, open-label, randomized dose escalation study followed by a Phase II study in renal cancer patients. Patients should not have had exposure to αCD70-linked dolastatin derivative prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v. CD70-2H5-HA119-NCA1 on days 1, 8, and 15 of each 28-day cycle. Doses of CD70-2H5-HA119-NCA1 may be held or modified for toxicity based on assessments as outlined below. Treatment repeats every 28 days in the absence of unacceptable toxicity. Cohorts of 3-6 patients receive escalating doses of CD70-2H5-HA119-NCA1 until the maximum tolerated dose (MTD) for CD70-2H5-HA119-NCA1 is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive CD70-2H5-HA119-NCA1 as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling: serial blood is drawn by direct vein puncture before and after administration of CD70-2H5-HA119-NCA1. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes Additional Assays for Cytotoxic, Cytostatic, and Immunomodulatory Activities Methods of determining whether an antibody mediates effector function against a target cell are known. Illustrative, non-limiting examples of such methods are described herein.

For determining whether an anti-CD70 antibody or derivative mediates antibody-dependent cellular cytotoxicity against activated immune cells or CD70-expressing cancer cells, an assay that measures target cell death in the presence of antibody and effector immune cells may be used. An assay used to measure this type of cytotoxicity can be based on determination of $^{51}$Cr release from metabolically-labeled targets cells after incubation in the presence of effector cells and target-specific antibody (see, e.g., Perussia and Loza, 2000, Methods in Molecular Biology 121:179-92; and "$^{51}$Cr Release Assay of Antibody-Dependent Cell-Mediated Cytotoxicity (ADCC)" in Current Potocols in Immunology, Coligan et al. eds., Wileyand Sons, 1993). For example, activated immune cells (e.g., activated lymphocytes) or CD70-expressing cancer cells labeled with $Na_2^{51}CrO_4$ and plated at a density of 5,000 cells per well of a 96-well plate can be treated with varying concentrations of anti-CD70 antibody for 30 minutes then mixed with normal human peripheral blood mononuclear cells (PBMC) for 4 hours. The membrane disruption that accompanies target cell death releases $^{51}$Cr into the culture supernatant which may be collected and assessed for radioactivity as a measure of cytotoxic activity. Other assays to measure ADCC may involve nonradioactive labels or be based on induced release of specific enzymes. For example, a non-radioactive assay based on time-resolved fluorometry is commercially available (Delphia, Perkin Elmer). This assay is based on loading target cells with an acetoxymethyl ester of fluorescence enhancing ligand (BATDA) that penetrates the cell membrane then hydrolyses to form a membrane impermeable hydrophilic ligand (TDA). When mixed with target specific antibody and PBMC effector cells, TDA is released from lysed cells and is available to form a highly fluorescent chelate when mixed with Europium. The signal, measured with a time-resolved fluorometer, correlates with the amount of cell lysis.

To determine whether an anti-CD70 antibody or derivative mediates antibody-dependent cellular phagocytosis against activated immune cells or CD70-expressing cancer cells, an assay that measures target cell internalization by effector immune cells (e.g., fresh cultured macrophages or established macrophage-like cell line) may be used (see, e.g., Munn and Cheung, 1990, J. Exp. Med. 172:231-37; Keler et al., 2000, J. Immunol. 164:5746-52; Akewanlop et al., 2001, Cancer Res. 61:4061-65). For example, target cells may be labeled with a lipophilic membrane dye such as PKH67 (Sigma), coated with target-specific antibody, and mixed with effector immune cells for 4-24 hours. The effector cells may then be identified by counterstaining with a fluorochrome-labeled antibody specific for a phagocytic cell surface marker (e.g., CD14) and the cells analyzed by two-color flow cytometry or fluoresence microscopy. Dual-positive cells represent effector cells that have internalized target cells. For these assays, effector cells may be monocytes derived from PBMC that have been differentiated into macrophages by culture for 5-10 days with M-CSF or GM-CSF (see, e.g., Munn and Cheung, supra). Human macrophage-like cell lines U937 (Larrick et al., 1980, J. Immunology 125:6-12) or THP-1 (Tsuchiya et al., 1980, Int. J. Cancer 26:171-76) which are available from ATCC may be used as an alternative phagocytic cell source.

Methods of determining whether an antibody mediates complement-dependent cytotoxicity upon binding to target cells are also known. The same methods can be applied to determine whether a CD70-binding agent mediates CDC on activated immune cells or CD70-expressing cancer cells. Illustrative examples of such methods are described infra.

The source of active complement can either be normal human serum or purified from laboratory animal including rabbits. In a standard assay, a CD70-binding agent is incubated with CD70-expressing activated immune cells (e.g., activated lymphocytes) or CD70-expressing cancer cells in the presence of complement. The ability of such CD70-binding agent to mediate cell lysis can be determined by several readouts. In one example, a Nasup.51CrO$_4$ release assay is used. In this assay, target cells are labeled with $Na^{51}CrO_4$. Unincorporated $Na^{51}CrO_4$ is washed off and cells are plated at a suitable density, typically between 5,000 to 50,000 cells/well, in a 96-well plate. Incubation with the CD70-binding agent in the presence of normal serum or purified complement typically last for 2-6 hours at 37.degree. C. in a 5% $CO_2$ atmosphere. Released radioactivity, indicating cell lysis, is determined in an aliquot of the culture supernatant by gamma ray counting. Maximum cell lysis is determined by releasing incorporated $Na^{51}CrO_4$ by detergent (0.5-1% NP-40 or Triton X-100) treatment. Spontaneous background cell lysis is determined in wells where only complement is present without any CD70-binding agents. Percentage cell lysis is calculated as (CD70-binding agent-induced lysis-spontaneous lysis)/maximum cell lysis. The second readout is a reduction of metabolic dyes, e.g., Alamar Blue, by viable cells. In this assay, target cells are incubated with CD70-binding agent with complement and incubated as described above. At the end of incubation, ⅒ volume of Alamar Blue (Biosource International, Camarillo, Calif.) is added. Incubation is continued for up to 16 hours at 37.degree. C. in a 5% $CO_2$ atmosphere. Reduction of Alamar Blue as an indication of metabolically active viable cells is determined by fluorometric analysis with excitation at 530 nm and emission at 590 nm. The third readout is cellular membrane permeability to propidium iodide (PI). Formation of pores in the plasma membrane as a result of complement activation facilitates entry of PI into cells where it will diffuse into the nuclei and bind DNA. Upon binding to DNA, PI fluorescence in the 600 nm significantly increases. Treatment of target cells with CD70-binding agent and complement is carried out as described above. At end of incubation, PI is added to a final concentration of 5.mu.g/ml. The cell suspension is then examined by flow cytometry using a 488 nm argon laser for excitation. Lysed cells are detected by fluorescence emission at 600 nm.

Additional Animal Models of Immunological Disorders or CD70-Expressing Cancers

The anti-CD70 binding agents of the present invention, e.g., antibodies or derivatives with one or more non-naturally encoded amino acids and ADCs of the invention, can be tested or validated in animal models of immunological disorders or CD70-expressing cancers. A number of established animal models of immunological disorders or CD70-expressing cancers are known to the skilled artisan, any of which can be used to assay the efficacy of the anti-CD70 antibody or derivative. Non-limiting examples of such models are described infra.

Examples for animal models of systemic and organ-specific autoimmune diseases including diabetes, lupus, systemic sclerosis, Sjogren's Syndrome, experimental autoimmune encephalomyelitis (multiple sclerosis), thyroiditis, myasthenia gravis, arthritis, uveitis, and inflammatory bowel disease have been described by Bigazzi, "Animal Models of Autoimmunity: Spontaneous and Induced," in The Autoimmune Diseases (Rose and Mackay eds., Academic Press, 1998) and in "Animal Models for Autoimmune and Inflammatory Disease," in Current Protocols in Immunology (Coligan et al. eds., Wiley and Sons, 1997).

Allergic conditions, e.g., asthma and dermatitis, can also be modeled in rodents. Airway hypersensitivity can be induced in mice by ovalbumin (Tomkinson et al., 2001, J. Immunol. 166:5792-800) or *Schistosoma mansoni* egg antigen (Tesciuba et al., 2001, J. Immunol. 167:1996-2003). The Nc/Nga strain of mice show marked increase in serum IgE and spontaneously develop atopic dermatitis-like leisons (Vestergaard et al., 2000, Mol. Med. Today 6:209-10; Watanabe et al., 1997, Int. Immunol. 9:461-66; Saskawa et al., 2001, Int. Arch. Allergy Immunol. 126:239-47).

Injection of immuno-competent donor lymphocytes into a lethally irradiated histo-incompatible host is a classical approach to induce GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, Bone Marrow Transpl. 26:931-938; Kataoka et al., 2001, Immunology 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, Science 241:1632-1639; Kamel-Reid and Dick, 1988, Science 242:1706-1709; Mosier et al., 1988, Nature 335:256-259). This has provided a small animal model system for the direct testing of potential therapeutic agents on human lymphoid cells. (See, e.g., Tournoy et al., 2001, J. Immunol. 166:6982-6991).

Moreover, small animal models to examine the in vivo efficacies of the anti-CD70 antibodies or derivatives can be created by implanting CD70-expressing human tumor cell lines into appropriate immunodeficient rodent strains, e.g., athymic nude mice or SCID mice. Examples of CD70-expressing human lymphoma cell lines include, for example, Daudi (Ghetie et al., 1994, Blood 83:1329-36; Ghetie et al., 1990, Int. J. Cancer 15:481-85; de Mont et al., 2001, Cancer Res. 61:7654-59), HS-Sultan (Cattan and Maung, 1996, Cancer Chemother. Pharmacol. 38:548-52; Cattan and Douglas, 1994, Leuk. Res. 18:513-22), Raji (Ochakovskaya et al., 2001, Clin. Cancer Res. 7:1505-10; Breisto et al., 1999, Cancer Res. 59:2944-49), and CA46 (Kreitman et al., 1999, Int. J. Cancer 81:148-55). Non-limiting example of a CD70-expressing Hodgkin's lymphoma line is L428 (Drexler, 1993, Leuk. Lymphoma 9:1-25; Dewan et al., 2005, Cancer Sci. 96:466-473). Non-limiting examples of CD70 expressing human renal cell carcinoma cell lines include 786-O (Ananth et al., 1999, Cancer Res. 59:2210-16; Datta et al., 2001, Cancer Res. 61:1768-75), ACHN (Hara et al., 2001, J. Urol. 166:2491-94; Miyake et al., 2002, J. Urol. 167:2203-08), Caki-1 (Prewett et al., 1998, Clin. Cancer Res. 4:2957-66; Shi and Siemann, 2002, Br. J. Cancer 87:119-26), and Caki-2 (Zellweger et al., 2001, Neoplasia 3:360-67). Non-limiting examples of CD70-expressing nasopharyngeal carcinoma cell lines include C15 and C17 (Busson et al., 1988, Int. J. Cancer 42:599-606; Bernheim et al., 1993, Cancer Genet. Cytogenet. 66:11-5). Non-limiting examples of CD70-expressing human glioma cell lines include U373 (Palma et al., 2000, Br. J. Cancer 82:480-7) and U87MG (Johns et al., 2002, Int. J. Cancer 98:398-408). Non-limiting examples of multiple myeloma cell lines include MM.1S (Greenstein et al., 2003, Experimental Hematology 31:271-282) and L363 (Diehl et al., 1978, Blut 36:331-338). (See also Drexler and Matsuo, 2000, Leukemia Research 24:681-703). These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD70 antibody or derivatives as described herein on modulating in vivo tumor growth.

CD70-Associated Disorders

The anti-CD70 antibodies and ADCs described herein are useful for treating or preventing a CD70-expressing cancer or an immunological disorder characterized by expression of CD70 by inappropriate activation of immune cells (e.g., lymphocytes or dendritic cells). Such expression of CD70 can be due to, for example, increased CD70 protein levels on the cells surface and/or altered antigenicity of the expressed CD70. Treatment or prevention of the immunological disorder, according to the methods described herein, is achieved by administering to a subject in need of such treatment or prevention an effective amount of the anti-CD70 antibody or derivative, whereby the antibody or derivative (i) binds to activated immune cells that express CD70 and that are associated with the disease state and (ii) exerts a cytotoxic, cytostatic, or immunomodulatory effect on the activated immune cells. In some embodiments, the cytotoxic, cytostatic, or immunomodulatory is exerted without conjugation to a cytotoxic, cytostatic, or immunomodulatory agent. In some embodiments, the cytotoxic, cytostatic, or immunomodulatory is exerted by conjugation to a cytotoxic, cytostatic, or immunomodulatory agent.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).)

Specific examples of such immunological diseases include the following: rheumatoid arthritis, psoriatic arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, *ascariasis*, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In some embodiments, the immunological disorder is a T cell-mediated immunological disorder, such as a T cell disorder in which activated T cells associated with the disorder express CD70. Anti-CD70 binding agents (e.g., antibodies or derivatives) can be administered to deplete such CD70-expressing activated T cells. In a specific embodiment, administration of anti-CD70 antibodies or derivatives can deplete CD70-expressing activated T cells, while resting T cells are not substantially depleted by the anti-CD70 or derivative. In this context, "not substantially depleted" means that less than about 60%, or less than about 70% or less than about 80% of resting T cells are not depleted.

The anti-CD70 antibodies and ADCs described herein are also useful for treating or preventing a CD70-expressing cancer. Treatment or prevention of a CD70-expressing cancer, according to the methods described herein, is achieved by administering to a subject in need of such treatment or prevention an effective amount of the anti-CD70 antibody or derivative, whereby the antibody or derivative (i) binds to CD70-expressing cancer cells and (ii) exerts a cytotoxic or cytostatic effect to deplete or inhibit the proliferation of the CD70-expressing cancer cells. In some embodiments, the cytotoxic, cytostatic, or immunomodulatory is exerted without conjugation to a cytotoxic, cytostatic, or immunomodulatory agent. In some embodiments, the cytotoxic, cytostatic, or immunomodulatory is exerted by conjugation to a cytotoxic, cytostatic, or immunomodulatory agent.

CD70-expressing cancers that can be treated or prevented by the methods described herein include, for example, different subtypes of Non-Hodgkin's Lymphoma (indolent NHLs, follicular NHLs, small lymphocytic lymphomas, lymphoplasmacytic NHLs, or marginal zone NHLs); Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas. The cancer can be, for example, newly diagnosed, pre-treated or refractory or relapsed. In some embodiments, a CD70-expressing cancer has at least about 15,000, at least about 10,000 or at least about 5,000 CD70 molecules/cell.

With respect to therapeutic regimens for combinatorial administration of conjugated or unconjugated anti-CD70 antibodies of the present invention, in a specific embodiment, an anti-CD70 binding agent is administered concurrently with a therapeutic agent. In another specific embodiment, the anti-CD70 antibody is conjugated to a therapeutic agent. In some embodiments, the subject is monitored following administration of the anti-CD70 binding agent, and optionally the therapeutic agent.

The therapeutic agent can be, for example, any agent that exerts a therapeutic effect on cancer cells or activated immune cells. Typically, the therapeutic agent is a cytotoxic or immunomodulatory agent. Such combinatorial administration can have an additive or synergistic effect on disease parameters (e.g., severity of a symptom, the number of symptoms, or frequency of relapse).

Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, rapamycin (Sirolimus), streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In some embodiments, the therapeutic agent can be a combined therapy, such as CHOP (Cyclophosphamide, Doxorubicin, Prednisolone and Vincristine), CHOP-R (Cyclophosphamide, Doxorubicin Vincristine, Prednisolone, and rituximab) or ABVD (Doxorubicin, Bleomycin, Vinblastine and Dacarbazine). Agents such as CC-1065 analogues, calicheamicin, maytansine, analogues of dolastatin 10, rhizoxin, and palytoxin can be linked to the anti-CD70 antibodies or derivatives thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. Patent Application Publication Nos. 20030083263 and 20050009751), International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin). Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, Cancer Res. 52:127-131). In some embodiments, the therapeutic agent is not a radioisotope. In some embodiments, the therapeutic agent is not ricin or saporin. In certain embodiments, the therapeutic agent is an anti-VEGF agent, such as AVASTIN (bevacizumab) or NEXAVAR (Sorafenib); a PDOF blocker, such as SUTENT (sunitinib malate); or a kinase inhibitor, such as NEXAVAR (sorafenib tosylateor). In some embodiments, the cytotoxic or immunomodulatory agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine or zoledronate.

In additional embodiments, the therapeutic agent is an antibody, such as a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (Medlmmune, Inc., MD; Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); CEAcide (Immunomedics, NJ; a humanized anti-CEA antibody); or an anti-CD40 antibody (e.g., as disclosed in U.S. Pat. No. 6,838,261).

Other suitable antibodies include, but are not limited to, antibodies against the following antigens: CA125, CA15-3, CA19-9, L6, Lewis Y, Lewis .lamda. alpha etoprotein, CA 242, placental alkaline phosphatase, prostate specific membrane antigen, prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen, IL-2 receptor, CD20, CD52, CD30, CD33, CD22, human chorionic gonadotropin, CD38, CD40, mucin, P21, MPG, and Neu oncogene product.

In some embodiments, the therapeutic agent is an immunomodulatory agent. The immunomodulatory agent can be, for example, gancyclovir, etanercept, tacrolimus, cyclosporine, rapamycin, REVLIMID (lenalidomide), cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists. In some embodiments, the immodulatory agent is a cytokine, such as G-CSF, GM-CSF or IL-2. Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products Way 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SKand F-104493, Leo Denmark SR-2566, Tanabe T-757 and Teijin TEI-1338.

The invention as described in the examples is not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or as otherwise known. Cell culture reagents were obtained from Invitrogen Corp., Carlsbad, Calif. The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING

```
<160> NUMBER OF SEQ ID NOS: 18

<210> SEQ ID NO 1
<211> LENGTH: 119
<212> TYPE: PRT
<213> ORGANISM: Homo sapiens
<220> FEATURE:
<221> NAME/KEY: MISC_FEATURE
<222> LOCATION: (119)..(119)
<223> OTHER INFORMATION: X is non-natural amino acid

<400> SEQUENCE: 1

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met Asn Trp Val Gln Gln Ala Pro Gly Lys Gly Leu Glu Trp Met
        35                  40                  45
```

```
Gly Ile Ile Asn Pro Tyr Asn Gly Gly Thr His Tyr Asn Gln Lys Phe
        50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ser Gly Tyr Asp Leu Tyr Phe Asp Tyr Trp Gly Gln Gly Thr
                100                 105                 110

Leu Val Thr Val Ser Ser Xaa
                115

<210> SEQ ID NO 2
<211> LENGTH: 107
<212> TYPE: PRT
<213> ORGANISM: Homo sapiens

<400> SEQUENCE: 2

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Asn Val Gly Thr Ala
                20                  25                  30

Val Ala Trp Tyr Gln Gln Lys Pro Gly Gln Ala Pro Arg Leu Leu Ile
             35                  40                  45

Tyr Ser Ala Phe Asn Arg Tyr Asn Gly Ile Pro Ala Arg Phe Ser Gly
 50                  55                  60

Ser Gly Pro Gly Thr Asp Phe Thr Leu Thr Ile Ser Ser Leu Gln Ser
 65                  70                  75                  80

Glu Asp Phe Ala Val Tyr Tyr Cys Gln Gln Tyr Ser Thr Tyr Pro Leu
                 85                  90                  95

Thr Phe Gly Gly Gly Thr Lys Val Glu Ile Lys
                100                 105

<210> SEQ ID NO 3
<211> LENGTH: 329
<212> TYPE: PRT
<213> ORGANISM: Homo sapiens
<220> FEATURE:
<221> NAME/KEY: MISC_FEATURE
<222> LOCATION: (329)..(329)
<223> OTHER INFORMATION: X is non-natural amino acid

<400> SEQUENCE: 3

Ser Thr Lys Gly Pro Ser Val Phe Pro Leu Ala Pro Ser Ser Lys Ser
 1               5                  10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
             35                  40                  45

Val His Thr Phe Pro Ala Val Leu Gln Ser Ser Gly Leu Tyr Ser Leu
 50                  55                  60

Ser Ser Val Val Thr Val Pro Ser Ser Ser Leu Gly Thr Gln Thr Tyr
 65                  70                  75                  80

Ile Cys Asn Val Asn His Lys Pro Ser Asn Thr Lys Val Asp Lys Lys
                 85                  90                  95

Val Glu Pro Lys Ser Cys Asp Lys Thr His Thr Cys Pro Pro Cys Pro
                100                 105                 110

Ala Pro Pro Val Ala Gly Gly Pro Ser Val Phe Leu Phe Pro Pro Lys
```

```
            115                 120                 125
Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Xaa
                325

<210> SEQ ID NO 4
<211> LENGTH: 328
<212> TYPE: PRT
<213> ORGANISM: Homo sapiens

<400> SEQUENCE: 4

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160
```

```
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
    210                 215                 220
Pro Arg Glu Pro Gln Val Tyr Thr Leu Pro Pro Ser Arg Asp Glu Leu
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly
                325

<210> SEQ ID NO 5
<211> LENGTH: 66
<212> TYPE: PRT
<213> ORGANISM: Homo sapiens
<220> FEATURE:
<221> NAME/KEY: MISC_FEATURE
<222> LOCATION: (66)..(66)
<223> OTHER INFORMATION: X is non-natural amino acid

<400> SEQUENCE: 5

Val Asp Asn Ala Leu Gln Ser Gly Asn Ser Gln Glu Ser Val Thr Glu
1               5                   10                  15
Gln Asp Ser Lys Asp Ser Thr Tyr Ser Leu Ser Ser Thr Leu Thr Leu
            20                  25                  30
Ser Lys Ala Asp Tyr Glu Lys His Lys Val Tyr Ala Cys Glu Val Thr
        35                  40                  45
His Gln Gly Leu Ser Ser Pro Val Thr Lys Ser Phe Asn Arg Gly Glu
    50                  55                  60
Cys Xaa
65

<210> SEQ ID NO 6
<211> LENGTH: 354
<212> TYPE: DNA
<213> ORGANISM: Homo sapiens

<400> SEQUENCE: 6
gaggtgcagc tggttcagtc tggggccgag gtgaaaaagc ctggggccac cgtgaaaatt      60
tcttgtaaag tttctggata taccttcacc gattactata tgaactgggt tcagcaagcc     120
cctggaaagg gactggagtg gatggggata attaacccat ataacggcgg caccactat     180 aaccaaaagt tcaaagggag ggttaccatc actgcagaca ccagcaccga caccgcttat     240
atggagctga gtagcctgag gtccgaggat actgcagttt actattgtgc gacttccggc     300
tacgatctgt actttgacta ctggggccag ggaaccctcg ttaccgtctc ctca           354
```

<210> SEQ ID NO 7
<211> LENGTH: 321
<212> TYPE: DNA
<213> ORGANISM: Homo sapiens

<400> SEQUENCE: 7

```
gaaattgtga tgacacagtc tccggccacc ctgtctgttt ctccggggga aagagctacc      60
ctgagttgca aagccagtca gaacgttggg accgccgttg cctggtacca acagaaacct     120
ggccaggccc cccgtctcct catctattcc gcattcaaca ggtataacgg catcccagca     180
aggttctccg gcagtgggcc agggacagac ttcactctca ccatcagcag cctgcagagc     240
gaggacttcg cagtttatta ttgtcagcag tacagtacct accctctcac tttcggagga     300
ggcactaaag ttgagatcaa a                                               321
```

<210> SEQ ID NO 8
<211> LENGTH: 651
<212> TYPE: DNA
<213> ORGANISM: Homo sapiens

<400> SEQUENCE: 8

```
gcacctcccg tcgccggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360
ctgcccccat cccgggatga gctgaccaag aaccaggtca gcctgacctg cctggtcaaa     420
ggcttctatc ccagcgacat cgccgtggag tgggagagca atgggcagcc ggagaacaac     480
tacaagacca cgcctcccgt gctggactcc gacggctcct tcttcctcta cagcaagctc     540
accgtggaca agagcaggtg gcagcagggg aacgtcttct catgctccgt gatgcatgag     600
gctctgcaca accactacac gcagaagagc ctctccctgt ctccgggttg a             651
```

<210> SEQ ID NO 9
<211> LENGTH: 324
<212> TYPE: DNA
<213> ORGANISM: Homo sapiens

<400> SEQUENCE: 9

```
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgcccT ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttga                                           324
```

<210> SEQ ID NO 10
<211> LENGTH: 122
<212> TYPE: PRT
<213> ORGANISM: Homo sapiens
<220> FEATURE:
<221> NAME/KEY: MISC_FEATURE
<222> LOCATION: (122)..(122)

<223> OTHER INFORMATION: X is non-natural amino acid

<400> SEQUENCE: 10

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Ser Asp Tyr
            20                  25                  30
Tyr Met Asn Trp Val Arg Gln Ala Pro Gly Gln Gly Leu Glu Trp Met
        35                  40                  45
Gly Glu Ile Asn Pro Thr Thr Gly Ala Thr Tyr Asn Gln Lys Phe
    50                  55                  60
Lys Ala Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Leu Phe Pro Ala Asn Tyr Ala Gly Phe Val Tyr Trp Gly
            100                 105                 110
Gln Gly Thr Leu Val Thr Val Ser Ser Xaa
        115                 120
```

<210> SEQ ID NO 11
<211> LENGTH: 106
<212> TYPE: PRT
<213> ORGANISM: Homo sapiens

<400> SEQUENCE: 11

```
Asp Ile Gln Met Thr Gln Ser Pro Ser Ser Leu Ser Ala Ser Val Gly
1               5                   10                  15
Asp Arg Val Thr Ile Thr Cys Ser Ala Ser Ser Ser Val Ser Tyr Met
            20                  25                  30
Tyr Trp Tyr Gln Gln Lys Pro Gly Lys Ala Pro Lys Leu Leu Ile Tyr
        35                  40                  45
Asp Thr Ser Lys Leu Ala Ser Gly Val Pro Ser Arg Phe Ser Gly Ser
    50                  55                  60
Gly Ser Gly Thr Asp Tyr Thr Phe Thr Ile Ser Ser Leu Gln Pro Glu
65                  70                  75                  80
Asp Ile Ala Thr Tyr Tyr Cys Gln Gln Trp Ser Ser Tyr Pro Trp Thr
                85                  90                  95
Phe Gly Gln Gly Thr Lys Val Glu Ile Lys
            100                 105
```

<210> SEQ ID NO 12
<211> LENGTH: 108
<212> TYPE: PRT
<213> ORGANISM: Homo sapiens
<220> FEATURE:
<221> NAME/KEY: MISC_FEATURE
<222> LOCATION: (108)..(108)
<223> OTHER INFORMATION: X is non-natural amino acid

<400> SEQUENCE: 12

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
```

```
              50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys Xaa
            100                 105
```

<210> SEQ ID NO 13
<211> LENGTH: 363
<212> TYPE: DNA
<213> ORGANISM: Homo sapiens

<400> SEQUENCE: 13

| | | | | | |
|---|---|---|---|---|---|
| caggtgcagc | tggttcagtc | tggggccgag | gtgaaaaagc | ctgggtcttc | tgtgaaagtt | 60 |
| tcttgtaaag | caagtggata | ttctttcagt | gattactata | tgaactgggt | taggcaggcc | 120 |
| cctggccaag | gactcgagtg | gatggggag | attaacccaa | ccaccggcgg | ggcaacctat | 180 |
| aaccaaaagt | tcaaagcaag | ggttaccatc | actgctgacg | agagcacttc | aactgcttat | 240 |
| atggagctga | gcagcctgag | gtccgaggat | accgcagttt | actattgtgc | gagatccctc | 300 |
| ttccctgcaa | actacgcagg | cttcgtttac | tggggacagg | gaaccctggt | caccgtctcc | 360 |
| tca | | | | | | 363 |

<210> SEQ ID NO 14
<211> LENGTH: 341
<212> TYPE: DNA
<213> ORGANISM: Homo sapiens

<400> SEQUENCE: 14

| | | | | | |
|---|---|---|---|---|---|
| gatattcaga | tgacacagtc | tccgtcttct | ctgtctgcca | gtgttgggga | tagagttacc | 60 |
| attacctgca | gtgccagttc | tagtgtttcc | tacatgtact | ggtaccaaca | gaaacctggc | 120 |
| aaggccccca | aactcctcat | ctatgacacc | tccaaactcg | caagtggcgt | tccatccagg | 180 |
| ttctccggca | gtgggagtgg | gacagactat | actttcacca | tcagcagcct | ccagcctgag | 240 |
| gacatcgcaa | cctattattg | tcagcagtgg | agtagctacc | cttggacttt | cggacaggga | 300 |
| acgaaagttg | agatcaaacg | tacggtggct | gcaccatctg | t | | 341 |

<210> SEQ ID NO 15
<211> LENGTH: 990
<212> TYPE: DNA
<213> ORGANISM: Homo sapiens

<400> SEQUENCE: 15

| | | | | | |
|---|---|---|---|---|---|
| tagagcacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | cacctcccgt | cgccggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcggaggga | gcagtacaac | 540 |
```

```
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggttga                                     990
```

```
<210> SEQ ID NO 16
<211> LENGTH: 301
<212> TYPE: DNA
<213> ORGANISM: Homo sapiens

<400> SEQUENCE: 16
cttcatcttc ccgccatctg atgagcagtt gaaatctgga actgcctctg ttgtgtgcct     60
gctgaataac ttctatccca gagaggccaa agtacagtgg aaggtggata acgccctcca    120
atcgggtaac tcccaggaga gtgtcacaga gcaggacagc aaggacagca cctacagcct    180
cagcagcacc ctgacgctga gcaaagcaga ctacgagaaa cacaaagtct acgcctgcga    240
agtcacccat caggggctga gctcgcccgt cacaaagagc ttcaacaggg gagagtgttg    300
a                                                                    301
```

```
<210> SEQ ID NO 17
<211> LENGTH: 118
<212> TYPE: PRT
<213> ORGANISM: Homo sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser
        115
```

```
<210> SEQ ID NO 18
<211> LENGTH: 107
<212> TYPE: PRT
<213> ORGANISM: Homo sapiens

<400> SEQUENCE: 18

Glu Ile Val Leu Thr Gln Ser Pro Ala Thr Leu Ser Leu Ser Pro Gly
1               5                   10                  15
```

| | | | | | | | | | | | | |
|---|---|---|---|---|---|---|---|---|---|---|---|---|
| Glu | Arg | Ala | Thr<br>20 | Leu | Ser | Cys | Arg | Ala<br>25 | Ser | Gln | Ser | Val<br>30 | Ser | Ser | Tyr |
| Leu | Ala | Trp<br>35 | Tyr | Gln | Gln | Lys | Pro<br>40 | Gly | Gln | Ala | Pro | Arg<br>45 | Leu | Leu | Ile |
| Tyr | Asp<br>50 | Ala | Ser | Asn | Arg | Ala<br>55 | Thr | Gly | Ile | Pro | Ala<br>60 | Arg | Phe | Ser | Gly |
| Ser<br>65 | Gly | Ser | Gly | Thr | Asp<br>70 | Phe | Thr | Leu | Thr | Ile<br>75 | Ser | Ser | Leu | Glu | Pro<br>80 |
| Glu | Asp | Phe | Ala | Val<br>85 | Tyr | Tyr | Cys | Gln | Gln<br>90 | Arg | Thr | Asn | Trp | Pro<br>95 | Leu |
| Thr | Phe | Gly | Gly<br>100 | Gly | Thr | Lys | Val | Glu<br>105 | Ile | Lys | | | | | |

What is claimed is:

1. A compound comprising Formula (VIII) or (IX), wherein the compound is an αCD70 antibody conjugated to a dolastatin, wherein the conjugation occurs via a non-naturally encoded amino acid in the antibody, wherein Formula (VIII) and (IX) correspond to:

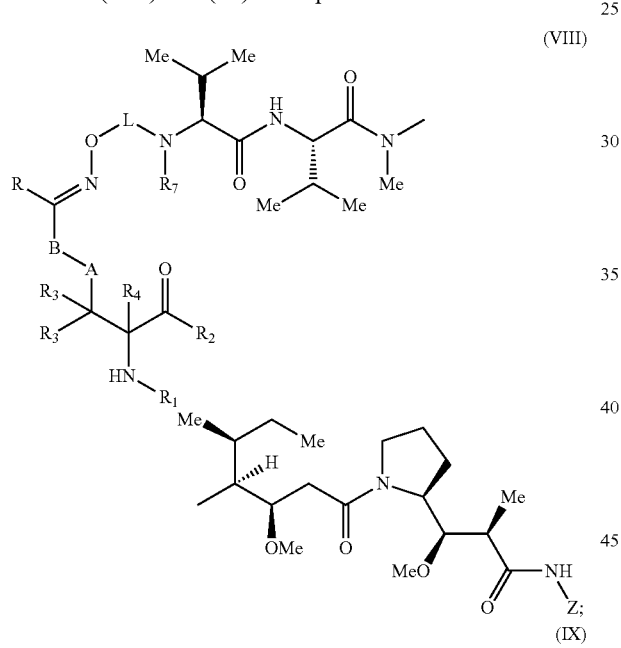

(VIII)

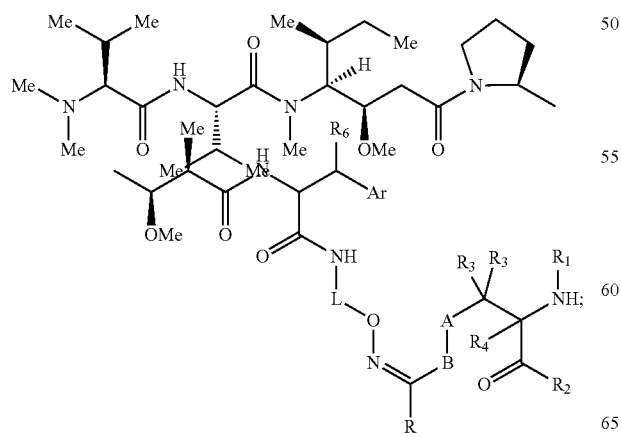

(IX)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is H, or an anti-CD70 (αCD70) antibody;

R$_2$ is OH, or an anti-CD70 (αCD70) antibody;

R$_3$ and R$_4$ are each independently H, halogen, lower alkyl, or substituted lower alkyl, or R$_3$ and R$_4$ or two R$_3$ groups optionally form a cycloalkyl or a heterocycloalkyl;

Z has the structure of:

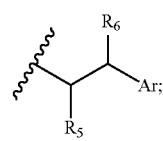

$R_5$ is H, $COR_8$, $C_1$-$C_6$alkyl, or thiazole;
$R_8$ is OH;
$R_6$ is OH or H;
Ar is phenyl or pyridine;
$R_7$ is $C_1$-$C_6$alkyl or hydrogen;
L is a linker selected from the group consisting of alkylene, -alkylene-C(O)—, -(alkylene-O)$_n$-alkylene-, -(alkylene-O)$_n$-alkylene-C(O)—, -(alkylene-O)$_n$—(CH$_2$)$_{n'}$—NHC(O)—(CH$_2$)$_{n''}$—C(Me)$_2$-S—S—(CH$_2$)$_{n'''}$—NHC(O)-(alkylene-O)$_{n''''}$-alkylene-, -(alkylene-O)$_n$-alkylene-W—, -alkylene-C(O)—W—, -(alkylene-O)$_n$-alkylene-U-alkylene-C(O)—, and -(alkylene-O)$_n$-alkylene-U-alkylene-;
W has the structure of:

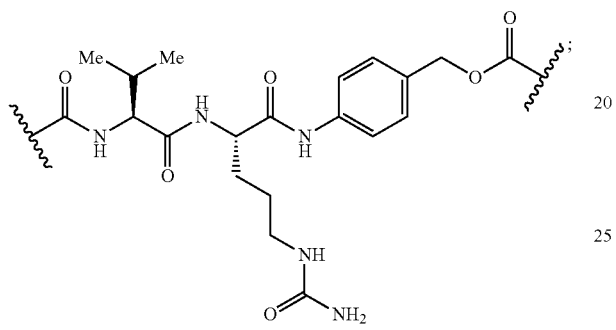

U has the structure of:

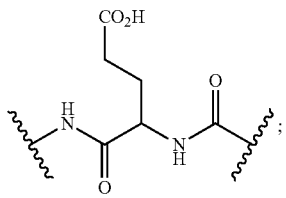 [SMILES: *NC(=O)C(CCC(=O)O)NC(*)=O]

and each n, n', n", n''' and n'''' are independently integers greater than or equal to one; with the proviso that one and only one of $R_1$ or $R_2$ is an anti-CD70 (αCD70) antibody; or a pharmaceutically acceptable prodrug thereof.

2. The compound of claim 1, wherein $R_1$ is H and $R_2$ is an anti-CD70 (αCD70) antibody.

3. The compound of claim 1, wherein $R_1$ is an anti-CD70 (αCD70) antibody and $R_2$ is OH.

4. The compound of claim 1, wherein the anti-CD70 (αCD70) antibody comprises no more than ten non-naturally encoded amino acids.

* * * * *

UNITED STATES PATENT AND TRADEMARK OFFICE
CERTIFICATE OF CORRECTION

PATENT NO. : 10,208,123 B2
APPLICATION NO. : 14/410021
DATED : February 19, 2019
INVENTOR(S) : R. S. Barnett et al.

Page 1 of 1

It is certified that error appears in the above-identified patent and that said Letters Patent is hereby corrected as shown below:

In the Claims

Column 359, Lines 27 to 48, replace " 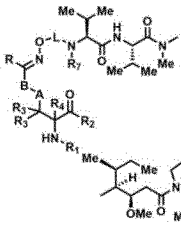 " with 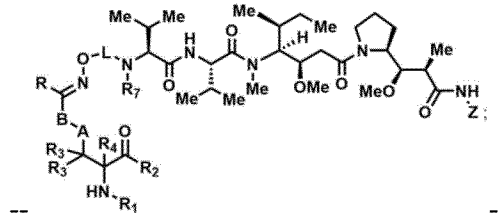 --.

Column 359, Lines 50 to 65, replace " 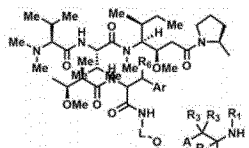 " with 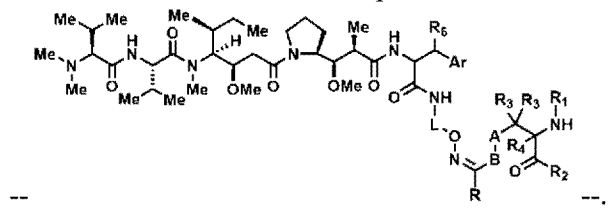 --.

Column 360, Line 48, replace "where" with --wherein--.

Signed and Sealed this
Twenty-eighth Day of June, 2022

Katherine Kelly Vidal
*Director of the United States Patent and Trademark Office*